United States Patent
Terauchi et al.

(10) Patent No.: US 8,268,848 B2
(45) Date of Patent: Sep. 18, 2012

(54) CYCLOPROPANE COMPOUND

(75) Inventors: Taro Terauchi, Tsukuba (JP); Ayumi Takemura, Tsukuba (JP); Takashi Doko, Tokyo (JP); Yu Yoshida, Tsukuba (JP); Toshiaki Tanaka, Tsukuba (JP); Keiichi Sorimachi, Tsukuba (JP); Yoshimitsu Naoe, Tsukuba (JP); Carsten Beuckmann, Tsukuba (JP); Yuji Kazuta, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/237,205

(22) Filed: Sep. 20, 2011

(65) Prior Publication Data

US 2012/0095031 A1     Apr. 19, 2012

Related U.S. Application Data

(60) Provisional application No. 61/385,342, filed on Sep. 22, 2010.

(30) Foreign Application Priority Data

Sep. 22, 2010   (JP) ................. 2010-211629

(51) Int. Cl.
*A01N 43/54*     (2006.01)
*A61K 31/505*    (2006.01)
(52) U.S. Cl. ...................... 514/269; 544/298
(58) Field of Classification Search ............ 514/269; 544/298
See application file for complete search history.

(56) References Cited

U.S. PATENT DOCUMENTS

| | | | |
|---|---|---|---|
| 5,935,814 A | 8/1999 | Bergsma et al. | |
| 6,001,963 A | 12/1999 | Bergsma et al. | |
| 6,020,157 A | 2/2000 | Bergsma et al. | |
| 6,166,193 A | 12/2000 | Yanagisawa | |
| 6,309,854 B1 | 10/2001 | Bergsma et al. | |
| 2008/0076771 A1* | 3/2008 | Reiter et al. | 514/245 |
| 2010/0261644 A1 | 10/2010 | DeFossa et al. | |
| 2012/0165339 A1* | 6/2012 | Terauchi et al. | 514/252.03 |

FOREIGN PATENT DOCUMENTS

| | | |
|---|---|---|
| JP | 10-229887 | 9/1998 |
| JP | 10-327888 | 12/1998 |
| JP | 10-327889 | 12/1998 |
| JP | 11-178588 | 7/1999 |
| JP | 06-328057 | 12/2006 |
| WO | WO 96/34877 | 11/1996 |
| WO | WO 2005/118548 | 12/2005 |
| WO | WO 2007/105177 | 9/2007 |
| WO | WO 2007/129188 | 11/2007 |
| WO | WO 2008/031772 | 3/2008 |
| WO | WO 2008/038251 | 4/2008 |
| WO | WO 2008/069997 | 6/2008 |
| WO | WO 2008/081399 | 7/2008 |
| WO | WO 2009/039942 | 4/2009 |
| WO | WO 2009/047723 | 4/2009 |

OTHER PUBLICATIONS

E. Mignot et al., 5 Nature Neuroscience Supplement 1071-1075 (2002).*
D.A. Prober et al., 26 The Journal of Neuroscience 13400-13410 (2006).*
Richey et al., "Pharmacological Advances in the Treatment of Insomnia," *Curr Pharm Des*. 17(15):1471-75 (2011).
Borgland et al., "Orexin A in the VTA is critical for the induction of synaptic plasticity and behavioral sensitization to cocaine," *Neuron*., 49:589-601 (2006).
Brisbare-Roch et al., "Promotion of sleep by targeting the orexin system in rats, dogs and humans," *Nat. Med.*, 13:150-155 (2007).
Chemelli et al., "Narcolepsy in orexin knockout mice: molecular genetics of sleep regulation," *Cell*, 98:437-451 (1999).
Dorffner et al., "Effect of almorexant treatment on sleep variables in patients with primary insomnia compared with healthy controls," *European Neuropsychopharmacology*, 20(Suppl 3):S252-S253 (2007).
Ida et al., "Possible involvement of orexin in the stress reaction in rats," *Biochem. Biophys. Res. Commun*., 270:318-323 (2000).
Sakurai et al., "Orexins and orexin receptors: a family of hypothalamic neuropeptides and G protein-coupled receptors that regulate feeding behavior," *Cell*, 92:573-585 (1998).
Shoblock et al., "Selective blockade of the orexin-2 receptor attenuates ethanol self-administration, place preference, and reinstatement," *Psychopharmacology*, 215:191-203 (2011).
Winrow et al., "Orexin receptor antagonism prevents transcriptional and behavioral plasticity resulting from stimulant exposure," *Neuropharmacology*, 58:185-194 (2010).

(Continued)

*Primary Examiner* — James O Wilson
*Assistant Examiner* — Alexander R Pagano
(74) *Attorney, Agent, or Firm* — Fish & Richardson P.C.

(57) ABSTRACT

A cyclopropane compound represented by the following formula (A) or a pharmaceutically acceptable salt thereof has orexin receptor antagonism, and therefore has a potencial of usefulness for the treatment of sleep disorder for which orexin receptor antagonism is effective, for example, insomnia:

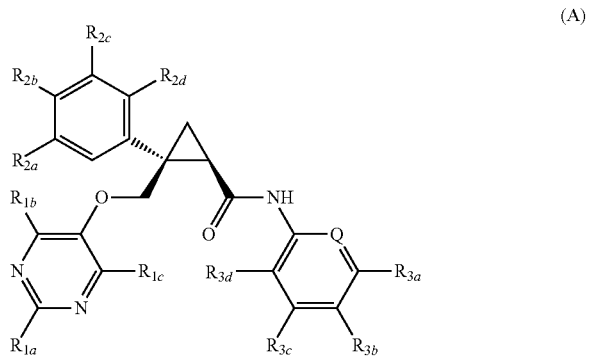

(A)

wherein Q represents —CH— or a nitrogen atom, $R_{1a}$ and $R_{1b}$ each independently represent a $C_{1-6}$ alkyl group and the like, $R_{1c}$ represents a hydrogen atom and the like, $R_{2a}$, $R_{2b}$, $R_{2c}$ and $R_{2d}$ each independently represent a hydrogen atom, a halogen atom, a $C_{1-6}$ alkyl group and the like, $R_{3a}$, $R_{3b}$ and $R_{3c}$ each independently represent a hydrogen atom, a halogen atom and the like, and $R_{3d}$ represents a hydrogen atom and the like.

27 Claims, 1 Drawing Sheet

OTHER PUBLICATIONS

English translation of the allowed claims in JP 2012-500752 dated Feb. 28, 2012.
Request for Expedited Examination of JP 2012-500752 dated Jan. 18, 2012 (in Japanese).
Request for Expedited Examination of JP 2012-500752 dated Jan. 18, 2012 (English translation).
International Search Report and Written opinion of PCT/JP2011/071325 dated Oct. 18, 2011 (in Japanese).
International Search Report and Written opinion of PCT/JP2011/071325 dated Oct. 18, 2011 (English Translation).
Decision to Grant JP 2012-500752 dated Feb. 28, 2012 (in Japanese).
Decision to Grant JP 2012-500752 dated Feb. 28, 2012 (English translation).

* cited by examiner

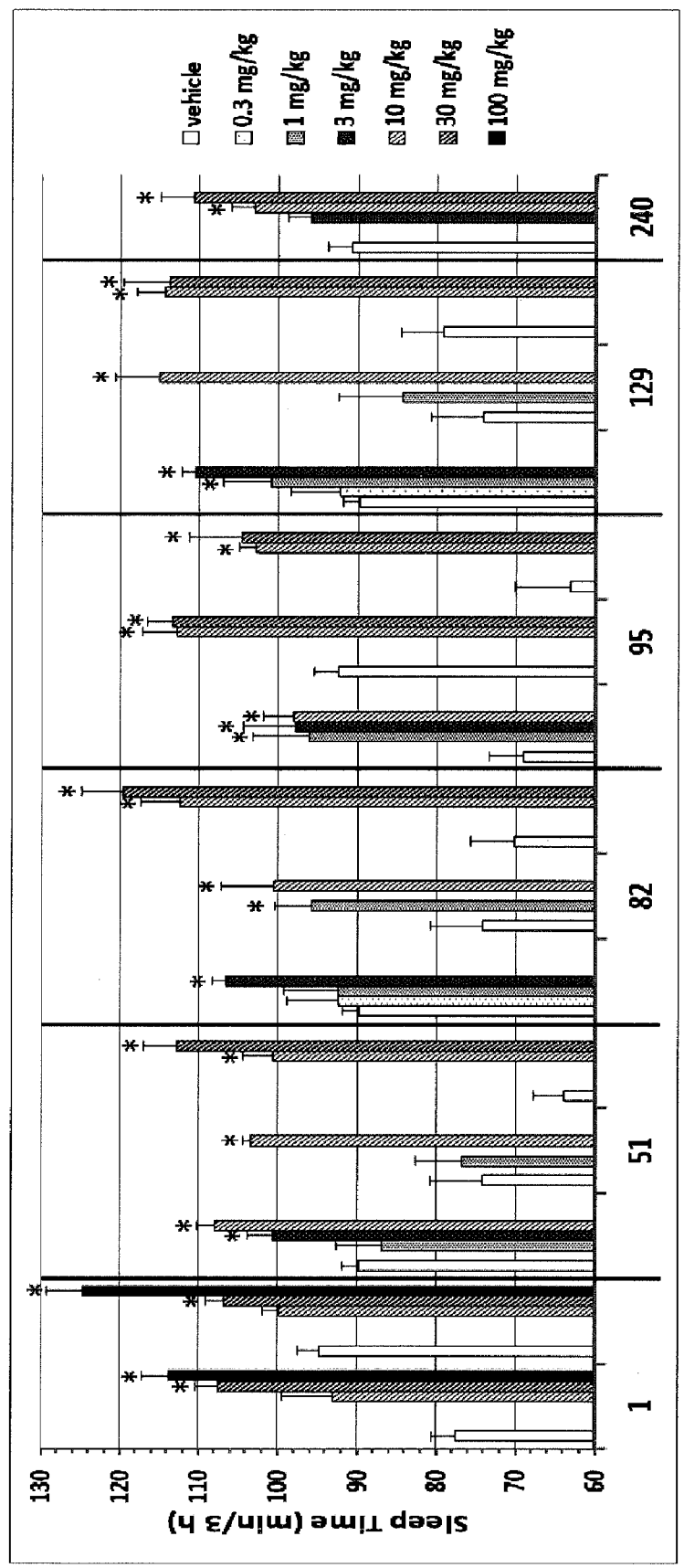

CYCLOPROPANE COMPOUND

CROSS REFERENCE TO RELATED APPLICATIONS

The present application claims priority from U.S. Provisional Application No. 61/385,342 filed Sep. 22, 2010 and Japanese Patent Applicaton No. 2010-211629 filed Sep. 22, 2010, all of the contents of which are incorporated herein by reference.

BACKGROUND OF THE INVENTION (1) Field of the Invention

The present invention relates to a cyclopropane compound having orexin receptor antagonism or a pharmaceutically acceptable salt thereof, and a medicinal use thereof. The present invention also relates to a pharmaceutical composition comprising the above-mentioned compound as an active ingredient.

(2) Description of Related Art

Orexin-A (OX-A, consisting of 33 amino acid peptides) and orexin-B (OX-B, consisting of 28 amino acid peptides), two types of intracerebral neuropeptides, which are expressed by neurons localized at the hypothalamus in the brain, have been discovered (Patent Document 5 and Non-Patent Document 1) as endogenous ligands of G protein-coupled receptors mainly existing in the brain, namely, orexin receptors (Patent Documents 14). It has been known that such orexin receptors include two subtypes, namely, an $OX_1$ receptor (OX1) as a type 1 subtype and an $OX_2$ receptor (OX2) as a type 2 subtype. OX1 binds OX-A more selectively than OX-B, and OX2 is able to bind OX-A as well as OX-B. Orexin has been found to stimulate the food consumption of rats, and thus, it has been suggested that orexin would play a physiological role as a mediator in a central feedback mechanism for controlling feeding behavior (Non-Patent Document 1). On the other hand, it has been observed that orexins control sleep-wake conditions. Thus, it is considered that orexins will potentially lead to new therapies for narcolepsy, as well as for insomnia and other sleep disorders (Non-Patent Document 2). In addition, it has been suggested that orexin signals in the ventral tegmental area regarding neural plasticity associated with opioid dependence and nicotine dependence play an important role in vivo (Non Patent Document 3 and Non Patent Document 4). It has been also reported that OX2 receptor was selectively inhibited to alleviate ethanol dependence in experiment using rats (Non Patent Document 5). Moreover, it has been reported that corticotropin-releasing factor (CRF), which involved in depression and anxiety disorder, is involved in orexin-induced behaviors in rats, and that orexin may play an important role in some stress reactions (Non Patent Document 6).

Orexin receptors are found in the mammalian brain and may have numerous implications in pathologies such as depression; dysphoria; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders; sleep disorders; cardiovascular diseases, diabetes; appetite/taste disorders; vomiting/nausea; asthma; Parkinson's disease; Cushing's syndrome/disease; basophil adenoma; prolactinoma; hyperprolactinemia; hypopituitarism; hypophysis tumour/adenoma; hypothalamic diseases; inflammatory bowel disease; gastric dyskinesia; gastric ulcers; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardial infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep apnea; narcolepsy; insomnia; parasomnia; and neurodegenerative disorders including nosological entities such as disinhibition-dementia-parkinsonism-amyotrophy complex; pallido-ponto-nigral degeneration epilepsy; seizure disorders and other diseases related to general orexin system dysfunction.

(2R)-2-{(1S)-6,7-dimethoxy-1-[2-(4-trifluoromethylphenyl)ethyl]-3,4-dihydro-1H-isoquinolin-2-yl}-N-methyl-2-phenylacetamide (ACT-078573; almorexant), a compound that functions as an orexin receptor antagonist, had been clinically developed as a therapeutic agent for insomnia (Patent Document 6). This compound causes a decrease in wakefulness in rats, which is characterized by decreased functions of awakening and spontaneous locomotor activity, and it dose-dependently increases both rapid eye movement (REM) sleep time and non-REM sleep time, and this compound, when administered to normal humans, exhibits dose-dependently a reduction of sleep latency, sleep efficacy and extension of total sleep time (Non Patent Document 7). There is also an article reporting that the compound, when administered to patients with insomnia, exhibits improvement of sleep efficacy, shortness of sleep latency, increase of REM sleep and improvement of REM sleep ratio (Non Patent Document 8). Furthermore, it has also been described that this compound improves the memory function of model rats (Patent Document 7), and that the compound is effective for posttraumatic stress disorder (Patent Document 8). On the other hand, 5-chloro-2-{(5R)-5-methyl-4-[5-methyl-2-(2H-1,2,3-triazol-2-yl)benzoyl]-1,4-diazepan-1-yl}-1,3-benzoxazole (MK-4305; suvorexant, Patent Document 9) and MK-6096, which have dual orexin antagonisms against OX1 and OX2, have been clinically developed as a medicine for insomnia.

RELATED ART DOCUMENTS

Patent Documents
Patent Document 1: International Publication No. WO1996/34877
Patent Document 2: JP 10-327888 A
Patent Document 3: JP 10-327889 A
Patent Document 4: JP 11-178588 A Patent Document 5: JP 10-229887 A
Patent Document 6: International Publication No. WO2005/118548
Patent Document 7: International Publication No. WO2007/105177
Patent Document 8: International Publication No. WO2009/047723
Patent Document 9: International Publication No. WO2008/069997

Non Patent Documents

Non Patent Document 1: Sakurai T. et al., Cell, 1998, 92, 573-585

Non Patent Document 2: Chemelli R. M. et al., Cell, 1999, 98, 437-451.

Non Patent Document 3: S. L. Borgland et al., Neuron, 2006, 49, 589-601

Non Patent Document 4: C. J. Winrow et al., Neuropharmacology, 2010, 58, 185-194

Non Patent Document 5: J. R. Shoblock et al., Psychopharmacology, 2011, 215, 191-203

Non Patent Document 6: T. Ida et al., Biochemical and Biophysical Research Communications, 2000, 270, 318-323

Non Patent Document 7: F. Jenck et al., Nature Medicine 2007, 13, 150-155

Non Patent Document 8: G Dorffner et al., European Neuropsychopharmacology, Vol. 20, Supplement, 3, 2007, S252-S253

BRIEF SUMMARY OF THE INVENTION

It is an object of the present invention to provide a cyclopropane compound or a pharmaceutically acceptable salt thereof having orexin receptor antagonism, and a pharmaceutical composition comprising the same.

The present invention relates to the following [1] to [20]:

[1] A compound represented by the following formula (I) or a pharmaceutically acceptable salt thereof:

[Formula 1]

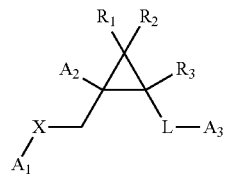

(I)

wherein $A_1$ represents a pyrimidinyl group or a N-oxide pyrimidinyl group, each of which may optionally have substituents selected from Substituent Group α, $A_2$ and $A_3$ each independently represent an aryl group selected from Group 1, which may optionally have 1 to 3 substituents selected from Substituent Group α, or a heterocyclic group selected from group 3, which may optionally have 1 to 3 substituents selected from Substituent Group β, $R_1$, $R_2$ and $R_3$ each independently represent a hydrogen atom, a halogen atom, a $C_{1-6}$ alkyl group which may optionally have 1 to 3 substituents selected from Substituent Group β, or a $C_{3-8}$ cycloalkyl group which may optionally have 1 to 3 substituents selected from Substituent Group β, X represents an oxygen atom, a $C_{1-6}$ alkylene group, a formula —$NR_4$— wherein $R_4$ represents a hydrogen atom or a $C_{1-6}$ alkyl group, L represents a bond or a formula —CONH—, wherein Substituent Group a: a cyano group, a halogen atom, a hydroxyl group, an oxo group, a formula —$NR_5R_6$ wherein $R_5$ and $R_6$ each independently represent a hydrogen atom or a $C_{1-6}$ alkyl group, a $C_{1-6}$ alkyl group which may optionally have 1 to 3 substituents selected from Substituent Group β, a $C_{1-6}$ alkoxy group which may optionally have 1 to 3 substituents selected from Substituent Group β, a $C_{1-6}$ alkylcarbonyl group which may optionally have 1 to 3 substituents selected from Substituent Group β, a $C_{1-6}$ alkylsulfonyl group which may optionally have 1 to 3 substituents selected from Substituent Group β, an aryl group selected from Group 1, which may optionally have 1 to 3 substituents selected from Substituent Group β, and a heteroaryl group selected from Group 2, which may optionally have 1 to 3 substituents selected from Substituent Group β;

Substituent Group β: a cyano group, a halogen atom, a hydroxyl group, a $C_{3-8}$ cycloalkyl group, and a $C_{1-6}$ alkoxy group;

Group 1: a phenyl group, a naphthyl group, an azulenyl group, an anthryl group, and a phenanthryl group;

Group 2: a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a triazinyl group, an indolyl group, an isoindolyl group, an indazolyl group, a benzoxazolyl group, a benzisoxadiazolyl group, a benzothiazolyl group, a benzisothiazolyl group, a quinolyl group, and an isoquinolyl group; and Group 3: a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a pyrimidinyl group, a triazinyl group, a 2-pyridonyl group, a 4-pyridonyl group, a pyridazidonyl group, a pyrimididonyl group, a purinyl group, a pteridinyl group, a quinolyl group, an isoquinolyl group, a naphthylidyl group, a quinoxalyl group, a cinnolyl group, a quinazolyl group, a phthalazyl group, an imidazopyridyl group, an imidazothiazolyl group, an imidazoxazolyl group, a benzimidazolyl group, an indolyl group, an isoindolyl group, an indazolyl group, a pyrrolopyridyl group, a thienopyridyl group, a fluoropyridyl group, a benzoxazolyl group, a benzisoxadiazolyl group, a benzothiazolyl group, a benzisothiazolyl group, a pyridopyrimidinyl group, an oxodihydropyridopyrimidinyl group, a benzofuryl group, a benzothienyl group, a benzothiadiazolyl group, a benzo[1,3]dioxolyl group, a thienofuryl group, a dihydrousobenzofuranyl group, a chromanyl group, an isochromanyl group, a 1,3-dioxaindanyl group, a 1,4-dioxatetralinyl group, and a dihydrobenzo[1,4]oxazinyl group.

[2] The compound according to [1] above, which is represented by the following formula (II), or a pharmaceutically acceptable salt thereof:

[Formula 2]

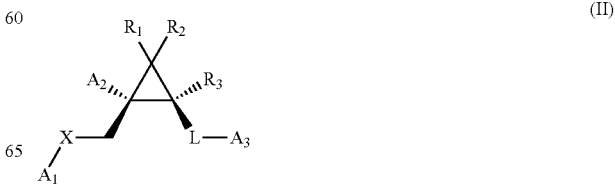

(II)

wherein $A_1$, $A_2$, $A_3$, $R_1$, $R_2$, $R_3$, X and L have the same definitions as those according to [1] above.

[3] The compound according to [1] or [2] above, which is represented by the following formula (III), or a pharmaceutically acceptable salt thereof:

[Formula 3]

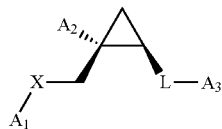

(III)

wherein
$A_1$ represents a pyrimidinyl group or a N-oxide pyrimidinyl group, each of which is substituted with $R_{1a}$, $R_{1b}$ and $R_{1c}$)
$A_2$ represents an aryl group selected from Group 1 or a heteroaryl group selected from Group 2, each of which is substituted with $R_{2a}$, $R_{2b}$, $R_{2c}$ and $R_{2d}$,
$A_3$ represents an aryl group selected from Group 1 or a heterocyclic group selected from Group 3, each of which is substituted with $R_{3a}$, $R_{3b}$, $R_{3c}$ and $R_{3d}$, wherein
$R_{1a}$, $R_{1b}$ and $R_{1c}$ each independently represent a hydrogen atom, a hydroxyl group, a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group, wherein
$R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group or a halo-$C_{1-6}$ alkyl group,
$R_{3a}$, $R_{3b}$, $R_{3c}$ and $R_{3d}$ each independently represent a hydrogen atom, a halogen atom, a hydroxyl group, a $C_{1-6}$ alkyl group, a $C_{1-6}$ alkoxy group, a halo-$C_{1-6}$ alkyl group, a $C_{1-6}$ alkoxy-$C_{1-6}$ alkyl group, a cyano group or a cyano-$C_{1-6}$ alkyl group, and
X, L, Group 1, Group 2 and Group 3 have the same definitions as those according to [1] above.

[4] The compound according to [3] above, or a pharmaceutically acceptable salt thereof, wherein L represents a formula —CONH—.

[5] The compound according to [4] above, or a pharmaceutically acceptable salt thereof, wherein X represents an oxygen atom.

[6] A compound represented by the following formula (IV) or a pharmaceutically acceptable salt thereof:

[Formula 4]

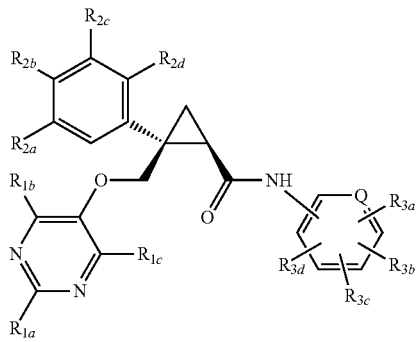

(IV)

wherein
Q represents —CH— or a nitrogen atom, $R_{1a}$ and $R_{1b}$ each independently represent a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group,
$R_{1c}$ represents a hydrogen atom or a hydroxyl group,
$R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group, a halo-$C_{1-6}$ alkyl group or a cyano group, and
$R_{3a}$, $R_{3b}$, $R_{3c}$ and $R_{3d}$ each independently represent a hydrogen atom, a halogen atom, a hydroxyl group, a $C_{1-6}$ alkyl group, a $C_{1-6}$ alkoxy group, a halo-$C_{1-6}$ alkyl group, a $C_{1-6}$ alkoxy-$C_{1-6}$ alkyl group, a cyano group or a cyano-$C_{1-6}$ alkyl group.

[7] A compound represented by the following formula (A) or a pharmaceutically acceptable salt thereof:

[Formula 5]

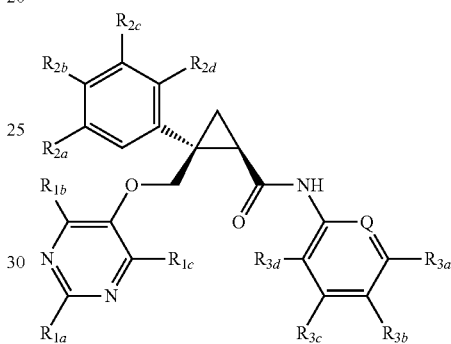

(A)

wherein
Q represents —CH— or a nitrogen atom, when Q represents —CH—,
$R_{1a}$ and $R_{1b}$ each independently represent a $C_{1-6}$ alkyl group, a halo-$C_{1-6}$ alkyl group or a $C_{1-6}$ alkoxy-$C_{1-6}$ alkyl group,
$R_{1c}$ represents a hydrogen atom,
$R_{2a}$, $R_{2b}$, $R_{2c}$, and $R_{2d}$ each independently represent a hydrogen atom, a halogen atom, a $C_{1-6}$ alkyl group, a $C_{1-6}$ alkoxy group or a halo-$C_{1-6}$ alkyl group,
$R_{3a}$ and $R_{3c}$ each independently represent a hydrogen atom, a halogen atom, a $C_{1-6}$ alkyl group, a halo-$C_{1-6}$ alkyl group, a $C_{1-6}$ alkoxy group, a $C_{1-6}$ alkoxy-$C_{1-6}$ alkyl group, a cyano group or a cyano-$C_{1-6}$ alkyl group,
$R_{3b}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and
$R_{3d}$ represents a hydrogen atom or a fluorine atom,
or
when Q represents a nitrogen atom,
$R_{1a}$ and $R_{1b}$ each independently represent a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group,
$R_{1c}$ represents a hydrogen atom or a hydroxyl group,
$R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group or a halo-$C_{1-6}$ alkyl group,
$R_{3a}$ represents a hydrogen atom, a halogen atom, a $C_{1-6}$ alkyl group, a $C_{1-6}$ alkoxy group or a $C_{1-6}$ alkoxy-$C_{1-6}$ alkyl group,
$R_{3b}$ represents a hydrogen atom, a halogen atom, a $C_{1-6}$ alkyl groupor a halo-$C_{1-6}$ alkyl group, $R_{3c}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom.

[8] The compound according to [7] above, which is represented by the following formula (B), or a pharmaceutically acceptable salt thereof:

[Formula 6]

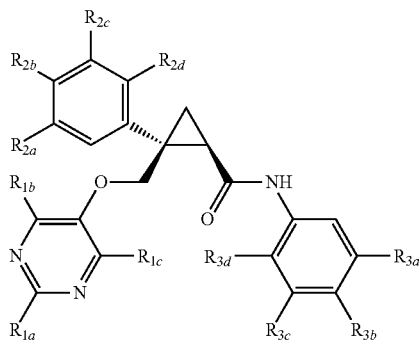

(B)

wherein $R_{1a}$ and $R_{1b}$ each independently represent a $C_{1-6}$ alkyl group, a halo-$C_{1-6}$ alkyl group or a $C_{1-6}$ alkoxy-$C_{1-6}$ alkyl group, $R_{1c}$ represents a hydrogen atom, $R_{2a}$, $R_{2b}$, $R_{2c}$ and $R_{2d}$ each independently represent a hydrogen atom, a halogen atom, a $C_{1-6}$ alkyl group, a $C_{1-6}$ alkoxy group or a halo-$C_{1-6}$ alkyl group, $R_{3a}$ and $R_{3c}$ each independently represent a hydrogen atom, a halogen atom, a $C_{1-6}$ alkyl group, a halo-$C_{1-6}$ alkyl group, a $C_{1-6}$ alkoxy group, a $C_{1-6}$ alkoxy-$C_{1-6}$ alkyl group, a cyano group or a cyano-$C_{1-6}$ alkyl group, $R_{3b}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom or a fluorine atom.

[9] The compound according to [7] above, which is represented by the following formula (C), or a pharmaceutically acceptable salt thereof:

[Formula 7]

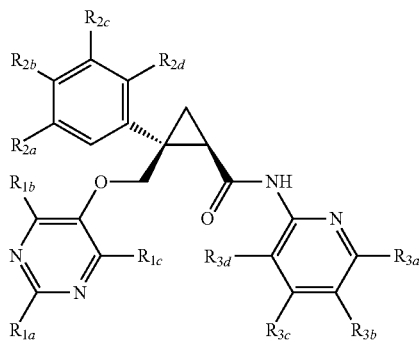

(C)

wherein $R_{1a}$ represents a $C_{1-6}$ alkyl group or a hydroxy-$C_{1-6}$ alkyl group, $R_{1b}$ represents a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group, $R_{1c}$ represents a hydrogen atom or a hydroxyl group, $R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group or a halo-$C_{1-6}$ alkyl group, $R_{3a}$ represents a substituent selected from a hydrogen atom, a halogen atom, a $C_{1-6}$ alkyl group, a $C_{1-6}$ alkoxy group and a $C_{1-6}$ alkoxy-$C_{1-6}$ alkyl group, $R_{3b}$ represents a hydrogen atom, a halogen atom, a $C_{1-6}$ alkyl group or a halo-$C_{1-6}$ alkyl group, $R_{3c}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom.

[10] The compound according to [9] above, or a pharmaceutically acceptable salt thereof, wherein $R_{1a}$ represents a methyl group, $R_{1b}$ represents a methyl group, an ethyl group, a hydroxymethyl group, a methoxymethyl group or a methoxyethyl group, and $R_{1c}$ represents a hydrogen atom.

[11] A compound, which is selected from the following compounds, or a pharmaceutically acceptable salt thereof:

1) (1R,2S)-2-{[(2,4-dimethylpyrimidin-5-yl)oxy]methyl}-N-(5-fluoropyridin-2-yl)-2-phenylcyclopropanecarboxamide (Example 1),
2) (1R,2S)-N-(5-chloropyridin-2-yl)-2-{[(2,4-dimethylpyrimidin-5-yl)oxy]methyl}-2-phenylcyclopropanecarboxamide (Example 16),
3) (1R,2S)-N-[3-(dimethylamino)phenyl]-2-{[(2,4-dimethylpyrimidin-5-yl)oxy]methyl}-2-phenylcyclopropanecarboxamide (Example 19),
4) (1R,2S)-N-(3-chlorophenyl)-2-{[(2,4-dimethylpyrimidin-5-yl)oxy]methyl}-2-phenylcyclopropanecarboxamide (Example 24),
5) (1R,2S)-N-(3-cyano-4-fluorophenyl)-2-{[(2,4-dimethylpyrimidin-5-yl)oxy]methyl}-2-phenylcyclopropanecarboxamide (Example 26),
6) (1R,2S)-N-(3-chloro-4-fluorophenyl)-2-{[(2,4-dimethylpyrimidin-5-yl)oxy]methyl}-2-phenylcyclopropanecarboxamide (Example 32),
7) (1R,2S)-2-{[(2,4-dimethylpyrimidin-5-yl)oxy]methyl}-N-(3-methoxyphenyl)-2-phenylcyclopropanecarboxamide (Example 36),
8) (1R,2S)-N-[3-(cyanomethyl)phenyl]-2-{[(2,4-dimethylpyrimidin-5-yl)oxy]methyl}-2-phenylcyclopropanecarboxamide (Example 39),
9) (1R,2S)-2-{[(2,4-dimethylpyrimidin-5-yl)oxy]methyl}-2-phenyl-N-[3-(trifluoromethyl)phenyl]cyclopropanecarboxamide (Example 43),
10) (1R,2S)-N-(5-chloro-4-methylpyridin-2-yl)-2-{[(2,4-dimethylpyrimidin-5-yl)oxy]methyl}-2-phenylcyclopropanecarboxamide (Example 45),
11) (1R,2S)-2-{[(2,4-dimethylpyrimidin-5-yl)oxy]methyl}-N-(5-fluoro-4-methylpyridin-2-yl)-2-phenylcyclopropanecarboxamide (Example 51),
12) (1R,2S)-2-{[(2,4-dimethylpyrimidin-5-yl)oxy]methyl}-N-[5-fluoro-4-(methoxymethyl)pyridin-2-yl]-2-phenylcyclopropanecarboxamide (Example 71),
13) (1R,2S)-2-{[(2,4-dimethylpyrimidin-5-yl)oxy]methyl}-N-(5-fluoro-4-methoxypyridin-2-yl)-2-phenylcyclopropanecarboxamide (Example 73),
14) (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (Example 82), 15) (1R,2S)-N-(3,4-difluorophenyl)-2-{[(2,4-dimethylpyrimidin-5-yl)oxy]methyl}-2-(3-fluorophenyl)cyclopropanecarboxamide (Example 84),
16) (1R,2S)-N-(4-chloropyridin-2-yl)-2-{[(2,4-dimethylpyrimidin-5-yl)oxy]methyl}-2-(3-fluorophenyl)cyclopropanecarboxamide (Example 85),
17) (1R,2S)-2-{[(2,4-dimethylpyrimidin-5-yl)oxy]methyl}-N-(5-fluoro-4-methoxymethylpyridin-2-yl)-2-(3-fluorophenyl)cyclopropanecarboxamide (Example 86),
18) (1R,2S)-2-{[(2,4-dimethylpyrimidin-5-yl)oxy]methyl}-2-(3-fluorophenyl)-N-(4-fluorophenyl)cyclopropanecarboxamide (Example 92),
19) (1R,2S)-2-{[(2,4-dimethylpyrimidin-5-yl)oxy]methyl}-2-(3-fluorophenyl)-N-phenylcyclopropanecarboxamide (Example 93),
20) (1R,2S)-2-{[(2,4-dimethylpyrimidin-5-yl)oxy]methyl}-N-(5-fluoro-4-methoxypyridin-2-yl)-2-(3-fluorophenyl)cyclopropanecarboxamide (Example 94),
21) (1R,2S)-2-{[(2,4-dimethylpyrimidin-5-yl)oxy]methyl}-2-(3-fluorophenyl)-N-(5-fluoropyridin-2-yl)cyclopropanecarboxamide (Example 95),
22) (1R,2S)-N-(5-cyanopyridin-2-yl)-2-{[(2,4-dimethylpyrimidin-5-yl)oxy]methyl}-2-(3-fluorophenyl)cyclopropanecarboxamide (Example 96),
23) (1R,2S)-2-{[(2,4-dimethylpyrimidin-5-yl)oxy]methyl}-2-(4-fluorophenyl)-N-(5-fluoropyridin-2-yl)cyclopropanecarboxamide (Example 100),
24) (1R,2S)-2-{[(2,4-dimethylpyrimidin-5-yl)oxy]methyl}-N-(5-fluoro-4-methoxypyridin-2-yl)-2-(4-fluorophenyl)cyclopropanecarboxamide (Example 104),
25) (1R,2S)-2-{[(2,4-dimethylpyrimidin-5-yl)oxy]methyl}-N-(5-fluoro-4-methoxymethylpyridin-2-yl)-2-(4-fluorophenyl)cyclopropanecarboxamide (Example 109),
26) (1R,2S)-2-{[(2,4-dimethylpyrimidin-5-yl)oxy]methyl}-N-(5-fluoro-4-methylpyridin-2-yl)-2-(4-fluorophenyl)cyclopropanecarboxamide (Example 111),
27) (1R,2S)-2-(3-cyanophenyl)-2-{[(2,4-dimethylpyrimidin-5-yl)oxy]methyl}-N-(5-fluoro-4-methylpyridin-2-yl)cyclopropanecarboxamide (Example 117),
28) (1R,2S)-2-{[(4-ethyl-2-methylpyrimidin-5-yl)oxy]methyl}-N-(5-fluoropyridin-2-yl)-2-phenylcyclopropanecarboxamide (Example 119),
29) (1R,2S)-N-(5-cyanopyridin-2-yl)-2-{[(4-ethyl-2-methylpyrimidin-5-yl)oxy]methyl}-2-phenylcyclopropanecarboxamide (Example 120),
30) (1R,2S)-N-(5-chloropyridin-2-yl)-2-{[(4-ethyl-2-methylpyrimidin-5-yl)oxy]methyl}-2-phenylcyclopropanecarboxamide (Example 121),
31) (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide (Example 129),
32) (1R,2S)-2-(3,5-difluorophenyl)-2-{[(2,4-dimethylpyrimidin-5-yl)oxy]methyl}-N-(4-fluorophenyl)cyclopropanecarboxamide (Example 130),
33) (1R,2S)-2-(3,5-difluorophenyl)-2-{[(2,4-dimethylpyrimidin-5-yl)oxy]methyl}-N-(pyridin-2-yl)cyclopropanecarboxamide (Example 131),
34) (1R,2S)-N-(5-chloropyridin-2-yl)-2-(3,5-difluorophenyl)-2-{[(2,4-dimethylpyrimidin-5-yl)oxy]methyl}cyclopropanecarboxamide (Example 132),
35) (1R,2S)-2-(3,5-difluorophenyl)-2-{[(2,4-dimethylpyrimidin-5-yl)oxy]methyl}-N-(5-fluoropyridin-2-yl)cyclopropanecarboxamide (Example 133),
36) (1R,2S)-N-(3,4-difluorophenyl)-2-(3,5-difluorophenyl)-2-{[(2,4-dimethylpyrimidin-5-yl)oxy]methyl}cyclopropanecarboxamide (Example 134),
37) (1R,2S)-N-(2,4-difluorophenyl)-2-(3,5-difluorophenyl)-2-{[(2,4-dimethylpyrimidin-5-yl)oxy]methyl}cyclopropanecarboxamide (Example 135),
38) (1R,2S)-N-(5-cyanopyridin-2-yl)-2-(3,5-difluorophenyl)-2-{[(2,4-dimethylpyrimidin-5-yl)oxy]methyl}cyclopropanecarboxamide (Example 137),
39) (1R,2S)-2-(3,5-difluorophenyl)-2-{[(2,4-dimethylpyrimidin-5-yl)oxy]methyl}-N-(5-fluoro-4-methoxypyridin-2-yl)cyclopropanecarboxamide (Example 138),
40) (1R,2S)-N-(5-chloropyridin-2-yl)-2-{[(4-(methoxymethyl)-2-methylpyrimidin-5-yl)oxy]methyl}-2-phenylcyclopropanecarboxamide (Example 139),
41) (1R,2S)-N-(5-cyanopyridin-2-yl)-2-{[(4-(methoxymethyl)-2-methylpyrimidin-5-yl)oxy]methyl}-2-phenylcyclopropanecarboxamide (Example 140),
42) (1R,2S)-N-(5-fluoropyridin-2-yl)-2-{[(4-(methoxymethyl)-2-methylpyrimidin-5-yl)oxy]methyl}-2-phenylcyclopropanecarboxamide (Example 141),
43) (1R,2S)-N-(5-fluoro-4-methylpyridin-2-yl)-2-{[(4-methoxymethyl-2-methylpyrimidin-5-yl)oxy]methyl}-2-phenylcyclopropanecarboxamide (Example 145),
44) (1R,2S)-N-(4-fluorophenyl)-2-{[(4-methoxymethyl-2-methylpyrimidin-5-yl)oxy]methyl}-2-phenylcyclopropanecarboxamide (Example 149),
45) (1R,2S)-N-(3,4-difluorophenyl)-2-{[(4-methoxymethyl-2-methylpyrimidin-5-yl)oxy]methyl}-2-phenylcyclopropanecarboxamide (Example 150),
46) (1R,2S)-2-(3,4-difluorophenyl)-2-{[(2,4-dimethylpyrimidin-5-yl)oxy]methyl}-N-(5-fluoro-4-methylpyridin-2-yl)cyclopropanecarboxamide (Example 164),
47) (1R,2S)-2-(3,4-difluorophenyl)-2-{[(2,4-dimethylpyrimidin-5-yl)oxy]methyl}-N-(4-fluorophenyl)cyclopropanecarboxamide (Example 165),
48) (1R,2S)-2-(3,4-difluorophenyl)-2-{[(2,4-dimethylpyrimidin-5-yl)oxy]methyl}-N-(pyridin-2-yl)cyclopropanecarboxamide (Example 166),
49) (1R,2S)-N-(5-cyanopyridin-2-yl)-2-(3,4-difluorophenyl)-2-{[(2,4-dimethylpyrimidin-5-yl)oxy]methyl}cyclopropanecarboxamide (Example 167),
50) (1R,2S)-N-(5-chloropyridin-2-yl)-2-(3,4-difluorophenyl)-2-{[(2,4-dimethylpyrimidin-5-yl)oxy]methyl}cyclopropanecarboxamide (Example 168),
51) (1R,2S)-2-(3,4-difluorophenyl)-2-{[(2,4-dimethylpyrimidin-5-yl)oxy]methyl}-N-(5-fluoropyridin-2-yl)cyclopropanecarboxamide (Example 169),
52) (1R,2S)-N,2-bis(3,4-difluorophenyl)-2-{[(2,4-dimethylpyrimidin-5-yl)oxy]methyl}cyclopropanecarboxamide (Example 170),
53) (1R,2S)-2-(3,4-difluorophenyl)-2-{[(2,4-dimethylpyrimidin-5-yl)oxy]methyl}-N-(5-fluoro-4-methoxypyridin-2-yl)cyclopropanecarboxamide (Example 173),
54) (1R,2S)-2-{[(2,4-dimethylpyrimidin-5-yl)oxy]methyl}-N-(5-fluoropyridin-2-yl)-2-(3-methoxyphenyl)cyclopropanecarboxamide (Example 186),
55) (1R,2S)-2-{[(2,4-dimethylpyrimidin-5-yl)oxy]methyl}-N-(5-fluoro-4-methylpyridin-2-yl)-2-(3-methoxyphenyl)cyclopropanecarboxamide (Example 189),
56) (1R,2S)-N-(3,4-difluorophenyl)-2-{[(2,4-dimethylpyrimidin-5-yl)oxy]methyl}-2-(3-methoxyphenyl)cyclopropanecarboxamide (Example 190),
57) (1R,2S)-2-(3-fluorophenyl)-N-(5-fluoropyridin-2-yl)-2-[(4-methoxymethyl-2-methylpyrimidin-5-yl)oxymethyl]cyclopropanecarboxamide (Example 191),
58) (1R,2S)-2-(3-fluorophenyl)-N-(4-fluorophenyl)-2-{[(4-methoxymethyl-2-methylpyrimidin-5-yl)oxy]methyl}cyclopropanecarboxamide (Example 192), 59) (1R,2S)-2-(3-fluorophenyl)-2-{[(4-methoxymethyl-2-methylpyrimidin-5-yl)oxy]methyl}-N-(pyridin-2-yl)cyclopropanecarboxamide (Example 193), 60) (1R,2S)-N-(3,4-difluorophenyl)-2-(3-fluorophenyl)-2-{[(4-methoxymethyl-2-methylpyrimidin-5-yl)oxy]methyl}cyclopropanecarboxamide (Example 194), 61) (1R,2S)-N,2-bis(3-fluorophenyl)-2-{[(4-methoxymethyl-2-methylpyrimidin-5-yl)oxy]methyl}cyclopropanecarboxamide (Example 195), 62) (1R,2S)-N-(2,4-difluorophenyl)-2-(3-fluorophenyl)-2-{[(4-methoxymethyl-2-methylpyrimidin-5-yl)oxy]methyl}cyclopropanecarboxamide (Example 196), 63) (1R,2S)-N-(2,5-difluorophenyl)-2-(3-fluorophenyl)-2-{[(4-methoxymethyl-2-methylpyrimidin-5-yl)oxy]methyl}cyclopropanecarboxamide (Example 197), 64) (1R,2S)-N-(5-chloropyridin-2-yl)-2-(3-fluorophenyl)-2-{[(4-methoxymethyl-2-methylpyrimidin-5-yl)oxy]methyl}cyclopropanecarboxamide (Example 198), 65) (1R,2S)-N-(5-fluoro-4-methylpyridin-2-yl)-2-(3-fluorophenyl)-2-{[(4-methoxymethyl-2-methylpyrimidin-5-yl)oxy]methyl}cyclopropanecarboxamide (Example 199), 66) (1R,2S)-2-(3-fluorophenyl)-2-{[(4-methoxymethyl-2-methylpyrimidin-5-yl)oxy]methyl}-N-[5-(trifluoromethyl)pyridin-2-yl]cyclopropanecarboxamide (Example 201), 67) (1R,2S)-2-(4-fluorophenyl)-N-(5-fluoropyridin-2-yl)-2-{[(4-methoxymethyl-2-methylpyrimidin-5-yl)oxy]methyl}cyclopropanecarboxamide (Example 202), 68) (1R,2S)-N,2-bis(4-fluorophenyl)-2-{[(4-methoxymethyl-2-methylpyrimidin-5-yl)oxy]methyl}cyclopropanecarboxamide (Example 203), 69) (1R,2S)-N-(5-chloropyridin-2-yl)-2-(4-fluorophenyl)-2-{[(4-methoxymethyl-2-methylpyrimidin-5-yl)oxy]methyl}cyclopropanecarboxamide (Example 204), 70) (1R,2S)-N-(5-fluoro-4-methylpyridin-2-yl)-2-(4-fluorophenyl)-2-{[(4-methoxymethyl-2-methylpyrimidin-5-yl)oxy]methyl}cyclopropanecarboxamide (Example 205), 71) (1R,2S)-N-(3,4-difluorophenyl)-2-(4-fluorophenyl)-2-{[(4-methoxymethyl-2-methylpyrimidin-5-yl)oxy]methyl}cyclopropanecarboxamide (Example 207), 72) (1R,2S)-2-(3,4-difluorophenyl)-2-{[(4-methoxymethyl-2-methylpyrimidin-5-yl)oxy]methyl}-N-(pyridin-2-yl)cyclopropanecarboxamide (Example 211), 73) (1R,2S)-2-(3,4-difluorophenyl)-N-(5-fluoro-4-methylpyridin-2-yl)-2-{[(4-methoxymethyl-2-methylpyrimidin-5-yl)oxy]methyl}cyclopropanecarboxamide (Example 212), 74) (1R,2S)-N,2-bis(3,4-difluorophenyl)-2-{[(4-methoxymethyl-2-methylpyrimidin-5-yl)oxy]methyl}cyclopropanecarboxamide (Example 214), 75) (1R,2S)-N-(2,4-difluorophenyl)-2-(3,4-difluorophenyl)-2-{[(4-methoxymethyl-2-methylpyrimidin-5-yl)oxy]methyl}cyclopropanecarboxamide (Example 216), 76) (1R,2S)-2-(3,5-difluorophenyl)-2-{[(4-methoxymethyl-2-methylpyrimidin-5-yl)oxy]methyl}-N-(pyridin-2-yl)cyclopropanecarboxamide (Example 218), 77) (1R,2S)-2-(3,5-difluorophenyl)-N-(4-fluorophenyl)-2-{[(4-methoxymethyl-2-methylpyrimidin-5-yl)oxy]methyl}cyclopropanecarboxamide (Example 219), 78) (1R,2S)-N-(3,4-difluorophenyl)-2-(3,5-difluorophenyl)-2-{[(4-methoxymethyl-2-methylpyrimidin-5-yl)oxy]methyl}cyclopropanecarboxamide (Example 221), 79) (1R,2S)-2-(3-chlorophenyl)-2-{[(4-methoxymethyl-2-methylpyrimidin-5-yl)oxy]methyl}-N-(pyridin-2-yl)cyclopropanecarboxamide (Example 225), 80) (1R,2S)-2-(3-chlorophenyl)-N-(5-fluoro-4-methylpyridin-2-yl)-2-{[(4-methoxymethyl-2-methylpyrimidin-5-yl)oxy]methyl}cyclopropanecarboxamide (Example 226), 81) (1R,2S)-N-(5-fluoro-4-methylpyridin-2-yl)-2-(3-fluorophenyl)-2-{[(4-methoxyethyl-2-methylpyrimidin-5-yl)oxy]methyl}cyclopropanecarboxamide (Example 229), 82) (1R,2S)-2-(3-fluoro-5-methoxyphenyl)-N-(4-fluorophenyl)-2-{[(4-methoxymethyl-2-methylpyrimidin-5-yl)oxy]methyl}cyclopropanecarboxamide (Example 231), 83) (1R,2S)-N-(3,4-difluorophenyl)-2-(3-fluoro-5-methoxyphenyl)-2-{[(4-methoxymethyl-2-methylpyrimidin-5-yl)oxy]methyl}cyclopropanecarboxamide (Example 232), 84) (1R,2S)-2-(3-fluoro-5-methoxyphenyl)-N-(5-fluoropyridin-2-yl)-2-[(4-methoxymethyl-2-methylpyrimidin-5-yl)oxymethyl]cyclopropanecarboxamide (Example 233), 85) (1R,2S)-2-(3-fluoro-5-methoxyphenyl)-N-(5-fluoro-4-methylpyridin-2-yl)-2-{[(4-methoxymethyl-2-methylpyrimidin-5-yl)oxy]methyl}cyclopropanecarboxamide (Example 234), 86) (1R,2S)-2-(3-fluoro-5-methoxyphenyl)-2-[(4-methoxymethyl-2-methylpyrimidin-5-yl)oxymethyl]-N-(pyridin-2-yl)cyclopropanecarboxamide (Example 235), 87) (1R,2S)-2-(3-fluoro-5-methoxyphenyl)-N-(3-fluorophenyl)-2-{[(4-methoxymethyl-2-methylpyrimidin-5-yl)oxy]methyl}cyclopropanecarboxamide (Example 236), 88) (1R,2S)-2-(4-fluoro-3-methoxyphenyl)-N-(5-fluoro-4-methylpyridin-2-yl)-2-{[(4-methoxymethyl-2-methylpyrimidin-5-yl)oxy]methyl}cyclopropanecarboxamide (Example 239), 89) (1R,2S)-2-{[(4-ethyl-2-methylpyrimidin-5-yl)oxy]methyl}-2-(3-fluorophenyl)-N-(pyridin-2-yl)cyclopropanecarboxamide (Example 240), 90) (1R,2S)-2-{[(4-ethyl-2-methylpyrimidin-5-yl)oxy]methyl}-2-(3-fluorophenyl)-N-(5-fluoropyridin-2-yl)cyclopropanecarboxamide (Example 241), 91) (1R,2S)-N-(5-cyanopyridin-2-yl)-2-{[(4-ethyl-2-methylpyrimidin-5-yl)oxy]methyl}-2-(3-fluorophenyl)cyclopropanecarboxamide (Example 242), 92) (1R,2S)-N-(5-chloropyridin-2-yl)-2-{[(4-ethyl-2-methylpyrimidin-5-yl)oxy]methyl}-2-(3-fluorophenyl)cyclopropanecarboxamide (Example 243), 93) (1R,2S)-2-{[(4-ethyl-2-methylpyrimidin-5-yl)oxy]methyl}-N-(5-fluoro-4-methylpyridin-2-yl)-2-(3-fluorophenyl)cyclopropanecarboxamide (Example 244), 94) (1R,2S)-2-{[(4-ethyl-2-methylpyrimidin-5-yl)oxy]methyl}-2-(4-fluorophenyl)-N-(pyridin-2-yl)cyclopropanecarboxamide (Example 245), 95) (1R,2S)-2-{[(4-ethyl-2-methylpyrimidin-5-yl)oxy]methyl}-2-(4-fluorophenyl)-N-(5-fluoropyridin-2-yl)cyclopropanecarboxamide (Example 246), 96) (1R,2S)-N-(4-chloropyridin-2-yl)-2-{[(4-ethyl-2-methylpyrimidin-5-yl)oxy]methyl}-2-(4-fluorophenyl)cyclopropanecarboxamide (Example 247), 97) (1R,2S)-2-{[(4-ethyl-2-methylpyrimidin-5-yl)oxy]methyl}-N-(5-fluoro-4-methylpyridin-2-yl)-2-(4-fluorophenyl)cyclopropanecarboxamide (Example 248), 98) (1R,2S)-2-{[(2,4-dimethylpyrimidin-5-yl)oxy]methyl}-2-(3-fluoro-5-methoxyphenyl)-N-(5-fluoro-4-methylpyridin-2-yl)cyclopropanecarboxamide (Example 256), 99) (1R,2S)-2-{[(2,4-dimethylpyrimidin-5-yl)oxy]methyl}-N-(5-fluoropyridin-2-yl)-2-(3-trifluoromethylphenyl)cyclopropanecarboxamide (Example 266), 100) (1R,2S)-2-(4-bromophenyl)-N-(5-chloropyridin-2-yl)-2-{[(2,4-dimethylpyrimidin-5-yl)oxy]methyl}cyclopropanecarboxamide (Example 273), 101) (1R,2S)-2-{[(2,4-dimethylpyrimidin-5-yl)oxy]methyl}-N-(5-fluoromethylpyridin-2-yl)-2-(3-fluorophenyl)cyclopropanecarboxamide (Example 282),
102) (1R,2S)-2-{[(2,4-dimethylpyrimidin-5-yl)oxy]methyl}-N-(5-fluoropyridin-2-yl)-2-(3-iodophenyl)cyclopropanecarboxamide (Example 283),
103) (1R,2S)-N-(5-fluoropyridin-2-yl)-2-{[(4-hydroxymethyl-2-methylpyrimidin-5-yl)oxy]methyl}-2-(3-fluorophenyl)cyclopropanecarboxamide (Example 286),
104) (1R,2S)-2-{[(4-ethyl-2-methylpyrimidin-5-yl)oxy]methyl}-2-(3-fluorophenyl)-N-(4-fluorophenyl)cyclopropanecarboxamide (Example 316),
105) (1R,2S)-2-{[(4-fluoromethyl-2-methylpyrimidin-5-yl)oxy]methyl}-2-(3-fluorophenyl)-N-(5-fluoropyridin-2-yl)cyclopropanecarboxamide (Example 320),
106) (1R,2S)-2-{[(2,4-dimethylpyrimidin-5-yl)oxy]methyl}-2-(3-fluoro-4-hydroxyphenyl)-N-(5-fluoropyridin-2-yl)cyclopropanecarboxamide (Example 321),
107) (1R,2S)-2-{[(2,4-dimethylpyrimidin-5-yl)oxy]methyl}-2-(3-fluoro-4-methoxyphenyl)-N-(5-fluoropyridin-2-yl)cyclopropanecarboxamide (Example 322),
108) (1R,2S)-2-(3-fluorophenyl)-N-(5-fluoropyridin-2-yl)-2-{[(2-hydroxymethyl-4-methylpyrimidin-5-yl)oxy]methyl}cyclopropanecarboxamide (Example 323),
109) (1R,2S)-2-{[(2,4-dimethylpyrimidin-5-yl)oxy]methyl-2-[5-fluoro-2-hydroxyphenyl]-N-(5-fluoropyridin-2-yl)cyclopropanecarboxamide (Example 324),
110) (1R,2S)-2-{[(2,4-dimethyl-6-oxo-1,6-dihydropyrimidin-5-yl)oxy]methyl}-2-(3-fluorophenyl)-N-(5-fluoropyridin-2-yl)cyclopropanecarboxamide (Example 326),
111) (1R,2S)-N-(2-cyanopyridin-4-yl)-2-{[(2,4-dimethylpyrimidin-5-yl)oxy]methyl}-2-phenylcyclopropanecarboxamide (Example 41),
112) (1R,2S)-2-[N-(2,4-dimethylpyrimidin-5-yl)methylaminomethyl]-N-(5-fluoropyridin-2-yl)-2-(3-fluorophenyl)cyclopropanecarboxamide (Example 293),
113) (1R,2S)-N-(5-chloro-4-methylpyridin-2-yl)-2-[N-(2,4-dimethylpyrimidin-5-yl)methylaminomethyl]-2-(3-fluorophenyl)cyclopropanecarboxamide (Example 295),
114) (1R,2S)-N-(3,4-fluoropyridin-2-yl)-2-[N-(2,4-dimethylpyrimidin-5-yl)methylaminomethyl]-2-(3-fluorophenyl)cyclopropanecarboxamide (Example 296),
115) (1R,2S)-2-(3-fluorophenyl)-N-(5-fluoropyridin-2-yl)-2-[N-(2-methyl-4-trifluoromethylpyrimidin-5-yl)methylaminomethyl] cyclopropanecarboxamide (Example 302), and
116) (1R,2S)-2-{[(2,4-dimethylpyrimidin-5-yl)oxy]methyl}-N-(6-fluoro-5-methoxypyridin-3-yl)-2-phenylcyclopropanecarboxamide (Example 327).

[12] A compound, which is selected from the following compounds, or a pharmaceutically acceptable salt thereof:
1) (1R,2S)-2-{[(2,4-dimethylpyrimidin-5-yl)oxy]methyl}-N-(5-fluoropyridin-2-yl)-2-phenylcyclopropanecarboxamide (Example 1),
11) (1R,2S)-2-{[(2,4-dimethylpyrimidin-5-yl)oxy]methyl}-N-(5-fluoro-4-methylpyridin-2-yl)-2-phenylcyclopropanecarboxamide (Example 51),
14) (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (Example 82),
21) (1R,2S)-2-{[(2,4-dimethylpyrimidin-5-yl)oxy]methyl}-2-(3-fluorophenyl)-N-(5-fluoropyridin-2-yl)cyclopropanecarboxamide (Example 95),
31) (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide (Example 129), and
89) (1R,2S)-2-{[(4-ethyl-2-methylpyrimidin-5-yl)oxy]methyl}-2-(3-fluorophenyl)-N-(pyridin-2-yl)cyclopropanecarboxamide (Example 240).

[13] (1R,2S)-2-{[(2,4-Dimethylpyrimidin-5-yl)oxy]methyl}-N-(5-fluoro-4-methylpyridin-2-yl)-2-(3-fluorophenyl)cyclopropanecarboxamide (Example 82) represented by the following formula or a pharmaceutically acceptable salt thereof

[Formula 8]

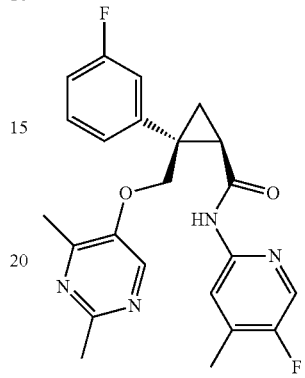

[14] (1R,2S)-2-{[(2,4-Dimethylpyrimidin-5-yl)oxy]methyl}-2-(3-fluorophenyl)-N-(5-fluoropyridin-2-yl)cyclopropanecarboxamide (Example 95) represented by the following formula or a pharmaceutically acceptable salt thereof:

[Formula 9]

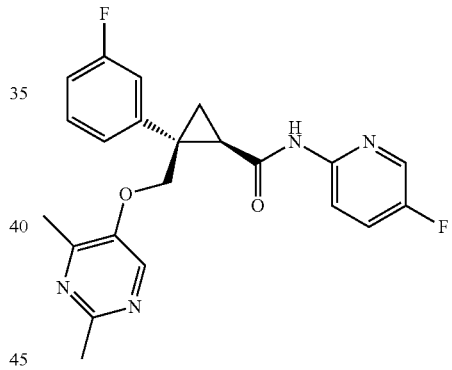

[15] (1R,2S)-2-(3,5-Difluorophenyl)-2-{[(2,4-dimethylpyrimidin-5-yl)oxy]methyl}-N-(5-fluoro-4-methylpyridin-2-yl)cyclopropanecarboxamide (Example 129) represented by the following formula or a pharmaceutically acceptable salt thereof:

[Formula 10]

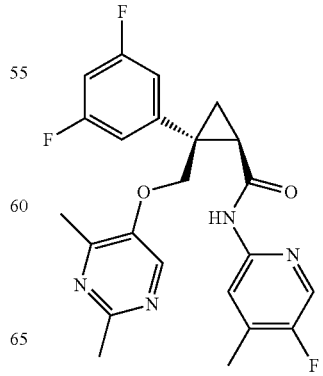

[16] A pharmaceutical composition comprising, as an active ingredient, the compound according to any one of [1] to [15] above or a pharmaceutically acceptable salt thereof

[17] The pharmaceutical composition according to [16] above, which is for the treatment of sleep disorder for which orexin receptor antagonism is effective.

[18] The pharmaceutical composition according to [17] above, wherein said sleep disorder is insomnia.

[19] A method for treating sleep disorder for which orexin receptor antagonism is effective, which comprises administering the compound according to any one of [1] to [15] above or a pharmaceutically acceptable salt thereof into a subject in need thereof

[20] The method according to [19] above, wherein said sleep disorder is insomnia The cyclopropane compound according to the present invention or a pharmaceutically acceptable salt thereof has orexin receptor antagonism. Therefore, the cyclopropane compound or a pharmaceutically acceptable salt thereof has a potential of usefulness for the treatment of sleep disorder for which orexin receptor antagonism is effective, for example, insomnia.

BRIEF EXPLANATION OF DRAWING

FIG. 1 shows results obtained by measuring the prolongation of sleep time for each of the compounds of Examples 1, 51, 82, 95, 129 and 240 when orally administered into mice.

DETAILED DESCRIPTION OF THE INVENTION

Hereinafter, the meanings of symbols, terms and the like used in the specification of the present application will be explained, and thus, the present invention will be described in detail.

In the specification of the present application, the structural formula of a compound may indicate a certain isomer for convenience sake. The present invention includes all isomers generated due to the structure of the compound, such as geometric isomers, optical isomers based on asymmetric carbon atoms, steric isomers or tautomers, and the isomeric mixtures thereof. Thus, the compound of the present invention is not limited to the descriptions of a formula given for convenience, and it may be either an isomer or a mixture. Accordingly, there may be a case in which the compound has asymmetric carbon atoms in a molecule thereof and an optically active form and a racemic form exist. However, the present invention is not limited thereto, but it includes all cases. Moreover, there may also be a case in which crystal polymorphisms exist. The present invention is not limited thereto, either, and it includes single crystals or the mixtures thereof. Other than anhydrides, hydrates may also be included. These substances are all included in the scope of claims in the specification of the present application.

The present invention includes a compound formed by isotopically labeling the compound of the formula (I). This compound is identical to the compound of the formula (I) with the exception that one or more atoms thereof are substituted with atom(s) having an atomic mass or mass number that are different from those generally found in the nature. Examples of an isotope that can be included in the compound of the present invention include the isotopes of hydrogen, carbon, nitrogen, oxygen, fluorine, phosphorus, sulfur, iodine and chloride. Specific examples include $^{2}H$, $^{3}H$, $^{11}C$, $^{14}C$, $^{13}N$, $^{15}O$, $^{18}F$, $^{35}S$, $^{123}I$, and $^{125}I$.

The compound of the present invention and a pharmaceutically acceptable derivative thereof (e.g. a salt), which include the above described isotopes and/or other isotopes, are included in the scope of claims in the specification of the present application. The isotopically labeled compound of the present invention, for example, a compound, into which a radioisotope(s) such as $^{3}H$ and/or $^{14}C$ are incorporated, is useful for the tissue distribution assay of a pharmaceutical agent and/or a substrate. Isotopes $^{3}H$ and $^{14}C$ are considered useful because of the easiness of preparation and detection. Isotopes $^{11}C$ and $^{18}F$ are considered useful for PET (positron-emission tomography), and isotope $^{125}I$ is considered useful for SPECT (single-photon-emission computed tomography). All of these isotopes are useful for brain imaging. Substitution with a heavy isotope such as $^{2}H$ is advantageous for a certain type of therapy, such as an increase in the in vivo half-life or a decrease in necessary dose due to its higher metabolic stability. Thus, such a heavy isotope is considered useful under certain circumstances. The isotopically labeled compound of the formula (I) of the present invention can be uniformly prepared by performing procedures disclosed in formulae and/or Examples as described below, using commonly used isotopically labeled reagents, instead of non-isotopically labeled reagents.

In the present specification, the term "halogen atom" is used to mean a fluorine atom, a chlorine atom, a bromine atom, an iodine atom, etc. It is preferably a fluorine atom or a chloride atom.

The term "$C_{1-6}$ alkyl group" is used to mean an alkyl group containing 1 to 6 carbon atoms. Examples of a preferred $C_{1-6}$ alkyl group include linear or branched alkyl groups such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group. Of these, a methyl group, an ethyl group and an n-propyl group are more preferable.

The term "$C_{1-6}$ alkylene group" is used to mean an alkylene group containing 1 to 6 carbon atoms. Examples of a preferred $C_{1-6}$ alkylene group include linear or branched alkylene groups such as a methylene group, an ethylene group, an n-propylene group, an isopropylene group, an n-butylene group, an isobutylene group, an n-pentylene group, an isopentylene group and a neopentylene group. Of these, a methylene group, an ethylene group and an n-propylene group are more preferable.

The term "$C_{1-6}$ alkoxy group" is used to mean an oxy group bound to the aforementioned "$C_{1-6}$ alkyl group". Specific examples of such a $C_{1-6}$ alkoxy group include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, an 2-ethyl-1-butyloxy group, a 3,3-dimethyl-2-butyloxy group and a 2,3-dimethyl-2-butyloxy group, preferably a methoxy group, an ethoxy group and a 1-propyloxy group.

The term "halo-$C_{1-6}$ alkyl group" is used to mean the aforementioned "$C_{1-6}$ alkyl group", in which hydrogen atom(s) are substituted with 1 to 5 aforementioned "halogen atoms". Specific examples of such a halo-$C_{1-6}$ alkyl group include a fluoromethyl group, a difluoromethyl group, a trifluoromethyl group, a trichloromethyl group, a 1-fluoroethyl group, a 2-fluoroethyl group, a 2-chloroethyl group, a 1,2-difluoroethyl group, a 2,2-difluoroethyl group, a 2,2,2-trifluoroethyl group, a 1-fluoropropyl group, a 2-fluoropropyl group, a 3-fluoropropyl group, a 3-chloropropyl group, a 2-fluoro-2-propyl group, a 4-fluorobutyl group, a 5-fluoropentyl group and a 6-fluorohexyl group, preferably a fluoromethyl group, a difluoromethyl group and a trifluoromethyl group.

The term "hydroxy-$C_{1-6}$ alkyl group" is used to mean the aforementioned "$C_{1-6}$ alkyl group", in which hydrogen atom (s) are substituted with 1 to 2 hydroxyl groups. Specific examples of such a hydroxy-$C_{1-6}$ alkyl group include a hydroxymethyl group, a 1-hydroxyethyl group, a 2-hydroxyethyl group, a 1,2-dihydroxyethyl group, a 1-hydroxypropyl group, a 2-hydroxypropyl group, a 3-hydroxypropyl group, a 2-hydroxy-2-propyl group, a 1,2-dihydroxypropyl group, a 1,3-dihydroxypropyl group, a 2,3-dihydroxypropyl group, a 4-hydroxybutyl group, a 5-hydroxypentyl group and a 6-hydroxyhexyl group, preferably a hydroxymethyl group, a 1-hydroxyethyl group and a 2-hydroxyethyl group.

The term "$C_{1-6}$ alkoxy-$C_{1-6}$ alkyl group" is used to mean the aforementioned "$C_{1-6}$ alkoxy group" bound to the aforementioned "$C_{1-6}$ alkyl group". Specific examples of such a $C_{1-6}$ alkoxy-$C_{1-6}$ alkyl group include a methoxymethyl group, a 1-methoxyethyl group, a 2-methoxyethyl group, a 1-methoxypropyl group, a 2-methoxypropyl group, a 3-methoxypropyl group, a 2-methoxy-2-propyl group, a (1-propyloxy)methyl group, a (2-propyloxy)methyl group, a 1-(1-propyloxy) ethyl group, a 2-(1-propyloxy)ethyl group, a 1-(2-propyloxy) ethyl group, a 2-(2-propyloxy)ethyl group, a 1-(1-propyloxy) propyl group, a 2-(1-propyloxy)propyl group, a 3-(1-propyloxy)propyl group, a 2-(1-propyloxy)-2-propyl group, a 1-(2-propyloxy)propyl group, a 2-(2-propyloxy)propyl group, a 3-(2-propyloxy)propyl group and a 2-(2-propyloxy)-2-propyl group, preferably a methoxyethyl group, a 1-methoxyethyl group and a 2-methoxyethyl group.

The term "$C_{1-6}$ alkylcarbonyl group" is used to mean an alkyl group containing 1 to 6 carbon atoms, in which one hydrogen atom is substituted with a carbonyl group. Examples of a preferred $C_{1-6}$ alkylcarbonyl group include an acetyl group, a propionyl group and a butyryl group.

The term "$C_{1-6}$ alkylsulfonyl group" is used to mean an alkyl group containing 1 to 6 carbon atoms, in which one hydrogen atom is substituted with a sulfonyl group. Examples of such a $C_{1-6}$ alkylsulfonyl group include a methylsulfonyl group, an ethylsulfonyl group, an n-propylsulfonyl group, an isopropylsulfonyl group, an n-butylsulfonyl group, an isobutylsulfonyl group, a t-butylsulfonyl group, an n-pentylsulfonyl group, an isopentylsulfonyl group, a neopentylsulfonyl group, an n-hexylsulfonyl group and a 1-methylpropylsulfonyl group.

The term "$C_{3-8}$ cycloalkyl group" is used to mean a cyclic alkyl group containing 3 to 8 carbon atoms, Examples of a preferred $C_{3-8}$ cycloalkyl group include a cyclopropyl group, a cyclobutyl group, a cyclopentyl group, a cyclohexyl group, a cycloheptyl group and a cyclooctyl group.

The term "aryl group" is used to mean an aryl group selected from Group 1. Group 1 means a phenyl group, a naphthyl group, an azulenyl group, an anthryl group and a phenanthryl group, preferably a phenyl group and a naphthyl group.

The term "heteroaryl group" is used to mean a heteroaryl group selected from Group 2. Group 2 means a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a triazinyl group, an indolyl group, an isoindolyl group, an indazolyl group, a benzoxazolyl group, a benzisoxadiazolyl group, a benzothiazolyl group, a benzisothiazolyl group, a quinolyl group and an isoquinolyl group, preferably a thienyl group and a pyridyl group.

The term "heterocyclic group" is used to mean an aryl group selected from Group 3. Group 3 means a furyl group, a thienyl group, a pyrrolyl group, an imidazolyl group, a triazolyl group, a tetrazolyl group, a thiazolyl group, a pyrazolyl group, an oxazolyl group, an isoxazolyl group, an isothiazolyl group, a furazanyl group, a thiadiazolyl group, an oxadiazolyl group, a pyridyl group, a pyrazinyl group, a pyridazinyl group, a pyrimidinyl group, a triazinyl group, a 2-pyridonyl group, a 4-pyridonyl group, a pyridazidonyl group, a pyrimididonyl group, a purinyl group, a pteridinyl group, a quinolyl group, an isoquinolyl group, a naphthylidyl group, a quinoxalyl group, a cinnolyl group, a quinazolyl group, a phthalazyl group, an imidazopyridyl group, an imidazothiazolyl group, an imidazoxazolyl group, a benzimidazolyl group, an indolyl group, an isoindolyl group, an indazolyl group, a pyrrolopyridyl group, a thienopyridyl group, a fluoropyridyl group, a benzoxazolyl group, a benzisoxadiazolyl group, a benzothiazolyl group, a benzisothiazolyl group, a pyridopyrimidinyl group, an oxodihydropyridopyrimidinyl group, a benzofuryl group, a benzothienyl group, a benzothiadiazolyl group, a benzo[1,3]dioxolyl group, a thienofuryl group, a dihydroisobenzofuranyl group, a chromanyl group, an isochromanyl group, a 1,3-dioxaindanyl group, a 1,4-dioxatetralinyl group, and a dihydrobenzo[1,4]oxazinyl group, preferably a thiazolyl group, an oxazolyl group, a pyridyl group, a pyrazinyl group, a pyridazinyl group, a pyrimidinyl group, a quinolyl group and an isoquinolyl group.

The term "Substituent Group α" is used to means a cyano group, a halogen atom, a hydroxyl group, an oxo group, a formula —$NR_6R_7$ wherein $R_6$ and $R_7$ each independently represent a hydrogen atom or a $C_{1-6}$ alkyl group, a $C_{1-6}$ alkyl group which may optionally have 1 to 3 substituents selected from Substituent Group β, a $C_{1-6}$ alkoxy group which may optionally have 1 to 3 substituents selected from Substituent Group β, a $C_{1-6}$ alkylcarbonyl group which may optionally have 1 to 3 substituents selected from Substituent Group β, a $C_{1-6}$ alkylsulfonyl group which may optionally have 1 to 3 substituents selected from Substituent Group β, an aryl group selected from Group 1, which may optionally have 1 to 3 substituents selected from Substituent Group β, and a heteroaryl group selected from Group 2, which may optionally have 1 to 3 substituents selected from Substituent Group β. Preferably, "Substituent Group α" is a cyano group, a fluorine atom, a chlorine atom, a bromine atom, a hydroxyl group, a dimethylamino group, a hydroxylmethyl group, a fluoromethyl group, a trifluoromethyl group, a methoxy group, an ethoxy group, a methoxymethyl group or a cyanomethyl group.

The term "Substituent Group β" is used to means a cyano group, a halogen atom, a hydroxyl group, a $C_{3-8}$ cycloalkyl group and a $C_{1-6}$ alkoxy group.

The cyclopropane compound of the formula (I) of the present invention may also be a pharmaceutically acceptable salt. Specific examples of such a pharmaceutically acceptable salt include: inorganic acid salts (for example, a sulfate, a nitrate, a perchlorate, a phosphate, a carbonate, a bicarbonate, a hydrofluoride, a hydrochloride, a hydrobromide, a hydroiodide); organic carboxylates (for example, an acetate, an oxalate, a maleate, a tartrate, a fumarate, a citrate); organic sulfonates (for example, a methanesulfonate, a trifluoromethanesulfonate, an ethanesulfonate, a benzenesulfonate, a toluenesulfonate, a camphorsulfonate); amino acid salts (for example, an aspartate, a glutamate); quaternary amine salts; alkaline metal salts (for example, a sodium salt, a potassium salt); and alkaline-earth metal salts (for example, a magnesium salt, a calcium salt).

The embodiments of the present invention include a compound represented by the following formula (IV) or a pharmaceutically acceptable salt thereof:

[Formula 11]

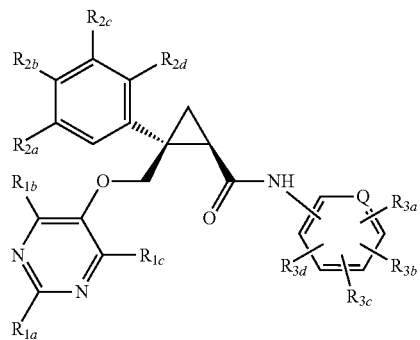

(IV)

wherein Q, $R_{1a}$, $R_{1b}$, $R_{1c}$, $R_{2a}$, $R_{2b}$, $R_{2c}$, $R_{2d}$, $R_{3a}$, $R_{3b}$, $R_{3c}$ and $R_{3d}$ have the same definitions as those according to [6] above.

The embodiments of the present invention include a compound represented by the following formula (A) or a pharmaceutically acceptable salt thereof:

[Formula 12]

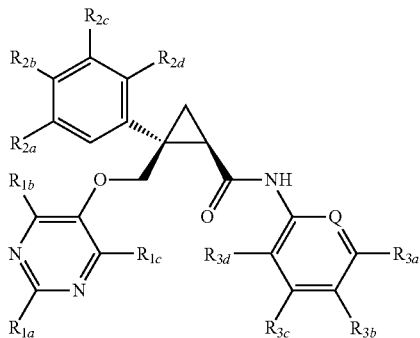

(A)

wherein Q, $R_{1a}$, $R_{1b}$, $R_{1c}$, $R_{2a}$, $R_{2b}$, $R_{2c}$ and $R_{2d}$ have the same definitions as those according to [7] above, and, when Q represents —CH— or a nitrogen atom, $R_{3a}$, $R_{3b}$, $R_{3c}$ and $R_{3b}$ have the same definitions as those according to [7] above.

The embodiments of the present invention include a compound represented by the following formula (B), or a pharmaceutically acceptable salt thereof:

[Formula 13]

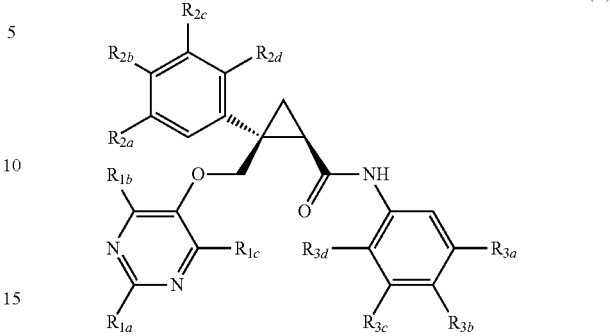

(B)

wherein $R_{1a}$, $R_{1b}$, $R_{1c}$, $R_{2a}$, $R_{2b}$, $R_{2c}$, $R_{2d}$, $R_{3a}$, $R_{3b}$, $R_{3c}$ and $R_{3b}$ have the same definitions as those according to [8] above.

The embodiments of the present invention include a compound represented by the following formula (C), or a pharmaceutically acceptable salt thereof:

[Formula 14]

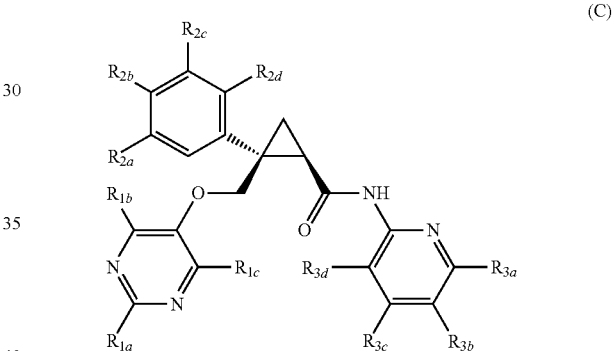

(C)

wherein $R_{1a}$, $R_{1b}$, $R_{1c}$, $R_{2a}$, $R_{2b}$, $R_{2c}$, $R_{2d}$, $R_{3a}$, $R_{3b}$, $R_{30}$ and $R_{3b}$ have the same definitions as those according to [9] above.

In the embodiment of the present invention, preferable is the compound of formula (IV) or a pharmaceutically acceptable salt thereof wherein Q is —CH— or a nitrogen atom, and, when Q is a nitrogen atom, —NH— of —CONH— may be bound to 2, 3 or 4-position in relation with Q of the phenyl ring.

In the embodiment of the present invention, preferable is the compound of formula (B) or a pharmaceutically acceptable salt thereof wherein $R_{1a}$ is a $C_{1-6}$ alkyl group; $R_{1b}$ is a $C_{1-6}$ alkyl group, a halo-$C_{1-6}$ alkyl group or a $C_{1-6}$ alkoxy-$C_{1-6}$ alkyl group; $R_{1c}$ is a hydrogen atom; $R_{2a}$, $R_{2b}$, $R_{2c}$ and $R_{2d}$ each independently are a hydrogen atom, a halogen atom, a $C_{1-6}$ alkyl group, a $C_{1-6}$ alkoxy group or a halo-$C_{1-6}$ alkyl group; $R_{3a}$ and $R_{3c}$ each independently are a hydrogen atom, a halogen atom, a $C_{1-6}$ alkyl group, a halo-$C_{1-6}$ alkyl group, a $C_{1-6}$ alkoxy group, a $C_{1-6}$ alkoxy-$C_{1-6}$ alkyl group, a cyano group or a cyano-$C_{1-6}$ alkyl group; $R_{3b}$ is a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group; and $R_{3d}$ represents a hydrogen atom or a fluorine atom.

In the embodiment of the present invention, preferable is the compound of formula (C) or a pharmaceutically acceptable salt thereof wherein $R_{1a}$ is a $C_{1-6}$ alkyl group or a hydroxy-$C_{1-6}$ alkyl group; $R_{1b}$ is a $C_{1-6}$ alkyl group, a hydroxy-$C_{1-6}$ alkyl group or a $C_{1-6}$ alkoxy-$C_{1-6}$ alkyl group; $R_{1c}$ is a hydrogen atom or a hydroxyl group; $R_{2a}$, $R_{2b}$, $R_{2c}$ and $R_{2d}$ each independently are a hydrogen atom, a halogen atom, a hydroxyl group, a $C_{1-6}$ alkyl group, a $C_{1-6}$ alkoxy group or a halo-$C_{1-6}$ alkyl group; $R_{3a}$ is a substituent selected from a hydrogen atom, a halogen atom, a $C_{1-6}$ alkyl group, a $C_{1-6}$ alkoxy group and a $C_{1-6}$ alkoxy-$C_{1-6}$ alkyl group; $R_{3b}$ is a hydrogen atom, a halogen atom, a $C_{1-6}$ alkyl group or a halo-$C_{1-6}$ alkyl group; $R_{3c}$ is a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group; and $R_{3d}$ is a hydrogen atom.

In the embodiment of the present invention, particularly preferable is the compound of formula (C) or a pharmaceutically acceptable salt thereof wherein $R_{1a}$ is a methyl group; $R_{1b}$ is a methyl group, an ethyl group, a hydroxymethyl group, a methoxymethyl group or a methoxyethyl group; and $R_{1c}$ is a hydrogen atom.

Specifically, the cyclopropane compound or a pharmaceutically acceptable salt thereof according to the present invention is preferably selected from the following compounds:

1) (1R,2S)-2-{[(2,4-dimethylpyrimidin-5-yl)oxy]methyl}-N-(5-fluoropyridin-2-yl)-2-phenylcyclopropanecarboxamide (Example 1),
2) (1R,2S)-N-(5-chloropyridin-2-yl)-2-{[(2,4-dimethylpyrimidin-5-yl)oxy]methyl}-2-phenylcyclopropanecarboxamide (Example 16),
3) (1R,2S)-N-[3-(dimethylamino)phenyl]-2-{[(2,4-dimethylpyrimidin-5-yl)oxy]methyl}-2-phenylcyclopropanecarboxamide (Example 19),
4) (1R,2S)-N-(3-chlorophenyl)-2-{[(2,4-dimethylpyrimidin-5-yl)oxy]methyl}-2-phenylcyclopropanecarboxamide (Example 24),
5) (1R,2S)-N-(3-cyano-4-fluorophenyl)-2-{[(2,4-dimethylpyrimidin-5-yl)oxy]methyl}-2-phenylcyclopropanecarboxamide (Example 26),
6) (1R,2S)-N-(3-chloro-4-fluorophenyl)-2-{[(2,4-dimethylpyrimidin-5-yl)oxy]methyl}-2-phenylcyclopropanecarboxamide (Example 32),
7) (1R,2S)-2-{[(2,4-dimethylpyrimidin-5-yl)oxy]methyl}-N-(3-methoxyphenyl)-2-phenylcyclopropanecarboxamide (Example 36),
8) (1R,2S)-N[3-(cyanomethyl)phenyl]-2-{[(2,4-dimethylpyrimidin-5-yl)oxy]methyl}-2-phenylcyclopropanecarboxamide (Example 39),
9) (1R,2S)-2-{[(2,4-dimethylpyrimidin-5-yl)oxy]methyl}-2-phenyl-N-[3-(trifluoromethyl)phenyl]cyclopropanecarboxamide (Example 43),
10) (1R,2S)-N-(5-chloro-4-methylpyridin-2-yl)-2-{[(2,4-dimethylpyrimidin-5-yl)oxy]methyl}-2-phenylcyclopropanecarboxamide (Example 45),
11) (1R,2S)-2-{[(2,4-dimethylpyrimidin-5-yl)oxy]methyl}-N-(5-fluoro-4-methylpyridin-2-yl)-2-phenylcyclopropanecarboxamide (Example 51),
12) (1R,2S)-2-{[(2,4-dimethylpyrimidin-5-yl)oxy]methyl}-N-[5-fluoro-4-(methoxymethyl)pyridin-2-yl]-2-phenyl-cyclopropanecarboxamide (Example 71),
13) (1R,2S)-2-{[(2,4-dimethylpyrimidin-5-yl)oxy]methyl}-N-(5-fluoro-4-methoxypyridin-2-yl)-2-phenylcyclopropanecarboxamide (Example 73),
14) (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (Example 82),
15) (1R,2S)-N-(3,4-difluorophenyl)-2-{[(2,4-dimethylpyrimidin-5-yl)oxy]methyl}-2-(3-fluorophenyl)cyclopropanecarboxamide (Example 84),
16) (1R,2S)-N-(4-chloropyridin-2-yl)-2-{[(2,4-dimethylpyrimidin-5-yl)oxy]methyl}-2-(3-fluorophenyl)cyclopropanecarboxamide (Example 85),
17) (1R,2S)-2-{[(2,4-dimethylpyrimidin-5-yl)oxy]methyl}-N-(5-fluoro-4-methoxymethylpyridin-2-yl)-2-(3-fluorophenyl)cyclopropanecarboxamide (Example 86),
18) (1R,2S)-2-{[(2,4-dimethylpyrimidin-5-yl)oxy]methyl}-2-(3-fluorophenyl)-N-(4-fluorophenyl)cyclopropanecarboxamide (Example 92),
19) (1R,2S)-2-{[(2,4-dimethylpyrimidin-5-yl)oxy]methyl}-2-(3-fluorophenyl)-N-phenylcyclopropanecarboxamide (Example 93),
20) (1R,2S)-2-{[(2,4-dimethylpyrimidin-5-yl)oxy]methyl}-N-(5-fluoro-4-methoxypyridin-2-yl)-2-(3-fluorophenyl)cyclopropanecarboxamide (Example 94),
21) (1R,2S)-2-{[(2,4-dimethylpyrimidin-5-yl)oxy]methyl}-2-(3-fluorophenyl)-N-(5-fluoropyridin-2-yl)cyclopropanecarboxamide (Example 95),
22) (1R,2S)-N-(5-cyanopyridin-2-yl)-2-{[(2,4-dimethylpyrimidin-5-yl)oxy]methyl}-2-(3-fluorophenyl)cyclopropanecarboxamide (Example 96),
23) (1R,2S)-2-{[(2,4-dimethylpyrimidin-5-yl)oxy]methyl}-2-(4-fluorophenyl)-N-(5-fluoropyridin-2-yl)cyclopropanecarboxamide (Example 100),
24) (1R,2S)-2-{[(2,4-dimethylpyrimidin-5-yl)oxy]methyl}-N-(5-fluoro-4-methoxypyridin-2-yl)-2-(4-fluorophenyl)cyclopropanecarboxamide (Example 104),
25) (1R,2S)-2-{[(2,4-dimethylpyrimidin-5-yl)oxy]methyl}-N-(5-fluoro-4-methoxymethylpyridin-2-yl)-2-(4-fluorophenyl)cyclopropanecarboxamide (Example 109),
26) (1R,2S)-2-{[(2,4-dimethylpyrimidin-5-yl)oxy]methyl}-N-(5-fluoro-4-methylpyridin-2-yl)-2-(4-fluorophenyl)cyclopropanecarboxamide (Example 111),
27) (1R,2S)-2-(3-cyanophenyl)-2-{[(2,4-dimethylpyrimidin-5-yl)oxy]methyl}-N-(5-fluoro-4-methylpyridin-2-yl)cyclopropanecarboxamide (Example 117),
28) (1R,2S)-2-{[(4-ethyl-2-methylpyrimidin-5-yl)oxy]methyl}-N-(5-fluoropyridin-2-yl)-2-phenylcyclopropanecarboxamide (Example 119),
29) (1R,2S)-N-(5-cyanopyridin-2-yl)-2-{[(4-ethyl-2-methylpyrimidin-5-yl)oxy]methyl}-2-phenylcyclopropanecarboxamide (Example 120),
30) (1R,2S)-N-(5-chloropyridin-2-yl)-2-{[(4-ethyl-2-methylpyrimidin-5-yl)oxy]methyl}-2-phenylcyclopropanecarboxamide (Example 121),
31) (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide (Example 129),
32) (1R,2S)-2-(3,5-difluorophenyl)-2-{[(2,4-dimethylpyrimidin-5-yl)oxy]methyl}-N-(4-fluorophenyl)cyclopropanecarboxamide (Example 130),
33) (1R,2S)-2-(3,5-difluorophenyl)-2-{[(2,4-dimethylpyrimidin-5-yl)oxy]methyl}-N-(pyridin-2-yl)cyclopropanecarboxamide (Example 131),
34) (1R,2S)-N-(5-chloropyridin-2-yl)-2-(3,5-difluorophenyl)-2-{[(2,4-dimethylpyrimidin-5-yl)oxy]methyl}cyclopropanecarboxamide (Example 132),
35) (1R,2S)-2-(3,5-difluorophenyl)-2-{[(2,4-dimethylpyrimidin-5-yl)oxy]methyl}-N-(5-fluoropyridin-2-yl)cyclopropanecarboxamide (Example 133),
36) (1R,2S)-N-(3,4-difluorophenyl)-2-(3,5-difluorophenyl)-2-{[(2,4-dimethylpyrimidin-5-yl)oxy]methyl}cyclopropanecarboxamide (Example 134),
37) (1R,2S)-N-(2,4-difluorophenyl)-2-(3,5-difluorophenyl)-2-{[(2,4-dimethylpyrimidin-5-yl)oxy]methyl}cyclopropanecarboxamide (Example 135), 38) (1R,2S)-N-(5-cyanopyridin-2-yl)-2-(3,5-difluorophenyl)-2-{[(2,4-dimethylpyrimidin-5-yl)oxy]methyl}cyclopropanecarboxamide (Example 137),
39) (1R,2S)-2-(3,5-difluorophenyl)-2-{[(2,4-dimethylpyrimidin-5-yl)oxy]methyl}-N-(5-fluoro-4-methoxypyridin-2-yl)cyclopropanecarboxamide (Example 138),
40) (1R,2S)-N-(5-chloropyridin-2-yl)-2-{[(4-(methoxymethyl)-2-methylpyrimidin-5-yl)oxy]methyl}-2-phenylcyclopropanecarboxamide (Example 139),
41) (1R,2S)-N-(5-cyanopyridin-2-yl)-2-{[(4-(methoxymethyl)-2-methylpyrimidin-5-yl)oxy]methyl}-2-phenylcyclopropanecarboxamide (Example 140),
42) (1R,2S)-N-(5-fluoropyridin-2-yl)-2-{[(4-(methoxymethyl)-2-methylpyrimidin-5-yl)oxy]methyl}-2-phenylcyclopropanecarboxamide (Example 141),
43) (1R,2S)-N-(5-fluoro-4-methylpyridin-2-yl)-2-{[(4-methoxymethyl-2-methylpyrimidin-5-yl)oxy]methyl}-2-phenylcyclopropanecarboxamide (Example 145),
44) (1R,2S)-N-(4-fluorophenyl)-2-{[(4-methoxymethyl-2-methylpyrimidin-5-yl)oxy]methyl}-2-phenylcyclopropanecarboxamide (Example 149),
45) (1R,2S)-N-(3,4-difluorophenyl)-2-{[(4-methoxymethyl-2-methylpyrimidin-5-yl)oxy]methyl}-2-phenylcyclopropanecarboxamide (Example 150),
46) (1R,2S)-2-(3,4-difluorophenyl)-2-{[(2,4-dimethylpyrimidin-5-yl)oxy]methyl}-N-(5-fluoro-4-methylpyridin-2-yl)cyclopropanecarboxamide (Example 164),
47) (1R,2S)-2-(3,4-difluorophenyl)-2-{[(2,4-dimethylpyrimidin-5-yl)oxy]methyl}-N-(4-fluorophenyl)cyclopropanecarboxamide (Example 165),
48) (1R,2S)-2-(3,4-difluorophenyl)-2-{[(2,4-dimethylpyrimidin-5-yl)oxy]methyl}-N-(pyridin-2-yl)cyclopropanecarboxamide (Example 166),
49) (1R,2S)-N-(5-cyanopyridin-2-yl)-2-(3,4-difluorophenyl)-2-{[(2,4-dimethylpyrimidin-5-yl)oxy]methyl}cyclopropanecarboxamide (Example 167),
50) (1R,2S)-N-(5-chloropyridin-2-yl)-2-(3,4-difluorophenyl)-2-{[(2,4-dimethylpyrimidin-5-yl)oxy]methyl}cyclopropanecarboxamide (Example 168),
51) (1R,2S)-2-(3,4-difluorophenyl)-2-{[(2,4-dimethylpyrimidin-5-yl)oxy]methyl}-N-(5-fluoropyridin-2-yl)cyclopropanecarboxamide (Example 169),
52) (1R,2S)-N,2-bis(3,4-difluorophenyl)-2-{[(2,4-dimethylpyrimidin-5-yl)oxy]methyl}cyclopropanecarboxamide (Example 170),
53) (1R,2S)-2-(3,4-difluorophenyl)-2-{[(2,4-dimethylpyrimidin-5-yl)oxy]methyl}-N-(5-fluoro-4-methoxypyridin-2-yl)cyclopropanecarboxamide (Example 173),
54) (1R,2S)-2-{[(2,4-dimethylpyrimidin-5-yl)oxy]methyl}-N-(5-fluoropyridin-2-yl)-2-(3-methoxyphenyl)cyclopropanecarboxamide (Example 186),
55) (1R,2S)-2-{[(2,4-dimethylpyrimidin-5-yl)oxy]methyl}-N-(5-fluoro-4-methylpyridin-2-yl)-2-(3-methoxyphenyl)cyclopropanecarboxamide (Example 189),
56) (1R,2S)-N-(3,4-difluorophenyl)-2-{[(2,4-dimethylpyrimidin-5-yl)oxy]methyl}-2-(3-methoxyphenyl)cyclopropanecarboxamide (Example 190),
57) (1R,2S)-2-(3-fluorophenyl)-N-(5-fluoropyridin-2-yl)-2-[(4-methoxymethyl-2-methylpyrimidin-5-yl)oxymethyl]cyclopropanecarboxamide (Example 191),
58) (1R,2S)-2-(3-fluorophenyl)-N-(4-fluorophenyl)-2-{[(4-methoxymethyl-2-methylpyrimidin-5-yl)oxy]methyl}cyclopropanecarboxamide (Example 192),
59) (1R,2S)-2-(3-fluorophenyl)-2-{[(4-methoxymethyl-2-methylpyrimidin-5-yl)oxy]methyl}-N-(pyridin-2-yl)cyclopropanecarboxamide (Example 193),
60) (1R,2S)-N-(3,4-difluorophenyl)-2-(3-fluorophenyl)-2-{[(4-methoxymethyl-2-methylpyrimidin-5-yl)oxy]methyl}cyclopropanecarboxamide (Example 194),
61) (1R,2S)-N,2-bis(3-fluorophenyl)-2-{[(4-methoxymethyl-2-methylpyrimidin-5-yl)oxy]methyl}cyclopropanecarboxamide (Example 195),
62) (1R,2S)-N-(2,4-difluorophenyl)-2-(3-fluorophenyl)-2-{[(4-methoxymethyl-2-methylpyrimidin-5-yl)oxy]methyl}cyclopropanecarboxamide (Example 196),
63) (1R,2S)-N-(2,5-difluorophenyl)-2-(3-fluorophenyl)-2-{[(4-methoxymethyl-2-methylpyrimidin-5-yl)oxy]methyl}cyclopropanecarboxamide (Example 197),
64) (1R,2S)-N-(5-chloropyridin-2-yl)-2-(3-fluorophenyl)-2-{[(4-methoxymethyl-2-methylpyrimidin-5-yl)oxy]methyl}cyclopropanecarboxamide (Example 198),
65) (1R,2S)-N-(5-fluoro-4-methylpyridin-2-yl)-2-(3-fluorophenyl)-2-{[(4-methoxymethyl-2-methylpyrimidin-5-yl)oxy]methyl}cyclopropanecarboxamide (Example 199),
66) (1R,2S)-2-(3-fluorophenyl)-2-{[(4-methoxymethyl-2-methylpyrimidin-5-yl)oxy]methyl}-N-[5-(trifluoromethyl)pyridin-2-yl]cyclopropanecarboxamide (Example 201),
67) (1R,2S)-2-(4-fluorophenyl)-N-(5-fluoropyridin-2-yl)-2-{[(4-methoxymethyl-2-methylpyrimidin-5-yl)oxy]methyl}cyclopropanecarboxamide (Example 202),
68) (1R,2S)-N,2-bis(4-fluorophenyl)-2-{[(4-methoxymethyl-2-methylpyrimidin-5-yl)oxy]methyl}cyclopropanecarboxamide (Example 203),
69) (1R,2S)-N-(5-chloropyridin-2-yl)-2-(4-fluorophenyl)-2-{[(4-methoxymethyl-2-methylpyrimidin-5-yl)oxy]methyl}cyclopropanecarboxamide (Example 204),
70) (1R,2S)-N-(5-fluoro-4-methylpyridin-2-yl)-2-(4-fluorophenyl)-2-{[(4-methoxymethyl-2-methylpyrimidin-5-yl)oxy]methyl}cyclopropanecarboxamide (Example 205),
71) (1R,2S)-N-(3,4-difluorophenyl)-2-(4-fluorophenyl)-2-{[(4-methoxymethyl-2-methylpyrimidin-5-yl)oxy]methyl}cyclopropanecarboxamide (Example 207),
72) (1R,2S)-2-(3,4-difluorophenyl)-2-{[(4-methoxymethyl-2-methylpyrimidin-5-yl)oxy]methyl}-N-(pyridin-2-yl)cyclopropanecarboxamide (Example 211),
73) (1R,2S)-2-(3,4-difluorophenyl)-N-(5-fluoro-4-methylpyridin-2-yl)-2-{[(4-methoxymethyl-2-methylpyrimidin-5-yl)oxy]methyl}cyclopropanecarboxamide (Example 212),
74) (1R,2S)-N,2-bis(3,4-difluorophenyl)-2-{[(4-methoxymethyl-2-methylpyrimidin-5-yl)oxy]methyl}cyclopropanecarboxamide (Example 214),
75) (1R,2S)-N-(2,4-difluorophenyl)-2-(3,4-difluorophenyl)-2-{[(4-methoxymethyl-2-methylpyrimidin-5-yl)oxy]methyl}cyclopropanecarboxamide (Example 216),
76) (1R,2S)-2-(3,5-difluorophenyl)-2-{[(4-methoxymethyl-2-methylpyrimidin-5-yl)oxy]methyl}-N-(pyridin-2-yl)cyclopropanecarboxamide (Example 218),
77) (1R,2S)-2-(3,5-difluorophenyl)-N-(4-fluorophenyl)-2-{[(4-methoxymethyl-2-methylpyrimidin-5-yl)oxy]methyl}cyclopropanecarboxamide (Example 219),
78) (1R,2S)-N-(3,4-difluorophenyl)-2-(3,5-difluorophenyl)-2-{[(4-methoxymethyl-2-methylpyrimidin-5-yl)oxy]methyl}cyclopropanecarboxamide (Example 221),
79) (1R,2S)-2-(3-chlorophenyl)-2-{[(4-methoxymethyl-2-methylpyrimidin-5-yl)oxy]methyl}-N-(pyridin-2-yl)cyclopropanecarboxamide (Example 225),
80) (1R,2S)-2-(3-chlorophenyl)-N-(5-fluoro-4-methylpyridin-2-yl)-2-{[(4-methoxymethyl-2-methylpyrimidin-5-yl)oxy]methyl}cyclopropanecarboxamide (Example 226), 81) (1R,2S)-N-(5-fluoro-4-methylpyridin-2-yl)-2-(3-fluorophenyl)-2-{[(4-methoxyethyl-2-methylpyrimidin-5-yl)oxy]methyl}cyclopropanecarboxamide (Example 229),
82) (1R,2S)-2-(3-fluoro-5-methoxyphenyl)-N-(4-fluorophenyl)-2-{[(4-methoxymethyl-2-methylpyrimidin-5-yl)oxy]methyl}cyclopropanecarboxamide (Example 231),
83) (1R,2S)-N-(3,4-difluorophenyl)-2-(3-fluoro-5-methoxyphenyl)-2-{[(4-methoxymethyl-2-methylpyrimidin-5-yl)oxy]methyl}cyclopropanecarboxamide (Example 232),
84) (1R,2S)-2-(3-fluoro-5-methoxyphenyl)-N-(5-fluoropyridin-2-yl)-2-[(4-methoxymethyl-2-methylpyrimidin-5-yl)oxymethyl]cyclopropanecarboxamide (Example 233),
85) (1R,2S)-2-(3-fluoro-5-methoxyphenyl)-N-(5-fluoro-4-methylpyridin-2-yl)-2-{[(4-methoxymethyl-2-methylpyrimidin-5-yl)oxy]methyl}cyclopropanecarboxamide (Example 234),
86) (1R,2S)-2-(3-fluoro-5-methoxyphenyl)-2-[(4-methoxymethyl-2-methylpyrimidin-5-yl)oxymethyl]-N-(pyridin-2-yl)cyclopropanecarboxamide (Example 235),
87) (1R,2S)-2-(3-fluoro-5-methoxyphenyl)-N-(3-fluorophenyl)-2-{[(4-methoxymethyl-2-methylpyrimidin-5-yl)oxy]methyl}cyclopropanecarboxamide (Example 236),
88) (1R,2S)-2-(4-fluoro-3-methoxyphenyl)-N-(5-fluoro-4-methylpyridin-2-yl)-2-{[(4-methoxymethyl-2-methylpyrimidin-5-yl)oxy]methyl}cyclopropanecarboxamide (Example 239),
89) (1R,2S)-2-{[(4-ethyl-2-methylpyrimidin-5-yl)oxy]methyl}-2-(3-fluorophenyl)-N-(pyridin-2-yl)cyclopropanecarboxamide (Example 240),
90) (1R,2S)-2-[(4-ethyl-2-methylpyrimidin-5-yl)oxy]methyl-2-(3-fluorophenyl)-N-(5-fluoropyridin-2-yl)cyclopropanecarboxamide (Example 241),
91) (1R,2S)-N-(5-cyanopyridin-2-yl)-2-{[(4-ethyl-2-methylpyrimidin-5-yl)oxy]methyl}-2-(3-fluorophenyl)cyclopropanecarboxamide (Example 242),
92) (1R,2S)-N-(5-chloropyridin-2-yl)-2-{[(4-ethyl-2-methylpyrimidin-5-yl)oxy]methyl}-2-(3-fluorophenyl)cyclopropanecarboxamide (Example 243),
93) (1R,2S)-2-{[(4-ethyl-2-methylpyrimidin-5-yl)oxy]methyl}-N-(5-fluoro-4-methylpyridin-2-yl)-2-(3-fluorophenyl)cyclopropanecarboxamide (Example 244),
94) (1R,2S)-2-{[(4-ethyl-2-methylpyrimidin-5-yl)oxy]methyl}-2-(4-fluorophenyl)-N-(pyridin-2-yl)cyclopropanecarboxamide (Example 245),
95) (1R,2S)-2-{[(4-ethyl-2-methylpyrimidin-5-yl)oxy]methyl}-2-(4-fluorophenyl)-N-(5-fluoropyridin-2-yl)cyclopropanecarboxamide (Example 246),
96) (1R,2S)-N-(4-chloropyridin-2-yl)-2-{[(4-ethyl-2-methylpyrimidin-5-yl)oxy]methyl}-2-(4-fluorophenyl)cyclopropanecarboxamide (Example 247),
97) (1R,2S)-2-{[(4-ethyl-2-methylpyrimidin-5-yl)oxy]methyl}-N-(5-fluoro-4-methylpyridin-2-yl)-2-(4-fluorophenyl)cyclopropanecarboxamide (Example 248),
98) (1R,2S)-2-{[(2,4-dimethylpyrimidin-5-yl)oxy]methyl}-2-(3-fluoro-5-methoxyphenyl)-N-(5-fluoro-4-methylpyrimidin-2-yl)cyclopropanecarboxamide (Example 256),
99) (1R,2S)-2-{[(2,4-dimethylpyrimidin-5-yl)oxy]methyl}-N-(5-fluoropyridin-2-yl)-2-(3-trifluoromethylphenyl)cyclopropanecarboxamide (Example 266),
100) (1R,2S)-2-(4-bromophenyl)-N-(5-chloropyridin-2-yl)-2-{[(2,4-dimethylpyrimidin-5-yl)oxy]methyl}cyclopropanecarboxamide (Example 273),
101) (1R,2S)-2-{[(2,4-dimethylpyrimidin-5-yl)oxy]methyl}-N-(5-fluoromethylpyridin-2-yl)-2-(3-fluorophenyl)cyclopropanecarboxamide (Example 282),
102) (1R,2S)-2-{[(2,4-dimethylpyrimidin-5-yl)oxy]methyl}-N-(5-fluoropyridin-2-yl)-2-(3-iodophenyl)cyclopropanecarboxamide (Example 283),
103) (1R,2S)-N-(5-fluoropyridin-2-yl)-2-{[(4-hydroxymethyl-2-methylpyrimidin-5-yl)oxy]methyl}-2-(3-fluorophenyl)cyclopropanecarboxamide (Example 286),
104) (1R,2S)-2-{[(4-ethyl-2-methylpyrimidin-5-yl)oxy]methyl}-2-(3-fluorophenyl)-N-(4-fluorophenyl)cyclopropanecarboxamide (Example 316),
105) (1R,2S)-2-{[(4-fluoromethyl-2-methylpyrimidin-5-yl)oxy]methyl}-2-(3-fluorophenyl)-N-(5-fluoropyridin-2-yl)cyclopropanecarboxamide (Example 320),
106) (1R,2S)-2-{[(2,4-dimethylpyrimidin-5-yl)oxy]methyl}-2-(3-fluoro-4-hydroxyphenyl)-N-(5-fluoropyridin-2-yl)cyclopropanecarboxamide (Example 321),
107) (1R,2S)-2-{[(2,4-dimethylpyrimidin-5-yl)oxy]methyl}-2-(3-fluoro-4-methoxyphenyl)-N-(5-fluoropyridin-2-yl)cyclopropanecarboxamide (Example 322),
108) (1R,2S)-2-(3-fluorophenyl)-N-(5-fluoropyridin-2-yl)-2-{[(2-hydroxymethyl-4-methylpyrimidin-5-yl)oxy]methyl}cyclopropanecarboxamide (Example 323),
109) (1R,2S)-2-{[(2,4-dimethylpyrimidin-5-yl)oxy]methyl}-2-[5-fluoro-2-hydroxyphenyl]-N-(5-fluoropyridin-2-yl)cyclopropanecarboxamide (Example 324),
110) (1R,2S)-2-{[(2,4-dimethyl-6-oxo-1,6-dihydropyrimidin-5-yl)oxy]methyl}-2-(3-fluorophenyl)-N-(5-fluoropyridin-2-yl)cyclopropanecarboxamide (Example 326),
111) (1R,2S)-N-(2-cyanopyridin-4-yl)-2-{[(2,4-dimethylpyrimidin-5-yl)oxy]methyl}-2-phenylcyclopropanecarboxamide (Example 41),
112) (1R,2S)-2-[N-(2,4-dimethylpyrimidin-5-yl)methylaminomethyl]-N-(5-fluoropyridin-2-yl)-2-(3-fluorophenyl)cyclopropanecarboxamide (Example 293),
113) (1R,2S)-N-(5-chloro-4-methylpyridin-2-yl)-2-[N-(2,4-dimethylpyrimidin-5-yl)methylaminomethyl]-2-(3-fluorophenyl)cyclopropanecarboxamide (Example 295),
114) (1R,2S)-N-(3,4-fluoropyridin-2-yl)-2-[N-(2,4-dimethylpyrimidin-5-yl)methylaminomethyl]-2-(3-fluorophenyl)cyclopropanecarboxamide (Example 296),
115) (1R,2S)-2-(3-fluorophenyl)-N-(5-fluoropyridin-2-yl)-2-[N-(2-methyl-4-trifluoromethylpyrimidin-5-yl)methylaminomethyl] cyclopropanecarboxamide (Example 302), and
116) (1R,2S)-2-{[(2,4-dimethylpyrimidin-5-yl)oxy]methyl}-N-(6-fluoro-5-methoxypyridin-3-yl)-2-phenylcyclopropanecarboxamide (Example 327).

More preferably, the cyclopropane compound or a pharmaceutically acceptable salt thereof is selected from the following compounds:

(1R,2S)-2-{[(2,4-dimethylpyrimidin-5-yl)oxy]methyl}-N-(5-fluoropyridin-2-yl)-2-phenylcyclopropanecarboxamide (Example 1), (1R,2S)-2-{[(2,4-dimethylpyrimidin-5-yl)oxy]methyl}-N-(5-fluoro-4-methylpyridin-2-yl)-2-phenylcyclopropanecarboxamide (Example 51), (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (Example 82), (1R,2S)-2-{[(2,4-dimethylpyrimidin-5-yl)oxy]methyl}-2-(3-fluorophenyl)-N-(5-fluoropyridin-2-yl)cyclopropanecarboxamide (Example 95), (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide (Example 129), and (1R,2S)-2-{[(4-ethyl-2-methylpyrimidin-5-yl)oxy]methyl}-2-(3-fluorophenyl)-N-(pyridin-2-yl)cyclopropanecarboxamide (Example 240).

Particularly preferably, the cyclopropane compound or a pharmaceutically acceptable salt thereof is selected from the following compounds:

(1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (Example 82) represented by the following formula or a pharmaceutically acceptable salt thereof:

[Formula 15]

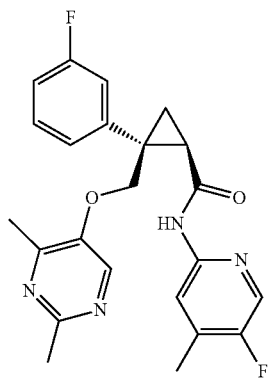

(1R,2S)-2-{[(2,4-dimethylpyrimidin-5-yl)oxy]methyl}-2-(3-fluorophenyl)-N-(5-fluoropyridin-2-yl)cyclopropanecarboxamide (Example 95) represented by the following formula or a pharmaceutically acceptable salt thereof:

[Formula 16]

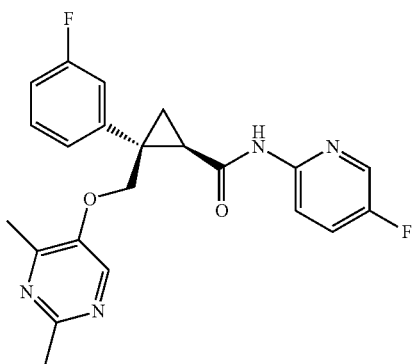

and,
(1R,2S)-2-(3,5-Difluorophenyl)-2-{[(2,4-dimethylpyrimidin-5-yl)oxy]methyl}-N-(5-fluoro-4-methylpyridin-2-yl)cyclopropanecarboxamide (Example 129) represented by the following formula or a pharmaceutically acceptable salt thereof:

[Formula 17]

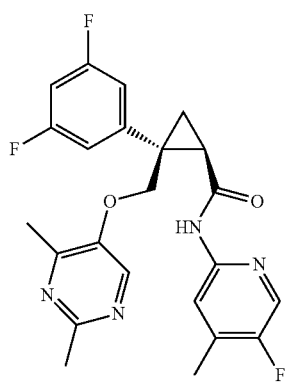

Next, a method for producing the compound of the formula (I) of the present invention [hereinafter referred to as a compound (I); compounds represented by other formulae will be referred to in the same manner] or a pharmaceutically acceptable salt thereof will be described.

In the formula (I), when L represents the formula —CONH—, the compound (I) or a pharmaceutically acceptable salt thereof can be produced by the following method.

The compound (I) represented by the following formula (I-1) and an intermediate thereof are synthesized, for example, by the following general production methods, and methods described in production examples and Examples, which will be described later.

Formula (I-1):

[Formula 18]

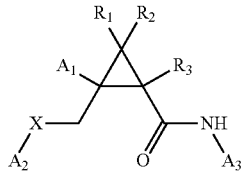

(I-1)

wherein $A_1$, $A_2$, $A_3$, $R_1$, $R_2$, $R_3$ and X have the same definitions as those described above.

The "leaving group" in a raw material compound used in production of the compound (I) of the present invention is not particularly limited, as long as it can be used in a nucleophilic substitution reaction. Preferred examples of such a leaving group include a halogen atom, a $C_{1-6}$ alkylsulfonyloxy group which may be substituted with the above described substituent group α, and an arylsulfonyloxy group which may be substituted with the above described substituent group α. Specific examples include a chlorine atom, a bromine atom, an iodine atom, a methanesulfonyloxy group, a trifluoromethanesulfonyloxy group and a p-toluenesulfonyloxy group.

1. General Production Method 1:

Scheme 1

[Formula 19]

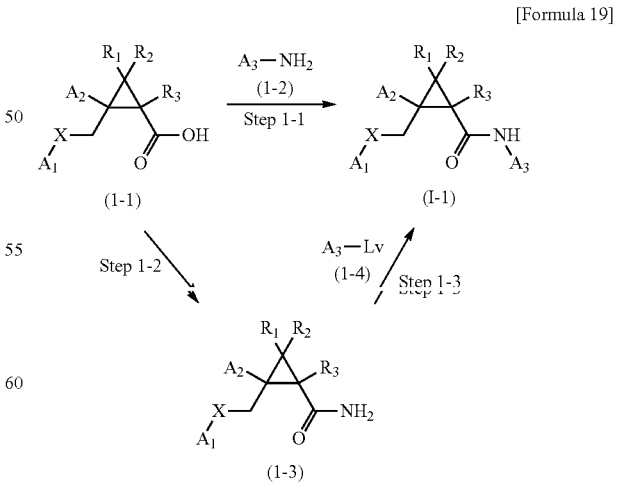

wherein $R_1$, $R_2$ and $R_3$ each represent hydrogen; Lv represents a leaving group including, for example, a halogen atom (a chlorine atom, a bromine atom, an iodine atom, etc.), and a sulfonyloxy group such as a methanesulfonyloxy group, a p-toluenesulfonyloxy group or a trifluoromethanesulfonyloxy group (which is represented by TfO in the formula); and $A_1, A_2, A_3$ and X have the same meanings as those described above.

Step 1-1:

The present step is a step of directly condensing the compound (1-1) with the compound (1-2) (method 1), or inducing the compound (1-1) to an acid halide (method 2), a mixed acid anhydride (method 3), an active ester (method 4) or the like, and then condensing the obtained product with the compound (1-2), so as to obtain the compound (I-1).

Method 1:

When the compound (1-1) is directly condensed with the compound (1-2), a condensing agent is used. Such a condensation reaction can be carried out under the same conditions as commonly used conditions described in publications as described below. Known methods are described, for example, in Rosowsky, A.; Forsch, R. A.; Moran, R. G; Freisheim, J. H.; J. Med. Chem., 34(1), 227-234 (1991), Brzostwska, M.; Brossi, A.; Flippen-Anderson, J. L.; Heterocycles, 32(10), 1968-1972 (1991), Romero, D. L.; Morge, R. A.; Biles, C.; Berrios-Pena, N.; May, P. D.; Palmer, J. R.; Johnson, P. D.; Smith, H. W; Busso, M.; Tan, C.-K.; Voorman, R. L.; Reusser, F.; Althaus, I. W.; Downey, K. M.; So, A. G; Resnick, L.; Tarpley, W. G, Aristoff, P. A.; J. Med. Chem., 37(7), 998-1014 (1994).

The compound (1-1) may be either a free form or a salt.

The solvent used in the present invention is not particularly limited, as long as it does not inhibit the reaction. Examples of such a solvent include tetrahydrofuran, 1,4-dioxane, ethyl acetate, methyl acetate, dichloromethane, chloroform, N,N-dimethylformamide, toluene and xylene. Examples of a condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC(N,N-dicyclohexylcarbodiimide), diethylphosphorylcyanide, and PyBOP (benzotriazol-1-yloxytris(pyrrolidino)phosphoniumhexafluorophosphate). The compound (1-2) is used in an amount from 1 equivalent to a largely excessive amount with respect to the compound (1-1). In addition, an organic base such as triethylamine may be added in an amount from 1 equivalent to a largely excessive amount to the compound (1-1), as necessary.

The reaction time is not particularly limited. It is generally from 0.5 to 48 hours, and preferably from 0.5 to 24 hours. The reaction temperature depends on a raw material used, a solvent used, and the like, and thus, it is not particularly limited. It is preferably from an ice cooling temperature to a solvent reflux temperature.

Method 2: (Synthetic Method Using Acid Halide)

In the present reaction, the compound (1-1) is converted to the corresponding acid halide according to a method known to a person skilled in the art, and the acid halide is then allowed to react with the compound (1-2) to obtain the compound (1-1).

Examples of a base used in the reaction include triethylamine, pyridine, potassium carbonate and diisopropylethylamine. The reaction temperature is not particularly limited. It is generally from −78° C. to a solvent reflux temperature, and preferably from −20° C. to room temperature. The solvent used in the reaction is not particularly limited, as long as it does not inhibit the reaction and is able to dissolve a starting substance to a certain extent. Preferred examples of such a solvent include tetrahydrofuran, ether, toluene and dichloromethane.

Method 3: (Synthetic Method Using Acid Anhydride)

After the compound (1-1) has been converted to a mixed acid anhydride, the mixed acid anhydride is allowed to react with the compound (1-2), so as to obtain the compound (1-1). The mixed acid anhydride can be synthesized by means known to a person skilled in the art. For example, it can be synthesized by reacting the compound (1-1) with a chloroformic acid ester such as ethyl chloroformate in the presence of a base such as triethylamine. Such a chloroformic acid ester and a base are used in an amount of 1 to 2 equivalents with respect to the compound (1-1). The reaction temperature is from −30° C. to room temperature, and preferably −20° C. to room temperature.

The step of condensing the mixed acid anhydride and the compound (1-2) is carried out, for example, by reacting the mixed acid anhydride with the compound (1-2) in a solvent such as dichloromethane, tetrahydrofuran or N,N-dimethylformamide. The compound (1-2) is used in an amount from 1 equivalent to a largely excessive amount with respect to the mixed acid anhydride The reaction time is not particularly limited. It is generally from 0.5 to 48 hours, and preferably from 0.5 to 12 hours. The reaction temperature is from −20° C. to 50° C., and preferably from −20° C. to room temperature.

Method 4: (Synthetic Method Using Active Ester)

After the compound (1-1) has been converted to an active ester, the active ester is allowed to react with the compound (1-2), so as to obtain the compound (1-1). The step of obtaining the active ester is carried out, for example, by reacting the compound (1-1) with an active ester-synthesizing reagent in a solvent such as 1,4-dioxane, tetrahydrofuran or N,N-dimethylformamide in the presence of a condensing agent such as DCC. An example of the active ester-synthesizing reagent is N-hydroxysuccinimide. Such an active ester-synthesizing reagent and a condensing agent are used in an amount of 1 to 1.5 equivalents with respect to the compound (1-1). The reaction time is not particularly limited. It is generally from 0.5 to 48 hours, and preferably from 0.5 to 24 hours.

The reaction temperature is from −20° C. to −50° C., and preferably from −20° C. to room temperature.

The step of condensing the active ester and the compound (1-2) is carried out, for example, by reacting the active ester with the compound (1-2) in a solvent such as dichloromethane, tetrahydrofuran or N,N-dimethylformamide. The compound (1-2) is used in an amount from 1 equivalent to a largely excessive amount with respect to the active ester. The reaction time is not particularly limited. It is generally from 0.5 to 48 hours, and preferably from 0.5 to 24 hours. The reaction temperature is from −20° C. to −50° C., and preferably from −20° C. to room temperature.

Step 1-2:

The present step is a step of obtaining the compound (1-3) from the compound (1-2).

The present step is a step of converting the compound (11) to the corresponding acid halide or acid anhydride by the methods described in Method 2 and Method 3 above and then reacting the acid halide or acid anhydride with ammonia, so as to obtain the compound (1-3). The ammonia used in the reaction may be either gas or an aqueous solution. It may also be an ammonia salt. The compound (1-3) can also be produced by reacting hexamethyl disilazane with an acid halide and then adding methanol to the reaction product, followed by an acid treatment (R. Pellegata et al., Synthesis, 1985, 517).

Moreover, the compound (1-3) can also be produced by heating the compound (1-1) and urea.

Step 1-3:

The present step is a step of obtaining the compound (I-1) from the compound (1-3).

This is a step of subjecting the compound (1-3) and the compound (1-4) to a coupling reaction using a transition metal, so as to obtain the compound (I-1).

In the present step, the reaction can be carried out under conditions that are commonly applied to the coupling reaction between an aryl halide or arylboronic acid and an acid amide, in which a transition metal is used.

A coupling reaction using copper is described, for example, in publications such as Hanhui Xu, Christian Wolf, Chem. Commun, 2009, 1715; and Suribabu Jammi et al., Synlett. 2009 (20), 3323. The type of a copper reagent used in the present reaction is not particularly limited. Preferred examples of such a copper reagent include cuprous iodide, cuprous oxide, and copper(II) trifluoromethanesulfonate.

A coupling reaction using a palladium complex is described, for example, in publications such as Van den Hoogenband, A et al., Tetrahedron Lett. 2004, 45, 8535; and Ghosh, A et al., Org. Lett. 2003, 5, 2207. The type of a palladium reagent used in the present reaction is not particularly limited. Preferred examples of such a palladium reagent include tris(dibenzylideneacetone)dipalladium, palladium chloride, and palladium(II) acetate. Examples of a ligand used in the present reaction include XantPhos (4,5-bis(diphenylphosphino)-9,9-dimethylxanthene), X-Phos (2-dicyclohexylphosphino-2',4',6'-triisopropylbiphenyl), BINAP (2,2'-bis(diphenylphosphino)-1,1'-binaphthyl), DPPF (1,1'-bis(diphenylphosphino)ferrocene), and tris(tert-butyloxy)phosphine. The transition metal reagent is used in an amount of approximately 0.001 to 0.1 equivalent with respect to the amount of a raw material. The type of a solvent used in the present reaction is not particularly limited, as long as it does not inhibit the reaction. Preferred examples of such a solvent include benzene, toluene, xylene, N,N-dimethylformamide, 1-methyl-2-pyrrolidone, tetrahydrofuran, 1,4-dioxane, acetonitrile, and propionitrile. The reaction temperature is not particularly limited. It is generally from an ice cooling temperature to a solvent reflux temperature, and preferably from room temperature to a solvent reflux temperature, for example. The reaction time is not particularly limited. It is generally from 0.5 to 48 hours, and preferably from 0.5 to 24 hours.

General Production Method 2:

wherein $A_1$, $A_2$, $R_1$, $R_2$, $R_3$ and X have the same meanings as those described above.

The general production method 2 is a method for producing the compound (1-1) that is a synthetic intermediate of the compound (1-1) according to the present invention, which uses the compound (2-1) as a raw material and involves [step 2-1] and [step 2-2] or [step 2-3].

The compound (2-1) can be produced from a commercially available product by a method known to a person skilled in the art. Further, it can also be produced by applying methods described in the production examples in the examples.

Step 2-1:

The present step is a step of subjecting the compound (2-1) to an oxidation reaction to obtain the compound (2-2). An aldehyde compound can be obtained from an alcohol compound according to a method known to a person skilled in the art.

Examples of a known oxidation method used in the reaction include Swern oxidation, Corey-Kim oxidation, Moffatt oxidation, PCC oxidation, PDC oxidation, Bess-Martin oxidation, $SO_3$-pyridine oxidation, and TEMPO oxidation.

The solvent used in the reaction is not particularly limited, as long as it does not inhibit the reaction and dissolves a starting substance to a certain extent. Examples of such a solvent include dimethyl sulfoxide, tetrahydrofuran, toluene, dichloromethane and chloroform.

The reaction temperature is not particularly limited. It is generally from −78° C. to a solvent reflux temperature, and preferably from −78° C. to room temperature. The reaction time is not particularly limited. It is generally from 5 minutes to 48 hours, and preferably from 5 minutes to 24 hours.

Step 2-2:

The present step is a step of subjecting the compound (2-3) to an oxidation reaction to obtain the compound (1-1). A carboxylic acid compound can be obtained from an aldehyde compound according to a method known to a person skilled in the art.

As an oxidation method, a commonly used oxidation method can be applied. For example, methods described in the production examples in the Examples can be applied.

Step 2-3:

The present step is a step of subjecting the compound (2-1) to an oxidation reaction to obtain the compound (1-1). As oxidation conditions, commonly used conditions can be applied. For example, oxidation can be carried out using TEMPO-bisacetyliodobenzene. The solvent used in the reaction is not particularly limited, as long as it does not inhibit the reaction and dissolves a starting substance to a certain extent.

Scheme 2

[Formula 20]

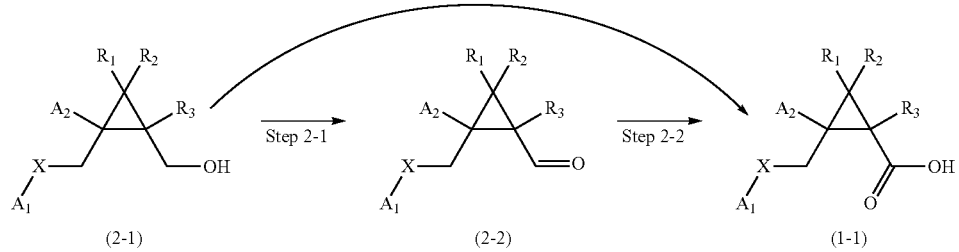

For example, dichloromethane, chloroform, acetonitrile, toluene or the like is mixed with water, and the mixed solvent can be used.

The reaction temperature is not particularly limited. It is generally from 0° C. to a solvent reflux temperature. The reaction time is not particularly limited. It is generally from 5 minutes to 48 hours, and preferably from 5 minutes to 24 hours.

Moreover, methods described in the production examples in the Examples can be applied.

General Production Method 3:

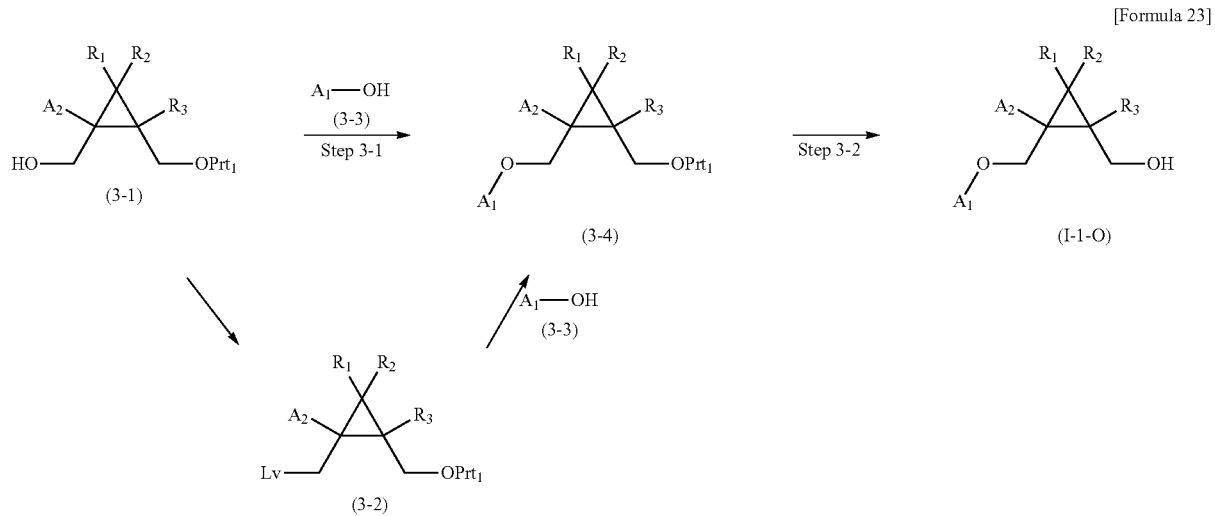

Scheme 3

[Formula 23]

wherein Lv represents a leaving group such as a halogen atom (a chlorine atom, a bromine atom, an iodine atom or the like), a sulfonyloxy group such as a methanesulfonyloxy group, a p-toluenesulfonyloxy group or a trifluoromethanesulfonyloxy group, or the like; $Prt_1$ represents a protecting group for a hydroxyl group; and $A_1$, $A_2$, $R_1$, $R_2$ and $R_3$ have the same meanings as those described above.

The general production method 3 is a method for producing the compound (I-1-O) that is a synthetic intermediate of the compound (I) according to the present invention, which uses the compound (3-1) as a raw material and involves [step 3-1] and [step 3-2].

The compound (I-1-O) can also be produced from a commercially available product according to a method known to a person skilled in the art. Further, it can also be produced by applying methods described in the production examples in the Examples.

Step 3-1:

The present step is a step of allowing the compound (3-1) to directly react with the compound (3-3), or of converting the compound (3-1) to the compound (3-2) and then allowing the compound (3-2) to react with the compound (3-3), so as to obtain the compound (3-4).

When the compound (3-1) is allowed to directly react with the compound (3-3), the present reaction can be carried out under conditions generally used in the Mitsunobu reaction (for example, conditions described in O. Mitsunobu, Synthesis, 1 (1981), D. L. Hughes, Organic Reactions, 42, 335 (1992), etc.).

The reaction is carried out using a phosphine derivative such as triphenylphosphine and an azodicarboxylic acid diester such as diethyl azodicarboxylate or diisopropyl azodicarboxylate. The solvent used in the reaction is not particularly limited, as long as it does not inhibit the reaction and dissolves a starting substance to a certain extent. For example, tetrahydrofuran, benzene, toluene or N,N-dimethylformamide can be used. The reaction temperature is not particularly limited. It is generally from an ice cooling temperature to room temperature.

Alternatively, the compound (3-4) can be produced by converting the compound (3-1) to the compound (3-2) having a leaving group and then performing a nucleophilic substitution reaction between the compound (3-2) and the compound (3-3). Specifically, a base is allowed to act on the compound (3-3) to form an anion, and the anion is then allowed to react with the compound (3-2), so as to obtain the compound (34), for example.

The solvent used in the reaction is not particularly limited, as long as it does not inhibit the reaction. The present reaction can be carried out by allowing a suitable base to act on the compound (3-3), in an amount of 1 equivalent to a largely excessive amount with respect to the compound, in an organic solvent such as diethyl ether, tetrahydrofuran, 1,4-dioxane, N,N-dimethylformamide or dimethyl sulfoxide. Examples of the used base include sodium hydroxide, potassium hydroxide, sodium hydride, potassium hydride, sodium methoxide, sodium ethoxide, and potassium tert-butoxide.

The reaction temperature is not particularly limited. It is generally from −78° C. to a solvent reflux temperature, and preferably from an ice cooling temperature to 100° C.

The compound (3-2) can be produced by converting the hydroxyl group of the compound (3-1) to a leaving group. Examples of such a leaving group include a halogen atom (a chlorine atom, a bromine atom or an iodine atom), and a sulfonyloxy group such as a methanesulfonyloxy group, a p-toluenesulfonyloxy group or a trifluoromethanesulfonyloxy group.

The reaction can be carried out under the same conditions as those generally used in a reaction of converting the hydroxyl group to such a leaving group (for example, conditions described in R. K. Crossland and K. L. Servis, Journal of Organic Chemistry, 35, 3195 (1970), Y Yoshida, Y. Sakakura, N. Aso, S. Okada, and Y. Tanabe, Tetrahedron, 55, 2183 (1999).

When the leaving group is a halogen atom for example, the compound (3-2) can be produced by allowing the compound (3-1) to react with thionyl chloride, thionyl bromide, phosphorus tribromide or tetrahalogenomethane triphenylphosphine. The solvent used in the reaction is not particularly limited, as long as it does not inhibit the reaction and dissolves a starting substance to a certain extent. Preferred examples of such a solvent include benzene, toluene, xylene, dichloromethane and chloroform. Further, there may be a case in which favorable results such as the improvement of a yield can be obtained by addition of a base. The base used in the reaction is not particularly limited, as long as it does not inhibit the reaction. Preferred examples of such a base include sodium carbonate, potassium carbonate, triethylamine, pyridine and N,N-diisopropylethylamine. The reaction temperature is generally from −78° C. to a solvent reflux temperature, and preferably from an ice cooling temperature to a solvent reflux temperature.

When the leaving group is a sulfonyloxy group, the compound (3-2) can be produced by allowing the compound (31) to react with methanesulfonyl chloride, p-toluenesulfonyl chloride, anhydrous trifluoromethanesulfonic acid, etc. The solvent used in the reaction is not particularly limited, as long as it does not inhibit the reaction and dissolves a starting substance to a certain extent. Preferred examples of such a solvent include tetrahydrofuran, toluene, xylene, dichloromethane, chloroform and N,N-dimethylformamide. The reaction temperature is generally from −78° C. to a solvent reflux temperature, and preferably from an ice cooling temperature to room temperature. Further, there may be a case in which favorable results such as the improvement of a yield can be obtained by addition of a base. The base used in the reaction is not particularly limited, as long as it does not inhibit the reaction. Preferred examples of such a base include sodium carbonate, potassium carbonate, triethylamine, pyridine and N,N-diisopropylethylamine.

Step 3-2:

The present step is a step of deprotecting the compound (3-4) to obtain the compound (I-1-O).

When $Prt_1$ is a tert-butyldimethylsilyl group or a tert-butyldiphenylsilyl group, the reaction can be carried out under the same conditions as those generally used in the deprotection reaction of a silyl group (for example, conditions described in publications such as T. W. Green and P. G. M. Wuts, "Protective Groups in Organic Chemistry, Third Edition," John Wiley & Sons (1999), pp. 113-148). Specifically, tetra-n-butylammonium fluoride is allowed to act on the compound (3-4) in an organic solvent such as tetrahydrofuran, or hydrochloric acid is allowed to act on the compound (3-4) in ethanol, so as to obtain the compound (I-1-O). The solvent used in the present reaction is not particularly limited, as long as it does not inhibit the reaction. Preferred examples of such a solvent include dichloromethane, methanol, ethanol, propanol, ethyl acetate, tetrahydrofuran and 1,4-dioxane. Further, there may be a case in which favorable results such as the improvement of a yield can be obtained by addition of an acetic acid.

When $Prt_1$ is a benzyl group, the reaction can be carried out under the same conditions as those generally used in the deprotection reaction of a benzyl group (for example, conditions described in publications such as T. W. Green and P. G. M. Wuts, "Protective Groups in Organic Chemistry, Third Edition," John Wiley & Sons (1999), pp. 76-86). Specifically, the reaction can be carried out, for example, by a catalytic reduction method, which uses palladium-carbon, palladium hydroxide-carbon or the like as a catalyst in an organic solvent such as ethanol in a hydrogen atmosphere.

The solvent used in the present reaction is not particularly limited, as long as it does not inhibit the reaction. Examples of such a solvent include methanol, ethanol, propanol, ethyl acetate, tetrahydrofuran and 1,4-dioxane. The reaction conditions are not particularly limited. The reaction can be carried out at a temperature from room temperature to a solvent reflux temperature at normal atmospheric pressure to 150 atmospheric pressures, and preferably at a temperature from room temperature to 60° C. at normal atmospheric pressure to 5 atmospheric pressures.

General Production Method 4:

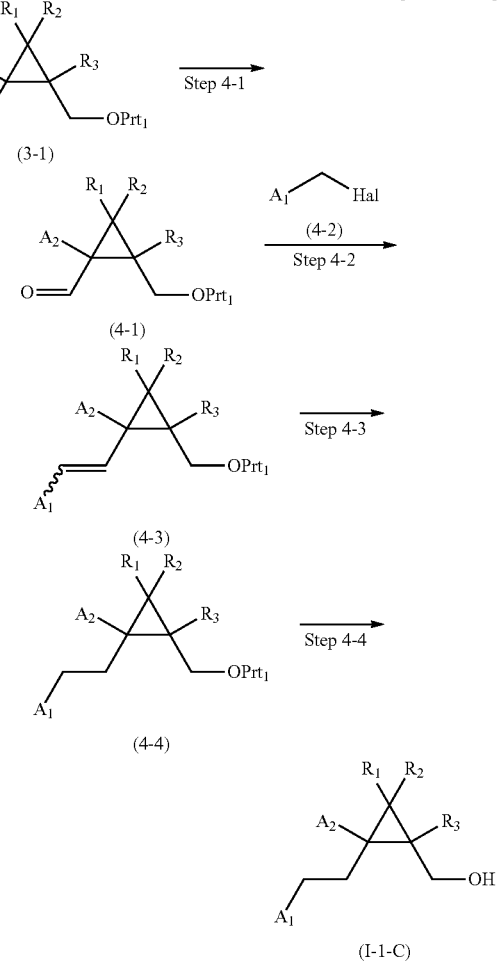

wherein $Prt_1$, $A_1$, $A_2$, $R_1$, $R_2$ and $R_3$ have the same meanings as those described above.

The general production method 4 is a method for producing the compound (I-1-C) that is a synthetic intermediate of the compound (I) according to the present invention, which uses the compound (3-1) as a raw material and involves 4 steps from [step 4-1] to [step 4-4].

The compound (I-1-C) can also be produced from a commercially available product by a method known to a person skilled in the art. Further, it can also be produced by applying methods described in the production examples in the examples.

Step 4-1

The present step is a step of oxidizing the alcohol of the compound (3-1) to obtain an aldehyde (4-1). The present reaction can be carried out under the same conditions as those in the step 2-1.

Step 4-2

The present step is a step of obtaining the olefin (4-3) from the aldehyde (4-1). The present reaction can be carried out under commonly used conditions. Specifically, the compound (4-2) and a Wittig reagent synthesized from triphenylphosphine are used for example, and these are allowed to react with the compound (4-1) in the presence of a base, so as to obtain the compound (4-3).

Step 4-3

The present step is a step of reducing olefin according to catalytic hydrogen reduction. The present reaction can be carried out under commonly used conditions.

Step 4-4

The present step is a step of deprotecting the compound (4-3) to obtain the compound (I-1-C). The present reaction can be carried out by the same method as that in the step 3-2.

5. General Production Method 5:

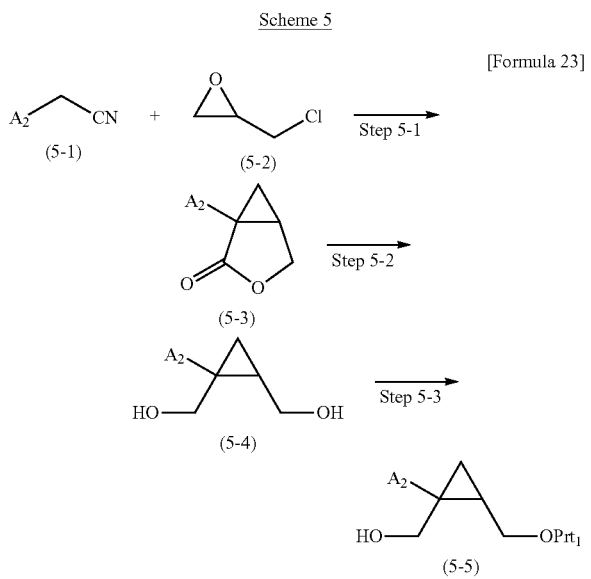

Scheme 5

[Formula 23]

wherein $Prt_1$ and $A_1$ have the same meanings as those described above.

The general production method 5 is a method for producing the compound (5-5) that is a synthetic intermediate of the compound (I) according to the present invention, which uses the compound (5-1) as a raw material and involves [step 5-1] to [step 5-3].

The compound (5-5) can also be produced from a commercially available product by a method known to a person skilled in the art. Further, it can also be produced by applying methods described in the production examples in the examples.

Step 5-1

The present step is a step of reacting an acetonitrile derivative (5-1) with the epichlorohydrin (5-2) to obtain the compound (5-3). The compound (5-3) can be produced under commonly used reaction conditions (for example, conditions described in S, Shuto, Bioorganic & Medicinal Chemistry, 10 (2002), 3829), or by applying methods described in the pro- duction examples in the examples. Moreover, an optically active substance of the compound (5-3) can be obtained using an optically active epichlorohydrin.

Step 5-2

The present step is a step of reducing the lactone (5-3) to obtain the compound (5-4). Examples of a reducing agent used in the reaction include sodium borohydride, lithium borohydride, and lithium aluminum hydride.

The solvent used in the present reaction is not particularly limited, as long as it does not inhibit the reaction and dissolves a starting substance to a certain extent. Examples of such a solvent include tetrahydrofuran and diethyl ether. In some cases, an alcoholic solvent such as methanol is mixed with such a solvent. The reaction temperature is not particularly limited. It is generally from −78° C. to a solvent reflux temperature, and preferably from −78° C. to room temperature. The reaction time is not particularly limited. It is generally from 5 minutes to 48 hours, and preferably from 5 minutes to 24 hours.

Step 5-3

The present step is a step of protecting the hydroxyl group of the compound (5-4). Examples of a protecting group used herein include an acetyl group, a methoxymethyl group, a trityl group, a benzyl group, a t-butyldiphenylsilyl group, and a triisopropylsilyl group. The present reaction can be carried out under the same conditions as those commonly used in the introduction of a protecting group into a hydroxyl group (for example, conditions described in publications such as T. W. Green and P. G. M. Wuts, "Protective Groups in Organic Chemistry, Third Edition," John Wiley & Sons (1999), pp. 17-245). In addition, as in the case of Example 49, the present reaction can also be carried out by acetylation using enzyme.

6. General Production Method 6:

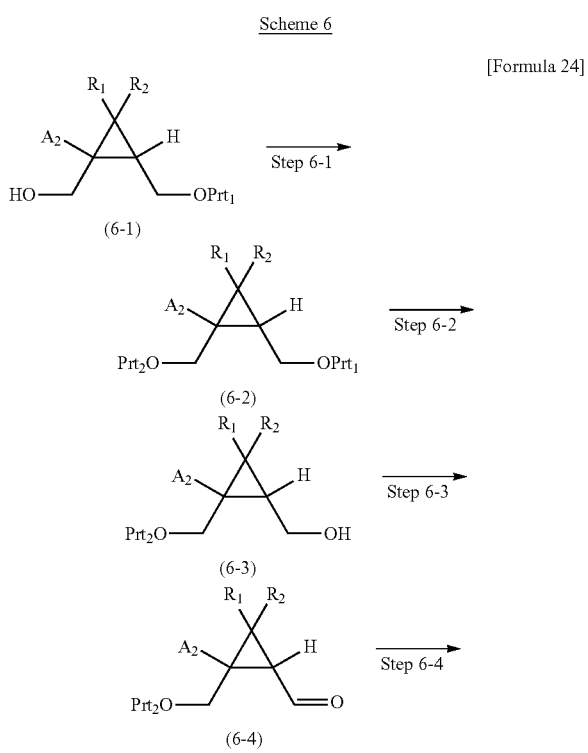

Scheme 6

[Formula 24]

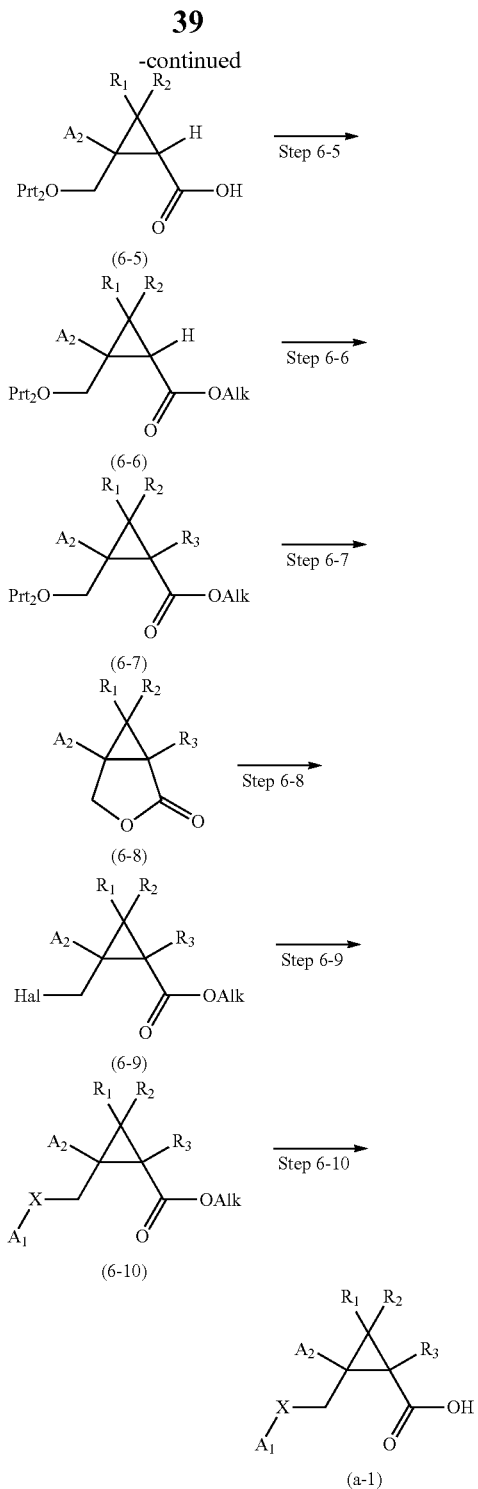

Step 6-1

The present step is a step of protecting of the hydroxyl group of the compound (6-1). Examples of a protecting group used herein include a methoxymethyl group, a trityl group and a benzyl group. Such a protecting group can be introduced under commonly used conditions described in the step 5-3.

Step 6-2

The present step is a step of selectively deprotecting the protecting group of the compound (6-2). The deprotection can be carried out under commonly used conditions.

Steps 6-3, 6-4

The present steps are steps of obtaining the carboxylic acid (6-5) from the compound (6-3) by the same methods as those of the step 2-1 and step 2-2 of the general production method 2.

Step 6-5

The present step is a step of esterifying the carboxylic acid (6-5) to obtain the compound (6-6). Esterification can be carried out under commonly used conditions.

Step 6-6

The present step is a step of introducing the substituent (R3) into the carbonyl α carbon of the ester (6-6). A preferred example of a base used herein is lithium diisopropylamide. As an alkylating agent, alkyl halide, aldehyde, ketone or the like is used. The solvent used in the reaction is not particularly limited, as long as it does not inhibit the reaction and dissolves a starting substance to a certain extent. Examples of such a solvent include tetrahydrofuran and diethyl ether. The reaction temperature is not particularly limited. It is generally from −78° C. to a solvent reflux temperature, and preferably from −78° C. to room temperature. The reaction time is not particularly limited. It is generally from 5 minutes to 48 hours, and preferably from 5 minutes to 24 hours.

Step 6-7

The present step is a step of selectively deprotecting the protecting group of the compound (6-7). In general, at the same time of deprotection, cyclization into lactone progresses in a molecule. The deprotection can be carried out under commonly used conditions.

Step 6-8

The present step is a step of reacting the compound (6-8) with thionyl halide in an alcoholic solvent, so as to obtain the haloester (6-9). The thionyl halide used in the reaction is preferably thionyl bromide. As a solvent, methanol or ethanol is preferable. The reaction temperature is not particularly limited. It is generally from −78° C. to a solvent reflux temperature, and preferably from −78° C. to room temperature. The reaction time is not particularly limited. It is generally from 5 minutes to 48 hours, and preferably from 5 minutes to 48 hours.

Step 6-9

The present step is a step of obtaining the compound (6-10) as a result of the nucleophilic substitution reaction between the compound (6-9) and the compound (3-3). The reaction conditions may be the same as those for the method for producing the compound (3-4) from the compound (3-2) in the general production method 3.

Step 6-10

The present step is a step of obtaining the compound (a-1) as a result of the ester hydrolysis of the compound (6-10). As reaction conditions, a sodium hydroxide aqueous solution or a potassium hydroxide aqueous solution may be used, for example. Also, an organic solvent such as methanol or ethanol is used, as necessary. The reaction temperature is not particularly limited. It is generally from −78° C. to a solvent reflux temperature, and preferably from room temperature to wherein Alk represents a $C_{1-6}$ alkyl group; Hal represents a halogen atom; $Prt_1$ represents a silyl group such as a t-butyldimethylsilyl group, a t-butyldiphenylsilyl group or a triisopropylsilyl group; $Prt_2$ represents a protecting group for a hydroxyl group, other than a silyl group; and X, $R_1$, $R_2$, $R_3$, $A_1$ and $A_2$ have the same meanings as those described above.

The general production method 6 is a method for producing the compound (a-1) that is a synthetic intermediate of the compound (I) according to the present invention, which uses the compound (6-1) as a raw material and involves 10 steps from [step 6-1] to [step 6-10].

a solvent reflux temperature. The reaction time is not particularly limited. It is generally from 5 minutes to 48 hours.

General Production Method 7:

The general production method 7 is a method for producing a compound (7-2) that is a synthetic intermediate of the compound (I) according to the present invention, which uses a compound (7-1) as a raw material and involves [step 7-1]. The compound (7-1) can also be produced from a commercially available product by a method known to a person skilled in the art. Further, it can also be produced by applying methods described in the production examples in the Examples.

[Formula 25]

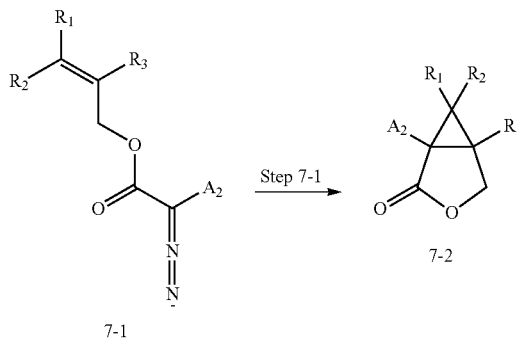

Step 7-1

The present step is a step of obtaining the compound (7-2), which involves intramolecular cyclization of the diazo compound (7-1). The reaction can be carried out under commonly used conditions for generating carbene from a diazo compound. The reaction can be carried out, for example, by the methods described in Doyle, M. P., Organic Letters, 2008, 2(8), 1145-1147; and Chen, C., Bioorganic & Medicinal Chemistry Letters, 2008, 18, 3328-3332.

General Synthetic Method 8:

[Formula 26]

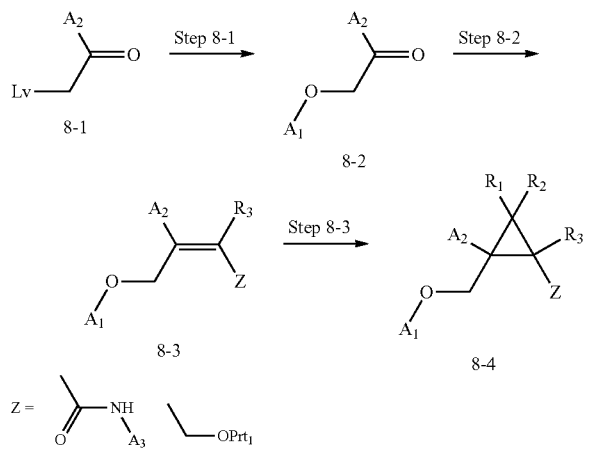

The general production method 8 is a method for producing the compound (8-4) from the compound (8-1) via [step 8-1], [step 8-2] and [step 8-3]. The compound (8-1) can be produced from a commercially available product by a method known to a person skilled in the art.

Step 8-1

The present step is a step of producing the compound (8-2) from the compound (8-1) by applying the method for producing the compound (3-4) from the compound (3-2) in the general production method 3.

Step 8-2

The present step is a step of obtaining the olefin (8-3) from the ketone (8-2) by the Wittig reaction or the Horner-Wadworth-Emmons reaction. The present reaction can be carried out under commonly used conditions.

Step 8-3

The present step is a step of obtaining the compound (8-4) by cyclopropanation of the olefin (8-3). Such cyclopropanation can be carried out, for example, by the Simmons-Smith reaction, or under conditions in which a diazo compound is combined with a metal catalyst such as rhodium acetate.

General Production Method 9:

[Formula 27]

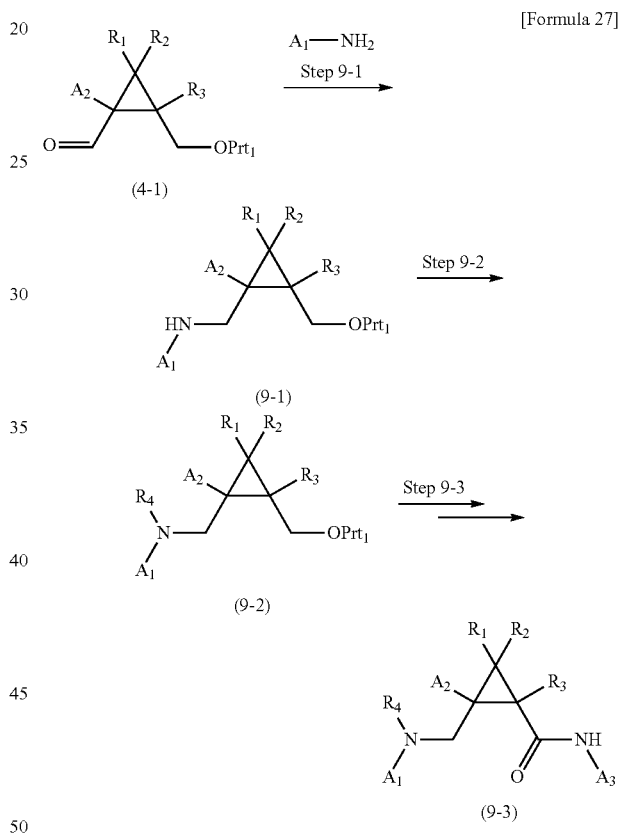

Step 9-1

The present step is a step of producing the compound (9-1) by reductive amination of the compound (4-1). As reaction conditions, ordinary conditions for reductive amination can be applied. Examples of a reducing agent include sodium borohydride and sodium triacetoxyborohydride.

The solvent used in the reaction is not particularly limited, as long as it does not inhibit the reaction and dissolves a starting substance to a certain extent. Examples of such a solvent include tetrahydrofuran and DMF. In some cases, an acid such as acetic acid may be mixed with such a solvent. The reaction temperature is not particularly limited. It is generally from −78° C. to a solvent reflux temperature, and preferably from 0° C. to room temperature. The reaction time is not particularly limited. It is generally from 5 minutes to 48 hours, and preferably from 5 minutes to 24 hours.

Step 9-2

The present step is a step of producing the compound (9-2) by reductive amination of the compound (9-1). The reaction conditions are the same as those applied in the step 9-1.

Step 9-3

The present step is a step of producing the compound (9-3) from the compound (9-2) according to the methods described in the step 3-2, step 2-1, step 2-2, and general production method 1.

General Production Method 10:

[Formula 28]

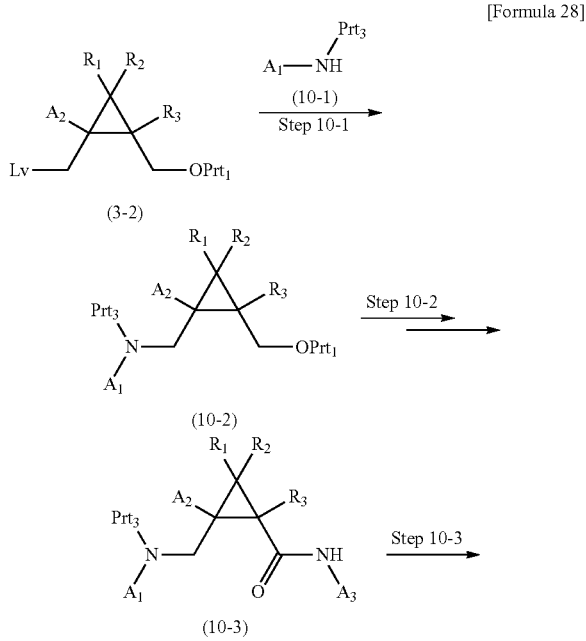

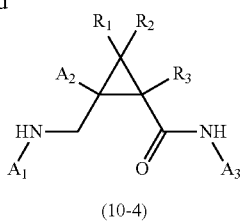

Step 10-1

The present step is a step of reacting the compound (3-2) with the amine (10-1) protected by amide or carbamate in the presence of a base, so as to produce the compound (10-2). Preferred examples of a base used herein include sodium hydride, cesium carbonate, and sodium hydroxide. The solvent used in the reaction is not particularly limited, as long as it does not inhibit the reaction and dissolves a starting substance to a certain extent. Examples of such a solvent include tetrahydrofuran, acetonitrile and DMF. The reaction temperature is not particularly limited. It is generally from 0° C. to a solvent reflux temperature. The reaction time is not particularly limited. It is generally from 5 minutes to 48 hours, and preferably from 5 minutes to 24 hours. In addition, preferred examples of the protecting group $Prt_3$ include: amide protecting groups such as a trifluoroacetyl group; and carbamate protecting groups such as t-butyl carbamate.

Step 10-2

The present step is a step of producing the compound (10-3) from the compound (10-2) according to the method described in the step 9-3.

Step 10-3

The present step is a step of producing the compound (10-4) by deprotection of the compound (10-3). The deprotection can be carried out under commonly used conditions.

General Production Method 11

[Formula 29]

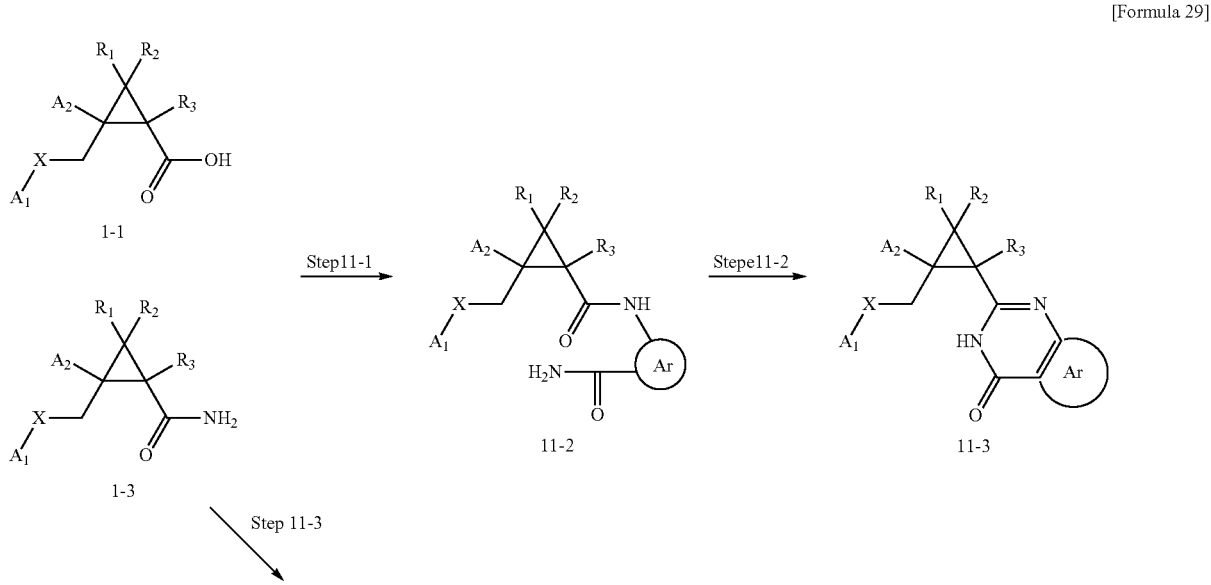

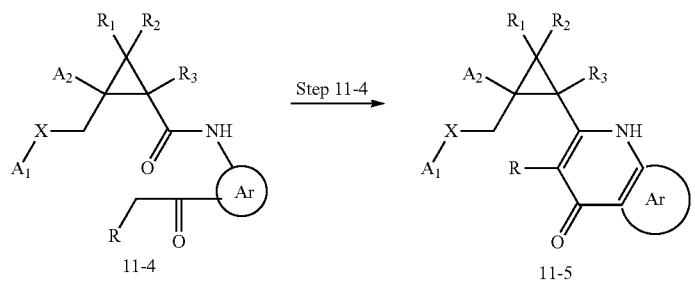

Step 11-1
The present step is a step of synthesizing the arylamide (11-2) from the compound (1-1) or the compound (1-3) under the conditions described in the general production method 1.

Step 11-2
The present step is a step of synthesizing the condensed pyrimidone derivative (11-3) from the compound (11-2) by an intramolecular cyclization reaction using a base. Preferred examples of a based used herein include potassium-tert-butoxide, sodium hydride, cesium carbonate, potassium carbonate, and sodium ethoxide. The solvent used in the reaction is not particularly limited, as long as it does not inhibit the reaction and dissolves a starting substance to a certain extent. Examples of such a solvent include tetrahydrofuran, 1,4-dioxane, DMF, MMP, acetonitrile, ethanol, and 2-propanol. The reaction temperature is not particularly limited. It is generally from 0° C. to a solvent reflux temperature, and preferably from room temperature to a solvent reflux temperature. The reaction time is not particularly limited. It is generally from 5 minutes to 48 hours, and preferably from 5 minutes to 24 hours.

Step 11-3
The present step is a step of synthesizing the arylamide (11-4) from the compound (1-1) or the compound (1-3) under the conditions described in the general production method 1.

Step 11-4
The present step is a step of synthesizing the condensed pyridone derivative (11-5) from the compound (11-4) by an intramolecular cyclization reaction using a base. Preferred examples of a based used herein include potassium-tert-butoxide, sodium hydride, cesium carbonate, potassium carbonate, and sodium ethoxide. The solvent used in the reaction is not particularly limited, as long as it does not inhibit the reaction and dissolves a starting substance to a certain extent. Examples of such a solvent include tetrahydrofuran, 1,4-dioxane, DMF, NMP, acetonitrile, ethanol, and 2-propanol. The reaction temperature is not particularly limited. It is generally from 0° C. to a solvent reflux temperature, and preferably from room temperature to a solvent reflux temperature. The reaction time is not particularly limited. It is generally from 5 minutes to 48 hours, and preferably from 5 minutes to 24 hours.

General Production Method 12:

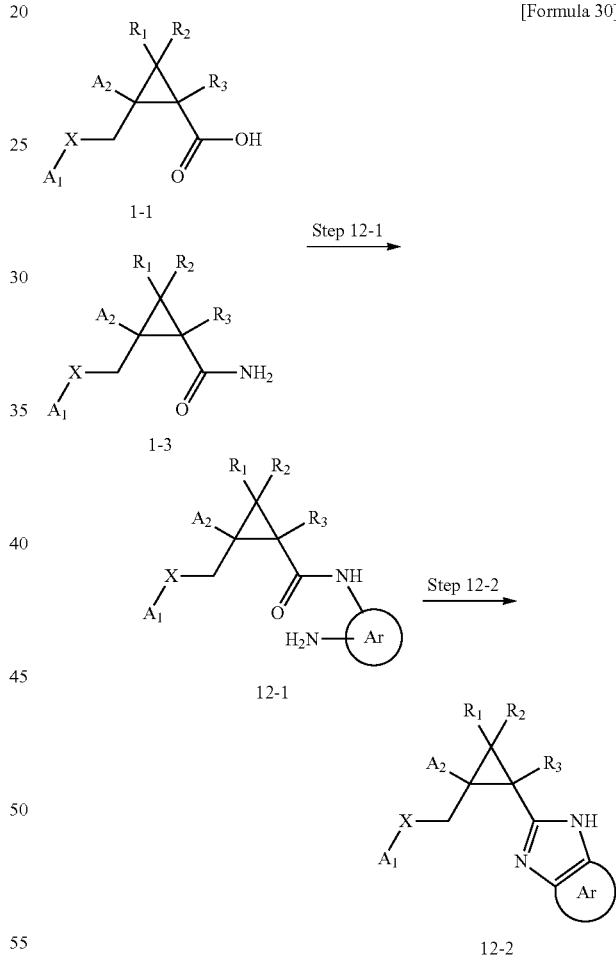

[Formula 30]

Step 12-1
The present step is a step of synthesizing the arylamide (12-1) from the compound (1-1) or the compound (1-3) under the conditions described in the general production method 1.

Step 12-2
The present step is a step of synthesizing the condensed imidazole derivative (12-2) from the compound (12-1) by an intramolecular cyclization reaction using an acid. Preferred examples of an acid used herein include acetic acid, trifluoroacetic acid, hydrochloric acid, and p-toluenesulfonic acid.

The solvent used in the reaction is not particularly limited, as long as it does not inhibit the reaction and dissolves a starting substance to a certain extent. For example, acetic acid is used as a solvent. Other examples of a solvent include tetrahydrofuran, 1,4-dioxane, DMF, NMP, acetonitrile, ethanol, and 2-propanol. The reaction temperature is not particularly limited. It is generally from 0° C. to a solvent reflux temperature, and preferably from room temperature to a solvent reflux temperature. The reaction time is not particularly limited. It is generally from 5 minutes to 48 hours, and preferably from 5 minutes to 24 hours.

General Production Method 13:

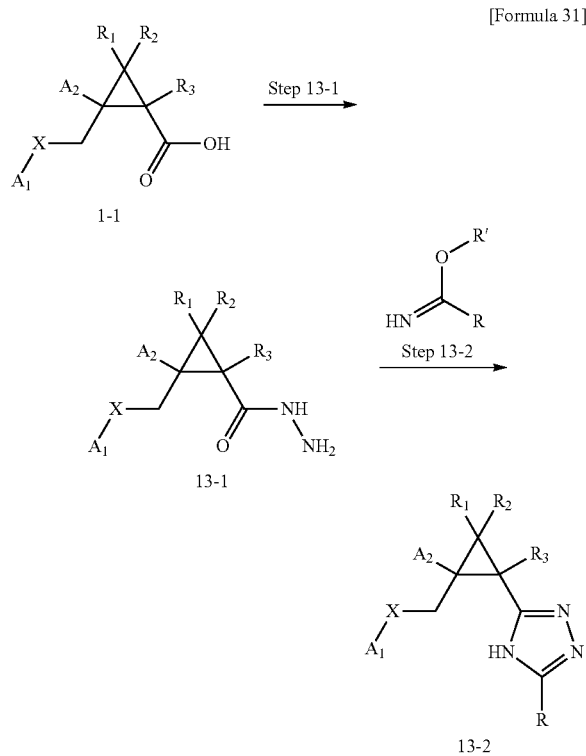

[Formula 31]

Step 13-1

The present step is a step of synthesizing the hydrazide (13-1) from the compound (1-1). As synthetic conditions used herein, a generally known method can be applied. For example, mono-protected hydrazine and the compound (1-1) are subjected to amide condensation, and then deprotection is then carried out, so as to synthesize the aforementioned compound. The amidation can be carried out by the method described in the step (1-1). The protecting group of hydrazine is not particularly limited. Examples of such a protecting group include tert-butoxycarbonyl, benzyloxycarbonyl, and trifluoroacetyl.

Step 13-2

The present step is a step of reacting the compound (13-1) with an imidate derivative to synthesize the triazole derivative (13-2). The reaction can be carried out under neutral conditions, or by adding an acid or a base. As an acid used herein, acetic acid, hydrochloric acid or the like is appropriate. As a base used herein, imidazole, triethylamine, potassium carbonate or the like is appropriate. The solvent used in the reaction is not particularly limited, as long as it does not inhibit the reaction and dissolves a starting substance to a certain extent. For example, acetic acid is used as a solvent.

Other examples of a solvent include tetrahydrofuran, 1,4-dioxane, D acetonitrile, ethanol, and 2-propanol. The reaction temperature is not particularly limited. It is generally from 0° C. to a solvent reflux temperature, and preferably from room temperature to a solvent reflux temperature. The reaction time is not particularly limited. It is generally from 5 minutes to 48 hours, and preferably from 5 minutes to 24 hours.

The thus obtained compound of the formula (I) of the present invention can be processed into a pharmaceutically acceptable salt according to an ordinary method, as necessary. Such a pharmaceutically acceptable salt can be produced by appropriately combining methods that are commonly used in the field of organic synthetic chemistry. Specifically, a free-type solution of the compound of the present invention is subjected to neutralization titration with an acid solution, for example. In addition, the compound of the formula (I) of the present invention is subjected to a well-known solvate formation reaction, as necessary, so that it can be converted to a solvate.

These methods are typical examples of the method for producing the compound (I). The raw material compounds or various reagents in the method for producing the compound (I) may form a salt or a hydrate, and all of them are different depending on a starting material, a solvent used, and the like and are not particularly limited, as long as they do not inhibit the reaction. The solvent used is also different depending on a starting material, a reagent, and the like and, needless to say, is not particularly limited, as long as it does not inhibit the reaction and is able to dissolve a starting substance to a certain extent. When the compound (I) is obtained as a free form, it can be converted, according to an ordinary method, to a state of the aforementioned salt that may be formed by the compound (I). Likewise, when the compound (I) is obtained as a salt of the compound (I), it can be converted to a free form of the compound (I) according to an ordinary method. Also, various isomers (for example, geometric isomers, optical isomers based on asymmetric carbon atoms, rotational isomers and steric isomers) obtained for the compound (I) can be purified and isolated by using ordinary separation means, for example, recrystallization, diastereomeric salt method, enzymatic resolution method and various chromatography techniques (for example, thin-layer chromatography, column chromatography and gas chromatography).

The term "composition" used herein includes a product comprising a particular ingredient in a particular amount and any product directly or indirectly brought about by the combination of particular ingredients in particular amounts. Such a term related to the pharmaceutical composition is intended to include a product comprising an active ingredient and an inert ingredient constituting a carrier and include every product directly or indirectly brought about by the combination, complexation or aggregation of any two or more ingredients or the dissociation, other kinds of reactions or interaction of one or more ingredients. Thus, the pharmaceutical composition of the present invention includes every composition prepared by mixing the compound of the present invention with a pharmaceutically acceptable carrier. The term "pharmaceutically acceptable" is used to mean that a carrier, a diluent or a vehicle must be compatible with other ingredients of a preparation and must be nontoxic to a taker.

As the ability of the compound of the present invention to bind to orexin receptors OX1R and/or OX2R, antagonism with respect to an orexin 1 receptor and/or an orexin 2 receptor mostly exhibits an IC50 value of 200 nM or lower, and a compound that exhibits an IC50 value of 100 nM or lower is preferable. A cyclopropane compound is thought to be more preferable, in which the ability to bind to an orexin 2 receptor (IC50 value) is 10 nM or lower in the sleep experiment by oral administration using mice, which is shown in Test Examples.

The cyclopropane compound according to the present invention or a pharmaceutically acceptable salt thereof, or a solvate thereof has orexin receptor antagonism. Thus, the cyclopropane compound according to the present invention or a pharmaceutically acceptable salt thereof, or a solvate thereof has applicability as a therapeutic agent for sleep disorder for which orexin receptor antagonism is effective. Examples of the sleep disorder for which orexin receptor antagonism is effective include insomnia The cyclopropane compound in this invention, a pharmaceutically acceptable salt thereof or a solvate thereof can be used to formulate a preparation according to an ordinary method. Examples of a preferred dosage form include oral preparations (tablets, granules, powders, capsules, syrups etc.), injections (for intravenous administration, for intramuscular administration, for subcutaneous sdministration, for intraperitoneal administration etc.), or topical products [transdermal absorptions (ointments, adhesive skin patch etc.), ophthalmic solutions, nasal preparations, suppositories etc.].

In the case of manufacturing oral solid preparations, for example, the cyclopropane compound in this invention, a pharmaceutically acceptable salt thereof or a solvate thereof is mixed with excipients, binders, disintegrators, lubricants, coloring agents etc., if necessary, and the obtained mixture is then processed into powders, fine granules, granules, tablets, coated tablets, capsules, etc. according to an ordinary method. In the case of production of tablets or granules, it may be coated with film, if necessary.

Examples of excipients used herein include lactose, corn starch and crystalline cellulose etc. Examples of binders used herein include hydroxypropyl cellulose, hydroxypropylmethyl cellulose etc. Examples of disintegrators used herein include calcium carboxymethyl cellulose, sodium croscarmellose etc. Examples of lubricants used herein include magnesium stearate, calcium stearate etc. Examples of coloring agents used herein include titanium oxide etc. Examples of coating agents used herein include hydroxypropyl cellulose, hydroxypropylmethyl cellulose, methyl cellulose etc. However, needless to say, examples of above agents are not limited thereto.

The aforementioned solid preparation such as tablets, capsules, granules or powders may comprise, as an active ingredient, the cyclopropane compound in this invention, a pharmaceutically acceptable salt thereof or a solvate thereof, in an amount of generally 0.001% to 99.5% by weight, and preferably 0.001% to 90% by weight.

In the case of manufacturing injections (for intravenous administration, for intramuscular administration, for subcutaneous sdministration, for intraperitoneal administration etc.), for example, pH adjusters, buffering agents, suspending agents, solubilizers, antioxidants, preventing agents (preservatives), tonicity agents, etc. are added to the cyclopropane compound in this invention, a pharmaceutically acceptable salt thereof or a solvate thereof, if necessary and the obtained mixture is then processed into such an injection according to an ordinary method. In addition, such an injection may be prepared as lyophilized preparation for dissolving when used.

Examples of pH adjusters and buffering agents used herein include organic acid or inorganic acid and/or a salt thereof. Examples of suspending agents used herein include methyl cellulose, polysolbate 80, sodium carboxymethyl cellulose, etc. Examples of solubilizers used herein include polysolbate 80, polyethylene solbitan monolaurate, etc. Examples of antioxidants used herein include α-tocopherol, etc. Examples of preventing agents used herein include methyl p-oxybenzoate, ethyl p-oxybenzoate, etc. Examples of tonicity agents used herein include glucose, sodium chloride, mannitol, etc. However, needless to say, examples of above agents are not limited thereto.

Such injection solutions may comprise an active ingredient in an amount of generally 0.000001% to 99.5% by weight, and preferably 0.000001% to 90% by weight.

In the case of manufacturing topical products, for example, the cyclopropane compound I this invention, a pharmaceutically acceptable salt thereof or a solvate thereof is mixed with base materials and the aforementioned adjuvants such as preventing agents, stabilizers, pH adjusters, antioxidants, coloring agents, etc. are added if necessary thereto and the obtained mixture is then processed into transdermal absorptions (ointments, adhesive skin patches, etc.), ophthalmic solutions, nasal preparations, supporsitoies, etc. according to an ordinary method.

As base materials used herein, various types of raw materials, which are generally used in pharmaceutical products, quasi drugs, cosmetic products, and other products, can be used. Examples of such raw materials include animal or vegetable oils, mineral oils, ester oils, waxes, emulsifiers, higher alcohols, fatty acids, silicon oils, surfactants, phospholipids, alcohols, polyhydric alcohols, water-soluble polymers, clay minerals, purified water etc.

Such external preparations may comprise an active ingredient in an amount of generally 0.000001% to 99.5% by weight, and preferably 0.000001% to 90% by weight.

The dose of the cyclopropane compound according to the present invention, a pharmaceutically acceptable salt thereof or a solvate thereof is different depending on the degree of symptoms, age, sex, body weight, administration route/the type of a salt, the specific type of disease, and the like. In general, in the case of oral administration, the cyclopropane compound according to the present invention, a pharmaceutically acceptable salt thereof or a solvate thereof is administered at a dose of approximately 30 μg to 10 g, preferably 100 μg to 5 g, and more preferably 100 μg to 1 g per adult per day. In the case of administration via injection, it is administered at a dose of approximately 30 μg to 1 g, preferably 100 μg to 500 mg, and more preferably 100 μg to 300 mg per adult per day. In both cases, it is administered once or divided over several administrations.

The compound of the present invention can be used as a chemical probe for capturing a target protein of a physiologically active low-molecular-weight compound. That is to say, the compound of the present invention can be converted to an affinity chromatography probe, a photoaffinity probe or the like, by introducing a labeling group, a linker or the like into a portion other than a structural portion essential for the expression of the activity of the compound according to the methods described in J. Mass Spectrum. Soc. Jpn. Vol. 51, No. 5, 2003, pp. 492-498; WO2007/139149; etc.

Examples of such a labeling group, a linker or the like used for such a chemical probe include groups described in the following groups (1) to (5).
(1) Protein labeling groups, such as photoaffinity labeling groups (for example, a benzoyl group, a benzophenone group, an azide group, a carbonyl azide group, a diaziridine group, an enone group, a diazo group, and a nitro group), and chemical affinity groups (for example, a ketone group in which the alpha carbon atom is replaced with a halogen atom, a carbamoyl group, an ester group, an alkylthio group, a Michael acceptor such as α,β-unsaturated ketone or ester, and an oxirane group), (2) Cleavable linkers such as —S—S—, —O—Si—O—, monosaccharide (a glucose group, a galactose group, etc.) or disaccharide (lactose, etc.), and oligopeptide linkers that can be cleaved by an enzyme reaction, (3) Fishing tag groups such as biotin and a 3-(4,4-difluoro-5,7-dimethyl-4H-3a,4a-diaza-4-bora-s-indacen-3-yl)propionyl group, (4) Radioactive labeling groups such as $^{125}$I, $^{32}$P, $^{3}$H and $^{14}$C; fluorescent labeling groups such as fluorescein, rhodamine, dansyl, umbelliferone, 7-nitrofurazanyl, and 3-(4,4-difluoro-5,7-dimethyl-4H-3a,4a-diaza-4-bora-s-indacen-3-yl)propionyl group; chemiluminescent groups such as lumiferin and luminol; and detectable markers including heavy metal ions such as a lanthanoid metal ion and a radium ion, or (5) Groups that are allowed to bind to solid-phase carriers, such as glass beads, a glass bed, a microtiter plate, agarose beads, an agarose bed, polystyrene beads, a polystyrene bed, nylon beads and a nylon bed.

A probe, which is prepared by introducing a labeling group or the like selected from the above described groups (1) to (5) into the compound of the present invention according to the methods described in the aforementioned publications and the like, can be used as a chemical probe for identifying a labeled protein useful for the search of a novel target of drug discovery.

Hereinafter, the present invention will be described more in detail in the following examples, production examples and test examples. However, these examples are not intended to limit the scope of the present invention. Moreover, abbreviations used in the examples are commonly used abbreviations that are well known to a person skilled in the art. Several abbreviations are as follows.

THF: tetrahydrofuran
DMF: N,N-dimethylformamide
TFA: trifluoroacetic acid
HATU: O-(7-azabenzotriazol-1-yl)-N,N,N,N-tetramethyluronium hexafluorophosphate
LC-MS: liquid chromatography-mass spectrometry
Pd$_2$DBA$_3$: tris(dibenzylideneacetone)dipalladium
LDA: lithium diisopropylamide
NaHMDS: sodium hexamethyldisilazide
TEMPO: (2,2,6,6-tetramethylpiperidin-1-yl)oxyl
DBU: 1,8-diazabicyclo[5.4.0]undec-7-ene
HOBt: 1-hydroxybenztriazole
WSC: 1-ethyl-3-(3-dimethylaminopropyl)carbodiimide hydrochloride
Xantphos: 4,5-bis(diphemylphosphino)-9,9-dimethylxanthene
NMP: 1-methyl-2-pyrrolidinoneChemical shifts in proton nuclear magnetic resonance spectrum are recorded by δ unit (ppm) with respect to tetramethylsilane. Coupling coefficients are recorded by hertz (Hz). With regard to pattern, s: singlet, d: doublet, t: triplet, q: quartette, and br: broad.

The term "room temperature" generally means approximately 10° C. to approximately 35° C. in the following examples and production examples. The symbol "%" means percent by weight, unless otherwise specified.

PRODUCTION EXAMPLE 1

Synthesis of 2-methoxy-4-methylpyrimidin-5-ol (Prep 1-5)

[Formula 32]

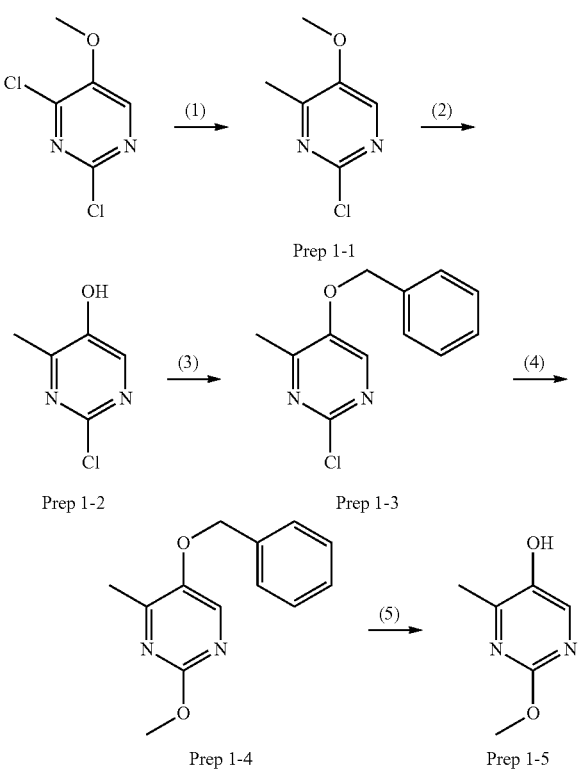

(1) 2-Chloro-5-methoxy-4-methylpyrimidine (Prep 1-1)

2,4-Dichloro-5-methoxypyrimidine (10 g) was dissolved in THF (100 ml), and while cooling, iron(III) acetylacetone (1.97 g), methyl magnesium chloride (3.0 M: 22.4 ml) were then added to the solution. The obtained mixture was stirred at room temperature overnight. Thereafter, iron(III) acetylacetone (1.97 g), and methyl magnesium chloride (3.0 M: 22.4 ml) were added to the reaction solution further twice. Thereafter, a 1 N hydrochloric acid aqueous solution was added to the reaction mixture, and diethyl ether was then added to the reaction solution to carry out liquid separation and extraction. The organic layer was dried over magnesium sulfate, and the solvent was then concentrated under reduced pressure. The obtained residue was purified by silica gel column chromatography (n-heptane:ethyl acetate), so as to obtain the title compound (6.6 g).

$^1$H-NMR (400 MHz, CDCl$_3$) δ (ppm): 2.46 (s, 3H), 3.92 (s, 3H), 8.06 (s, 1H).

(2) 2-Chloro-4-methylpyrimidin-5-ol (Prep 1-2)

A dichloromethane solution (50 ml) of the compound Prep 1-1 (6.6 g) was added dropwise to a dichloromethane solution (1.0 M: 100 ml) of boron tribromide, and the obtained mixture was then stirred at room temperature for 4 days. Thereafter, methanol was added to the reaction mixture, and a 5 N sodium hydroxide aqueous solution was then added to the reaction solution for neutralization. Liquid separation and extraction were carried out successively using chloroform and ethyl acetate at a pH value of approximately pH 2 to 3. The organic layer was dried over magnesium sulfate, and the solvent was then concentrated under reduced pressure. Diethyl ether was added to the obtained residue to solidify it, and the solidified product was collected by filtration and was then dried, so as to obtain the title compound.

$^1$H-NMR (400 MHz, DMSO-$d_6$) δ (ppm): 2.32 (s, 3H), 8.09 (s, 1H), 10.61 (s, 1H).

(3) 5-Benzyloxy-2-chloro-4-methylpyrimidine (Prep 1-3)

Sodium hydride (60% oil dispersion; 66.2 mg) was added to a THF solution (4.0 ml) of the compound Prep 1-2 (200 mg), and the obtained mixture was then stirred at room temperature for 10 minutes. Thereafter, benzyl bromide (197 ul) was added to the reaction solution. The obtained mixture was stirred at room temperature for 2 hours. Thereafter, DMF (2.0 ml) was added to the reaction solution, and the obtained mixture was then stirred for 4 hours. Thereafter, a saturated ammonium chloride aqueous solution was added to the reaction mixture, and liquid separation and extraction were carried out with diethyl ether. The obtained organic layer was dried over magnesium sulfate, and the solvent was then concentrated under reduced pressure. The obtained residue was purified by silica gel column chromatography (n-heptane:ethyl acetate), so as to obtain the title compound (317 mg).

$^1$H-NMR (400 MHz, CDCl$_3$) δ (ppm): 2.51 (s, 3H), 5.15 (s, 2H), 7.37-7.40 (m, 5I), 8.10 (s, 1H).

(4) 5-Benzyloxy-2-methoxy-4-methylpyrimidine (Prep 1-4)

Sodium methoxide (143 mg) was added to a DMF solution (4.0 ml) of Prep 1-3 (310 mg), and the obtained mixture was then stirred at 70° C. for 2 hours. Thereafter, the reaction mixture was cooled, a 1 N hydrochloric acid aqueous solution was then added thereto, and liquid separation and extraction were then carried out with diethyl ether. The obtained organic layer was dried over magnesium sulfate, and the solvent was then concentrated under reduced pressure. The obtained residue was purified by silica gel column chromatography (n-heptane:ethyl acetate), so as to obtain the title compound (220 mg).

$^1$H-NMR (400 MHz, CDCl$_3$) δ (ppm): 2.44 (s, 3H), 3.93 (s, 1H), 5.07 (s, 2H), 7.35-7.41 (m, 5H), 7.99 (s, 1H).

(5) 2-Methoxy-4-methylpyrimidin-5-ol (Prep 1-5)

Palladium hydroxide was added to a methanol solution (8.0 ml) of the compound Prep 1-4 (220 mg), and the obtained mixture was then stirred in a hydrogen atmosphere for 2.5 hours. Thereafter, the reaction mixture was filtered with Celite, and the obtained filtrate was then concentrated under reduced pressure, so as to obtain the title crude compound (130 mg).

$^1$H-NMR (400 MHz, DMSO-$d_6$) δ (ppm): 2.26 (s, 3H), 3.77 (s, 1H), 7.95 (s, 1H).

PRODUCTION EXAMPLE 2

Synthesis of 2-ethyl-4-methylpyrimidin-5-ol (Prep 2-2)

[Formula 33]

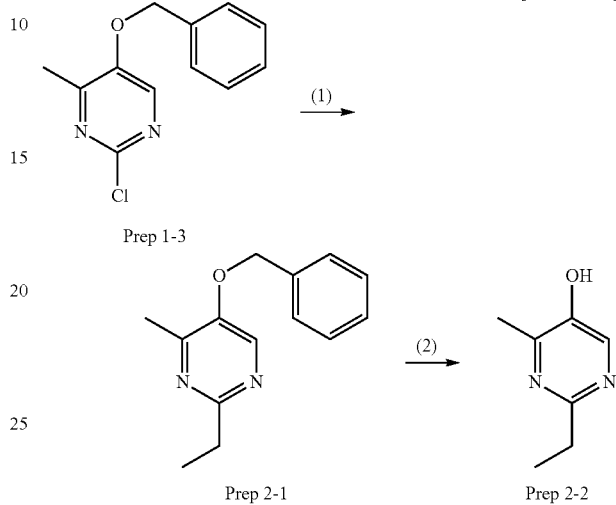

(1) 5-Benzyloxy-2-ethyl-4-methylpyrimidine (Prep 2-1)

Potassium carbonate (1.4 g), 1,1-bis(diphenylphosphino)ferrocenedichloro palladium(II), (dichloromethane complex) (276 mg) were added to a THF solution (10 ml) of the compound Prep 1-3 (793 mg), and diethylzinc (1 M: 3.72 ml) was then added thereto. The obtained mixture was stirred at 65° C. overnight. Thereafter, water was added to the reaction mixture, and liquid separation and extraction were then carried out with ethyl acetate. The obtained organic layer was dried over magnesium sulfate, and the solvent was then concentrated under reduced pressure. The obtained residue was purified by silica gel column chromatography (n-heptane:ethyl acetate), so as to obtain the title compound (400 mg).

$^1$H-NMR (400 MHz, CDCl$_3$) δ (ppm): 1.32 (t, J=8.0 Hz, 1H), 2.49 (s, 3H), 2.86 (d, J=8.0 Hz, 1H), 2.90 (d, J=7.6 Hz, 1H), 5.13 (s, 2H), 7.33-7.43 (m, 5H), 8.16 (s, 1H).

(2) 2-Ethyl-4-methylpyrimidin-5-ol (Prep 2-2)

Palladium hydroxide was added to a methanol solution (8.0 ml) of the compound Prep 2-1 (220 mg), and the obtained mixture was then stirred in a hydrogen atmosphere for 2.5 hours. Thereafter, the reaction mixture was filtered with Celite, and the obtained filtrate was then concentrated under reduced pressure, so as to obtain the title crude compound (130 mg).

$^1$H-NMR (400 MHz, CDCl$_3$) δ (ppm): 1.30 (t, J=8.0 Hz, 1H), 2.48 (s, 3H), 2.83 (d, J=8.0 Hz, 1H), 2.88 (d, J=8.0 Hz, 1H), 8.04 (s, 1H).

PRODUCTION EXAMPLE 3

Synthesis of 4-ethyl-2-methylpyrimidin-5-ol (Prep 3-3)

[Formula 34]

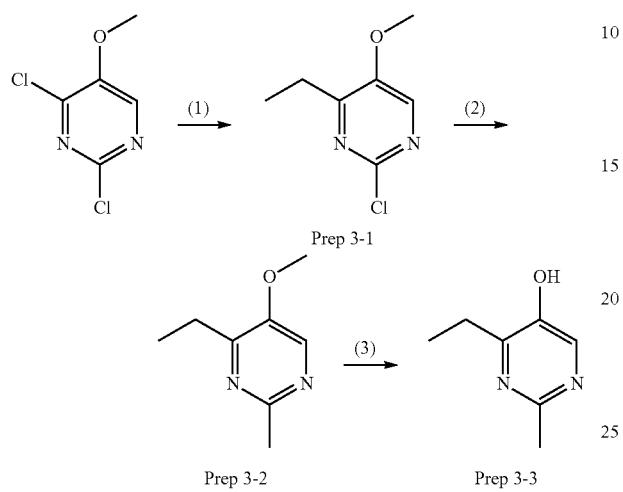

(1) 2-Chloro-4-ethyl-5-methoxypyrimidine (Prep 3-1)

2,4-Dichloro-5-methoxypyrimidine (5 g) was dissolved in THF (50 ml), and while cooling, iron(III) acetylacetone (985 mg) and ethyl magnesium chloride (0.91 M: 36.9 ml) were then added to the solution. The obtained mixture was stirred at room temperature overnight. Thereafter, iron(III) acetylacetone (985 mg) and methyl magnesium chloride (0.91 M: 36.9 ml) were added to the reaction solution further twice. A 1 N hydrochloric acid aqueous solution was added to the reaction mixture, and liquid separation and extraction were then carried out with diethyl ether. The organic layer was dried over magnesium sulfate, and the solvent was then concentrated under reduced pressure. The obtained residue was purified by silica gel column chromatography (n-heptane: ethyl acetate), so as to obtain the title compound (1 g).

$^1$H-NMR (400 MHz, CDCl$_3$) δ (ppm): 1.25 (t, J=8.0 Hz, 1H), 2.78 (d, J=7.6 Hz, 1H), 2.82 (d, J=8.0 Hz, 1H), 3.92 (s, 3H), 8.06 (s, 1H).

(2) 4-Ethyl-5-methoxy-2-methylpyrimidine (Prep 3-2)

Trimethyl aluminum (2.0 M: 6.95 ml) and tetrakistriphenylphosphine palladium(0) (335 mg) were added to a THF solution (15.0 ml) of the compound Prep 3-1 (1.0 g), and the obtained mixture was then stirred at 70° C. for 2 days. Thereafter, the reaction solution was added dropwise to ice water, and it was then converted to the neutral to mild acidic range by addition of 1 N hydrochloric acid. Subsequently, liquid separation and extraction were carried out with ethyl acetate. The organic layer was dried over magnesium sulfate, and the solvent was then concentrated under reduced pressure. The obtained residue was purified by silica gel column chromatography (n-heptane:ethyl acetate), so as to obtain the title compound (736 mg).

$^1$H-NMR (400 MHz, CDCl$_3$) δ (ppm): 1.24 (t, J=7.6 Hz, 1H), 2.64 (s, 3H), 2.76 (d, J=7.6 Hz, 1H), 2.80 (d, J=7.6 Hz, 1H), 3.89 (s, 1H), 8.10 (s, 1H).

(3) 4-Ethyl-2-methylpyrimidin-5-ol (Prep 3-3)

Boron tribromide (1.0 M, 118 ml) was added dropwise to a dichloromethane solution (69.6 ml) of the compound Prep 3-2 (5.12 g). The obtained mixture was stirred at room temperature for 4 days. Thereafter, ammonia/methanol was added to the reaction solution, followed by quenching. The reaction solution that had been converted to the neutral to mild acidic range was filtered, and the filtrate was then concentrated under reduced pressure. The obtained residue was purified by silica gel column chromatography (ethyl acetate to ethyl acetate:methanol), so as to obtain the title compound (4.0 g).

$^1$H-NMR (400 MHz, CDCl$_3$) δ (ppm): 1.13 (t, J=8.0 Hz, 1H), 2.43 (s, 3H), 2.61 (d, J=8.0 Hz, 1H), 2.65 (d, J=7.6 Hz, 1H), 8.04 (s, 1H), 9.85 (s, 1H).

PRODUCTION EXAMPLE 4

Synthesis of 2,4-dimethylpyrimidin-5-ol (Prep 4-2)

[Formula 35]

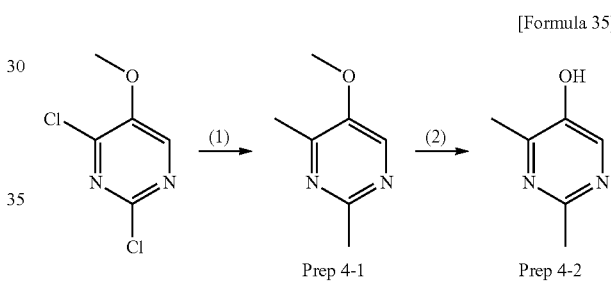

(1) 5-Methoxy-2,4-dimethylpyrimidine (Prep 4-1)

2,4-Dichloro-5-methoxypyrimidine (5.3 g) was dissolved in THF (51.3 ml), and tetrakis(triphenylphosphine)palladium (1.71 g) and trimethylaluminum (2.0 M: 51.8 ml) were then added to the solution. The temperature of the obtained mixture was heated to 75° C., and the obtained mixture was then stirred overnight. Thereafter, 1 equivalent of trimethyl aluminum was added to the reaction solution, and the obtained mixture was then stirred for 6 hours. Thereafter, saturated ammonium chloride aqueous solution was added dropwise to the reaction solution under cooling on ice, and liquid separation and extraction were carried out with chloroform. The organic layer was dried over magnesium sulfate, and the solvent was then concentrated under reduced pressure. The obtained residue was purified by silica gel column chromatography (n-heptane:ethyl acetate to ethyl acetate), so as to obtain the title compound (4.2 g).

$^1$H-NMR (400 MHz, CDCl$_3$) δ (ppm): 2.42 (s, 3H), 2.63 (s, 3H), 3.88 (s, 3H), 8.08 (s, 1H).

(2) 2,4-Dimethylpyrimidin-5-ol (Prep 4-2)

A dichloromethane solution (100.0 ml) of the compound Prep 4-1 (15.5 g) was added dropwise to a boron tribromide (1.0 M in dichloromethane, 400.0 ml). The obtained mixture was stirred at room temperature for 4 days, and the reaction solution was then quenched with methanol. The reaction solution that had been converted to the neutral to mild acidic range was filtered, and the filtrate was then concentrated under reduced pressure. The obtained residue was purified by silica gel column chromatography (ethyl acetate to ethanol), so as to obtain the title compound (10.1 g).

$^1$H-NMR (400 MHz, DMSO-$d_6$) δ (ppm): 2.26 (s, 3H), 2.41 (s, 3H), 8.02 (s, 1H).

PRODUCTION EXAMPLE 5

Synthesis of 6-fluoro-5-methoxymethylpyridin-3-amine (Prep 5-3)

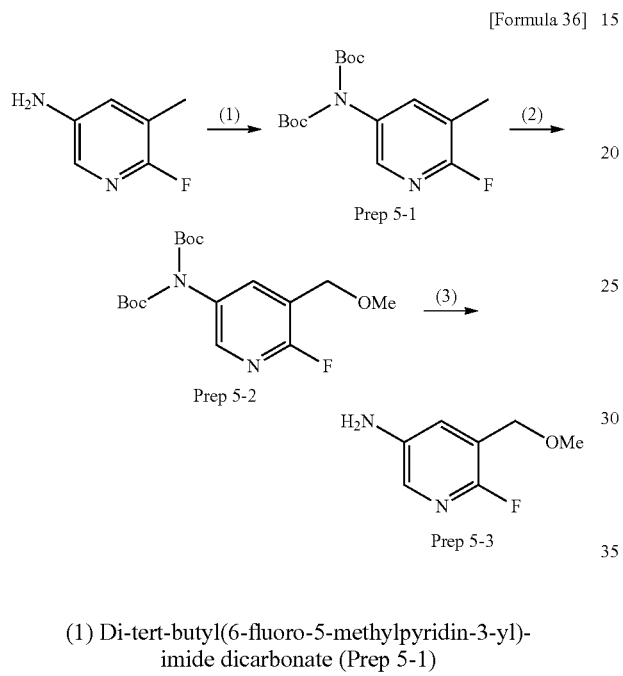

[Formula 36]

(1) Di-tert-butyl(6-fluoro-5-methylpyridin-3-yl)-imide dicarbonate (Prep 5-1)

Di-tert-butyl carbonate (2.59 g) and a catalytic amount of 4-dimethylaminopyridine (0.01 g) were added to a THF solution (10 ml) of 5-amino-2-fluoro-3-picoline (0.5 g), and the obtained mixture was then stirred at room temperature for 67 hours. Thereafter, water was added to the reaction solution, and the mixture was then extracted with ethyl acetate. The resultant extract was washed with water, and was then dried over anhydrous sodium sulfate. The solvent was distilled off under reduced pressure, and the residue was then purified by silica gel column chromatography (chloroform), so as to obtain the title compound (1.14 g).

(2) Di-tert-butyl[6-fluoro-5-methoxymethylpyridin-3-yl]-imide dicarbonate (Prep 5-2)

The compound Prep 5-1 (500 mg) and N-bromosuccinimide (272 mg) were dissolved in tetrachloromethane (5 ml), and 2,2'-azobis(isobutyl nitrate) (25.1 mg) was then added to the solution. The obtained mixture was stirred at 80° C. for 5 hours. Thereafter, water was added to the reaction solution, and the mixture was then extracted with ethyl acetate. The resultant extract was washed with water, and was then dried over anhydrous sodium sulfate. The solvent was distilled off under reduced pressure, and the residue was then dissolved in methanol (5 ml). Then, sodium methoxide (413 mg) was added to the solution, and the obtained mixture was then stirred at room temperature for 1 hour. Thereafter, water was added to the reaction solution, and the mixture was then extracted with ethyl acetate. Thereafter, the resultant extract was washed with water, and was then dried over anhydrous sodium sulfate. The solvent was distilled off under reduced pressure, and the residue was then purified by silica gel column chromatography (n-heptane:ethyl acetate=20:1 to 2:1), so as to obtain the title compound.

(3) 6-Fluoro-5-methoxymethylpyridin-3-amine (Prep 5-3)

Trifluoroacetic acid (1 ml) was added to a dichloromethane solution (5 ml) of the compound Prep 5-2, and the obtained mixture was then stirred at room temperature for 1 hour. Thereafter, a saturated sodium bicarbonate aqueous solution was added to the reaction solution, and the mixture was then extracted with dichloromethane. The resultant extract was washed with water, and was then dried over anhydrous sodium sulfate. The solvent was distilled off under reduced pressure, so as to obtain the target compound (60 mg).

$^1$H-NMR (400 MHz, CDCl$_3$) δ (ppm): 3.43 (s, 3H), 4.43 (s, 3H), 7.20 (ddt, J=8.0, 2.4, 0.8 Hz, 1H), 7.53 (t, J=2.4, Hz, 1H).

PRODUCTION EXAMPLE 6

Synthesis of 4-methoxymethylpyridin-2-amine (Prep 6-3)

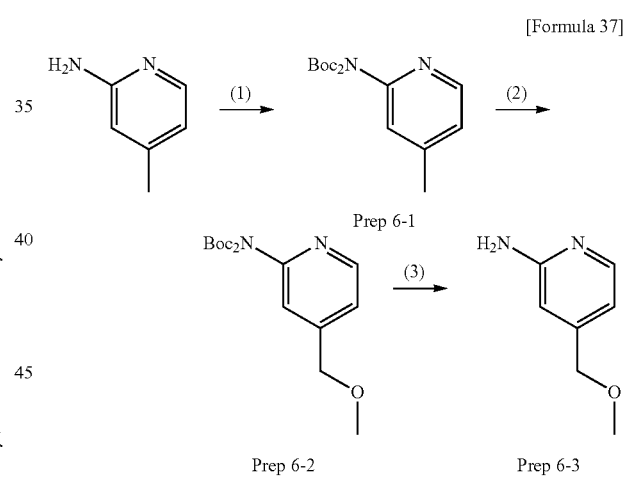

[Formula 37]

(1) Di-tert-butyl(4-methylpyridin-2-yl)imide dicarbonate (Prep 6-1)

Di-tert-butyl carbonate (4.04 g), 4-dimethylaminopyridine (226 mg), and triethylamine (5.17 ml) were added to a dichloromethane solution (50 ml) of 2-amino-4-methylpyridine (1.0 g), and the obtained mixture was then stirred at room temperature for 72 hours. Thereafter, water was added to the reaction solution, and the mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate), so as to obtain the title compound (1.7 g).

¹H-NMR (400 MHz, CDCl₃) δ (ppm): 1.45 (s, 18H), 2.37 (s, 3H), 7.03 (dd, J=5.2, 0.8 Hz, 1H), 7.05 (d, J=0.8H, 1H), 8.34 (d, J=5.2 Hz, 1H).
MS [M+H]⁺=309

(2) Tert-butyl(4-methoxymethylpyridin-2-yl) carbamate (Prep 6-2)

Benzoyl peroxide (23.6 mg) was added to a tetrachloromethane solution (10 ml) of the compound Prep 6-1 (300 mg) and N-bromosuccinimide (173 mg), and the obtained mixture was then heated to reflux for 1 hour. Thereafter, 2,2'-azobis(isobutyl nitrate) (16.0 mg) was added to the reaction solution, and the obtained mixture was further heated to reflux for 5 hours. Thereafter, the reaction solution was cooled to room temperature, and it was then filtered with Celite. The filtrate was concentrated under reduced pressure, and the residue was then purified by silica gel column chromatography (n-heptane:ethyl acetate), so as to obtain the corresponding benzyl bromide.

Sodium methoxide (25% methanol solution: 1 ml) was added to a methanol solution (3 ml) of the obtained bromide, and the obtained mixture was then stirred at room temperature for 19 hours. Thereafter, the reaction solvent was distilled off under reduced pressure, and the residue was then purified by silica gel column chromatography (n-heptane:ethyl acetate=4:1 to 3:2), so as to obtain the title compound (62 mg).
¹H-NMR (400 MHz, CDCl₃) δ (ppm): 1.53 (s, 9H), 3.42 (s, 3H), 4.46 (s, 2H), 6.96-6.97 (m, 1H), 7.91 (brs, 1H), 8.24-8.25 (m, 1H).
MS [M+H]⁺=239

(3) 4-Methoxymethylpyridin-2-amine (Prep 6-3)

Trifluoroacetic acid (1 ml) was added to a dichloromethane solution (3 ml) of the compound Prep 6-2 (62 mg), and the obtained mixture was then stirred at room temperature for 3 hours. Thereafter, a 5 N sodium hydroxide aqueous solution was added to the reaction solution, and the mixture was then extracted with ethyl acetate. The organic layer was washed with a saturated sodium chloride aqueous solution, and was then dried over anhydrous magnesium sulfate, followed by filtration. The filtrate was concentrated under reduced pressure, so as to obtain the target compound (35 mg).
¹H-NMR (400 MHz, CDCl₃) δ (ppm): 3.41 (s, 3H), 4.37 (s, 2H), 4.66 (brs, 2H), 6.51 (s, 1H), 6.59 (d, J=5.6 Hz, 1H), 7.99 (d, J=5.6 Hz, 1H).

PRODUCTION EXAMPLE 7

Synthesis of 4-(difluoromethyl)pyridin-2-amine (Prep 7-4)

[Formula 38]

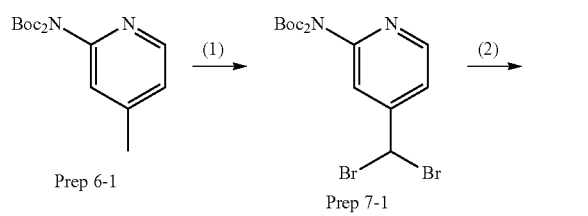

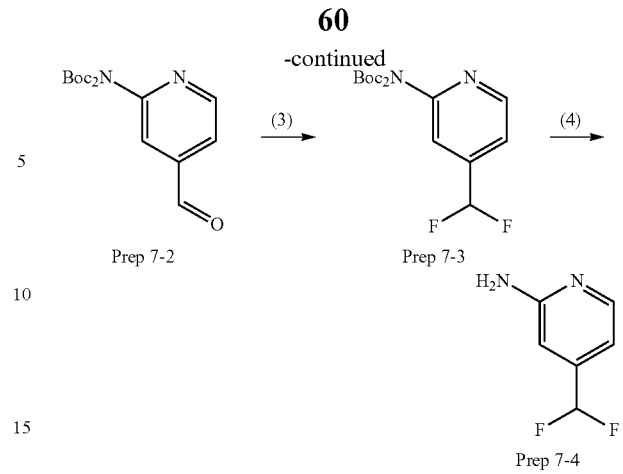

(1) Di-tert-butyl[4-(dibromomethyl)pyridin-2-yl] imide dicarbonate (Prep 7-1)

2,2'-Azobis(isobutyl nitrate) (74.7 mg) was added to a tetrachloromethane solution (47 ml) of the compound Prep 6-1 (1.4 g) and N-bromosuccinimide (807 mg), and the obtained mixture was then heated to reflux for 4 hours. Thereafter, the reaction solution was cooled to room temperature, and it was then filtered with Celite. The filtrate was concentrated under reduced pressure, and the residue was purified by silica gel column chromatography (n-heptane:ethyl acetate), so as to obtain the title compound (210 mg).
¹H-NMR (400 MHz, CDCl₃) δ (ppm): 1.46 (s, 18H), 6.54 (s, 1H), 7.36 (dd, J=5.2, 1.6 Hz, 1H), 7.45 (d, J=1.6 Hz, 1H), 8.48 (d, J=5.2 Hz, 1H).
MS [M+H]⁺=467

(2) Di-tert-butyl(4-formylpyridin-2-yl)imide dicarbonate (Prep 7-2)

Dimethyl sulfoxide (500 ul) and silver nitrate (692 mg) were added to a toluene solution (5 ml) of the compound Prep 7-1 (210 mg), and the obtained mixture was then stirred at 60° C. for 2 hours. The temperature of the reaction solution was heated to 80° C., and the reaction solution was further stirred for 19 hours. Thereafter, the reaction solution was cooled to room temperature, and was then filtered with silica gel. The filtrate was concentrated under reduced pressure, so as to obtain the title compound (100 mg).
¹H-NMR (400 MHz, CDCl₃) δ (ppm): 1.47 (s, 18H), 7.61 (dd, J=5.2, 1.2 Hz, 1H), 7.74 (d, J=1.2H, 1H), 8.70 (d, J=5.2 Hz, 1H), 10.08 (s, 1H).

(3) Di-tert-butyl(4-difluoromethylpyridin-2-yl)imide dicarbonate (Prep 7-3)

Diethylaminosulfate trifluoride (122 ul) was added to a dichloromethane solution (3 ml) of the compound Prep 7-2 (100 mg) at 0° C. The temperature of the reaction solution was warmed to room temperature, and the reaction solution was then stirred for 3.5 hours. Thereafter, a saturated sodium bicarbonate aqueous solution was added to the reaction solution, and the obtained mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate), so as to obtain the title compound (78 mg).

$^1$H-NMR (400 MHz, CDCl$_3$) δ (ppm): 1.46 (s, 18H), 6.65 (t, J=55.6 Hz, 1H), 7.32 (d, J=5.2 Hz, 1H), 7.43 (s, 1H), 8.58 (d, J=5.2 Hz, 1H).

MS [2M+Na]$^+$=711

(4) 4-Difluoromethylpyridin-2-amine (Prep 7-4)

Trifluoroacetic acid (0.5 ml) was added to a dichloromethane solution (2 ml) of the compound Prep 7-3 (78 mg), and the obtained mixture was then stirred at room temperature for 3 hours. Thereafter, a 5 N sodium hydroxide aqueous solution was added to the reaction solution, and the obtained mixture was then extracted with chloroform. The organic layer was washed with a saturated sodium chloride aqueous solution, and was then dried over anhydrous magnesium sulfate, followed by filtration. The filtrate was concentrated under reduced pressure, so as to obtain the target compound (30 mg).

$^1$H-NMR (400 MHz, CDCl$_3$) δ (ppm): 4.61 (brs, 2H), 6.51 (t, J=56.0 Hz, 1H), 6.60 (brs, 1H), 6.74-6.76 (m, 1H), 8.17 (d, J=5.2 Hz, 1H).

PRODUCTION EXAMPLE 8

Synthesis of 5-fluoro-4-methoxymethylpyridin-2-amine (Prep 8-3)

[Formula 39]

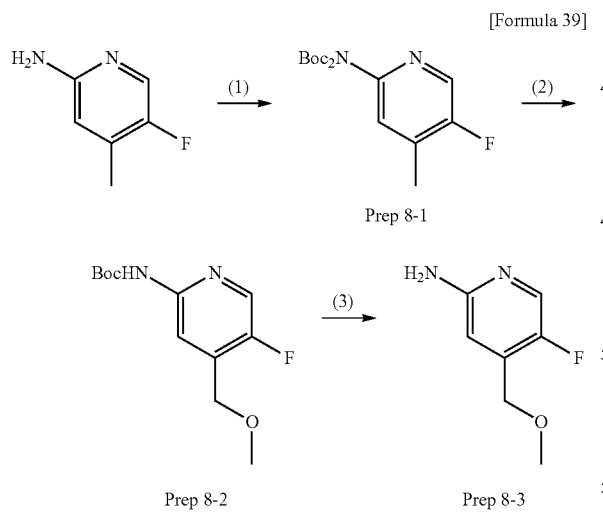

(1) Di-tert-butyl(5-fluoro-4-methylpyridin-2-yl) imide dicarbonate (Prep 8-1)

Di-tert-butyl carbonate (1.73 g), 4-dimethylaminopyridine (242 mg), and triethylamine (1.66 ml) were added to a dichloromethane solution (50 ml) of 2-amino-5-fluoro-4-methylpyridine (500 mg), and the obtained mixture was then stirred at room temperature for 6 days. Thereafter, water was added to the reaction solution, and the obtained mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was purified by silica gel column chromatography (n-heptane:ethyl acetate), so as to obtain the title compound (737 mg).

$^1$H-NMR (400 MHz, CDCl$_3$) δ (ppm): 1.45 (s, 18H), 2.32-2.33 (m, 3H), 7.08 (brd, J=5.6 Hz, 1H), 8.23 (d, J=1.2 Hz, 1H).

MS [2M+Na]$^+$=675

(2) Tert-butyl(5-fluoro-4-methoxymethylpyridin-2-yl) carbamate (Prep 8-2)

2,2'-azobis(isobutyl nitrate) (158 mg) was added to a tetrachloromethane solution (20 ml) of the compound Prep 8-1 (630 mg) and N-bromosuccinimide (377 mg), and the obtained mixture was then heated to reflux for 11 hours. Thereafter, the reaction solution was cooled to room temperature, and it was then filtered with Celite. The filtrate was concentrated under reduced pressure, and the residue was then purified by silica gel column chromatography (n-heptane:ethyl acetate), so as to obtain the corresponding bromide.

Sodium methoxide (104 mg) was added to a methanol solution (10 ml) of the obtained bromide, and the obtained mixture was then stirred at room temperature for 3 hours. Thereafter, water was added to the reaction solution, and the obtained mixture was then extracted with ethyl acetate. The organic layer was dried over anhydrous magnesium sulfate and was then filtered. The filtrate was concentrated under reduced pressure, and the residue was then purified by silica gel column chromatography (n-heptane:ethyl acetate), so as to obtain the title compound (180 mg).

$^1$H-NMR (400 MHz, CDCl$_3$) δ (ppm): 1.53 (s, 9H), 3.46 (s, 3H), 4.52 (brs, 2H), 7.21 (brs, 1H), 8.02-8.03 (m, 2H).

MS [M-tBu+H]$^+$=201

(3) 5-Fluoro-4-methoxymethylpyridin-2-amine (Prep 8-3)

Trifluoroacetic acid (2 ml) was added to a dichloromethane solution (6 ml) of the compound Prep 8-2 (180 mg), and the obtained mixture was then stirred at room temperature for 17 hours. Thereafter, a 5 N sodium hydroxide aqueous solution was added to the reaction solution, and the obtained mixture was then extracted with chloroform. The organic layer was dried over anhydrous magnesium sulfate and was then filtered. The filtrate was concentrated under reduced pressure, so as to obtain the target compound (90 mg).

$^1$H-NMR (400 MHz, CDCl$_3$) δ (ppm): 3.45 (s, 3H), 4.32 (brs, 2H), 4.47 (s, 2H), 6.58 (d, J=4.8 Hz, 1H), 7.86 (d, J=1.6 Hz, 1H).

MS [M+H]$^+$=157

PRODUCTION EXAMPLE 9

Synthesis of 5-fluoro-4-methoxypyridin-2-amine (Prep 9-3)

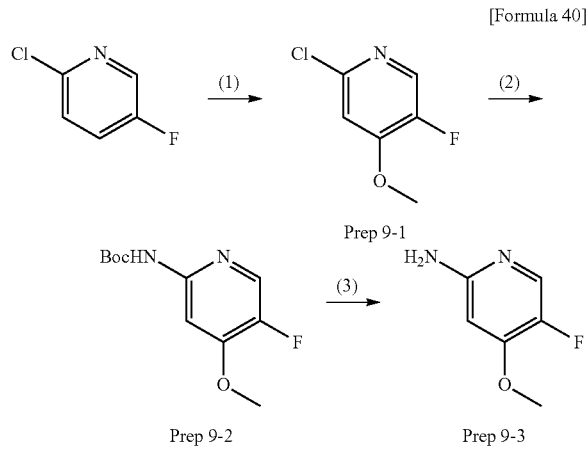

[Formula 40]

Prep 9-1

Prep 9-2

Prep 9-3

(1) 2-Chloro-5-fluoro-4-methoxypyridine (Prep 9-1)

A THF solution (20 ml) of n-butyllithium (2.64 M n-hexane solution: 10.4 ml) was cooled to −78° C., and a THF solution (20 ml) of 2-chloro-5-fluoropyridine (3.0 g) and N,N-diisopropylamine (4.49 ml) was then added dropwise to the solution. The obtained mixture was stirred at the same temperature as described above for 2 hours. Thereafter, a THF solution (10 ml) of trimethyl borate (4.74 g) was added to the reaction solution, and the temperature was then warmed to room temperature, followed by stirring for 1.5 hours. Thereafter, the reaction solution was cooled to 0° C., and acetic acid (3.92 ml) was added thereto, followed by stirring for 20 minutes. Thereafter, hydrogen peroxide (30% aqueous solution; 7.05 ml) was added to the reaction solution, and the temperature was warmed to room temperature again, followed by stirring for 15 hours. Thereafter, the reaction solution was cooled to 0° C., and a saturated sodium thiosulfate aqueous solution was then added thereto, followed by stirring for 2 hours. Thereafter, 5 N hydrochloric acid was added to the reaction solution, and the obtained mixture was then extracted with ethyl acetate and with chloroform. The combined organic layer was dried over magnesium sulfate and was then filtered. The solvent was concentrated under reduced pressure, so as to obtain the corresponding alcohol.

Iodomethane (4.18 ml) was added to a chloroform solution (100 ml) of the obtained alcohol and silver carbonate (16.4 g). The temperature of the obtained mixture was then heated to 40° C., and the mixture was then stirred for 4 hours. Thereafter, the reaction solution was cooled to room temperature, and was then filtered with Celite-silica gel. The filtrate was concentrated under reduced pressure, and the residue was then purified by silica gel column chromatography (n-heptane:ethyl acetate), so as to obtain the title compound (1.9 g).

$^1$H-NMR (400 MHz, CDCl$_3$) δ (ppm): 3.95 (s, 3H), 6.91 (d, J=6.0 Hz, 1H), 8.11 (d, J=2.4 Hz, 1H).

MS [M+H]$^+$=162

(2) Tert-butyl(5-fluoro-4-methoxypyridin-2-yl) carbamate (Prep 9-2)

The temperature of a 1,4-dioxane solution (50 ml) of the compound Prep 9-1 (1.0 g), tert-butyl carbamate (870 mg), xantphos (1.07 g), potassium triphosphate (1.97 g) and Pd$_2$DBA$_3$ (567 mg) was heated to 100° C. Thereafter, the solution was then stirred for 3.5 hours. Subsequently, the reaction solution was cooled to room temperature, and was then filtered with Celite. The filtrate was concentrated under reduced pressure, and the residue was then purified by silica gel column chromatography (n-heptane:ethyl acetate), so as to obtain the title compound (470 mg).

$^1$H-NMR (400 MHz, CDCl$_3$) δ (ppm): 1.53 (s, 9H), 3.97 (s, 3H), 7.51 (brs, 1H), 7.69 (d, J=6.4 Hz, 1H), 7.96 (d, J=3.2 Hz, 1H).

MS [M+H]$^+$=243

(3) 5-Fluoro-4-methoxypyridin-2-amine (Prep 9-3)

Trifluoroacetic acid (1 ml) was added to a dichloromethane solution (2 ml) of the compound Prep 9-2 (200 mg), and the obtained mixture was then stirred at room temperature for 1.5 hours. Thereafter, a 5 N sodium hydroxide aqueous solution was added to the reaction solution, and the obtained mixture was then extracted with ethyl acetate. The organic layer was dried over anhydrous magnesium sulfate and was then filtered. The filtrate was concentrated under reduced pressure, so as to obtain the target compound (110 mg).

$^1$H-NMR (400 MHz, CDCl$_3$) δ (ppm): 3.87 (s, 3H), 4.27 (brs, 2H), 6.06 (d, J=5.6 Hz, 1H), 7.80 (d, J=3.2 Hz, 1H).

PRODUCTION EXAMPLE 10

Synthesis of 3-bromo-5-(difluoromethoxy)pyridine (Prep 10)

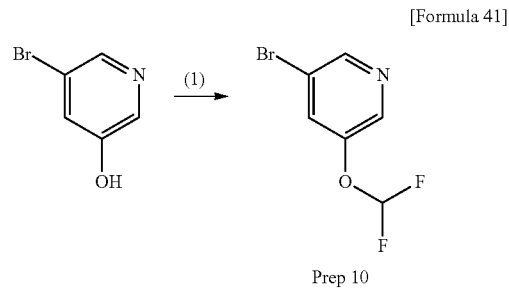

[Formula 41]

Prep 10

(1) 3-Bromo-5-(difluoromethoxy)pyridine (Prep 10)

Potassium carbonate (7.13 g) and chlorodifluoroacetic acid (1.75 ml) were added to a DMF solution (40 ml) of 3-bromo-5-hydroxypyridine (3.0 g). The temperature of the obtained mixture was heated to 100° C., and the mixture was then stirred for 24 hours. Thereafter, water was added to the reaction solution, and the obtained mixture was then extracted with diethyl ether. The organic layer was successively washed with a saturated sodium bicarbonate aqueous solution and a saturated sodium chloride aqueous solution, and was then dried over magnesium sulfate, followed by filtration. The solvent was concentrated under reduced pressure, and the residue was then purified by silica gel column chromatography (n-hexane:diethyl ether), so as to obtain the title compound (670 mg).

$^1$H-NMR, (400 MHz, CDCl$_3$) δ (ppm): 6.56 (t, J=72.0 Hz, 1H), 7.67-7.68 (m, 1H), 8.43 (d, J=2.4 Hz, 1H), 8.56 (d, J=2.0 Hz, 1H).

MS [M+H]$^+$=224

PRODUCTION EXAMPLE 11

Synthesis of 4-methoxymethyl-2-methylpyrimidin-5-ol (Prep 11-3)

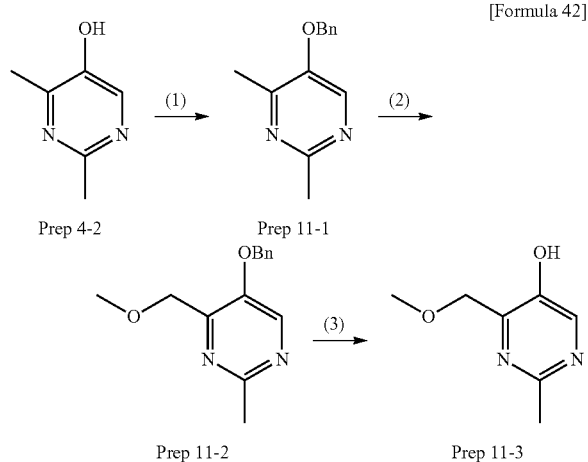

[Formula 42]

(1) 5-Benzyloxy-2,4-dimethylpyrimidine (Prep 11-1)

A THF solution (80 ml) of Prep 4-2 (5.0 g) was cooled to 0° C., and potassium tert-butoxide (5.43 g) was then added to the solution. The obtained mixture was stirred at 0° C. for 30 minutes. Thereafter, benzyl bromide (5.73 ml) was added to the reaction solution at the same temperature as described above, and the temperature of the mixture was then warmed to room temperature, followed by stirring for 20 hours. Thereafter, water was added to the reaction solution, and the obtained mixture was then extracted with ethyl acetate. The organic layer was dried over anhydrous magnesium sulfate and was then filtered. The filtrate was concentrated under reduced pressure, and the residue was then purified by silica gel column chromatography (n-heptane:ethyl acetate, to ethyl acetate), so as to obtain the title compound (6.0 g).

$^1$H-NMR (400 MHz, CDCl$_3$) δ (ppm): 2.48 (s, 3H), 2.62 (s, 3H), 5.13 (s, 2H), 7.33-7.42 (m, 5H), 8.13 (s, 1H).

MS [M+H]$^+$=215

(2) 5-Benzyloxy-4-methoxymethyl-2-methylpyrimidine (Prep 11-2)

A chloroform solution (200 ml) of the compound Prep 11-1 (13 g) was cooled to 0° C., and thereafter, bromine (3.11 ml) was slowly added dropwise thereto. The temperature of the reaction solution was warmed to room temperature, and the solution was then stirred for 18 hours. Thereafter, a saturated sodium bicarbonate aqueous solution was added to the reaction solution, and the obtained mixture was then extracted with chloroform. The organic layer was dried over anhydrous magnesium sulfate and was then filtered. The filtrate was concentrated under reduced pressure, the residue was then purified by silica gel column chromatography (n-heptane: ethyl acetate to ethyl acetate), so as to obtain the corresponding bromide.

Sodium methoxide (2.56 g) was added to a methanol solution (180 ml) of the obtained bromide, and the obtained mixture was then heated to reflux for 21 hours. Thereafter, the reaction solution was concentrated under reduced pressure, and ethyl acetate and water were then added to the concentrate. The obtained mixture was extracted with ethyl acetate. The organic layer was dried over anhydrous magnesium sulfate and was then filtered. The filtrate was concentrated under reduced pressure, and the residue was then purified by silica gel column chromatography (n-heptane:ethyl acetate), so as to obtain the title compound (9.0 g).

$^1$H-NMR (400 MHz, CDCl$_3$) δ (ppm): 2.70 (s, 3H), 3.52 (s, 3H), 4.63 (s, 2H), 5.16 (s, 2H), 7.34-7.41 (m, 5H), 8.24 (s, 1H).

MS [M+H]$^+$=245

(3) 4-Methoxymethyl-2-methylpyrimidin-5-ol (Prep 11-3)

10% palladium-carbon (900 mg) was added to an ethyl acetate solution (300 ml) of the compound Prep 11-2 (8.8 g), and the obtained mixture was then stirred in a hydrogen atmosphere at room temperature for 2 hours. Thereafter, the reaction solution was filtered with Celite, and the filtrate was then concentrated under reduced pressure, so as to obtain the title compound (5.3 g).

$^1$H-NMR (400 MHz, CDCl$_3$) δ (ppm): 2.61 (s, 3H), 3.56 (s, 3H), 4.79 (s, 2H), 7.90 (brs, 1H), 8.25 (s, 1H).

PRODUCTION EXAMPLE 12

Synthesis of 4-(2-methoxyethyl)-2-methylpyrimidin-5-ol (Prep 12-2)

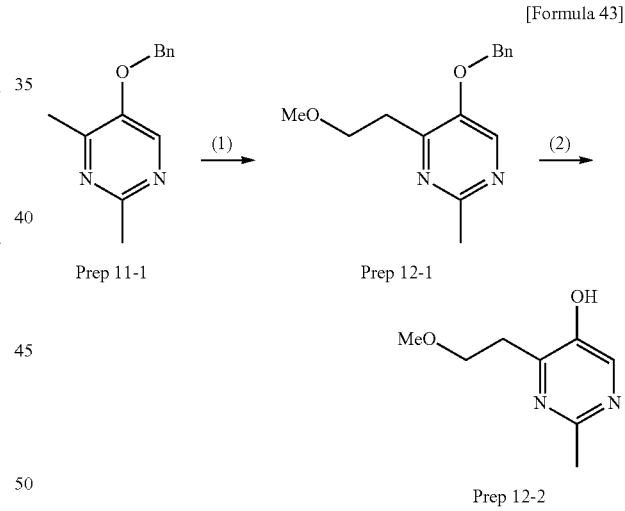

[Formula 43]

(1) 5-Benzyloxy-4-(2-methoxyethyl)-2-methylpyrimidine (Prep 12-1)

The compound Prep 11-1 (1.66 g) was dissolved in THF (130 ml), and the obtained solution was then cooled to 0° C. A THF solution (8.5 ml) of 1 N LDA was added dropwise to the solution, and the obtained mixture was then stirred for 30 minutes. Thereafter, chloromethyl methyl ether (0.88 ml) was added to the reaction solution. The obtained mixture was further stirred at room temperature for 12 hours. Thereafter, water was added to the reaction solution, and the obtained mixture was then extracted with ethyl acetate. The resultant extract was washed with water, and was then dried over anhydrous sodium sulfate. The solvent was distilled off under reduced pressure, and the residue was then purified by silica gel column chromatography (n-heptane:ethyl acetate), so as to obtain the title compound (0.65 g).

$^1$H-NMR (400 MHz, CDCl$_3$) δ (ppm): 2.63 (s, 3H), 3.11 (t, J=7.2 Hz, 2H), 3.35 (s, 3H), 3.79 (t, J=7.2 Hz, 2H), 5.13 (s, 2H), 7.33-7.42 (m, 5H), 8.16 (s, 1H).

(2) 4-(2-Methoxyethyl)-2-methylpyrimidin-5-ol (Prep 12-2)

The compound Prep 12-1 (0.65 g) was dissolved in ethyl acetate (9 ml), and the obtained solution was then cooled to 0° C. Thereafter, 5% palladium carbon (0.31 g) was added to the solution, followed by hydrogen substitution. Then, the resultant product was stirred at room temperature for 2 hours. Thereafter, the reaction solution was filtered, and the solvent was then distilled off under reduced pressure. The residue was purified by silica gel column chromatography (n-heptane: ethyl acetate to ethyl acetate:methanol), so as to obtain the title compound (0.36 g).

$^1$H-NMR (400 MHz, CDCl$_3$) δ (ppm): 2.61 (s, 3H), 3.09 (t, J=5.6 Hz, 2H), 3.64 (s, 3H), 3.80 (t, J=5.6 Hz, 2H), 8.24 (s, 1H), 8.39 (brs, 1H).

PRODUCTION EXAMPLE 13

Synthesis (1R,2S)-2{[(2,4-dimethylpyrimidin-5-yl)oxy]methyl}-2-phenylcyclopropanecarboxylic acid (Prep 13-7)

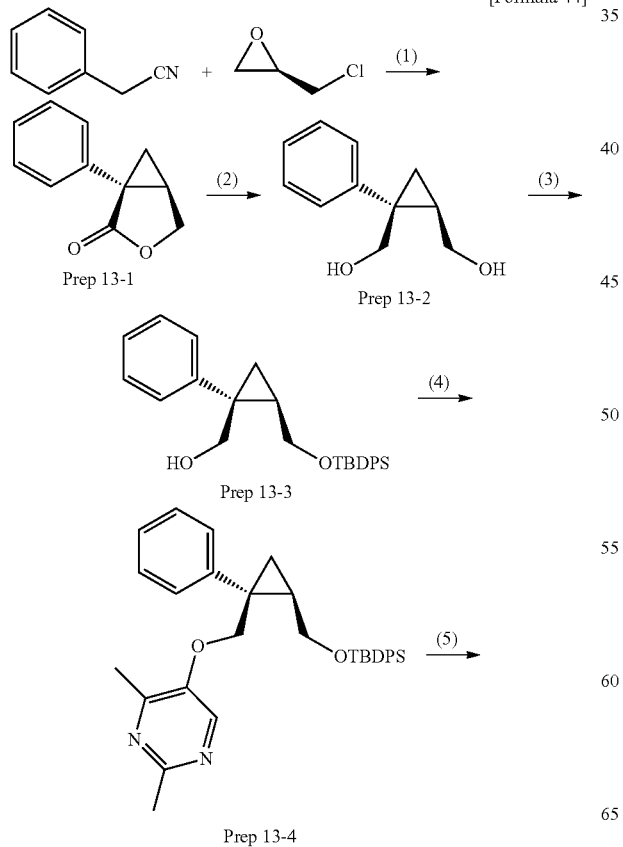

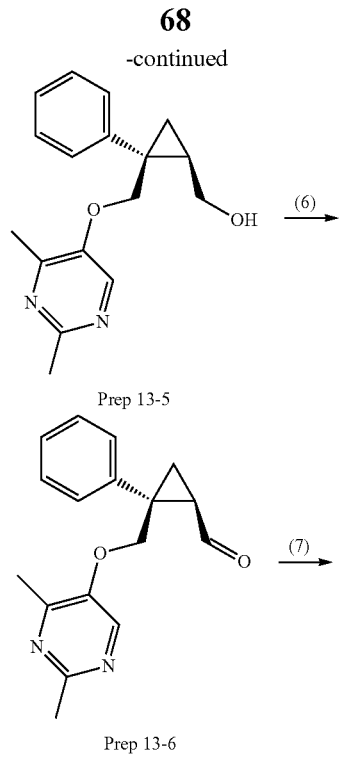

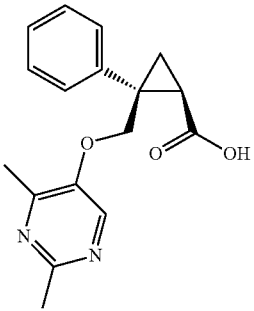

(1) (1S,5R)-1-phenyl-3-oxabicyclo[3.1.0]hexan-2-one (Prep 13-1)

Phenylacetonitrile (20 g) was dissolved in THF (500 ml), and NaHMDS (323 ml, 1.06 M) was then added dropwise to the solution under cooling in an ice-salt bath. The obtained mixture was stirred for 2 hours, and R-(−)-epichlorohydrin (15.8 g) was then added dropwise to the reaction solution (3 hours, 0° C.). The obtained mixture was stirred for 2 hours (wherein the internal temperature was maintained around 0° C.), and it was then stirred at room temperature overnight. Thereafter, the reaction solution was cooled on ice, and a small amount of water was added dropwise thereto. The reaction solution was concentrated under reduced pressure, and thereafter, ethanol (200 ml) and a 1 N potassium hydroxide aqueous solution (200 ml) were added to the residue. The obtained mixture was heated to reflux for 8 hours. Thereafter, the temperature of the reaction solution was returned to room temperature, and concentrated hydrochloric acid was then added to the solution, so that the pH value was adjusted to pH<2. Thereafter, the mixture was stirred at 0° C. for 2 hours. Thereafter, the reaction solution was stirred at room temperature for 1 hour. Subsequently, the reaction solution was concentrated under reduced pressure, and ethyl acetate and water were added to the concentrate to carry out liquid separation. The organic layer was successively washed with a saturated sodium bicarbonate aqueous solution and a saturated sodium chloride aqueous solution. The resultant organic layer was dried over magnesium sulfate, and the solvent was then concentrated under reduced pressure. The residue was purified by silica gel column chromatography (n-heptane:ethyl acetate), so as to obtain the title compound (24.7 g).

¹H-NMR (400 MHz, CDCl₃) δ (ppm): 1.37 (t, J=4.8 Hz, 1H), 1.65 (dd, J=7.8, 4.4 Hz, 1H), 2.54-2.58 (m, 1H), 4.30 (d, J=9.2 Hz, 1H), 4.47 (dd, J=9.4, 4.4 Hz, 1H), 7.25-7.45 (m, 5H).

(2) (1S,2R)-1-phenylcyclopropan-1,2-dimethanol (Prep 13-2)

Sodium borohydride (10.7 g) was added to a THF-methanol solution (200 ml-100 ml) of the compound Prep 13-1 (24.7 g) at 0° C., and the obtained mixture was then stirred at room temperature for 1 hour. Under cooling on ice, water was added to the reaction solution, and the obtained mixture was concentrated under reduced pressure and was then extracted with ethyl acetate. The organic layer was washed with a saturated sodium chloride aqueous solution and was then dried over magnesium sulfate. The solvent was concentrated under reduced pressure, and the residue was then purified by silica gel column chromatography (n-heptane:ethyl acetate), so as to obtain the title compound (20.5 g).

¹H-NMR (400 MHz, CDCl₃) δ (ppm): ¹H-NMR (400 MHz, CDCl₃) δ (ppm): 0.78 (t, J=5.2 Hz, 1H), 1.87 (dd, J=8.6, 5.2, 1H), 1.60-1.76 (m, 1H), 3.42 (t, J=11.6, 1H), 3.57 (dd, J=9.4, 4.4 Hz, 2H) 7.22-7.44 (m, 5H).

(3) (1S,2R)-2-(tert-butyldiphenylsilyloxymethyl)-1-phenylcyclopropylmethanol (Prep 13-3)

The compound Prep 13-2 (10 g) and imidazole (4.01 g) were dissolved in DMF (90 ml), and the obtained mixture was cooled to -15° C. Thereafter, a DMF solution (20 ml) of tert-butyldiphenylsilyl chloride was added dropwise to the reaction solution (for approximately 30 minutes; insoluble matters were precipitated almost at the same time after completion of dropping). After the mixture had been stirred for 1 hour, methanol was added to the reaction solution, and the obtained mixture was then stirred at room temperature for 30 minutes. Thereafter, water was added to the organic layer, and the obtained mixture was then extracted with ethyl acetate. The resultant extract was successively washed with a saturated ammonium chloride aqueous solution, water and a saturated sodium chloride aqueous solution, and was then dried over anhydrous magnesium sulfate. The solvent was distilled off under reduced pressure, and the residue was then purified by silica gel column chromatography (n-heptane:ethyl acetate), so as to obtain the title compound (10.5 g).

¹H-NMR (400 MHz, CDCl₃) δ (ppm): ¹H-NMR (400 MHz, CDCl₃) δ (ppm): 0.71 (t, J=5.6 Hz, 1H), 1.04 (dd, J=9.6, 5.2 Hz, 1H), 1.50-1.58 (m, 1H), 3.50 (dd, J=12.4, 1.6 Hz, 1H), 3.53 (dd, J=11.6, 1.6 Hz, 1H), 3.71 (dd, J=12.4, 1.6 Hz, 1H), 4.10 (t, J=12.0 Hz, 1H), 4.20 (dd, J=12.0, 5.6 Hz, 1H), 7.21-7.46 (m, 10H). 7.7-7.76 (m, 5H)

(4) 5-[(1S,2R)-2-(tert-butyldiphenylsilyloxymethyl)-1-phenylcyclopropylmethoxy]-2,4-dimethylpyrimidine (Prep 13-4)

Diisopropyl azodicarboxylate (1.13 ml) was added dropwise to a THF solution (15 ml) of the compound Prep 13-3 (1.50 g), triphenylphosphine (1.42 g) and the 2,4-dimethylpyrimidin-5-ol (0.58 g) obtained in Production Example 4 at 0° C., and the obtained mixture was then stirred at room temperature for 1 day. Thereafter, the reaction solution was concentrated under reduced pressure, and the residue was then purified by silica gel column chromatography (n-heptane:ethyl acetate), so as to obtain the title compound (1.76 g).

MS [M+Na]⁺-545.

(5) [(1R,2S)-2-{[(2,4-dimethylpyrimidin-5-yl)oxy]methyl}-2-phenylcyclopropyl]methanol (Prep 13-5)

Tetrabutylammonium fluoride (1 M THF solution: 4.24 ml) was added dropwise to a THF solution (21 ml) of the compound Prep 13-4 (1.76 g) at room temperature, and the obtained mixture was then stirred at room temperature for 17 hours. Thereafter, the reaction solution was concentrated under reduced pressure, and the residue was then purified by NH-silica gel column chromatography (n-heptane:ethyl acetate to ethyl acetate), so as to obtain the title compound (0.98 g).

MS [M+H]⁺-285.

(6) [(1R,2S)-2-{[(2,4-dimethylpyrimidin-5-yl)oxy]methyl}-2-phenyl]cyclopropanecarbaldehyde (Prep 13-6)

A dichloromethane solution (10 ml) of oxalyl chloride (593 ul) was cooled to -78° C., and a dichloromethane solution (2 ml) of dimethyl sulfoxide (981 ul) was added dropwise to the resultant solution. Fifteen minutes later, a dichloromethane solution (3 ml) of the compound Prep 13-5 (981 mg) was added dropwise to the reaction solution at -78° C., and the obtained mixture was then stirred at the same temperature as described above for 75 minutes. Thereafter, triethylamine (3.83 ml) was added to the reaction solution, and the temperature of the obtained mixture was raised to 0° C. Water and a saturated ammonium chloride aqueous solution were added to the reaction solution, and the obtained mixture was then extracted with dichloromethane. The organic layer was dried over anhydrous magnesium sulfate and was then filtered. The filtrate was concentrated under reduced pressure, and the residue was then purified by silica gel column chromatography (n-heptane:ethyl acetate to ethyl acetate), so as to obtain the title compound (753.4 mg).

¹H-NMR™ (400 MHz, CDCl₃) δ (ppm): 1.69 (dd, J=8.0, 4.8 Hz, 1H), 1.97 (dd, J=6.0, 5.2 Hz, 1H), 2.35 (s, 3H), 2.50-2.53 (m, 1H), 2.59 (s, 3H), 4.19 (d, J=10.0 Hz, 1H), 4.45 (d, J=9.6 Hz, 1H), 7.25-7.52 (m, 5H), 7.94 (s, 1H), 9.86 (d, J=3.6 Hz, 1H).

(7) (1R,2S)-2-{[(2,4-dimethylpyrimidin-5-yl)oxy]methyl}-2-phenylcyclopropanecarboxylic acid (Prep 13-7)

2-Methyl-2-butene (2.25 ml), anhydrous sodium dihydrogen phosphate (318 mg) and sodium chlorite (482 mg) were added to an acetone-water solution (12 ml) of the compound 13-6 at room temperature, and the obtained mixture was then stirred for 100 minutes. The reaction solution was concentrated under reduced pressure, and the residue was then purified by silica gel column chromatography (n-heptane:ethyl acetate=1:1 to chloroform:methanol=10:1), so as to obtain the title compound (639 mg).

¹H-NMR (400 MHz, CDCl₃) δ (ppm): 1.57 (dd, J=8.0, 4.8 Hz, 1H), 1.75 (t, J=4.8 Hz, 1H), 2.27 (dd, J=8.0, 5.6 Hz, 1H), 2.33 (s, 3H), 2.56 (s, 3H), 4.45 (d, J=9.6 Hz, 1H), 4.50 (d, J=9.2 Hz, 1H), 7.26-7.52 (m, 5H), 8.16 (s, 1H).

PRODUCTION EXAMPLE 14

Synthesis of (1R,2S)-2-{[(2,4-dimethylpyrimidin-5-yl)oxy]methyl}-2-(3-fluorophenyl)cyclopropanecarboxylic acid (Prep 14-6)

[Formula 45]

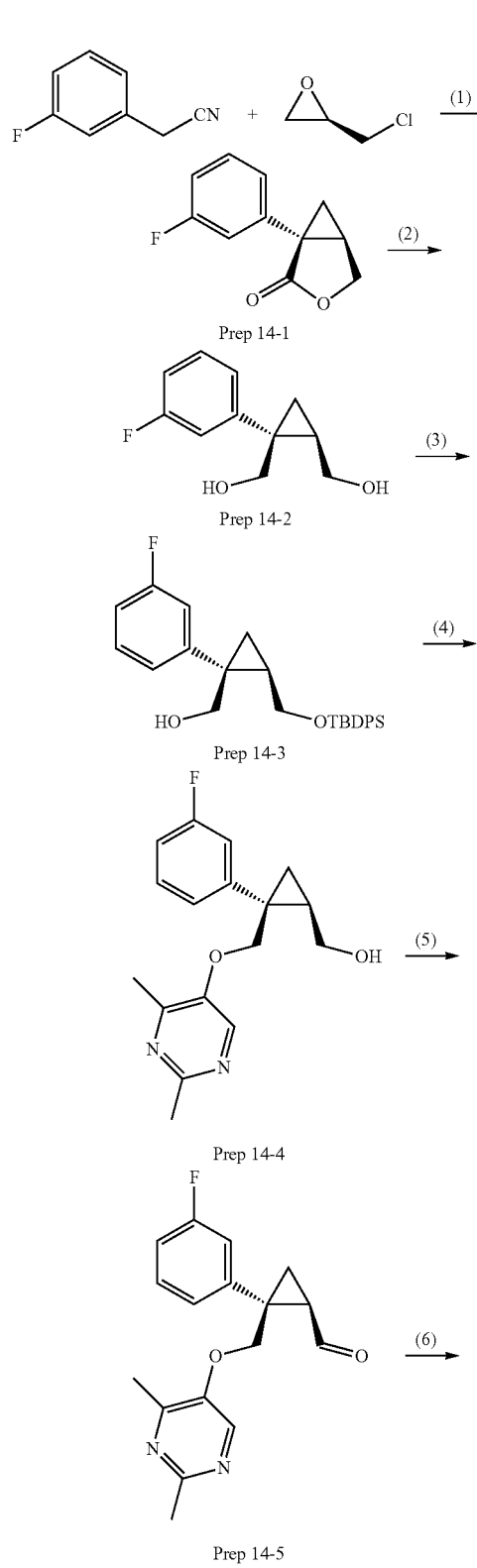

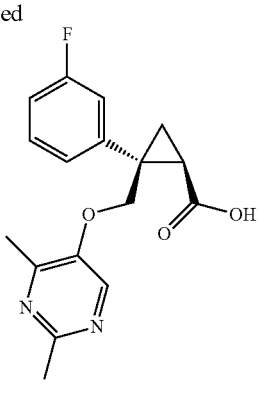

Prep 14-6

(1) (1S,5R)-1-(3-fluorophenyl)-3-oxabicyclo[3.1.0]hexan-2-one (Prep 14-1)

3-Fluoro phenyl acetonitrile (70 g) was dissolved in THF (500 ml), and NaHMDS (1000 ml, 1.06 M) was then added dropwise to the solution under cooling in an ice-salt bath. The obtained mixture was stirred for 1 hour, and R-(−)-epichlorohydrin (40.6 ml) was then added dropwise to the reaction solution (approximately 10 minutes, internal temperature<10° C.). The obtained mixture was stirred for 2 hours (wherein the internal temperature was maintained around 0° C.), and it was then stirred at room temperature for 14 hours. Thereafter, the reaction solution was cooled on ice, and a small amount of water was added dropwise thereto. The reaction solution was concentrated under reduced pressure, and thereafter, ethanol (700 ml) and a 1 N potassium hydroxide aqueous solution (1000 ml) were added to the residue. The obtained mixture was heated to reflux for 5 hours. Thereafter, the temperature of the reaction solution was returned to room temperature, and 5 N hydrochloric acid (400 ml) was then added to the solution. The obtained mixture was stirred at 60° C. for 1 hour. Thereafter, the reaction solution was concentrated under reduced pressure, and ethyl acetate and water were added to the concentrate to carry out liquid separation. The organic layer was successively washed with a saturated sodium bicarbonate aqueous solution and a saturated sodium chloride aqueous solution. The resultant organic layer was dried over magnesium sulfate, and the solvent was then concentrated under reduced pressure. The residue was purified by silica gel column chromatography (n-heptane:ethyl acetate), so as to obtain the title compound (84.9 g).

$^1$H-NMR (400 MHz, CDCl$_3$) δ (ppm): 1.41 (t, J=5.2 Hz, 1H), 1.64 (dd, J=8.0, 5.2 Hz, 1H), 2.56-2.63 (m, 1H), 4.30 (d, J=9.2 Hz, 1H), 4.47 (dd, J=9.2, 4.8 Hz, 1H), 6.96-7.02 (m, 1H), 7.16-7.21 (m, 2H), 7.28-7.35 (m, 1H).

(2) (1S,2R)-1-(3-fluorophenyl)cyclo propan-1,2-dimethanol (Prep 14-2)

Sodium borohydride (25 g) was added to a THF-methanol solution (440 ml-220 ml) of the compound Prep 14-1(72.7 g) at 0° C., and the obtained mixture was then stirred at room temperature for 65 hours. Under cooling on ice, water and 5 N hydrochloric acid were added to the reaction solution, and the obtained mixture was then extracted with ethyl acetate. The organic layer was washed with a saturated sodium chloride aqueous solution, and was then dried over magnesium sulfate.

The solvent was concentrated under reduced pressure, and the residue was then purified by silica gel column chromatography (n-heptane:ethyl acetate), so as to obtain the title compound (72.7 g).

¹H-NMR (400 MHz, CDCl₃) δ (ppm): 0.80 (t, J=5.0 Hz, 1H), 1.10 (dd, J=8.6, 5.0 Hz, 1H), 1.62-1.71 (m, 1H), 3.41 (t, J=11.4 Hz, 1H), 3.58 (d, J=12.0 Hz, 1H), 4.12-4.25 (m, 2H), 690-696 (m, 1H), 7.08-7.14 (m, 1H), 7.16-7.21 (m, 1H) 7.24-7.32 (m, 1H).

(3) {(1S,2R)-[2-(tert-butyldiphenylsilyloxymethyl)-1-(3-fluorophenyl)cyclopropyl]}methanol (Prep 14-3)

The compound Prep 14-2 (42.4 g) and triethylamine (33.0 ml) were dissolved in dichloromethane (216 ml), and the obtained mixture was then cooled to −20° C. Thereafter, tert-butyldiphenylsilyl chloride (56.3 ml) was added dropwise to the reaction solution (approximately 30 minutes; insoluble matters were precipitated almost at the same time after completion of dropping). After the mixture had been stirred for 1 hour, the reaction solution was further stirred at room temperature for 20 hours. Thereafter, water was added to the reaction solution, and the obtained mixture was then extracted with dichloromethane. The resultant extract was washed with water, and was then dried over anhydrous magnesium sulfate. The solvent was distilled off under reduced pressure, and the residue was then purified by silica gel column chromatography (n-heptane:ethyl acetate), so as to obtain the title compound (67.8 g).

¹H-NMR (400 MHz, CDCl₃) δ (ppm): 0.73 (t, J=5.2 Hz, 1H), 1.04 (dd, J=8.4, 5.2 Hz, 1H), 1.09 (s, 9H), 1.48-1.53 (m, 1H), 3.52 (t, J=12.0 Hz, 1H), 3.56 (dd, J=9.6, 1.6 Hz, 1H), 3.70 (dd, J=9.6, 1.6 Hz, 1H), 4.18 (t, J=12.0 Hz, 1H), 4.20 (dd, J=12.0, 5.2 Hz, 1H), 6.93 (tdd, J=8.0, 2.4, 1.2 Hz, 1H), 7.11 (dt, J=9.6, 2.4 Hz, 1H), 7.20 (dt, J=8.0, 1.2 Hz, 1H), 7.28 (td, J=8.0, 6.0 Hz, 1H), 7.37-7.49 (m, 6H), 7.69-7.74 (m, 4H).

(4) {(1R,2S)-2-{[(2,4-dimethylpyrimidin-5-yl)oxy]methyl}-2-(3-) fluorophenyl)cyclopropyl}methanol (Prep 14-4)

Diisopropyl azodicarboxylate (0.316 ml) was added dropwise to a THF solution (10 ml) of the compound Prep 14-3 (581 mg), triphenylphosphine (1.3 g) and the 2,4-dimethyl-pyrimidin-5-ol (183 mg) obtained in Production Example 4 at 0° C., and the obtained mixture was then stirred at room temperature for 2 days. Thereafter, the reaction solution was concentrated under reduced pressure, and was then purified by silica gel column chromatography (n-heptane:ethyl acetate=19:1 to 7:3). The obtained (1S,2R)-2-(tert-butyl-diphenylsilyloxymethyl)-1-{[(2,4-dimethylpyrimidin-5-yl)oxy]methyl}-1-(3-fluorophenyl)cyclopropane was dissolved in THF (15 ml), and tetrabutyl ammonium fluoride (1 M THF solution: 1.61 ml) was then added dropwise to the solution at room temperature. The obtained mixture was stirred at room temperature for 14 hours. Thereafter, the reaction solution was concentrated under reduced pressure, and was then purified by silica gel column chromatography (n-heptane:ethyl acetate=10: lto 0:1), so as to obtain the title compound (238 mg).

¹H-NMR (400 MHz, CDCl₃) δ (ppm): 1.00 (t, J=5.6 Hz, 1H), 1.25-1.33 (m, 1H), 1.78-1.88 (m, 1H), 2.39 (s, 3H), 2.61 (s, 3H), 3.58 (dd, J=12.0, 9.6 Hz, 1H), 4.02-4.11 (m, 1H), 4.12 (d, J=10.4 Hz, 1H), 4.43 (d, J=9.6 Hz, 1H), 6.92-6.98 (m, 1H), 7.10-7.16 (m, 1H), 7.18-7.23 (m, 1H), 7.29 (td, J=8.0, 6.0 Hz, 1H), 8.00 (s, 1H).

4-Alternative Method

{(1R,2S)-2-{[(2,4-dimethylpyrimidin-5-yl)oxy]methyl}-2-(3-fluorophenyl)cyclopropyl}methanol (Prep 14-4) (Alternative Method)

Triethylamine (14.5 ml) was added to a dichloromethane solution (200 ml) of the compound Prep 14-3 (41.3 g), and the obtained mixture was then cooled to 0° C. Methanesulfonyl chloride (7.34 ml) was added dropwise to the reaction solution, and the obtained mixture was then stirred for 1 hour. Thereafter, water was added to the reaction solution, and the obtained mixture was then extracted with dichloromethane. The resultant extract was dried over anhydrous sodium sulfate, and the solvent was then distilled off under reduced pressure. The 2,4-dimethyl-pyrimidin-5-ol (14.1 g) obtained in Production Example 4-(2) and cesium carbonate (61.8 g) were added to an acetonitrile solution (200 ml) of the obtained residue, and the obtained mixture was then heated to 70° C. The reaction solution was stirred at 70° C. for 4 hours, and it was then cooled to 0° C. Tetrabutyl ammonium fluoride (1 M THF solution: 190 ml) was added dropwise to the reaction solution, and the obtained mixture was then stirred at room temperature for 1 hour. Thereafter, water was added to the reaction solution, and the obtained mixture was then extracted with ethyl acetate. The resultant extract was dried over anhydrous sodium sulfate, and the solvent was then distilled off under reduced pressure.

The residue was purified by NH-silica gel column chromatography (n-heptane:ethyl acetate=9:1 to 1:1), so as to obtain the title compound (20.7 g).

(5) (1R,2S)-2-{[(2,4-dimethylpyrimidin-5-yl)oxy]methyl}-2-(3-fluorophenyl)cyclopropanecarbaldehyde (Prep 14-5)

A dichloromethane solution (7 ml) of oxalyl chloride (137 ul) was cooled to −78° C., and dimethyl sulfoxide (226 ul) was then added dropwise thereto (internal temperature: −60° C. or lower). The obtained mixture was stirred at the same temperature as described above for 10 minutes. Thereafter, a dichloromethane solution (3 ml) of the compound Prep 14-4 (238 mg) was added dropwise to the reaction solution at −78° C., and the obtained mixture was then stirred at the same temperature as described above for 30 minutes. Thereafter, triethylamine (671 ul) was added to the reaction solution, and the obtained mixture was then stirred for 15 minutes. Thereafter, the temperature of the reaction solution was warmed to room temperature. A saturated sodium chloride aqueous solution was added to the reaction solution, and the obtained mixture was then extracted with ethyl acetate. The organic layer was dried over anhydrous magnesium sulfate, and was then concentrated under reduced pressure, so as to obtain the crude title compound (236 mg).

¹H-NMR (400 MHz, CDCl₃) δ (ppm): 1.67 (dd, J=8.0, 4.8 Hz, 1H), 1.96-2.00 (m, 1H), 2.36 (s, 3H), 2.49-2.55 (m, 1H), 2.59 (s, 3H), 4.19 (d, J=9.6 Hz, 1H), 4.44 (d, J=10.0 Hz, 1H), 6.97-7.04 (m, 1H), 7.14-7.20 (m, 1H), 7.21-7.25 (m, 1H), 7.30-7.37 (m, 1H), 7.95 (s, 1H), 9.87 (d, J=3.2 Hz, 1H).

(6) (1R,2S)-2-{[(2,4-dimethylpyrimidin-5-yl)oxy]methyl}-2-(3-fluorophenyl)cyclopropanecarboxylic acid (Prep 14-6)

The compound Prep 14-5 (18.9 g), 2-methyl-2-butene (26.1 ml), and sodium hydrogen phosphate (9.07 g) were dissolved in a mixed solvent of acetone and water (200 ml/40 ml), and sodium chlorite (6.26 g) was added by portions to the solution. The obtained mixture was stirred at room temperature for 2 hours, and the reaction solution was then concentrated under reduced pressure. The precipitated solid was collected by filtration, and was then washed with dichloromethane. Thereafter, the solvent was distilled off under reduced pressure. The residue was purified by silica gel column chromatography (n-heptane:ethyl acetate=1:1 to 0:1, and then, ethyl acetate:methanol=10:1), so as to obtain the title compound (16.2 g).

$^1$H-NMR (400 MHz, CDCl$_3$) δ (ppm): 1.55 (dd, J=8.4, 5.6 Hz, 1H), 1.76 (t, J=5.6 Hz, 1H), 2.25 (dd, J=8.4, 6.4 Hz, 1H), 2.33 (s, 3H), 2.55 (s, 3H), 4.47 (t, J=9.6 Hz, 1H), 4.50 (d, J=9.6 Hz, 1H), 6.99 (tdd, J=8.0, 2.4, 1.2 Hz, 1H), 7.21 (dt, J=9.6, 2.4 Hz, 1H), 7.26 (td, J=8.0, 1.2 Hz, 1H), 7.32 (td, J=8.0, 6.0 Hz, 1H), 8.21 (s, 1H).

The compound Prep 14-6 can be directly produced from the compound Prep 14-4 by the following method.

The compound Prep 14-4 (300 mg) and TEMPO (5 mol %, 7.74 mg) were dissolved in an acetonitrile-phosphate (pH 6.4) buffer (5 ml, 5 ml), and 2 N HCl (150 ul) and sodium chlorite (180 mg) were then added to the solution. The obtained solution was heated to 40° C., and a 5w % hypochlorous acid aqueous solution (2 mol %, 26.5 ul) was then added to the reaction solution, followed by stirring for 2 hours. Thereafter, the reaction solution was cooled to room temperature, and an excessive amount of 2-methyl-2-butene was then added to the reaction solution, followed by stirring for 5 minutes. Thereafter, the reaction solution was subjected to liquid separation and extraction with dichloromethane, and the solvent was then distilled off under reduced pressure. The residue was purified by silica gel column chromatography (n-heptane:ethyl acetate=1:1 to 0:1, and then, ethyl acetate:methanol=9:1), so as to obtain the title compound (215 mg).

PRODUCTION EXAMPLE 15

Synthesis of (1R,2S)-2-{[(2,4-dimethylpyrimidin-5-yl)oxy]methyl}-2-(4-fluorophenyl)cyclopropanecarboxylic acid (Prep 15-5)

The title compound was synthesized from 4-fluoro phenyl acetonitrile by the same method as that of Production Example 13.

[Formula 46]

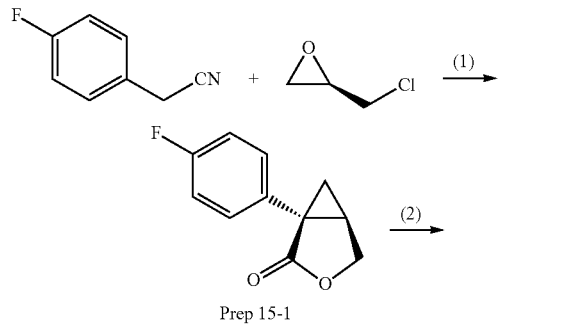

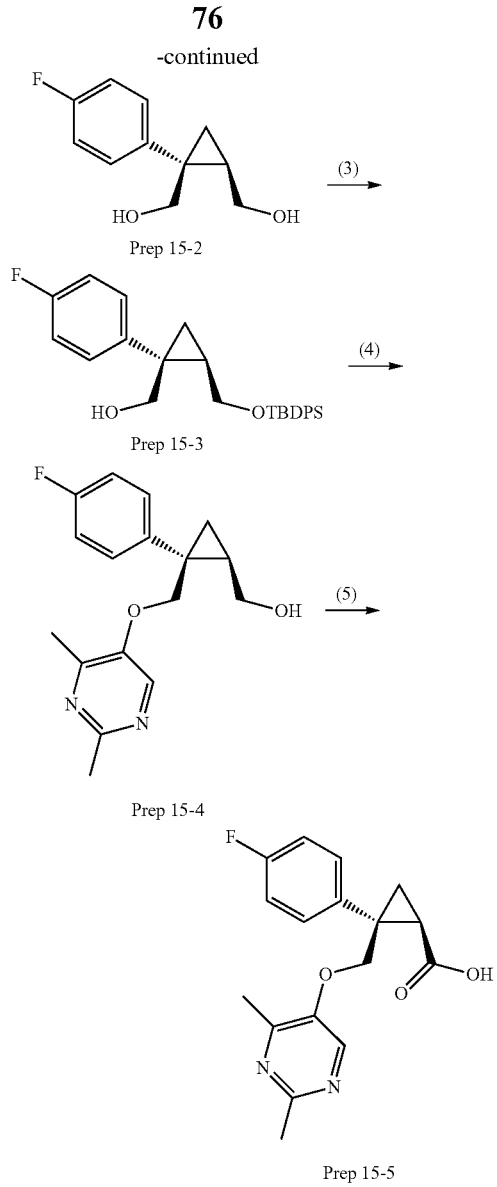

TABLE 1

| Compound No. | Compound name | Data (NMR and/or MS) |
|---|---|---|
| Prep 15-1 | (1S,5R)-1-(4-fluorophenyl)-3-oxabicyclo[3.1.0]hexan-2-one | $^1$H-NMR (400 MHz, CDCl$_3$) δ (ppm): 1.37 (t, J = 5.2 Hz, 1H), 1.60 (dd, J = 8.0, 4.8 Hz, 1H), 2.50-2.60 (m, 1H), 4.30 (d, J = 9.6 Hz, 1H), 4.48 (dd, J = 9.6, 4.8 Hz, 1H), 6.96-7.18 (m, 2H), 7.30-7.46 (m, 2H). |
| Prep 15-2 | (1S,2R)-1-(4-fluorophenyl)cyclopropan-1,2-dimethanol | $^1$H-NMR (400 MHz, CDCl$_3$) δ (ppm): 0.78 (t, J = 5.2 Hz, 1H), 1.06 (dd, J = 8.8, 5.2 Hz, 1H), 1.54-1.72 (m, 1H), 3.42 (dd, J = 11.6, 10.8 Hz, 1H), 3.57 (d, J = 12.0 Hz, 1H), 3.98-4.26 (m, 2H), 6.94-7.09 (m, 2H), 7.33-7.46 (m, 2H). |
| Prep 15-3 | {(1S,2R)-2-{[(tert-butyl-diphenyl-silyl)oxy]-methyl}-1-(4-fluoro-phenyl)cyclopropyl}methanol | $^1$H-NMR (400 MHz, CDCl$_3$) δ (ppm): 0.70 (t, J = 5.6 Hz, 1H), 0.92-1.16 (m, 10H), 1.40-1.60 (m, 1H), 3.42-3.58 (m, 2H), 3.69 (dd, J = 12.4, 1.6 Hz, 1H), 4.03 (t, J = 11.6 Hz, 1H), 4.20 (dd, J = 11.6, 5.2 Hz, 1H), 6.94-7.06 (m, 2H), 7.20-7.53 (m, 8H), 7.66-7.78 (m, 4H). |

TABLE 1-continued

| Compound No. | Compound name | Data (NMR and/or MS) |
|---|---|---|
| Prep 15-4 | {(1R,2S)-2-{[(2,4-dimethyl-pyrimidin-5-yl)oxy]methyl}-2-(4-fluoro-phenyl)cyclo-propyl}-methanol | $^1$H-NMR (400 MHz, CDCl$_3$) δ (ppm): 0.97 (t, J = 5.6 Hz, 1H), 1.20-1.30 (m, 1H), 1.72-1.86 (m, 1H), 2.14-2.26 (m, 1H), 2.38 (s, 3H), 2.60 (s, 3H), 3.50-3.62 (m, 1H), 4.00-4.16 (m, 2H), 4.39 (d, J = 10.0 Hz, 1H), 6.94-7.12 (m, 2H), 7.32-7.46 (m, 2H), 7.98 (s, 1H). |
| Prep 15-5 | (1R,2S)-2-{[(2,4-dimethyl-pyrimidin-5-yl)oxy]methyl}-2-(4-fluoro-phenyl)cyclo-propane-carboxylic acid | $^1$H-NMR (400 MHz, CDCl$_3$) δ (ppm): 1.52 (dd, J = 8.0, 4.8 Hz, 1H), 1.74 (dd, J = 5.6, 5.2 Hz, 1H), 2.22 (dd, J = 8.4, 6.0 Hz, 1H), 2.33 (s, 3H), 2.56 (s, 3H), 4.36-4.50 (m, 2H), 6.96-7.12 (m, 2H), 7.32-7.54 (m, 2H), 8.18 (s, 1H). MS [M + H]$^+$ = 317. |

PRODUCTION EXAMPLE 16

Synthesis of (1R,2S)-2-{[(3,5-difluorophenyl)-2-[(2,4-dimethylpyrimidin-5-yl)oxy]methyl]cyclopropan-ecarboxylic acid (Prep 16-7)

[Formula 47]

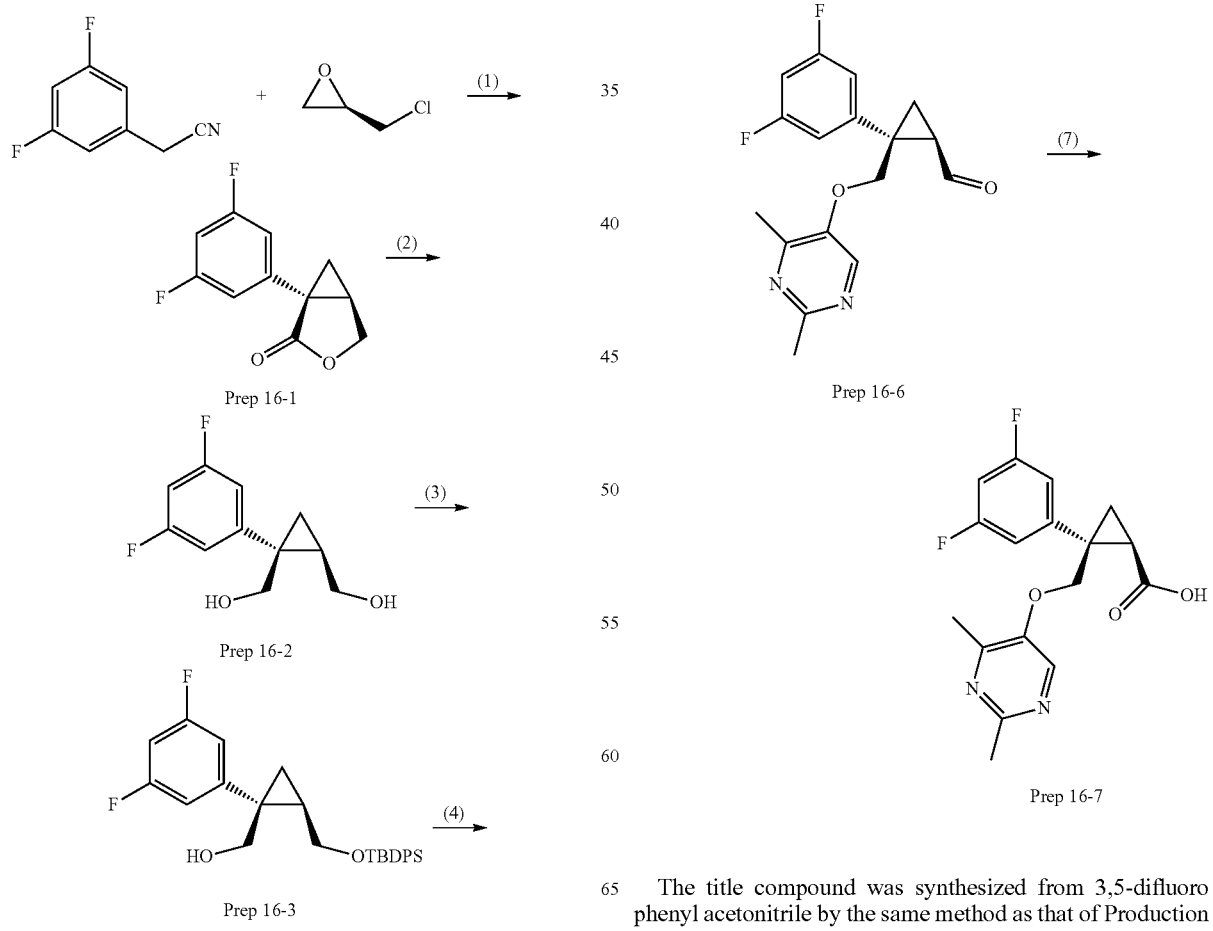

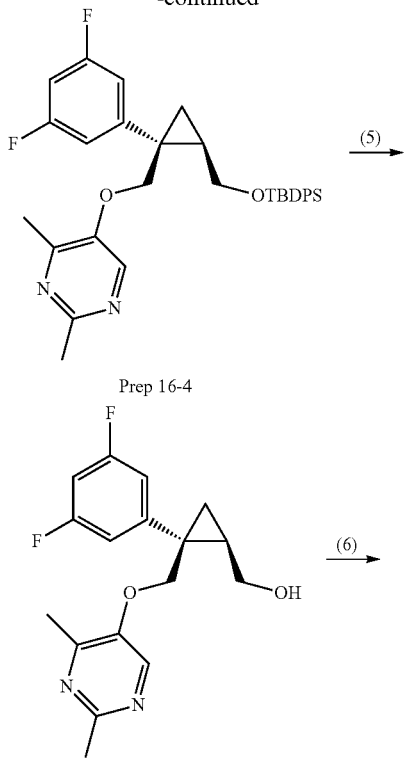

The title compound was synthesized from 3,5-difluoro phenyl acetonitrile by the same method as that of Production Example 13.

TABLE 2

| Compound No. | Compound name | Data (NMR and/or MS) |
|---|---|---|
| Prep 16-1 | (1S,5R)-1-(3,5-difluorophenyl)-3-oxabicyclo[3.1.0]hexan-2-one | $^1$H-NMR (400 MHz, CDCl$_3$) δ (ppm): 1.45 (t, J = 4.8 Hz, 1H), 1.63 (dd, J = 8.4, 5.2 Hz, 1H), 2.58-2.63 (m, 1H), 4.30 (d, J = 9.2 Hz, 1H), 4.46 (dd, J = 4.4, 9.2 Hz, 1H), 6.71-6.77 (m, 1H), 6.97-7.02 (m, 2H). |
| Prep 16-2 | (1S,2R)-1-(3,5-difluorophenyl)-1,2-cyclopropanedimethanol | MS [M + Na]$^+$ = 237. |
| Prep 16-3 | (1S,2R)-2-(tert-butyldiphenylsilyloxymethyl)-1-(3,5-difluorophenyl)cyclopropylmethanol | $^1$H-NMR (400 MHz, CDCl$_3$) δ (ppm): 0.74 (t, J = 5.2 Hz, 1H), 1.03 (dd, J = 8.4, 5.2 Hz, 1H), 1.09 (s, 9H), 1.42-1.50 (m, 1H), 3.51 (t, J = 11.6 Hz, 1H), 3.59-3.70 (m, 2H), 4.08-4.22 (m, 2H), 6.65-6.71 (m, 1H), 6.91-6.95 (m, 2H), 7.36-7.49 (m, 6H), 7.49-7.73 (m, 4H). |
| Prep 16-4 | 5-[(1S,2R)-2-(tert-butyldiphenylsilyloxymethyl)-1-(3,5-difluorophenyl)cyclopropylmethyloxy]-2,4-dimethylpyrimidine | MS [M + Na]$^+$ = 559. |
| Prep 16-5 | (1R,2S)-2-(3,5-difluorophenyl)-2-{[(2,4-dimethylpyrimidin-5-yl)oxy]methyl}cyclopropylmethanol | MS [M + H]$^+$ = 321. |
| Prep 16-6 | (1R,2S)-2-(3,5-difluorophenyl)-2-{[(2,4-dimethylpyrimidin5-yl)oxy]methyl}cyclopropanecarbaldehyde | $^1$H-NMR (400 MHz, CDCl$_3$) δ (ppm): 1.66 (dd, J = 8.4, 5.2 Hz, 1H), 1.98 (t, J = 5.2 Hz, 1H), 2.36 (s, 3H), 2.49-2.53 (m, 1H), 2.60 (s, 3H), 4.17 (d, J = 9.6 Hz, 1H), 4.41 (d, J = 9.6 Hz, 1H), 6.73-6.80 (m, 1H), 6.96-7.00 (m, 2H), 7.96 (s, 1H), 9.88 (d, J = 3.2 Hz, 1H). |
| Prep 16-7 | (1R,2S)-2-(3,5-difluorophenyl)-2-{[(2,4-dimethylpyrimidin-5-yl)oxy]methyl}cyclopropanecarboxylic acid | $^1$H-NMR (400 MHz, CDCl$_3$) δ (ppm): 1.59 (dd, J = 8.4, 6.0 Hz, 1H), 1.74 (t, J = 6.0 Hz, 1H), 2.22 (dd, J = 8.0, 6.0 Hz, 1H), 2.39 (s, 3H), 2.59 (s, 3H), 4.44 (d, J = 9.6 Hz, 1H), 4.58 (d, J = 9.6 Hz, 1H), 6.75 (t, J = 9.2 Hz, 1H), 6.99-7.03 (m, 2H), 8.28 (s, 1H). MS [M + H]$^+$ = 335 |

PRODUCTION EXAMPLE 17

Synthesis of 2-{[(2,4-dimethylpyrimidin-5-yl)oxy]methyl}-2-(2-methoxyphenyl)cyclopropanecarboxylic acid (Prep 17-4)

[Formula 48]

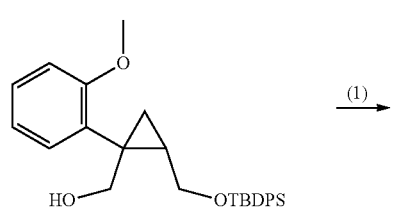

(1) →

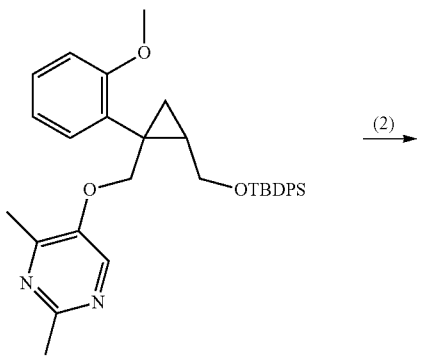

Prep 17-1

(2) →

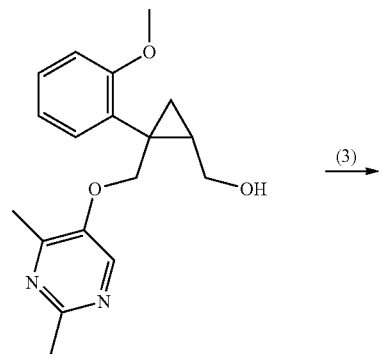

Prep 17-2

(3) →

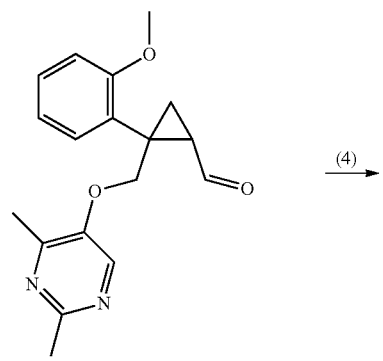

Prep 17-3

(4) →

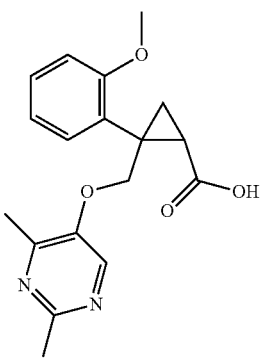

Prep 17-4

(1) 5-{(1S,2R)-2-[tert-butyl(diphenyl)silyloxymethyl]-1-(2-methoxyphenyl)cyclopropyl}methoxy-2,4-dimethylpyrimidine (Prep 17-1)

Triphenylphosphine (610 mg) was added to a toluene solution (15 ml) of the [2-({[tert-butyl(diphenyl)silyl]oxy}methyl)-1-(2-methoxyphenyl)cyclopropyl]methanol (800 mg) synthesized from (2-methoxyphenyl)acetonitrile and epichlorohydrin according to the method of Production Example 13 and tetrabromomethane (772 mg) at room temperature. The temperature of the obtained mixture was heated to 40° C., and the mixture was then stirred for 2 hours. Thereafter, a saturated sodium bicarbonate aqueous solution was added to the reaction solution, and the obtained mixture was then extracted with ethyl acetate. The organic layer was successively washed with water and a saturated sodium chloride aqueous solution, and was then anhydrous magnesium sulfate, followed by filtration. The filtrate was concentrated under reduced pressure, and the residue was then purified by silica gel column chromatography (n-heptane:ethyl acetate=19:1 to 9:1), so as to obtain the corresponding bromide.

Potassium carbonate (210 mg) was added to a DMF solution (10 ml) of the obtained bromide and the compound Prep 4-2 (113 mg) at room temperature, and the temperature of the obtained mixture was heated to 50° C., followed by stirring for 2 hours. Thereafter, the temperature of the reaction solution was heated to 70° C., and the reaction solution was further stirred for 11 hours. Thereafter, water was added to the reaction solution, and the obtained mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate=9:1 to 1:4), so as to obtain the title compound (148 mg).

$^1$H-NMR (400 MHz, CDCl$_3$) δ (ppm): 0.94 (dd, J=6.2, 5.2 Hz, 1H), 1.07 (s, 9H), 1.10 (dd, J=8.8, 5.2 Hz, 1H), 1.54-1.61 (m, 1H), 2.21 (s, 3H), 2.58 (s, 3H), 3.80 (s, 3H), 3.95 (d, J=6.8 Hz, 2H), 4.11 (d, J=9.8 Hz, 1H), 4.25 (d, J=9.8 Hz, 1H), 6.82-6.91 (m, 2H), 7.19-7.42 (m, 8H), 7.65-7.69 (m, 4H), 7.87 (s, 1H).

MS [M+Na]$^+$=575

(2) {2-{[(2,4-Dimethylpyrimidin-5-yl)oxy]methyl}-2-(2-methoxyphenyl) cyclopropyl}methanol (Prep 17-2)

Tetrabutyl ammonium fluoride (1 M THF solution: 322 ul) was added dropwise to a THF solution (1.3 ml) of the compound Prep 17-1 (148 mg) at room temperature, and the obtained mixture was then stirred at room temperature for 23 hours. The reaction solution was concentrated under reduced pressure, and the residue was then purified by silica gel column chromatography (n-heptane:ethyl acetate=1:1, to ethyl acetate, to ethyl acetate:methanol=9:1), so as to obtain the title compound (75 mg).

$^1$H-NMR (400 MHz, CDCl$_3$) δ (ppm): 0.99 (dd, J=6.2, 5.2 Hz, 1H), 1.21 (dd, J=8.8, 5.2 Hz, 1H), 1.68-1.76 (m, 1H), 2.32 (s, 3H), 2.45 (dd, J=8.8, 2.4 Hz, 1H), 2.58 (s, 3H), 3.48-3.54 (m, 1H), 3.88 (s, 3H), 4.13 (dt, J=8.8, 6.4 Hz, 1H), 4.18 (d, J=10.0 Hz, 1H), 4.33 (d, J=10.0 Hz, 1H), 6.87 (dd, J=8.0, 1.2 Hz, 1H), 6.94 (dt, J=8.0, 1.2 Hz, 1H), 7.24-7.29 (m, 1H), 7.34 (dd, J=8.0, 1.6 Hz, 1H), 7.94 (s, 1H).

(3) 2-{[(2,4-Dimethylpyrimidin-5-yl)oxy]methyl}-2-(2-methoxyphenyl)cyclopropanecarbaldehyde (Prep 17-3)

A dichloromethane solution (0.5 ml) of oxalyl chloride (82 ul) was cooled to −78° C., and thereafter, a dichloromethane solution (0.5 ml) of dimethyl sulfoxide (136 ul) was added dropwise thereto. Ten minutes later, a dichloromethane solution of the compound Prep 17-2 (75 mg) was added dropwise to the reaction solution at −78° C., and the obtained mixture was then stirred at the same temperature as described above for 40 minutes. Thereafter, triethylamine (534 ul) was added to the reaction solution, and the temperature of the obtained mixture was then raised to 0° C., followed by stirring for 15 minutes. Thereafter, water was added to the reaction solution, and the obtained mixture was then extracted with ethyl acetate). The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate=9:1 to ethyl acetate), so as to obtain the title compound (41 mg).

$^1$H-NMR (400 MHz, CDCl$_3$) δ (ppm): 1.55 (dd, J=8.4, 5.2 Hz, 1H), 1.97 (dd, J=6.2, 5.2 Hz, 1H), 2.28 (s, 3H), 2.42 (ddd, J=8.4, 6.2, 4.0 Hz, 1H), 2.56 (s, 3H), 3.87 (s, 3H), 4.17 (d, J=9.6 Hz, 1H), 4.41 (d, J=9.6 Hz, 1H), 6.88 (dd, J=8.0, 0.8 Hz, 1H), 6.94 (dt, J=8.0, 0.8 Hz, 1H), 7.26-7.30 (m, 1H), 7.37 (dd, J=8.0, 1.8 Hz, 1H), 7.90 (s, 1H), 9.82 (d, J=4.0 Hz, 1H).

(4) 2-{[(2,4-Dimethylpyrimidin-5-yl)oxy]methyl}-2-(2-methoxyphenyl)cyclopropanecarboxylic acid (Prep 17-4)

2-Methyl-2-butene (139 ul), anhydrous sodium dihydrogen phosphate (23.6 mg), and sodium chlorite (44.4 mg) were added to an acetone-water solution (1.3 ml) of the compound Prep 17-3 (41 mg) at room temperature. The obtained mixture was stirred for 2.5 hours. Thereafter, the reaction solution was concentrated under reduced pressure, and the residue was then purified by silica gel column chromatography (n-heptane:ethyl acetate=1:1 to chloroform:methanol=9:1), so as to obtain the title compound (35 mg).

$^1$H-NMR (400 MHz, CDCl$_3$) δ (ppm): 1.50 (dd, J=8.0, 5.2 Hz, 1H), 1.70 (dd, J=6.4, 5.2 Hz, 1H), 2.13 (dd, J=8.0, 6.4 Hz, 1H), 2.31 (s, 3H), 2.56 (s, 3H), 3.89 (s, 3H), 4.40 (d, J=9.2 Hz, 1H), 4.57 (d, J=9.2 Hz, 1H), 6.89 (dd, J=8.0, 1.2 Hz, 1H), 6.95 (dt, J=8.0, 1.2 Hz, 1H), 7.27-7.30 (m, 1H), 7.42 (dd, J=8.0, 1.2 Hz, 1H), 8.19 (s, 1H),

PRODUCTION EXAMPLE 18

Synthesis of 2-(3-cyanophenyl)-2-{[(2,4-dimethylpyrimidin-5-yl)oxy]methyl}cyclopropanecarboxylic acid (Prep 18-4)

[Formula 49]

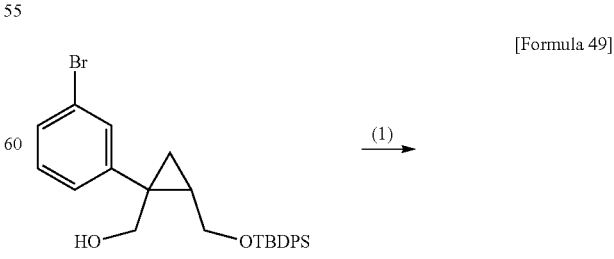

-continued

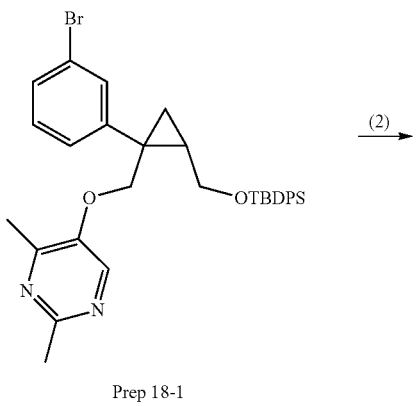

Prep 18-1

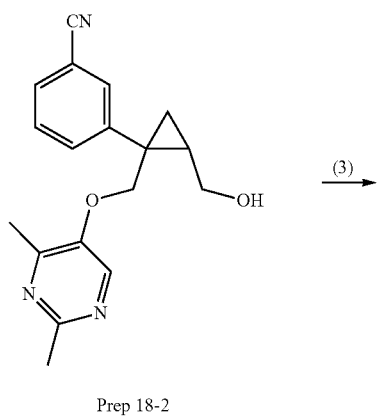

Prep 18-2

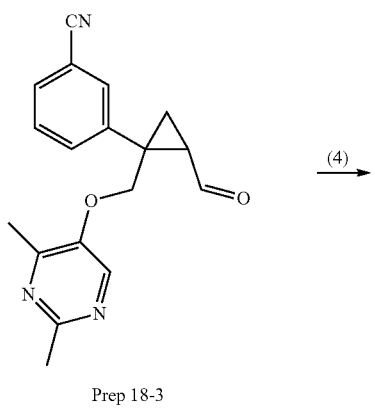

Prep 18-3

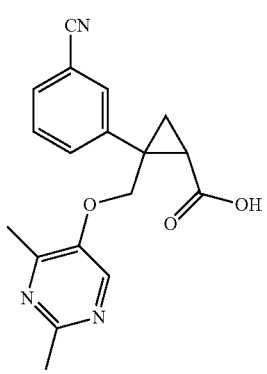

Prep 18-4

(1) 5-[1-(3-Bromophenyl)-2-(tert-butyldiphenylsilyloxymethyl)cyclopropylmethoxy-2,4-dimethylpyrimidine (Prep 18-1)

Diisopropyl azodicarboxylate (0.706 ml) was added dropwise to a THF solution (13 ml) of the [1-(3-bromophenyl)-2-(tert-butyldiphenylsilyloxymethyl)]cyclopropylmethanol (1.3 g) synthesized from (3-bromophenyl)acetonitrile and epichlorohydrin according to the same method as that of Production Example 13, triphenylphosphine (893 mg), and the 2,4-dimethyl-pyrimidin-5-ol (390 mg) synthesized in Production Example 4-(2) at 0° C. The obtained mixture was then stirred at room temperature for 14 hours. Thereafter, water was added to the reaction solution, and the obtained mixture was then extracted with ethyl acetate. The organic layer was washed with a saturated sodium chloride aqueous solution, was then dried over magnesium sulfate, and was then concentrated under reduced pressure. The residue was purified by silica gel column chromatography n-heptane:ethyl acetate=1:0 to 3:2), so as to obtain the title compound (880 mg).

$^1$H-NMR (400 MHz, CDCl$_3$) δ (ppm): 0.95 (t, J=5.8 Hz, 1H), 1.08 (s, 9H), 1.17-1.35 (m, 1H), 1.55-1.65 (m, 1H), 2.30 (s, 3H), 2.61 (s, 3H), 3.75 (dd, J=11.2, 8.0 Hz, 1H), 4.04 (dd, $^1$H, J=11.2, 5.4 Hz, 1H), 4.11 (d, J=9.6 Hz, 1H), 4.19 (d, J=9.6 Hz, 1H), 7.17 (t, J=7.8 Hz, 1H), 7, (m, 6H), 7.40-7.46 (m, 2H), 7.59 (t, J=2.0 Hz, 1H), 7.62-7.68 (m, 4H), 7.88 (s, 1H).

(2) 3-(1-{[(2,4-dimethylpyrimidin-5-yl)oxy]methyl}-2-hydroxymethylcyclopropan-1-yl}benzonitrile (Prep 18-2)

Zinc cyanide (172 mg) and tetrakistriphenylphosphinepalladium (169 mg) were added to a DMF solution (20 ml) of the compound Prep 18-1 (880 mg), and the obtained mixture was then stirred in a nitrogen atmosphere at 90° C. for 7 hours. Thereafter, the temperature of the reaction solution was returned to room temperature, and a saturated sodium bicarbonate aqueous solution was added thereto. The obtained mixture was then extracted with ethyl acetate. The organic layer was washed with a saturated sodium chloride aqueous solution, was then dried over magnesium sulfate, and was then concentrated under reduced pressure. The residue was dissolved in THF (10 ml), and tetrabutyl ammonium fluoride (1 M THE solution: 2.19 ml) was then added dropwise to the solution at room temperature. The obtained mixture was then stirred at room temperature for 5 hours. Thereafter, the reaction solution was concentrated under reduced pressure, and the residue was then purified by silica gel column chromatography (n-heptane:ethyl acetate (1:0 to 0:1) to ethyl acetate:methanol (9:1)), so as to obtain the title compound (415 mg).

$^1$H-NMR (400 MHz, CDCl$_3$) δ (ppm): 1.07 (t, J=6.0 Hz, 1H), 1.31 (dd, J=8.6, 5.4 Hz, 1H), 1.74-1.84 (m, 1H), 2.38 (s, 3H), 2.60 (s, 3H), 3.63 (dd, J=12.0, 9.2 Hz, 1H), 4.09 (dd, J=12.0, 5.4 Hz, 1H), 4.16 (d, J=10.0 Hz, 1H), 4.38 (d, J=10.0 Hz, 1H), 7.45 (t, J=7.6 Hz, 1H), 7.54-7.58 (m, 1H), 7.68-7.72 (m, 1H), 7.73-7.75 (m, 1H), 8.01 (s, 1H).

(3) 3-(1-{[(2,4-dimethylpyrimidin-5-yl)oxy]methyl}-2-formylcyclopropan-1-yl}benzonitrile (Prep 18-3)

A dichloromethane solution (7 ml) of oxalyl chloride (239 ul) was cooled to −78° C., and dimethyl sulfoxide (394 ul) was then added dropwise thereto (internal temperature: −60° C. or lower). The obtained mixture was stirred at the same temperature as described above for 10 minutes. Thereafter, a dichloromethane solution (7 ml) of the compound Prep 18-2 (415 mg) was added dropwise to the reaction solution at −78° C., and the obtained mixture was then stirred at the same temperature as described above for 30 minutes. Thereafter, triethylamine (1.17 ml) was added to the reaction solution, and the mixture was then stirred for 15 minutes. Thereafter, the temperature of the reaction solution was warmed to room temperature. A saturated sodium chloride aqueous solution was added to the reaction solution, and the obtained mixture was then extracted with ethyl acetate. The organic layer was dried over anhydrous magnesium sulfate and was then concentrated under reduced pressure, so as to obtain a crude title compound (236 mg).

$^1$H-NMR (400 MHz, CDCl$_3$) δ (ppm): 1.41 (t, J=7.2 Hz, 1H), 1.69 (dd, J=8.4, 5.2 Hz, 1H), 2.03 (t, J=5.8 Hz, 1H), 2.35 (s, 3H), 2.59 (s, 3H), 4.22 (d, J=10.0 Hz, 1H), 4.42 (d, J=10.0 Hz, 1H), 7.50 (t, J=8.2 Hz, 1H), 7.59-7.65 (m, 1H), 7.70-7.75 (m, 1H), 7.76-7.79 (m, 1H), 7.96 (s, 1H), 9.92 (d, J=2.8 Hz, 1H).

(4) 2-(3-Cyanophenyl)-2-{1-{[(2,4-dimethylpyrimidin-5-yl)oxy]methyl}cyclopropanecarboxylic acid (Prep 18-4)

The compound Prep 18-3 (415 mg), 2-methyl-2-butene (0.717 ml) and sodium dihydrogen phosphate (243 mg) were dissolved in a mixed solvent of acetone and water (10 ml/2 ml). Sodium chlorite (244 mg) was added by portions to the solution. The obtained mixture was then stirred at room temperature for 14 hours, and the reaction solution was then concentrated under reduced pressure. The residue was purified by silica gel column chromatography (ethyl acetate: methanol 1:0 to 17:3), so as to obtain the title compound (265 mg).

$^1$H-NMR (400 MHz, CDCl$_3$) δ (ppm): 1.61 (dd, J=8.4, 5.6 Hz, 1H), 1.79 (t, J=5.6 Hz, 1H), 2.20-2.27 (m, 1H), 2.37 (s, 3H), 2.60 (s, 3H), 4.46 (d, J=9.6 Hz, 1H), 4.59 (d, J=9.6 Hz, 1H), 7.49 (t, J=7.8 Hz, 1H), 7.59-7.63 (m, 1H), 7.72-7.77 (m, 1H), 7.80 (t, J=1.8 Hz, 1H), 8.28 (s, 1H).

PRODUCTION EXAMPLE 19

Synthesis of (1R,2S)-2-{[(4-ethyl-2-methylpyrimidin-5-yl)oxy]methyl}-2-phenylcyclopropanecarboxylic acid (Prep 19-3)

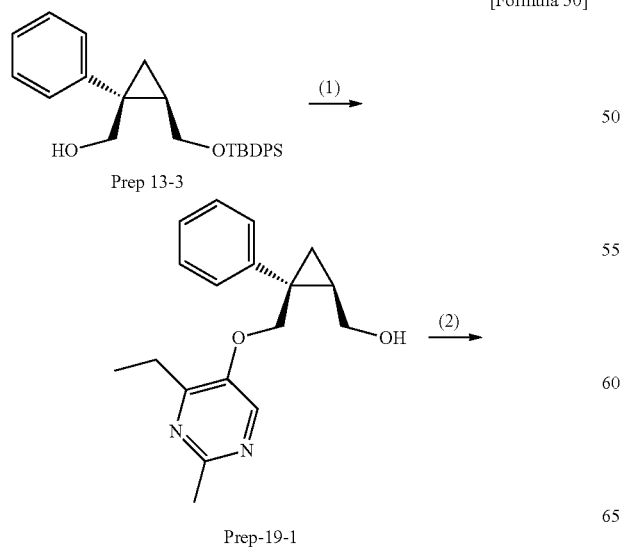

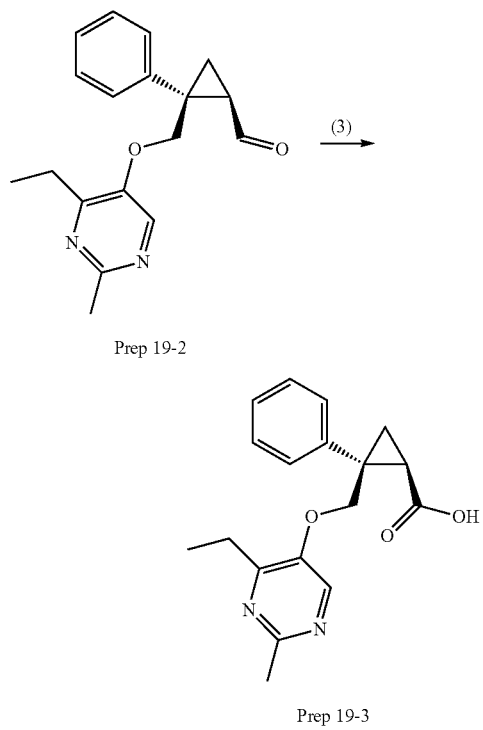

The title compound was synthesized from the compound Prep 13-3 and the compound Prep 3-3 by the same method as that of Production Example 13.

TABLE 3

| Compound No. | Compound name | Data (NMR and/or MS) |
|---|---|---|
| Prep 19-1 | (1R,2S)-2-{[(4-ethyl-2-methylpyrimidin-5-yl)oxy]methyl}-2-phenylcyclopropyl-methanol | $^1$H-NMR (400 MHz, CDCl$_3$) δ (ppm): 0.97 (t, J = 5.4 Hz, 1H), 1.15 (t, J = 7.8 Hz, 3H), 1.27 (dd, J = 8.8, 5.2 Hz, 1H), 1.80-1.90 (m, 1H), 2.19 (dd, J = 9.6, 3.2 Hz, 1H), 2.60 (s, 3H), 2.70 (ddd, J = 15.2, 7.6, 3.2 Hz, 2H), 3.54-3.63 (m, 1H), 4.03-4.15 (m, 1H), 4.11 (d, J = 10.0 Hz, 1H), 4.44 (d, J = 9.6 Hz, 1H), 7.21-7.29 (m, 1H), 7.29-7.36 (m, 2H), 7.42-7.46 (m, 2H), 7.99 (s, 1H). |
| Prep 19-2 | (1R,2S)-2-{[(4-ethyl-2-methylpyrimidin-5-yl)oxy]methyl}-2-phenylcyclopropan-1-yl}carbaldehyde | $^1$H-NMR (400 MHz, CDCl$_3$) δ (ppm): 1.16 (t, J = 7.6 Hz, 3H), 1.64-1.74 (m, 1H), 1.97 (t, J = 5.6 Hz, 1H), 2.50-2.55 (m, 1H), 2.60 (s, 3H), 2.70 (q, J = 7.6 Hz, 2H), 4.20 (d, J = 10.0 Hz, 1H), 4.44 (d, J = 9.6 Hz, 1H), 7.27-7.38 (m, 3H), 7.42-7.47 (m, 2H), 7.95 (s, 1H), 9.86 (d, J = 3.6 Hz, 1H). |
| Prep 19-3 | (1R,2S)-2-{[(4-ethyl-2-methylpyrimidin-5-yl)oxy]methyl}-2-phenylcyclopropane-carboxyic acid | $^1$H-NMR (400 MHz, CDCl$_3$) δ (ppm): 1.08 (t, J = 7.4 Hz, 3H), 1.53-1.58 (m, 1H), 1.76 (t, J = 5.2 Hz, 1H), 2.24-2.29 (m, 1H), 2.57 (s, 3H), 2.60-2.71 (m, 2H), 4.49 (dd, J = 13.2, 9.2 Hz, 2H), 7.25-7.32 (m, 1H), 7.32-7.39 (m, 2H), 7.46-7.52 (m, 2H), 8.23 (s, 1H). |

PRODUCTION EXAMPLE 20

Synthesis of (1R,2R)-2-{[(2,4-dimethylpyrimidin-5-yl)oxy]methyl}-2-phenylcyclopropanecarboxylic acid (Prep 20-6)

[Formula 51]

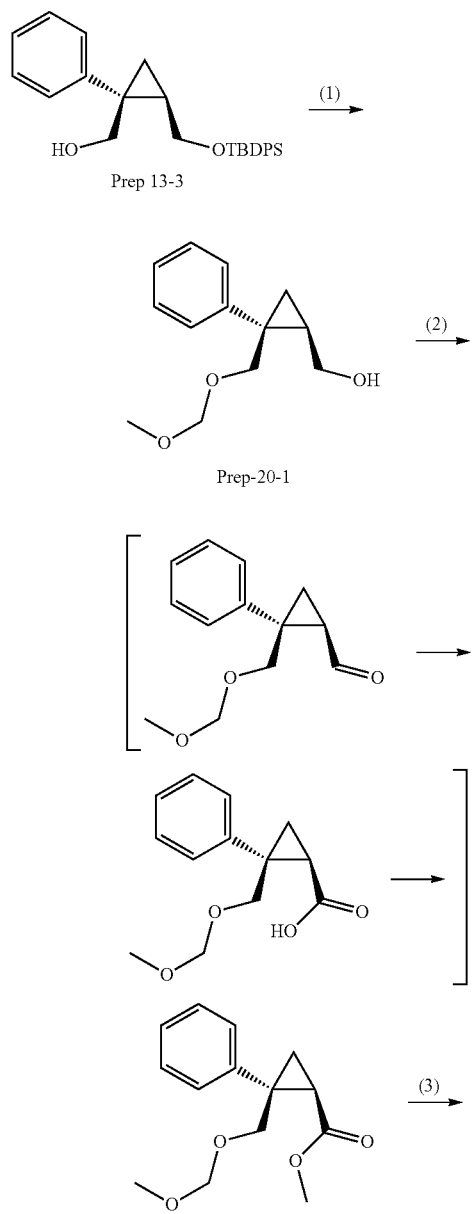

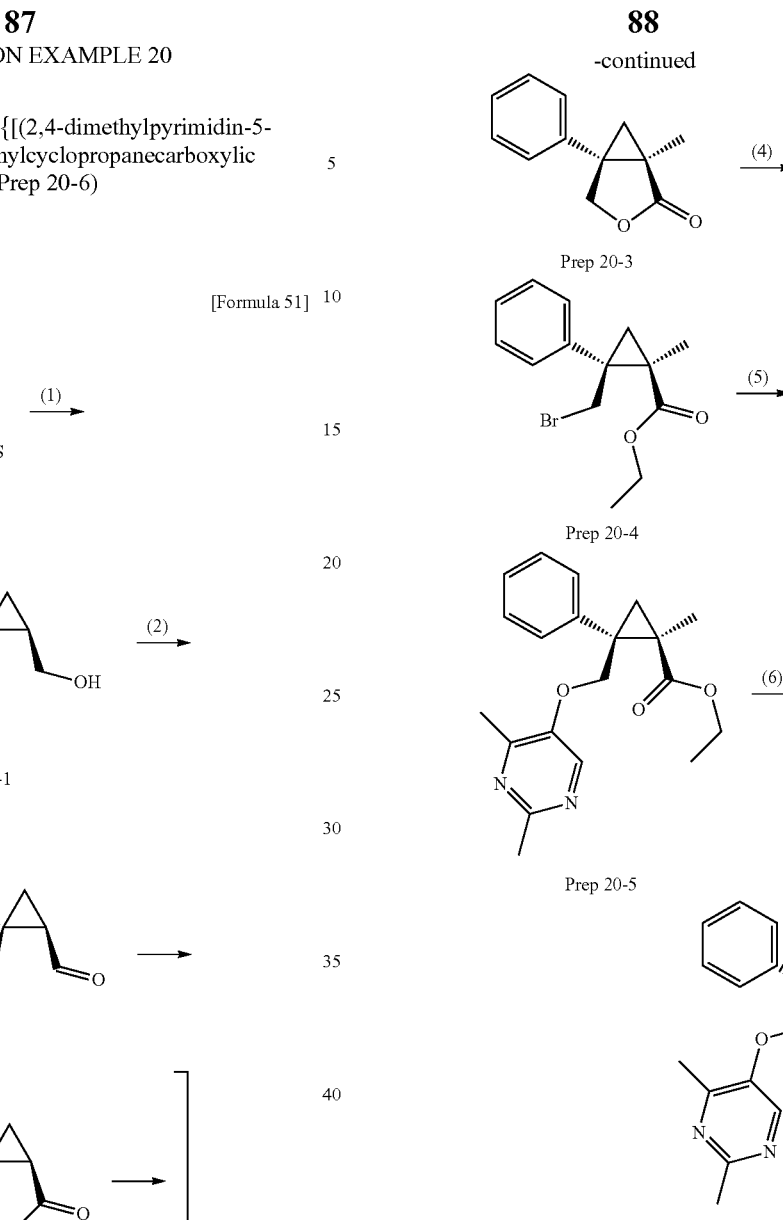

(1) [(1R,2S)-2-(methoxymethoxymethyl)-2-phenylcyclopropyl]methanol (Prep 20-1)

N,N-diisopropylethylamine (4.35 ml) and chloromethyl methyl ether (1.52 ml) were added to a dichloromethane solution (40 ml) of the compound Prep 13-3 (4 g), while the solution was stirred under cooling on ice. The obtained mixture was stirred at room temperature for 14 hours. Thereafter, water was added to the reaction solution, and the mixture was then extracted with dichloromethane. The organic layer was dried over magnesium sulfate, and the solvent was then distilled off under reduced pressure. The obtained residue was dissolved in THF (40 ml), and tetrabutyl ammonium fluoride (1 M THF solution: 1.61 ml) was then added to the solution at room temperature. The obtained mixture was stirred at room temperature for 2 hours. Thereafter, the reaction solution was concentrated under reduced pressure, and the residue was then purified by silica gel column chromatography (n-heptane:ethyl acetate=9:1 to 1:1), so as to obtain the title compound (1.93 g).

¹H-NMR (400 MHz, CDCl₃) δ (ppm): 0.79 (t, J=5.6 Hz, 1H), 1.11 (dd, J=8.8, 5.2 Hz, 1H), 1.70-1.80 (m, 1H), 3.19 (s, 3H), 3.35-3.45 (m, 1H), 3.57 (d, J=10.4 Hz, 1H), 4.04-4.16 (m, 2H), 4.52 (d, J=6.4 Hz, 1H), 4.59 (d, J=6.8 Hz, 1H), 7.18-7.24 (m, 1H), 7.25-7.34 (m, 2H), 7.35-7.42 (m, 2H).

(2) Methyl (1R,2S)-2-methoxymethoxymethyl-2-phenylcyclopropanecarboxylate (Prep 20-2)

A dichloromethane solution (15 ml) of oxalyl chloride (1.5 ml) was cooled to −78° C., and a dichloromethane solution (5 ml) of dimethyl sulfoxide (2.49 ml) was then added dropwise thereto (internal temperature: −65° C. or lower). The obtained mixture was stirred at the same temperature as described above for 5 minutes. Thereafter, a dichloromethane solution (20 ml) of the compound Prep 20-1 (1.93 g) was added dropwise to the reaction solution at −78° C., and the obtained mixture was then stirred at the same temperature as described above for 30 minutes. Thereafter, triethylamine (7.33 ml) was added to the reaction solution, and the obtained mixture was then stirred for 15 minutes. Thereafter, the temperature of the reaction solution was warmed to room temperature. A saturated sodium chloride aqueous solution was added to the reaction solution, and the obtained mixture was then extracted with ethyl acetate. The organic layer was dried over anhydrous magnesium sulfate, and was then concentrated under reduced pressure, so as to obtain an aldehyde (1.93 g). The obtained aldehyde (1.93 g), 2-methyl-2-butene (4.65 ml) and sodium dihydrogen phosphate were dissolved in a mixed solvent of acetone and water (60 ml/15 ml), and sodium chlorite (1.58 g) was then added by portions to the solution, while the solution was stirred under cooling on ice. The obtained mixture was stirred at room temperature for 5 hours. Thereafter, water was added to the reaction solution, and the obtained mixture was then extracted with ethyl acetate. The organic layer was washed with a saturated sodium chloride aqueous solution, was then dried over magnesium sulfate, and was then concentrated under reduced pressure. The residue was dissolved in a mixed solvent of methanol and THF (20 ml/20 ml), and while stirring at room temperature, trimethylsilyldiazomethane (2 M hexane solution: 8.76 ml) was added to the solution. The obtained mixture was stirred at room temperature for 14 hours. Thereafter, a small amount of acetic acid was added to the reaction solution, and thereby excessive trimethylsilyldiazomethane was decomposed. The resultant product was concentrated under reduced pressure, and the residue was then purified by silica gel column chromatography (n-heptane:ethyl acetate=1:0 to 4:1), so as to obtain the title compound (1.65 g).

¹H-NMR (400 MHz, CDCl₃) δ (ppm): 1.43 (dd, J=8.0, 4.8 Hz, 1H), 1.60 (dd, J=6.2, 4.8 Hz, 1H), 2.12 (dd, J=8.0, 6.2 Hz, 1H), 3.14 (s, 3H), 3.75 (s, 3H), 3.85 (d, J=10.0 Hz, 1H), 3.98 (d, J=9.6 Hz, 1H), 4.48 (s, 2H), 7.21-7.28 (m, 1H), 729-7.34 (m, 2H), 7.37-7.42 (m, 2H).

(3) (1S,5R)-1-methyl-5-phenyl-3-oxabicyclo[3.1.0]hexan-2-one (Prep 20-3)

While stirring at −78° C., n-butyllithium (2.69 M hexane solution: 3.3 ml) was added to a THF solution (22 ml) of diisopropylamine (1.25 ml). The obtained mixture was stirred at −78° C. for 30 minutes. Thereafter, a THF solution (11 ml) of the compound Prep 20-2 (1.11 g) was added to the reaction solution, and the obtained mixture was then stirred at −78° C. for 1 hour. Thereafter, iodomethane (703 ul) was added to the reaction solution, and the obtained mixture was stirred for 3 hours, while the temperature was warmed to room temperature. Thereafter, a saturated ammonium chloride aqueous solution was added to the reaction solution, and the obtained mixture was then extracted with ethyl acetate. The obtained layer was washed with a saturated sodium chloride aqueous solution, was then dried over magnesium sulfate, and was then concentrated under reduced pressure. The residue was dissolved in THF (10 ml), and while stirring at room temperature, 7.5 N hydrochloric acid (10 ml) was added to the solution. The obtained mixture was stirred at room temperature for 2 hours. Thereafter, water was added to the reaction solution, and the obtained mixture was then extracted with ethyl acetate. The obtained organic layer was successively washed with a saturated sodium bicarbonate aqueous solution and a saturated sodium chloride aqueous solution, and was then dried over magnesium sulfate. After completion of vacuum concentration, the residue was purified by silica gel column chromatography (n-heptane:ethyl acetate=1:0 to 4:1), so as to obtain the title compound (314 mg).

¹H-NMR (400 MHz, CDCl₃) δ (ppm): 1.15 (s, 3H), 1.36 (d, J=5.2 Hz, 1H), 1.51 (d, J=4.8 Hz, 1H), 4.38 (dd, J=12.4, 9.2 Hz, 2H), 7.20-7.44 (m, 5H).

(4) Ethyl (1R,2R)-2-bromomethyl-1-methyl-2-phenylcyclopropanecarboxylate (Prep 20-4)

While stirring at −15° C., thionyl bromide (247 ul) was added dropwise to ethanol (2 ml). Thereafter, the compound Prep 20-3 (150 mg) was added to the solution, and the obtained mixture was then stirred at −15° C. overnight. Thereafter, the reaction solution was concentrated under reduced pressure, and was then purified by silica gel column chromatography (n-heptane:ethyl acetate=1:0 to 3:17), so as to obtain the title compound (131 mg).

¹H-NMR (400 MHz, CDCl₃) δ (ppm): 1.02 (s, 3H), 1.31-1.37 (m, 1H), 1.34 (t, J=7.0 Hz, 3H), 1.91 (d, J=5.2 Hz, 1H), 3.79 (d, J=10.0 Hz, 1H), 3.87 (dd, J=10.0, 1.0 Hz, 1H), 4.24 (q, J=7.0 Hz, 2H), 7.26-7.43 (m, 5H).

(5) Ethyl (1R,2R)-2-{[(2,4-dimethylpyrimidin-5-yl)oxy]methyl}-1-methyl-2-phenylcyclopropanecarboxylate (Prep 20-5)

Potassium carbonate (91.4 mg), the 2,4-dimethyl-pyrimidin-5-ol (71.2 mg) synthesized in Production Example 4-(2), and tetrabutyl ammonium iodide (81.4 mg) were added to a DMF solution (3 ml) of the compound Prep 20-4 (131 mg). The reaction solution was stirred at 70° C. for 5 hours, and the temperature of the reaction solution was then returned to room temperature. Water was added to the reaction solution, and the obtained mixture was then extracted with ethyl acetate. The organic layer was washed with a saturated sodium chloride aqueous solution, was then dried over magnesium sulfate, and was then concentrated under reduced pressure. The residue was purified by silica gel column chromatography (n-heptane:ethyl acetate=19:1 to 2:3), so as to obtain the title compound (133 mg).

¹H-NMR (400 MHz, CDCl₃) δ (ppm): 1.08 (s, 3H), 1.22 (t, J=7.0 Hz, 3H), 1.30 (d, J=4.8 Hz, 1H), 1.96 (d, J=4.8 Hz, 1H), 2.40 (s, 3H), 2.58 (s, 3H), 4.04-4.17 (m, 2H), 4.30 (dd, J=12.2, 5.4 Hz, 2H), 7.26-7.48 (m, 5H), 7.90 (s, 1H).

(6) (1R,2R)-2-{[(2,4-dimethylpyrimidin-5-yl)oxy]methyl}-1-methyl-2-phenylcyclopropanecarboxylic acid (Prep 20-6)

A 5 N sodium hydroxide aqueous solution (235 ul) was added to an ethanol solution (2 ml) of the compound Prep 20-5 (133 mg), and the obtained mixture was then stirred at 80° C. for 5 hours. After the temperature of the reaction solution had been returned to room temperature, the reaction solution was neutralized with 5 N hydrochloric acid, followed by vacuum concentration. The residue was fully washed with THF, and was then filtered. The filtrate was dried over magnesium sulfate, and was then concentrated under reduced pressure, so as to obtain the title compound (144 mg).

$^1$H-NMR (400 MHz, CDCl$_3$) δ (ppm): 1.10 (s, 3H), 1.24-1.34 (m, 1H), 1.95 (brd, J=4.4 Hz, 1H), 2.34 (s, 3H), 2.51 (s, 3H), 4.36 (brd, J=9.2 Hz, 1H), 4.44 (brd, J=9.6 Hz, 1H), 7.26-7.47 (m, 5H), 8.04 (s, 1H).

The carboxylic acids of Production Example 21-47 were synthesized by the same method as that of Production Example 13, with the exception that (±)-epichlorohydrin was used as a racemic form, instead of using R-(−)-epichlorohydrin.

TABLE 4

| Production example | Structural formula | Compound name | Data (MS) |
|---|---|---|---|
| Prep 21 | | (1R,2S)-2-{[(2,4-dimethylpyrimidin-5-yl)oxy]methyl}-2-phenylcyclopropanecarboxylic acid | MS [M + H]$^+$ = 315 |
| Prep 22 | | (1R,2S)-2-{[(2-ethyl-4-methylpyrimidin-5-yl)oxy]methyl}-2-phenylcyclopropanecarboxylic acid | MS [M + H]$^+$ = 313 |
| Prep 23 | | (1R,2S)-2-{[(4-methoxymethyl-2-methylpyrimidin-5-yl)oxy]methyl}-2-phenylcyclopropanecarboxylic acid | MS [M + H]$^+$ = 329 |

TABLE 5

| Production example | Structural formula, MS |
|---|---|
| Prep 24 | 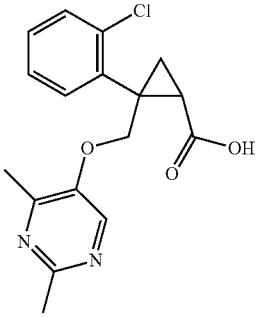<br>MS [M + H]+ = 333 |
| Prep 25 | 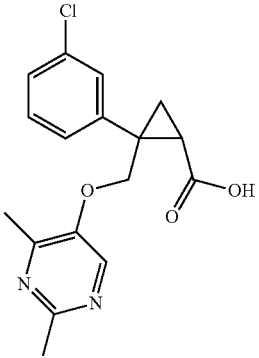<br>MS [M + H]+ = 333 |

TABLE 5-continued

| Production example | Structural formula, MS |
|---|---|
| Prep 26 | 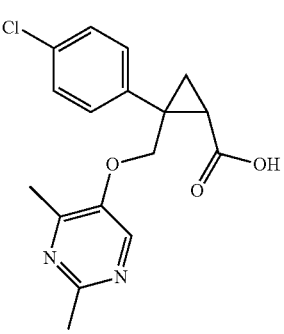<br>MS [M + H]+ = 333 |

TABLE 6

| Production example | Structural formula | NMR and/or MS |
|---|---|---|
| Prep 27 | 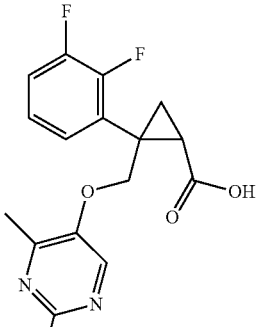 | $^1$H-NMR (400 MHz, CDCl$_3$) δ (ppm): 1.59 (dd, J = 8.4, 5.2 Hz, 1H), 1.77 (t, J = 5.6 Hz, 1H), 2.20-2.25 (m, 1 H), 2.33 (s, 3H), 2.59 (s, 3H), 4.43 (d, J = 9.6 Hz, 1H), 4.61 (d, J = 10.0 Hz, 1H), 7.01-7.30 (m, 3H), 8.26 (s, 1H).<br>MS [M + H]+ = 335 |
| Prep 28 | 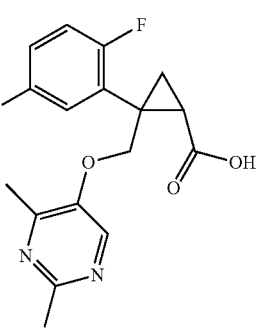 | $^1$H-NMR (400 MHz, CDCl$_3$) δ (ppm): 1.58 (dd, J = 8.4, 5.6 Hz, 1H), 1.76 (t, J = 6.0 Hz, 1H), 2.21 (dd, J = 8.4, 6.4 Hz, 1H), 2.35 (s, 3H), 2.59 (s, 3H), 4.43 (d, J = 9.6 Hz, 1H), 4.61 (d, J = 10.0 Hz, 1H), 6.95-7.20 (m, 3H), 8.28 (s, 1H).<br>MS [M + H]+ = 335 |

TABLE 6-continued

| Production example | Structural formula | NMR and/or MS |
|---|---|---|
| Prep 29 | | ¹H-NMR (400 MHz, CDCl₃) δ (ppm): 1.56 (dd, J = 8.0, 5.6 Hz, 1H), 1.72 (t, J = 5.6 Hz, 1H), 2.20 (dd, J = 8.4, 6.0 Hz, 1H), 2.38 (s, 3H), 2.58 (s, 3H), 4.41 (d, J = 9.2 Hz, 1H), 4.55 (d, J = 9.6 Hz, 1H), 7.11-7.34 (m, 3H), 8.26(s, 1H). MS [M + H]⁺ = 335 |
| Prep 30 | | ¹H-NMR (400 MHz, CDCl₃) δ (ppm): 1.48-1.60 (m, 1 H), 1.70 (dd, J = 6.0, 5.2 Hz, 1H), 2.22 (dd, J = 8.4, 6.0 Hz, 1H), 2.28-2.44 (m, 6H), 2.57 (s, 3H), 4.32-4.62 (m, 2H), 7.10-7.44 (m, 4H), 8.20 (s, 1H). MS [M + H]⁺ = 313 |
| Prep 31 | | ¹H-NMR (400 MHz, CDCl₃) δ (ppm): 1.59 (dd, J = 7.6, 5.2 Hz, 1H), 1.71 (dd, J = 5.8, 5.0 Hz, 1H), 2.24 (dd, J = 8.2, 6.2 Hz, 1H), 2.37 (s, 3H), 2.38 (s, 3H), 2.59 (s, 3H), 4.43 (d, J = 9.2 Hz, 1H), 4.57 (d, J = 9.6 Hz, 1H), 7.08-7.13 (m, 1H), 7.21-7.33 (m, 3H), 8.22 (s, 1H). |
| Prep 32 | | ¹H-NMR (400 MHz, CDCl₃) δ (ppm): 1.55 (dd, J = 8.2, 4.6 Hz, 1H), 1.78 (dd, J = 6.0, 5.2 Hz, 1H), 2.21 (dd, J = 8.2, 6.2 Hz, 1H), 2.35 (s, 3H), 2.52 (s, 3H), 2.59 (s, 3H), 4.37 (d, J = 9.6 Hz, 1H), 4.55 (d, J = 9.2 Hz, 1H), 7.16-7.23 (m, 3H), 7.43-7.49 (m, 1H), 8.22 (s, 1H). |

TABLE 6-continued

| Production example | Structural formula | NMR and/or MS |
|---|---|---|
| Prep 33 | | $^1$H-NMR (400 MHz, CDCl$_3$) δ (ppm): 1.46-1.58 (m, 1H), 1.69 (t, J = 4.8 Hz, 1H), 2.14-2.28 (m, 1H), 2.37 (s, 3H), 2.56 (s, 3H), 3.81 (s, 3H), 4.30-4.56 (m, 2H), 6.78-6.96 (m, 2H), 7.20-7.46 (m, 2H), 8.17 (s, 1H). MS [M + H]$^+$ = 329 |

TABLE 7

| Production example | Structural formula, MS |
|---|---|
| Prep 34 | MS [M + H]$^+$ = 329 |
| Prep 35 | MS [M + H]$^+$ = 347 |
| Prep 36 | MS [M + H]$^+$ = 347 |
| Prep 37 | MS [M + H]$^+$ = 365 |

TABLE 7-continued

| Production example | Structural formula, MS |
|---|---|
| Prep 38 | (3,5-difluorophenyl cyclopropane derivative) MS [M + H]⁺ = 365 |
| Prep 39 | (3-chlorophenyl cyclopropane derivative) MS [M + H]⁺ = 363 |
| Prep 40 | (3-fluorophenyl cyclopropane with methoxyethyl pyrimidine) MS [M + H]⁺ = 361 |
| Prep 41 | (3-fluoro-5-methoxyphenyl derivative) MS [M + H]⁺ = 377 |
| Prep 42 | (4-fluoro-3-methoxyphenyl derivative) MS [M + H]⁺ = 377 |
| Prep 43 | (3-fluorophenyl cyclopropane with ethyl pyrimidine) MS [M + H]⁺ = 331 |
| Prep 44 | (4-fluorophenyl cyclopropane with ethyl pyrimidine) MS [M + H]⁺ = 331 |

TABLE 7-continued

| Production example | Structural formula, MS |
|---|---|
| Prep 45 | 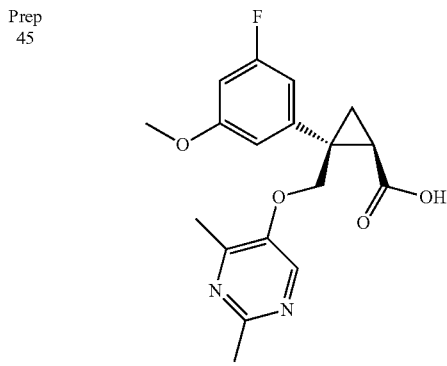<br>MS [M + H]⁺ = 347 |
| Prep 46 | 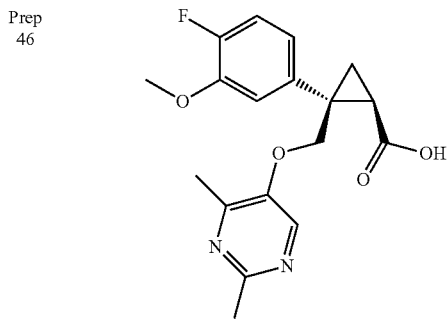<br>MS [M + H]⁺ = 347 |
| Prep 47 | 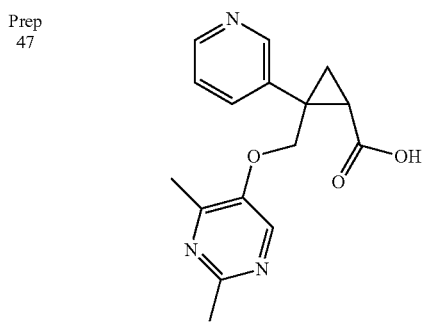<br>MS [M + H]⁺ = 300 |

PRODUCTION EXAMPLE 48

Synthesis of 2-{[(2,4-dimethylpyrimidin-5-yl)oxy]methyl}-3,3-dimethyl-2-phenylcyclopropanecarboxylic acid (Prep 48-5)

[Formula 52]

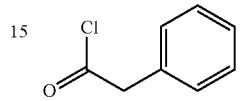

Prep 48-2

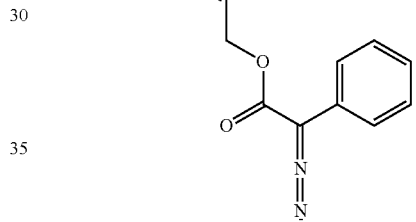

Prep 48-3    Prep 48-4

Prep 48-5

(1) 3-Methyl-2-buten-1-yl phenylacetate (Prep 48-1)

Triethylamine (9.7 ml) and phenylacetyl chloride (7.67 ml) were added to a dichloromethane solution (50 ml) of 3-methyl-2-buten-1-ol (5 g), while the solution was stirred under cooling on ice. The obtained mixture was stirred under cooling on ice for 3 hours. Thereafter, water was added to the reaction solution, and the obtained mixture was then extracted with dichloromethane. The obtained organic layer was dried over magnesium sulfate, and was then concentrated under reduced pressure. The residue was purified by silica gel column chromatography (n-heptane:ethyl acetate=1:0 to 19:1), so as to obtain the title compound (11.5 g).

$^1$H-NMR (400 MHz, CDCl$_3$) δ (ppm): 1.69 (s, 3H), 1.75 (s, 3H), 3.63 (s, 2H), 4.59 (d, J=7.2 Hz, 2H), 5.30-5.37 (m, 1H), 7.23-7.36 (m, 5H).

(2) 3-Methyl-2-buten-1-yl diazophenylacetate (Prep 48-2) Prep 48-1

DBU (9.26 ml) and 4-acetamidebenzenesulfonyl azide (13.5 g) were added to an acetonitrile solution (100 ml) of the compound Prep 48-1 (11.5 g), while the solution was stirred under cooling on ice. The obtained mixture was stirred at room temperature for 15 hours. The reaction solution was concentrated under reduced pressure, and water was then added thereto. The obtained mixture was then extracted with ethyl acetate. The obtained organic layer was washed with a saturated sodium chloride aqueous solution, dried over magnesium sulfate, and concentrated under reduced pressure. The residue was purified by silica gel column chromatography (n-heptane:ethyl acetate=1:0 to 19:1), so as to obtain the title compound (8.45 g).

$^1$H-NMR (400 MHz, CDCl$_3$) δ (ppm): 1.75 (s, 3H), 1.78 (s, 3H), 4.77 (d, J=7.6 Hz, 2H), 5.36-5.44 (m, 1H), 7.15-7.20 (m, 1H), 7.35-7.41 (m, 2H), 7.45-7.51 (m, 2H).

(3) 6,6-Dimethyl-1-phenyl-3-oxabicyclo[3.1.0]hexan-2-one (Prep 48-3)

While stirring at 50° C., a dichloromethane solution (180 ml) of Prep 48-2 (8.45 g) was added dropwise to a dichloromethane solution (360 ml) of rhodium(II) acetate dimer (324 mg) over 2 hours. Thereafter, the reaction solution was stirred at 50° C. for 1 hour. Thereafter, the reaction solution was cooled to room temperature, and was then concentrated under reduced pressure, so as to obtain a crude title compound (8 g).

$^1$H-NMR (400 MHz, CDCl$_3$) δ (ppm): 0.88 (s, 3H), 1.32 (s, 3H), 2.39 (d, J=5.2 Hz, 1H), 4.25 (d, J=9.6 Hz, 1H), 4.53 (dd, J=9.6, 5.2 Hz, 1H), 7.27-739 (m, 5H).

(4) (3,3-Dimethyl-1-phenylcyclopropan-1,2-diyl)dimethanol (Prep 48-4)

Lithium aluminum hydride (1.5 g) was added to a THF solution (100 ml) of Prep 48-3 (8 g), while the solution was stirred under cooling on ice. The obtained mixture was stirred for 1 hour. Thereafter, ice and a small amount of 27% ammonia aqueous solution were added to the reaction solution, and the obtained mixture was then stirred at room temperature for 10 minutes. Thereafter, Celite and magnesium sulfate were added to the reaction solution, and the obtained mixture was then stirred for 10 minutes. Thereafter, the reaction solution was filtered, and the filtrate was then concentrated under reduced pressure, so as to obtain the title compound (6.52 g).

$^1$H-NMR (400 MHz, CDCl$_3$) δ (ppm): 0.78 (s, 3H), 1.25 (s, 3H), 1.49 (dd, J=7.0, 5.8 Hz, 1H), 3.72 (dd, J=12.2, 11.0 Hz, 1H), 3.89 (d, J=12.0 Hz, 1H), 4.03 (d, J=12.2 Hz, 1H), 4.10 (dd, J=11.8, 5.8 Hz, 1H), 7.21-7.37 (m, 5H).

(5) 2-{[(2,4-Dimethylpyrimidin-5-yl)oxy]methyl}-3,3-dimethyl-2-phenylcyclopropanecarboxylic acid (Prep 48-5)

The title compound was synthesized from Prep 48-4 according to the method of Production Examples 13-(6) and 13-(7).

MS [M+H]$^+$=327

PRODUCTION EXAMPLE 49

Synthesis of (1R,2S)-2-{[(2,4-dimethylpyrimidin-5-yl)oxy]methyl}-2-(3-fluorophenylcyclopropyl)methanol (Prep 14-4)

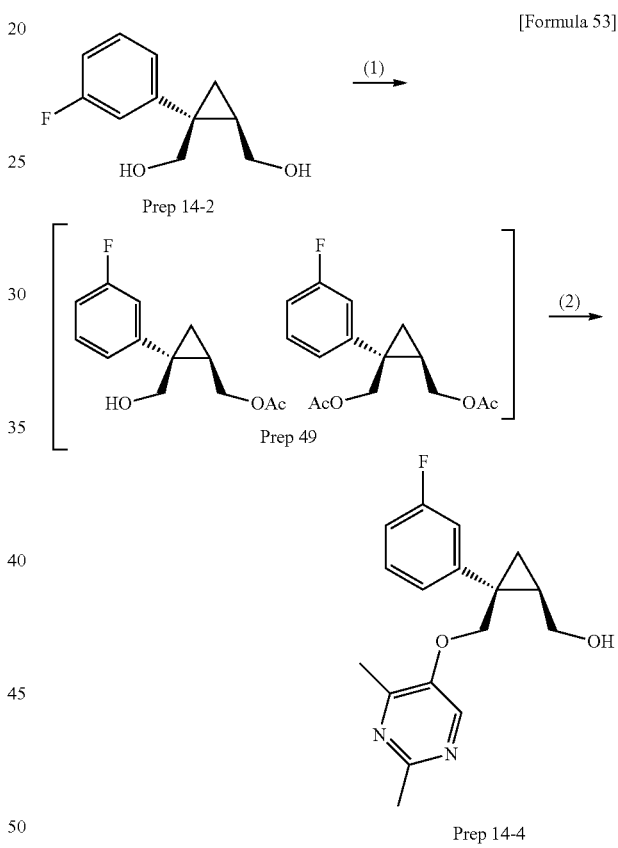

(1)[1(1R,2S)-2-(3-fluorophenyl)-2-(hydroxymethyl)cyclopropyl]methyl acetate, [(1S,2R)-1-(3-fluorophenyl)-1,2-diyl]bis(methylene)diacetate mixture (Prep 49)

Lipase acrylic resin from *candida antarctica* (SIGMA, 1.78 g) was added to a THF (110 ml)-vinyl acetate (25 ml) solution of the compound Prep 14-2 (35.5 g) under cooling on ice. The obtained mixture was stirred at room temperature for 17 hours. Thereafter, the reaction solution was filtered, and the obtained filtrate was then concentrated, so as to obtain the title compound (43.7 g).

MS [M+H]$^+$=239, 281

105

(2) (1R,2S)-2-{[(2,4-dimethylpyrimidin-5-yl)oxy]methyl}-2-(3-fluorophenylcyclopropyl)methanol (Prep 14-4)

Diisopropyl azodicarboxylate (45.8 ml) was added dropwise to a THF solution (400 ml) of the compound Prep 49 (43.7 g), triphenylphosphine (57 g) and 2,4-dimethyl-pyrimidin-5-ol (Prep 4-2, 24.7 g) at 0° C. The obtained mixture was stirred at room temperature for 15 hours. Thereafter, a saturated sodium bicarbonate aqueous solution was added to the reaction solution, and the obtained mixture was then extracted with ethyl acetate. The organic layer was washed with a saturated sodium chloride aqueous solution, was then dried over magnesium sulfate, and was then concentrated. The obtained reaction product was dissolved in EtOH-1 N sodium hydroxide aqueous solution (200 ml-200 ml), and the obtained mixture was then stirred at room temperature for 1 hour. Thereafter, a 5 N sodium hydroxide aqueous solution (100 ml) was added to the reaction solution, and the obtained mixture was then stirred at room temperature for 1 hour. Subsequently, the reaction solution was concentrated under reduced pressure at room temperature, and the obtained residue was then extracted with ethyl acetate. The organic layer was washed with a saturated sodium chloride aqueous solution, and was then dried over magnesium sulfate. The solvent was concentrated under reduced pressure, and the residue was then purified by silica gel column chromatography (heptane: ethyl acetate=1:4, to ethyl acetate:methanol=1:1). The obtained crude product was filtered through NH-silica gel pad (ethyl acetate), followed by concentration of the solvent under reduced pressure, so as to obtain the title compound (39.3 g).

$^1$H-NMR (400 MHz, CDCl$_3$) δ (ppm): 1.00 (t, J=5.2 Hz, 1H), 1.24-1.30 (m, 1H), 1.79-1.85 (m, 1H), 2.39 (s, 3H), 2.60 (s, 3H), 3.55-3.61 (m, 1H), 4.03-4.13 (m, 1H), 4.12 (d, J=9.6 Hz, 1H), 4.43 (d, J=9.6 Hz, 1H), 6.92-6.98 (m, 1H), 7.11-7.15 (m, 1H), 7.19-7.22 (m, 1H), 7.25-7.31 (m, 1H), 8.00 (s, 1H).

PRODUCTION EXAMPLE 50

Synthesis of (1R,2S)-2-(3,5-difluorophenyl)-2-[2-(4-methoxybenzyloxy)-4-(trifluoromethylpyrimidin-5-yl)oxymethyl]cyclopropanecarboxylic acid (Prep 50-7)

[Formula 54]

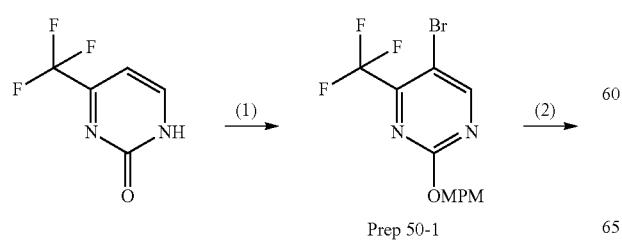

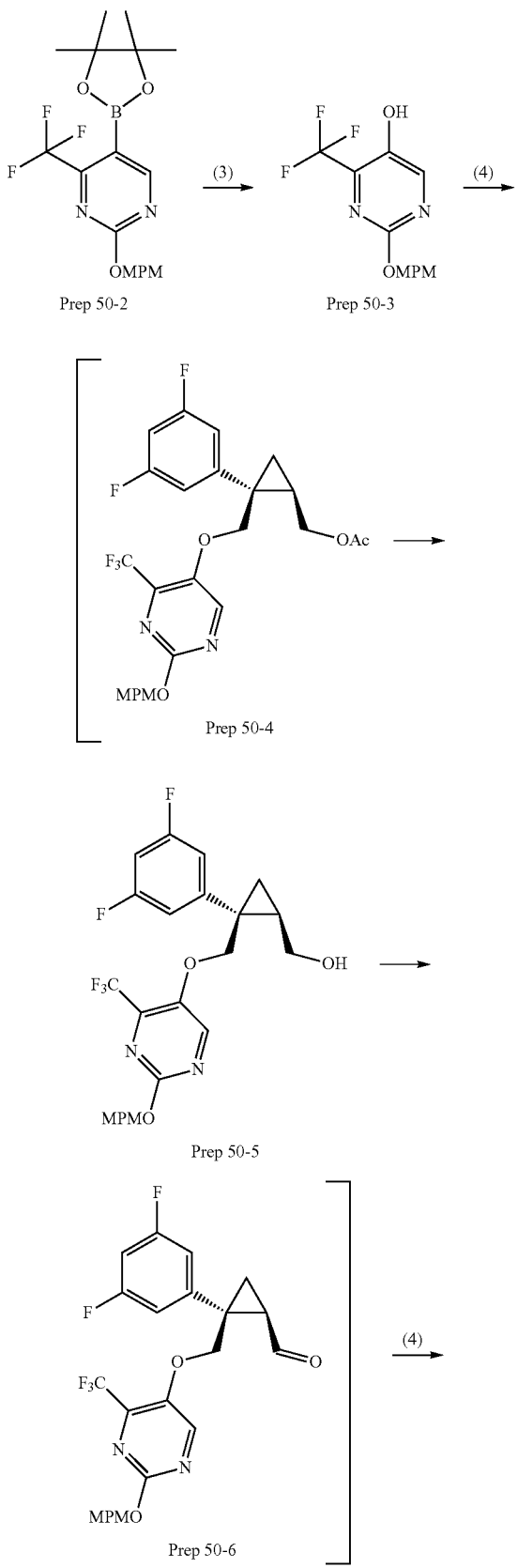

-continued

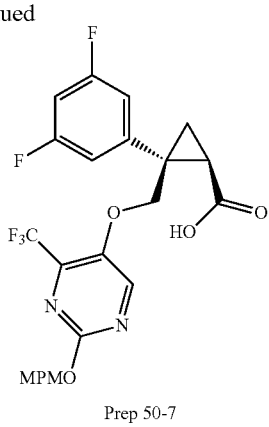

Prep 50-7

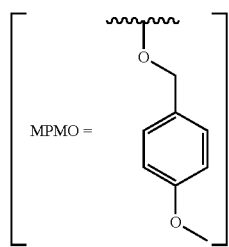

1) 5-Bromo-2-(4-methoxybenzyloxy)-4-trifluoromethylpyrimidine (Prep 50-1)

Potassium acetate (15.3 g) was added to an acetic acid solution (50 ml) of 4-(trifluoromethyl)pyrimidin-2(1H)-one (CAS No. 104048-92-2; 8.4 g), and thereafter, bromine (2.6 ml) was added dropwise to the solution at 40° C. The obtained mixture was stirred at 70° C. for 1.5 hours. Thereafter, the reaction mixture was concentrated under reduced pressure, and water and ethyl acetate were then added to the residue to carry out liquid separation and extraction. The obtained organic layer was dried over magnesium sulfate and was then concentrated under reduced pressure. Phosphorous oxychloride (40 ml) was added to the obtained residue, and the thus obtained mixture was then stirred for 1.5 hours under heating to reflux. The reaction mixture was concentrated under reduced pressure, and phosphorous oxychloride was then distilled off. Thereafter, ice was added to the residue, and liquid separation and extraction were then carried out with hexane. The obtained organic layer was dried over magnesium sulfate and then filtered. The resultant filtrate was concentrated under reduced pressure, so as to obtain a crude product.

Sodium hydride (60% Oil dispersion: 2.05 g) was added to a THF solution (150 ml) of 4-methoxybenzyl alcohol (7.07 g), and the obtained mixture was then stirred at room temperature for 30 minutes. A THF solution of the above obtained crude product was added dropwise to the reaction mixture, and the obtained mixture was then stirred overnight. Thereafter, a saturated ammonium chloride aqueous solution was added to the reaction mixture, followed by quenching. THF was distilled off under reduced pressure, and liquid separation and extraction were then carried out with ethyl acetate. The obtained organic layer was dried over magnesium sulfate and was then concentrated under reduced pressure. The obtained residue was purified by silica gel column chromatography (n-heptane:ethyl acetate=19:1 to 3:1), so as to obtain the title compound (12.5 g).

$^1$H-NMR (400 MHz, CDCl$_3$) δ (ppm): 3.81 (s, 3H), 5.40 (s, 2H), 6.87-6.90 (m, 2H), 7.43 (brbrd, J=7.6 Hz, 2H), 8.76 (s, 1H).

(2) 2-(4-Methoxybenzyloxy)-5-(4,4,5,5-tetramethyl-1,3,2-dioxaborolan-2-yl)-4-trifluoromethylpyrimidine (Prep 50-2)

Potassium acetate (9.3 g) and bis(pinacolato)diboron (9.63 g) were added to a 1,4-dioxane solution (130 ml) of the compound Prep 50-1 (11.5 g), and deaeration and nitrogen substitution were then performed on the obtained solution. Thereafter, 1,1-bis(diphenylphosphino)ferrocene dichloropalladium(II) was added to the reaction solution, and the obtained mixture was heated to reflux at 110° C. for 6 hours. Thereafter, the reaction mixture was moderately concentrated under reduced pressure, and 1,4-dioxane was distilled off. Then, ethyl acetate was added to the resultant product, and the reaction solution was then filtered. The filtrate was concentrated under reduced pressure, and the obtained residue was then purified by silica gel column chromatography (n-heptane:ethyl acetate=19:1 to 1:2), so as to obtain the title compound (8.0 g).

MS [M+H]$^+$=433.

(3) 2-(4-Methoxybenzyloxy)-4-trifluoromethylpyrimidin-5-ol (Prep 50-3)

A 30% hydrogen peroxide water (502 ul) and a 2 N sodium hydroxide aqueous solution (2.44 ml) were added to a THF solution (20 ml) of the compound Prep 50-2 (2 g) under cooling on ice, and the obtained mixture was then stirred for 15 minutes. Thereafter, the reaction solution was further stirred at room temperature for 30 minutes. Thereafter, a 1 N hydrochloric acid aqueous solution was added to the reaction mixture, and the pH of the mixed solution was adjusted around pH 5. Liquid separation and extraction were carried out on the reaction solution with diethyl ether. The obtained organic layer was dried over magnesium sulfate and was then concentrated under reduced pressure. The obtained residue was purified by silica gel column chromatography (n-heptane:ethyl acetate=9:1 to 1:1), so as to obtain the title compound (980 mg).

MS [M+Na]$^+$=323.

(4) (1R,2S)-2-(3,5-difluorophenyl)-2-[2-(4-methoxybenzyloxy)]-4-(trifluoromethylpyrimidin-5-yl)oxymethyl)cyclopropanecarboxylic acid (Prep 50-7)

The title compound was obtained from the compound Prep 49 and the compound Prep 50-3 according to the methods of Production Example 1,3-(4) to 13-(7).

MS [M+Na]$^+$=533.

PRODUCTION EXAMPLE 51

Synthesis of (1R,2S)-2-[2-(2,4-dimethylpyrimidin-5-yl)ethyl]-2-phenylcyclopropanecarboxylic acid (Prep 51-9)

[Formula 55]

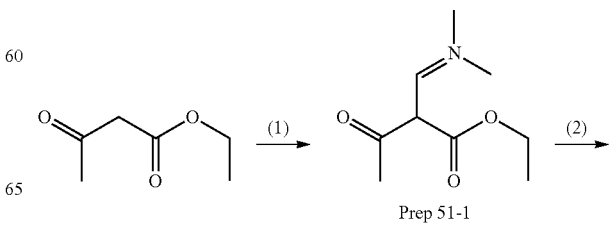

Prep 51-1

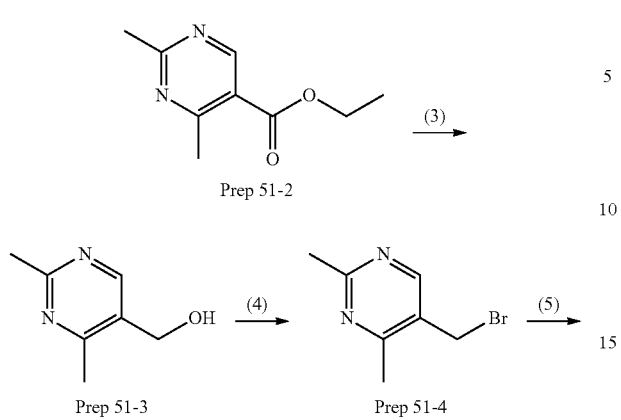

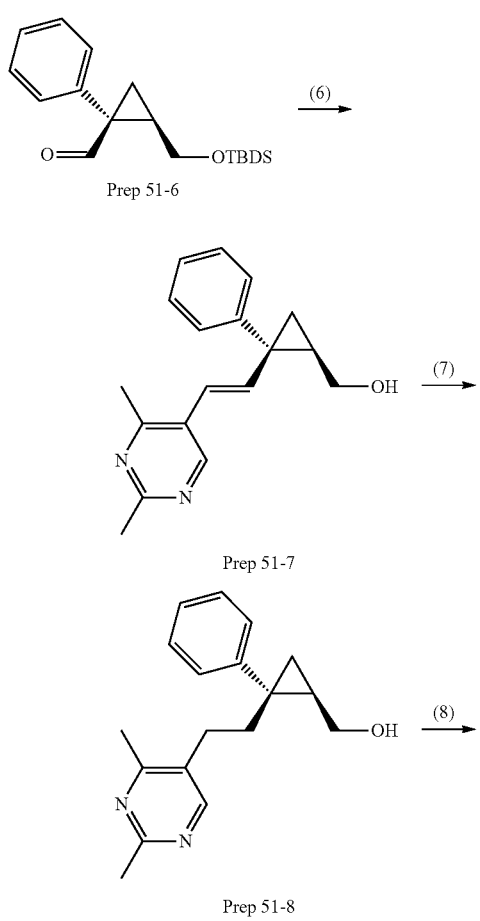

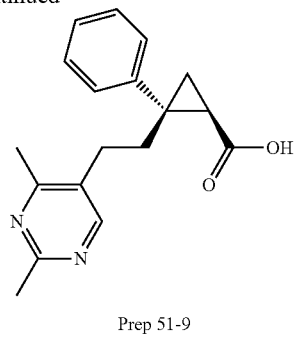

(1) Ethyl 2-[(dimethylamino)methylene]-3-oxobutanoate (Prep 51-1)

N,N-dimethylformamide dimethyl acetal (80.4 ml) was added dropwise to ethyl acetoacetate (63 g), and the obtained mixture was then stirred at room temperature for 14 hours. Thereafter, the reaction solution was concentrated under reduced pressure, and azeotropy with toluene was then performed three times, so as to obtain a crude title compound (89 g).

$^1$H-NMR (400 MHz, CDCl$_3$) δ (ppm): 1.33 (t, J=7.2 Hz, 3H), 2.33 (s, 3H), 3.07 (brs, 6H), 4.23 (q, J=7.2 Hz, 2H), 7.68 (s, 1H).

(2) Ethyl 2,4-dimethylpyrimidin-5-carboxylate (Prep 51-2)

The compound Prep 51-1 (10 g), acetamidine hydrochloride (5.11 g) and sodium ethoxide (3.67 g) were dissolved in ethanol (100 ml), and the obtained mixture was then stirred at 100° C. for 5 hours. Thereafter, the temperature of the reaction solution was returned to room temperature, and the reaction solution was then concentrated under reduced pressure. Water was added to the residue, and the obtained mixture was then extracted with ethyl acetate. The organic layer was washed with a saturated sodium chloride aqueous solution and was then dried over magnesium sulfate, followed by vacuum concentration, so as to obtain a crude title compound (8.76 g).

$^1$H-NMR (400 MHz, CDCl$_3$) δ (ppm): 1.41 (t, J=7.0 Hz, 3H), 2.75 (s, 3H), 2.80 (s, 3H), 4.40 (q, J=7.0 Hz, 2H), 9.05 (s, 1H).

(3) (2,4-Dimethylpyrimidin-5-yl)methanol (Prep 51-3)

A THF solution (30 ml) of the compound Prep 51-2 (8.76 g) was added dropwise to a THF suspension (50 ml) of lithium aluminum hydride (1.84 g), while the solution was stirred under cooling on ice. The obtained mixture was stirred at room temperature for 3 hours. Thereafter, while the reaction solution was stirred under cooling on ice, a 27% ammonia aqueous solution and Celite were successively added thereto, and the obtained mixture was then stirred for 30 minutes. Thereafter, magnesium sulfate was added to the reaction solution, followed by filtration. The filtrate was then concentrated under reduced pressure. The residue was purified by silica gel column chromatography (n-heptane:ethyl acetate (9:1 to 3:2) to ethyl acetate:methanol (9:1)) so as to obtain the title compound (670 mg).

¹H-NMR (400 MHz, CDCl₃) δ (ppm): 2.52 (s, 3H), 2.68 (s, 3H), 4.71 (s, 2H), 8.50 (s, 1H).

(4) 5-Bromomethyl-2,4-dimethylpyrimidine (Prep 51-4)

Phosphorus tribromide (0.912 ml) was added to a toluene dichloromethane solution (10 ml-5 ml) of the compound Prep 51-3 (670 mg), and the obtained mixture was then stirred at room temperature for 3 hours. Thereafter, ice was added to the reaction solution, while the solution was stirred under cooling on ice, and a saturated sodium bicarbonate aqueous solution was then added to the reaction solution. The obtained mixture was extracted with ethyl acetate. The obtained organic layer was washed with a saturated sodium chloride aqueous solution and was dried over magnesium sulfate, followed by vacuum concentration, so as to obtain a crude title compound (354 mg).
¹H-NMR (400 MHz, CDCl₃) δ (ppm): 2.58 (s, 3H), 2.70 (s, 3H), 4.44 (s, 2H), 8.48 (s, 1H).

(5) [(2,4-Dimethylpyrimidin-5-yl)methyl]triphenylphosphonium bromide (Prep 51-5)

Triphenylphosphine (462 mg) was added to a toluene solution (15 ml) of the compound Prep 51-4 (354 mg), and the obtained mixture was then stirred at 140° C. for 5 hours. The temperature of the reaction solution was returned to room temperature, and a precipitated solid was then collected by filtration, followed by washing with tert-butyl methyl ether, so as to obtain the title compound (610 mg).
¹H-NMR (400 MHz, CDCl₃) δ (ppm): 1.87 (d, J=1.2 Hz, 3H), 2.62 (d, J=1.6 Hz, 3H), 5.68 (d, J=14.4 Hz, 2H), 7.64-7.75 (m, 6H), 7.77-7.88 (m, 9H), 8.36 (d, J=2.4 Hz, 1H).

(6) (1R,2S)-2-[(E,Z)-2-(2,4-dimethylpyrimidin-5-yl)vinyl]-2-phenylcyclopropylmethanol (Prep 51-7)

To a THF solution (7 ml) of the compound Prep 51-5 (610 mg), n-butyllithium (2.64 M n-hexane solution: 0.5 ml) was added, while stirring at −78° C. The obtained mixture was stirred at the same temperature as described above for 30 minutes. Thereafter, a THF solution (4 ml) of the (1S,2R)-2-(tert-butyldiphenylsilyloxymethyl)-1-phenylcyclopropanecarbaldehyde (Prep 51-6, 602 mg) that had been obtained from the compound Prep 13-3 according to the method of Production Example 5,3-(1) was added to the reaction solution, and the obtained mixture was then stirred at 0° C. for 4 hours. Thereafter, water and a small amount of acetic acid were added to the reaction solution, and the obtained mixture was then extracted with ethyl acetate. The obtained organic layer was washed with a saturated sodium chloride aqueous solution and was then dried over magnesium sulfate, followed by vacuum concentration. The residue was purified by silica gel column chromatography (n-heptane:ethyl acetate=1:0 to 4:1). The obtained compound was dissolved in THF (10 ml), and tetrabutyl ammonium fluoride (1 M THF solution: 2.64 ml) was then added to the obtained solution. The obtained mixture was stirred at room temperature for 12 hours. Thereafter, the reaction solution was concentrated under reduced pressure, and the residue was then purified by silica gel column chromatography (n-heptane:ethyl acetate (9:1 to 0:1) to ethyl acetate:methanol (19:1)), so as to obtain the title compound (113 mg).
MS [M+H]⁺=281

(7) (1R,2S)-2-[2-(2,4-dimethylpyrimidin-5-yl)ethyl]-2-phenylcyclopropylmethanol (Prep 51-8)

10% palladium-carbon (water content: 50%, 100 mg) was added to an ethyl acetate solution (20 ml) of the compound Prep 51-7 (113 mg), and catalytic hydrogen reduction was then carried out on the obtained solution at room temperature at an ordinary pressure for 30 minutes. Thereafter, the reaction solution was filtered with Celite, and the filtrate was then concentrated under reduced pressure, so as to obtain a crude title compound (80 mg).
MS [M+H]⁺=283

(8) (1R,2S)-2-[2-(2,4-dimethylpyrimidin-5-yl)ethyl]-2-phenylcyclopropanecarboxylic acid (Prep 51-9)

The title compound was synthesized from the compound Prep 51-8 according to the method of Production Examples 13-(6) and 13-(7).
MS [M+H]⁺=297

PRODUCTION EXAMPLE 52

Synthesis of 2,4-dimethylpyrimidin-5-amine (Prep 52-2)

The starting substance was synthesized according to the method described in Heterocycles, 57(11), 2045-2064, 2002.

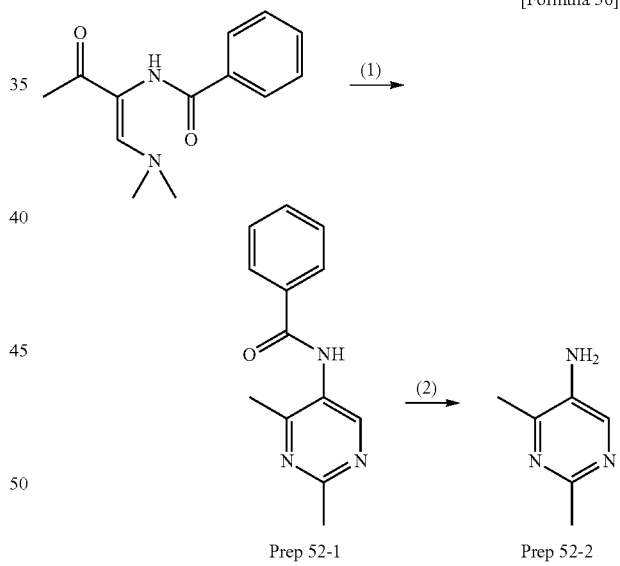

[Formula 56]

Prep 52-1          Prep 52-2

(1) N-(2,4-dimethylpyrimidin (Prep 52-1)

Acetamidine hydrochloride (8.31 g) and potassium carbonate (6.06 g) were added to an ethanol solution (55.6 ml) of N-{(1Z)-1-[(dimethylamino)methylene]-2-oxopropyl}benzamide (6.8 g), and the temperature of the obtained mixture was then heated to 70° C., followed by stirring for 15 hours. Thereafter, the reaction solution was concentrated under reduced pressure, and the residue was then purified by silica gel column chromatography (n-heptane:ethyl acetate=4:1 to 0:10), so as to obtain the title compound (4.1 g).

$^1$H-NMR (400 MHz, CDCl$_3$) δ (ppm): $^1$H-NMR (400 MHz, CDCl$_3$) δ (ppm): 2.53 (s, 3H), 2.72 (s, 3H), 7.44-7.64 (m, 3H), 7.89-7.92 (m, 2H), 8.01 (s, 1H).

(2) 2,4-Dimethylpyrimidin-5-amine (Prep 52-2)

The compound Prep 52-1 (4.0 g) was dissolved in an ethanol (20 ml)-2 N sodium hydroxide aqueous solution (20 ml), and the obtained solution was then stirred at 70° C. for 1 day. Thereafter, the reaction solution was extracted with ethyl acetate and chloroform, and the organic layer was then dried over magnesium sulfate, followed by filtration. The organic layer was concentrated under reduced pressure, so as to obtain the title compound (1.63 g).

$^1$H-NMR (400 MHz, CDCl$_3$) δ (ppm) $^1$H-NMR (400 MHz, CDCl$_3$) δ (ppm): 2.38 (s, 3H), 2.59 (s, 3H), 3.52 (brs, 2H), 8.01 (s, 1H).

PRODUCTION EXAMPLE 53

Synthesis of (1R,2S)-2-{[(2,4-dimethylprymidin-5-yl)(methyl)amino]methyl}-2-(3-fluorophenyl)cyclopropanecarboxylic acid (Prep 53-6)

[Formula 57]

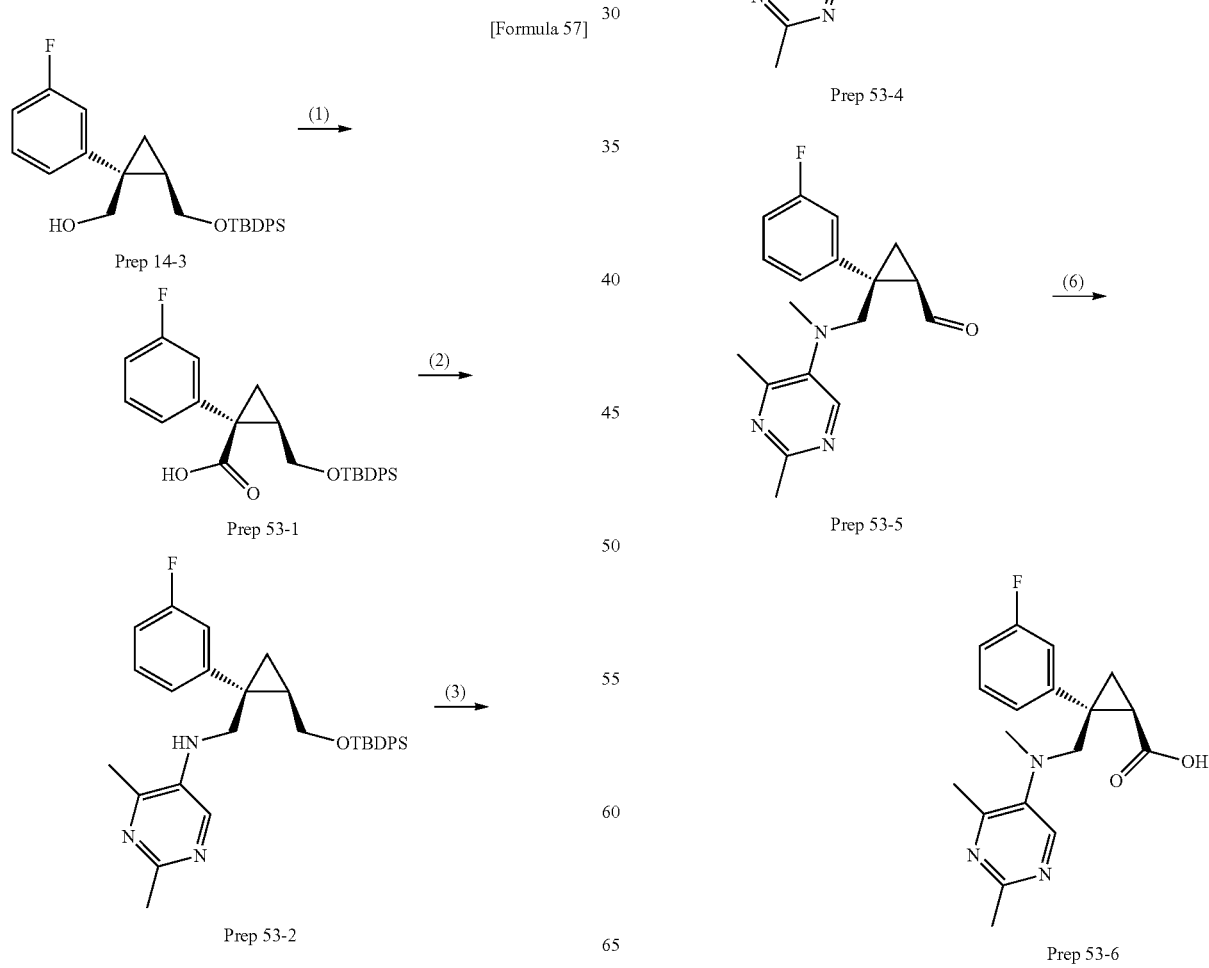

(1) (1R,2S)-2-(tert-butyldiphenylsilyloxymethyl)-1-(3-fluorophenyl)cyclopropanecarbaldehyde (Prep 53-1)

A dichloromethane solution (50 ml) of oxalyl chloride (1.26 ml) was cooled to −78° C., and a dichloromethane solution (10 ml) of dimethyl sulfoxide (2.04 ml) was then added dropwise to the reaction solution. Fifteen minutes later, a dichloromethane solution (12 ml) of the compound Prep 14-3 (3.0 g) was added dropwise to the reaction solution at −78° C., and the obtained mixture was then stirred at the same temperature as described above for 60 minutes. Thereafter, triethylamine (8.03 ml) was added to the reaction solution, and the temperature of the obtained mixture was then raised to 0° C., followed by stirring for 2 hours. Thereafter, a saturated ammonium chloride aqueous solution was added to the reaction solution, and the obtained mixture was then extracted with ethyl acetate. The organic layer was washed with a saturated sodium bicarbonate aqueous solution and a saturated sodium chloride aqueous solution. The organic layer was dried over anhydrous magnesium sulfate and was then filtered. The filtrate was concentrated under reduced pressure, and the residue was then purified by silica gel column chromatography (n-heptane:ethyl acetate=10:0 to 4:1), so as to obtain the title compound (3.7 g).
$^1$H-NMR (400 MHz, CDCl$_3$) δ (ppm): $^1$H-NMR (400 MHz, CDCl$_3$) δ (ppm): 1.07 (s, 9H), 1.53 (dd, J=8.2, 4.8 Hz, 1H), 1.76 (dd, J=7.2, 5.2 Hz, 1H), 1.90-2.10 (m, 1H), 3, 68 (dd, J=12.4, 9.6 Hz, 1H), 4.08 (dd, J=11.6, 9.6 Hz, 1H), 6.98-7.16 (m, 3H), 7.46-7.63 (m, 7H), 7.64-7.73 (m, 4H), 9.59 (s, 1H).

(2) N[(1S,2R)-2-(tert-butyldiphenylsilyloxmethyl)-1-(3-fluorophenyl)cyclopropylmethyl}-2,4-dimethylpyrimidin-5-amine (Prep 53-2)

Acetic acid (1.5 ml) was added to a chloroform solution (60 ml) of the compound Prep 53-1 (3.7 g) and the compound Prep 52-2 (1.37 g), and the obtained mixture was then stirred at room temperature for 30 minutes. Thereafter, sodium triacetoxyborohydride (5.44 g) was added to the reaction solution, and the obtained mixture was then stirred for 15 hours. Thereafter, a saturated sodium bicarbonate aqueous solution was added to the reaction solution, and the obtained mixture was then extracted with ethyl acetate. The resultant extract was dried over anhydrous magnesium sulfate. The solvent was distilled off under reduced pressure, and the residue was then purified by silica gel column chromatography (n-heptane:ethyl acetate=9:1 to 0:10), so as to obtain the title compound (4.26 g).
$^1$H-NMR (400 MHz, CDCl$_3$) δ (ppm): $^1$H-NMR (400 MHz, CDCl$_3$) δ (ppm): 0.75 (t, J=5.2 Hz, 1H), 1.09-1.13 (m, 1H), 1.11 (s, 9H), 1.54-1.62 (m, 1H), 2.08 (s, 3H), 2.56 (s, 3H), 3, 32 (d, J=12.8 Hz, 1H), 3.50 (d, J=12.8 Hz, 1H), 3.59 (dd, J=11.6, 10.0 Hz, 1H), 4.16 (dd, J=11.6, 6.0 Hz, 1H), 6.90-6.96 (m, 1H), 7.04-7.08 (m, 1H), 7.13-7.16 (m, 1H), 7.25-7.47 (m, 7H), 7.63-7.69 (m, 4H), 7.79 (s, 1H).

(3) N-{[(1S,2R)-2-(tert-butyldiphenylsilyloxymethyl)-1-(3-fluorophenyl)cyclopropylmethyl}-N,2,4-trimethylpyrimidin-5-amine (Prep 53-3)

Formaldehyde (1.59 ml) and sodium triacetoxyborohydride (3.71 g) were added to an acetonitrile solution (30 ml) of the compound Prep 53-2 (4.62 g), and the obtained mixture was then stirred for 1 hour. Thereafter, formaldehyde (1.59 ml) and sodium triacetoxyborohydride (3.71 g) were further added to the reaction solution, and the obtained mixture was then stirred for 30 minutes. Thereafter, a saturated sodium bicarbonate aqueous solution was added to the reaction solution, and the obtained mixture was then extracted with ethyl acetate. The resultant extract was dried over anhydrous magnesium sulfate. The solvent was distilled off under reduced pressure, and the residue was then purified by silica gel column chromatography (n-heptane:ethyl acetate=9:1 to 0:10), so as to obtain the title compound (4.26 g).
MS [M+H]$^+$=555

(4) (1R,2S)-2-{[(2,4-dimethylpyrimidin-5-yl)(methyl)amino]methyl}-2-(3-fluorophenyecyclopropyl] methanol (Prep 53-4)

Tetrabutylammonium fluoride (1 M THF solution: 17.5 ml) was added dropwise to a THF solution (30 ml) of the compound Prep 53-3 (3.23 g) at room temperature, and the obtained mixture was then stirred at room temperature for 17 hours. Thereafter, the reaction solution was concentrated under reduced pressure, the residue was then purified by silica gel column chromatography (n-heptane:ethyl acetate=1:1 to 0:10), so as to obtain the title compound (1.84 g).
$^1$H-NMR (400 MHz, CDCl$_3$) δ (ppm): $^1$H-NMR (400 MHz, CDCl$_3$) δ (ppm): 0.80 (t, J=5.2 Hz, 1H), 1.18 (dd, J=9.2, 5.2 Hz, 1H), 1.54-1.64 (m, 1H), 2.20 (s, 3H), 2.57 (s, 3H), 2.69 (s, 3H), 3, 35 (d, J=13.6 Hz, 1H), 3.47 (d, J=13.6 Hz, 1H), 3.60 (dd, J=11.6, 9.2 Hz, 1H), 4.03 (dd, J=11.6, 9.2 Hz, 1H), 6.82-6.87 (m, 1H), 6.92-6.96 (m, 1H), 7.01-7.04 (m, 1H), 7.13-7.19 (m, 1H), 8.10 (s, 1H).

(5) [1R,2S)2-{[(2,4-dimethylpryimidin-5-yl)(methyl)amino]methyl}-2-(3-fluorophenyl)cyclopropanecarbaldehyde (Prep 53-5)

A dichloromethane solution (40 ml) of oxalyl chloride (343 ul) was cooled to −78° C., and a dichloromethane solution (10 ml) of dimethyl sulfoxide (560 ul) was then added dropwise thereto. Thirty minutes later, a dichloromethane solution (9.6 ml) of the compound Prep 53-4 (620 mg) was added dropwise to the reaction solution at −78° C., and the obtained mixture was then stirred at the same temperature as described above for 30 minutes. Thereafter, triethylamine (8.03 ml) was added to the reaction solution, and the obtained mixture was then stirred for 30 minutes. Thereafter, the temperature of the reaction solution was raised to 0° C., and the reaction solution was then stirred for 2 hours. Thereafter, a saturated sodium bicarbonate aqueous solution was added to the reaction solution, and the obtained mixture was then extracted with ethyl acetate. The organic layer was washed with a saturated sodium chloride aqueous solution. The organic layer was dried over anhydrous magnesium sulfate and was then filtered. The filtrate was concentrated under reduced pressure, and the residue was then purified by silica gel column chromatography (n-heptane:ethyl acetate=2:3 to 0:10), so as to obtain the title compound (617 mg).
$^1$H-NMR (400 MHz, CDCl$_3$) δ (ppm): $^1$H-NMR (400 MHz, CDCl$_3$) δ (ppm): 1.60-1.67 (m, 1H), 1.78 (t, J=5.6 Hz, 1H), 2.08 (s, 3H), 2, 262.32 (m, 1H), 2.58 (s, 3H), 2.66 (s, 3H), 3, 42 (d, J=14.0 Hz, 1H), 3.53 (d, J=14.0 Hz, 1H) 6.91-7.06 (m, 3H), 7.21-7.27 (m, 1H), 8.07 (s, 1H), 9.74 (d, J=4.0 Hz, 1H).

(6) (1R,2S)-2-{[(2,4-dimethylpyrimidin-5-yl)(methyl)amino]methyl}-2-(3-fluorophenyl)cyclopropanecarboxylic acid (Prep 53-6)

2-Methyl-2-butene (1.08 ml), anhydrous sodium dihydrogen phosphate (731 mg) and sodium chlorite (367 mg) were added to an acetone-water solution (10 ml) of the compound Prep 53-5 (617 mg) at room temperature, and the obtained mixture was then stirred for 2 hours. Thereafter, the reaction solution was extracted with ethyl acetate, and the organic layer was then washed with a saturated sodium chloride aqueous solution. The organic layer was dried over anhydrous magnesium sulfate and was then filtered. The filtrate was concentrated under reduced pressure, and the residue was then purified by silica gel column chromatography (n-heptane:ethyl acetate=1:4 to ethyl acetate:methanol=4:1), so as to obtain the title compound (632 mg).

$^1$H-NMR (400 MHz, CDCl$_3$) δ (ppm): $^1$H-NMR (400 MHz, CDCl$_3$) δ (ppm): 1.60-1.63 (m, 2H), 2.03-2.08 (m, 1H), 2.08 (s, 3H), 2.60 (s, 3H), 2.66 (s, 3H), 3, 56 (d, J=12.8 Hz, 1H), 3.64 (d, J=12.8 Hz, 1H), 6.91-6.97 (m, 1H), 7.04-7.08 (m, 1H), 7.11-7.14 (m, 1H), 7.23-7.29 (m, 1H), 8.39 (s, 1H).

PRODUCTION EXAMPLE 54

Synthesis of (1R,2S)-2-[(2,4-dimethoxypyrimidin-5-yl)(methyl)amino]methyl-2-phenylcyclopropanecarboxylic acid (Prep 54)

The title compound was synthesized in the same manner as that of Production Example 53.

[Formula 58]

Prep 54

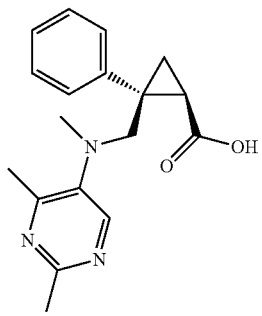

MS [M+H]$^+$-312

PRODUCTION EXAMPLE 55

Synthesis of (1S,2R)-2-[(tert-butoxycarbonyl)(2-methyl-4-trifluoromethylpyrimidin-5-yl)amino]methyl-2-(3-fluorophenyl)cyclopentanecarboxylic acid (Prep 55-6)

[Formula 59]

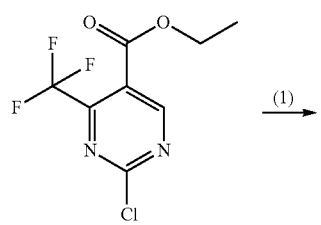

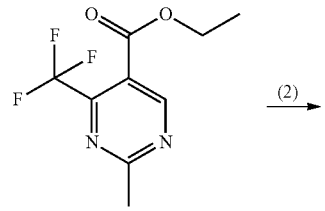

Prep 55-1

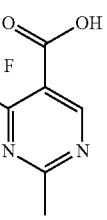

Prep 55-2

Prep 55-3

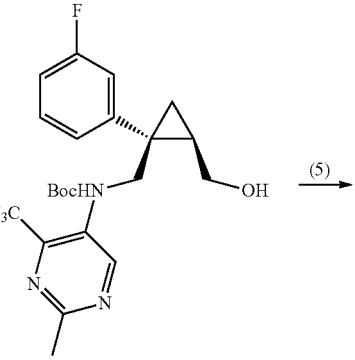

Prep 55-4

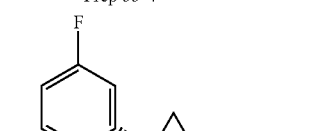

Prep 55-5

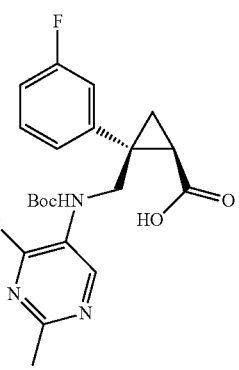

Prep 55-6

(1) Ethyl 2-methyl-4-trifluoromethylpyrimidinecarboxylate (Prep 55-1)

Ethyl 2-chloro-4-(trifluoromethyl)pyrimidin-5-carboxylate (9.7 g) was dissolved in THF (100 ml), and thereafter, trimethylaluminum (38.1 ml, 2 M) and tetrakis(triphenylphosphine)palladium(0) were added to the obtained solution. The obtained mixture was stirred at 70° C. overnight. Thereafter, the reaction mixture was cooled to room temperature, and a saturated ammonium chloride aqueous solution and a 5 N hydrochloric acid aqueous solution were added dropwise to the reaction solution under cooling on ice. Thereafter, water was added to the reaction solution at a time point at which foaming was terminated, and liquid separation and extraction were then carried out with ethyl acetate. The organic layer was dried over magnesium sulfate, and the solvent was then concentrated under reduced pressure. The residue was purified by silica gel column chromatography (n-heptane:ethyl acetate=19:1 to 2:1), so as to obtain the title compound (8.1 g).

MS [M+H]$^+$=235.

(2) 2-Methyl-4-trifluoromethylpyrimidin-5-carboxylate (Prep 55-2)

A 2 N sodium hydroxide aqueous solution (26 ml) was added to a THF-ethanol solution (80 ml-20 ml) of the compound Prep 55-1 (8.1 g), and the obtained mixture was then stirred at room temperature for 2 hours. Thereafter, termination of the reaction was confirmed by LC-MS, and a 1 N hydrochloric acid aqueous solution was then added to the reaction solution to neutralize it. Subsequently, the reaction solution was concentrated under reduced pressure, and THF and ethanol were then distilled off. A 2 N hydrochloric acid aqueous solution was added to the residue to adjust the pH value thereof to pH 2 to 3, and liquid separation and extraction were then carried out with ethyl acetate. The organic layer was dried over magnesium sulfate. The solvent was concentrated under reduced pressure, so as to obtain a crude title compound (6.2 g).

MS [M+H]$^+$=207.

(3) Tert-butyl(2-methyl-4-trifluoromethylpyrimidin-5-yl)carbamate (Prep 55-3)

Triethylamine (10.3 ml) and diphenylphosphoryl azide (9.55 ml) were added to a toluene-tert-butanol solution (50 ml-50 ml) of the compound Prep 55-2 (6.2 g). The obtained mixture was stirred at 100° C. overnight. Thereafter, the reaction mixture was cooled, and water was then added thereto, followed by vacuum concentration. A saturated sodium bicarbonate aqueous solution was added to the residue, and liquid separation and extraction were then carried out with ethyl acetate. The obtained organic layer was dried over magnesium sulfate and was then concentrated under reduced pressure. The obtained residue was purified by silica gel column chromatography (n-heptane:ethyl acetate=19:1 to 3:1), so as to obtain the title compound (8.0 g).

MS [M+H]$^+$=278.

(4) Tert-butyl{[(1S,2R)-1-(3-fluorophenyl)-2-hydroxymethylcyclopropyl]methyl}(2-methyl-4-trifluoromethylpyrimidin-5-yl)carbamate (Prep 55-4)

Triethylamine (322 ul) and methane sulfonyl chloride (171 ul) were added to a dichloromethane solution (6.0 ml) of the compound Prep 49 (500 mg) under cooling on ice, and the obtained mixture was then stirred at room temperature for 1 hour. Thereafter, water was added to the reaction mixture, and liquid separation and extraction were then carried out with dichloromethane. The obtained organic layer was dried over magnesium sulfate and was then concentrated under reduced pressure, so as to obtain a crude product. Thereafter, cesium carbonate and the compound Prep 55-3 (699 mg) were added to an acetonitrile solution (10 ml) of the crude product, and the obtained mixture was then stirred at 80° C. overnight. Thereafter, the reaction mixture was cooled, and water was then added thereto. Subsequently, liquid separation and extraction were carried out with ethyl acetate. The obtained organic layer was dried over magnesium sulfate and was then concentrated under reduced pressure. The obtained residue was dissolved in methanol (5 ml), and a 1 N sodium hydroxide aqueous solution (1.26 ml) was then added to the solution, followed by stirring at room temperature for 30 minutes. Thereafter, water was added to the reaction mixture, and liquid separation and extraction were then carried out with ethyl acetate. The obtained organic layer was dried over magnesium sulfate and was then concentrated under reduced pressure. The residue was purified by silica gel column chromatography (n-heptane:ethyl acetate=19:1 to 1:1), so as to obtain the title compound (200 mg).

MS [M+Na]$^+$=478.

(5) Tert-butyl{[(1S,2R)-1-(3-fluorophenyl)-2-formylcyclopropyl]methyl}(2-methyl-4-trifluoromethylpyrimidin-5-yl)carbamate (Prep 55-5)

A Dess-Martin reagent was added to a dichloromethane solution (5 ml) of the compound Prep 55-4 (200 mg) under cooling on ice. The obtained mixture was stirred for 1 hour, and a mixed solution of a sodium bicarbonate aqueous solution and a sodium sulfite aqueous solution was then added to the reaction mixture. The obtained mixture was stirred until it became transparent. The reaction mixture was subjected to liquid separation and extraction with dichloromethane. The obtained organic layer was dried over magnesium sulfate and was then concentrated under reduced pressure. The residue was purified by silica gel column chromatography (n-heptane:ethyl acetate=4:1 to 1:1), so as to obtain the title compound (180 mg).

MS [M+Na]$^+$=476.

(6) (1S,2R)-2-[(tert-butoxycarbonyl)(2-methyl-4-trifluoromethylpyrimidin-5-yl)amino]methyl-2-(3-fluorophenyl)cyclopropanecarboxylic acid (Prep 55-6)

2-Methyl-2-butene (210 ul), sodium dihydrogen phosphate (57.2 mg) and sodium chlorite (53.9 mg) were added to an acetone-water mixed solvent (4 ml-2 ml) of the compound Prep 55-5 (180 mg). The obtained mixture was stirred at room temperature for 1 hour. Thereafter, water was added to the reaction solution, and liquid separation and extraction were then carried out with dichloromethane. The obtained organic layer was dried over magnesium sulfate. The organic layer was dried over anhydrous magnesium sulfate and was then filtered. The filtrate was concentrated under reduced pressure, so as to obtain a crude product of the title compound (186 mg).

MS [M+Na]$^+$=492.

The compound of Production Example 56 (Prep 56) was produced according to the method of Production Example 13. However, an alcohol corresponding to Prep 13-5 was synthesized from a diol corresponding to Prep 13-2 according to the method of Production Example 49.

TABLE 8

| Production example | Structural formula | NMR (400 MHz, CDCl$_3$) and/or MS |
|---|---|---|
| Prep 56 | | $^1$H-NMR (400 MHz, CDCl$_3$) δ (ppm): 1.52-1.59 (m, 1H), 1.73-1.78 (m, 1H), 2.22-2.27 (m, 1H), 2.37 (s, 3H), 2.58 (s, 3H), 4.47 (s, 2H), 7.11 (t, J = 7.8 Hz, 1H), 7.43-7.48 (m, 1H), 7.62-7.67 (m, 1H), 7.89 (t, J = 1.6 Hz, 1H), 8.22 (s, 1H) MS [M + H]$^+$ = 425 |

EXAMPLE 1

Synthesis of (1R,2S)-2-{[(2,4-dimethylpyrimidin-5-yl)oxy]methyl}-N-(5-fluoropyridin-2-yl)-2-phenyl-cyclopropanecarboxamide (1)

[Formula 60]

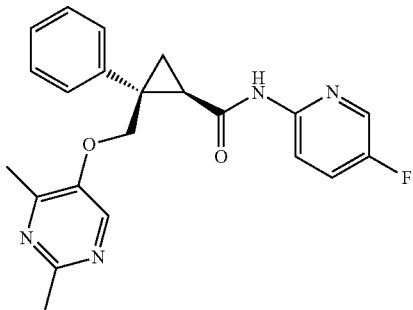

The carboxylic acid Prep 13-7 (639 mg) was dissolved in dichloromethane (10 ml), and thereafter, oxalyl chloride (367 ul) and DMF (a catalytic amount) were added to the solution. The reaction solution was stirred at room temperature for 1 hour. Thereafter, the reaction solution was concentrated under reduced pressure to obtain a crude acid chloride. Subsequently, diisopropylethylamine (848 ul) was added to a THF solution (10.0 ml) of 2-amino-5-fluoropyridine (360 mg), and the temperature of the obtained mixture was then heated to 60° C. A THF solution (5.0 ml) of the crude acid chloride was added dropwise to the reaction solution, and the obtained mixture was then stirred at the same temperature as described above for 1 hour. Thereafter, the reaction mixture was cooled to room temperature, and it was then stirred for 1 hour. Thereafter, the reaction solution was concentrated under reduced pressure, and it was then distributed to ethyl acetate and water, so as to separate an organic layer. The organic layer was dried over anhydrous magnesium sulfate, and the filtrate was then concentrated under reduced pressure. The residue was purified by NH-silica gel column chromatography (n-heptane:ethyl acetate=19:1 to 3:2). Then, diethyl ether was added to the obtained product of interest. The precipitated solid was collected by filtration and was then dried, so as to obtain the title compound (418 mg).

$^1$H-NMR (400 MHz, CDCl$_3$) δ (ppm): 1.60-1.64 (m, 1H), 1.90 (t, J=5.2 Hz, 1H), 2.12 (brt, 1H), 2.20 (s, 3H), 2.54 (s, 3H), 4.40 (d, J=9.2 Hz, 1H), 4.51 (d, J=9.2 Hz, 1H), 7.26-7.47 (m, 6H), 7.96 (s, 1H), 8, 06-8.12 (m, 2H), 8.33 (brs, 1H).

MS [M+H]$^+$=393

* The compounds of Examples 2 to 45 were synthesized by reacting the carboxylic acid Prep 13-7 with any amine by the same method as that of Example 1.

TABLE 9

| Example | Structural formula | NMR(400 MHz, CDCl$_3$) and/or MS |
|---|---|---|
| 2 | | $^1$H-NMR δ (ppm): 1.78 (dd, J = 8.0, 5.6 Hz, 1H), 2.01 (t, J = 5.6 Hz, 1H), 2.17 (s, 3H), 2.18 (s, 3H), 2.25 (brt, 1H), 2.57 (s, 3H), 4.44 (d, J = 9.6 Hz, 1H), 4,63 (d, J = 9.6 Hz, 1H), 6.46 (brs, 1H), 7.32-7.41 (m, 3H), 7.44-7.47 (m, 2H), 8.02 (s, 1H). MS [M + H]$^+$ = 395 |

TABLE 9-continued

| Example | Structural formula | NMR(400 MHz, CDCl₃) and/or MS |
|---|---|---|
| 3 | 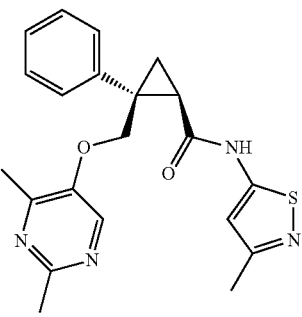 | $^1$H-NMR δ (ppm): 1.72 (dd, J = 8.0, 5.6 Hz, 1H), 1.98(t, J = 5.6 Hz, 1H), 2.16 (dd, J = 8.0, 5.6 Hz, 1H), 2.20 (s, 3H), 2.41 (s, 3H), 2.56 (s, 3H), 4.43 (d, J = 9.6 Hz, 1 H), 4.52 (d, J = 9.6 Hz, 1H), 6.59 (s, 1H), 7.30-7.38 (m, 3H), 7.42-7.45 (m, 2H), 7.98 (s, 1H), 8.91 (brs, 1 H).<br>MS [M + H]⁺ = 395 |
| 4 | 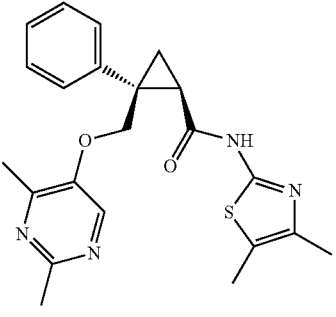 | $^1$H-NMR δ (ppm): 1.66 (dd, J = 8.0, 5.6 Hz, 1H), 1.94 (t, J = 5.6 Hz, 1H), 2.09 (dd, J = 8.0, 5.6 Hz, 1H), 2.15 (brs, 3H), 2.21 (s, 3H), 2.23 (s, 3H), 2.55 (s, 3H) 4.40 (d, J = 9.6 Hz, 1H), 4.50 (d, J = 9.6 Hz, 1H), 7.29-7.42 (m, 5H), 7.97(s, 1H).<br>MS [M + H]⁺ = 409 |
| 5 | 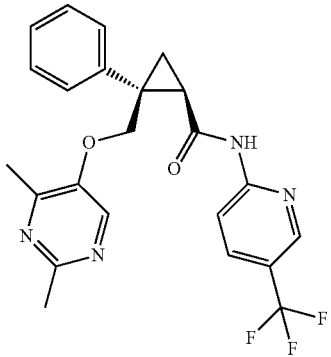 | $^1$H-NMR δ (ppm): 1.67 (dd, J = 8.0, 5.6 Hz, 1H), 1.94 (t, J = 5.6 Hz, 1H), 2.16 (dd, J = 8.0, 5.6Hz, 1H), 2.22(s, 3 H), 2.55 (s, 3H), 4.41 (d, J = 9.6 Hz, 1H), 4.51 (d, J = 9.6 Hz, 1H), 7.36-7.40 (m, 3H), 7.46-7.48 (m, 2H), 7.88 (dd, J = 8.6, 2.4 Hz, 1H), 7.97 (s, 1H), 8.21 (d, J = 8.6 Hz, 1H), 8.41 (brs, 1H), 8.54-8.55 (m, 1H).<br>MS [M + H]⁺ = 443 |

TABLE 10

| Example | Structural formula | NMR(400 MHz, CDCl₃) and/or MS |
|---|---|---|
| 6 | 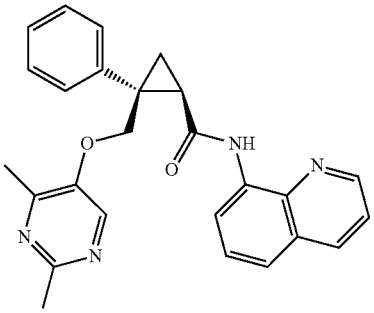 | $^1$H-NMR δ (ppm): 1.66 (dd, J = 8.2, 5.0 Hz, 1H), 1.97 (dd, J = 5.8, 5.0 Hz, 1H), 2.08 (s, 3H), 2.40 (dd, J = 8.2, 5.8 Hz, 1H), 2.51 (s, 3H), 4.51 (d, J = 9.6 Hz, 1H), 4.59 (d, J = 9.6 Hz, 1H), 7.29-7.34 (m, 1H), 7.37-7.42 (m, 2 H), 7.47-7.55 (m, 5H), 7.99 (s, 1H), 8.18 (dd, J = 8.2, 1.8 Hz, 1H), 8.62 (dd, J = 6.2, 2.6 Hz, 1H), 8.84 (dd, J = 4.2, 1.8 Hz, 1H), 10.21 (brs, 1H).<br>MS [M + Na]⁺ = 447 |

TABLE 10-continued

| Example | Structural formula | NMR(400 MHz, CDCl₃) and/or MS |
|---|---|---|
| 7 | | MS [M + H]⁺ = 425 |
| 8 | | ¹H-NMR δ (ppm): 1.67 (dd, J = 8.0, 5.6 Hz, 1H), 1.96 (t, J = 5.6 Hz, 1H), 2.15 (dd, J = 8.0, 5.6 Hz, 1H), 2.21 (s, 3H), 2.53 (s, 3H), 4.52 (d, J = 9.6 Hz, 1H), 4.59 (d, J = 9.6 Hz, 1H), 7.29-7.40 (m, 4H), 7.47-7.49 (m, 2H), 7.54 (dd, J = 8.8, 2.4 Hz, 1H), 7.90 (brs, 1H), 8.02-8.08 (m, 3H), 8.27 (d, J = 1.8 Hz, 1H), 8.83 (dd, J = 4.0, 1.8 Hz, 1H).<br>MS [M + Na]⁺ = 447 |
| 9 | | MS [M + H]⁺ = 425 |

TABLE 11

| Example | Structural formula | NMR(400 MHz, CDCl₃) and/or MS |
|---|---|---|
| 10 | | ¹H-NMR δ (ppm): 1.66 (dd, J = 8.0, 5.6 Hz, 1H), 1.93 (t, J = 5.6 Hz, 1H), 2.15 (dd, J = 8.0, 5.6Hz, 1H), 2.20 (s, 3H), 2.54 (s, 3H), 4.42 (d, J = 9.6 Hz, 1H), 4.51 (d, J = 9.6 Hz, 1H), 7.24-7.39 (m, 4H), 7.45-7.48 (m, 2H), 7.97 (s, 1H), 8.36 (brs, 1H), 8.43-8.44 (m, 2H). |

TABLE 11-continued

| Example | Structural formula | NMR(400 MHz, CDCl$_3$) and/or MS |
|---|---|---|
| 11 | | $^1$H-NMR δ (ppm): 1.63 (dd, J = 8.0, 5.6 Hz, 1H), 1.91 (t, J = 5.6 Hz, 1H), 2.11-2.15 (m, 1H), 2.23 (s, 3H), 2.56 (s, 3H), 3.87 (s, 3H), 4.43 (d, J = 9.6 Hz, 1H), 4.55 (d, J = 9.6 Hz, 1H), 6.48 (d, J = 8.8 Hz, 1H), 7.28-7.39 (m, 3H), 7.46-7.56 (m, 4H), 7.98-8.00 (m, 2H). MS [M + H]$^+$ = 405 |
| 12 | | $^1$H-NMR δ (ppm): 1.62 (dd, J = 8.0, 5.2Hz, 1H), 1.91(t, J = 5.2 Hz, 1H), 2.09 (brt, 1H), 2.22 (s, 3H), 2.55 (s, 3H), 4.38 (d, J = 9.4 Hz, 1H), 4.47 (d, J = 9.4 Hz, 1H), 7.06 (d, J = 8.0 Hz, 1H), 7.30-7.38 (m, 3H), 7.45-7.46 (m, 2H), 7.62 (t, J = 8.0 Hz, 1H), 7.95 (s, 1H), 7.99 (d, J = 8.0 Hz, 1H), 8.25 (brs, 1H). MS [M + H]$^+$ = 409 |
| 13 | | $^1$H-NMR δ (ppm): 1.65 (t, J = 6.0 Hz, 1H), 1.95 (t, J = 6.0 Hz, 1H), 2.16 (t, J = 6.0 Hz, 1H), 2,21 (s, 3H), 2.5 2 (s, 3H), 4.50 (d, J = 9.4 Hz, 1H), 4.58 (d, J = 9.4 Hz, 1H), 7.28-7.36 (m, 3H), 7.44-7.46 (m, 2H), 7.58 (d, J = 5.8 Hz, 1H), 7.64-7.66 (m, 1H), 7.76 (d, J = 8.8 Hz, 1H), 8.01 (s, 1H), 8.27 (brs, 1H), 8.45 (d, J = 5.8 Hz, 1H), 9.14 (brs, 1H). MS [M + H]$^+$ = 425 |

TABLE 12

| Example | Structural formula | NMR (400 MHz, CDCl$_3$) and/or MS |
|---|---|---|
| 14 | | $^1$H-NMR δ (ppm): 1.62 (dd, J = 8.0, 5.2 Hz, 1H), 1.91 (t, J = 5.2 Hz, 1H), 2.12-2.15 (m, 1H), 2.20 (s, 3H), 2.54 (s, 3H), 3.39 (s, 3H), 4.41-4.43 (m, 3H), 4.51 (d, J = 9.2 Hz, 1H), 7.03-7.04 (m, 1H), 7.27-7.38 (m, 3H), 7.44-7.47 (m, 2H), 7.97 (s, 1H), 8.00 (brs, 1H), 8.22 (d, J = 5.2 Hz, 1H), 8.48 (brs, 1H). MS[M + H]$^+$ = 419 |

TABLE 12-continued
| Example | Structural formula | NMR (400 MHz, CDCl₃) and/or MS |
|---|---|---|
| 15 | 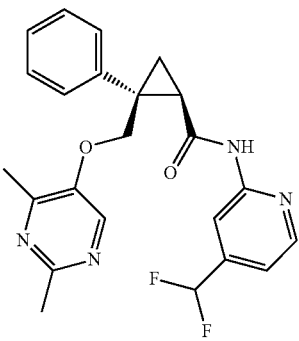 | ¹H-NMR δ (ppm): 1.64 (dd, J = 8.0, 5.6 Hz, 1H), 1.92 (t, J = 5.6 Hz, 1H), 2.15 (dd, J = 8.0, 5.6 Hz, 1H), 2.20 (s, 3H), 2.54 (s, 3H), 4.41 (d, J = 9.6 Hz, 1H), 4.50(d, J = 9.6 Hz, 1H), 6.56 (t, J = 56.0 Hz, 1H), 7.18-7.39 (m, 4H), 7.46-7.48 (m, 2H), 7.96 (s, 1H), 8.21 (brs, 1H), 8.38-8.40 (m, 1H).<br>MS[M + H]⁺ = 425 |
TABLE 13
| Example | Structural formula, MS |
|---|---|
| 16 | 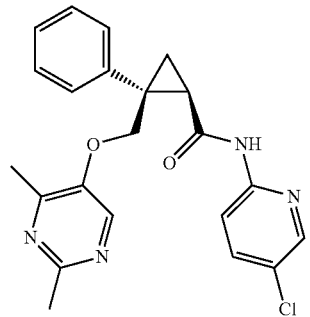<br>MS [M + H]⁺ = 409 |
| 17 | 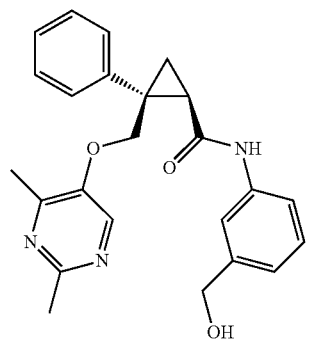<br>MS [M + H]⁺ = 404 |
TABLE 13-continued
| Example | Structural formula, MS |
|---|---|
| 18 | 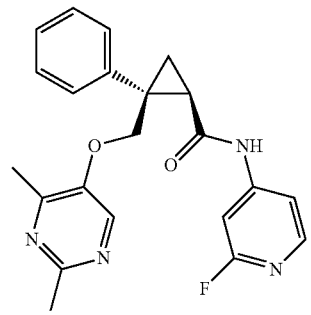<br>MS [M + H]⁺ = 393 |
| 19 | 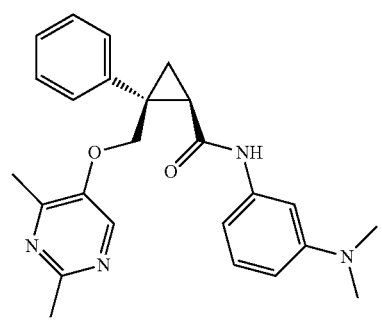<br>MS [M + H]⁺ = 417 |

TABLE 13-continued
| Example | Structural formula, MS |
|---|---|
| 20 | 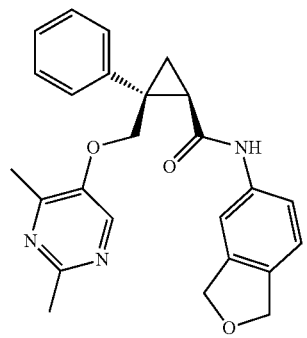 MS [M + H]$^+$ = 416 |
| 21 | 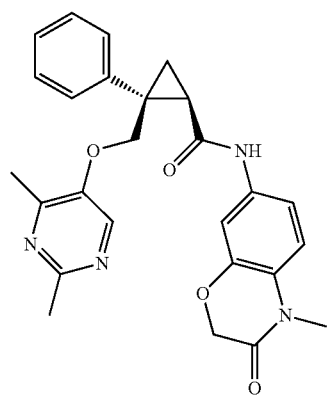 MS [M + H]$^+$ = 459 |
| 22 | 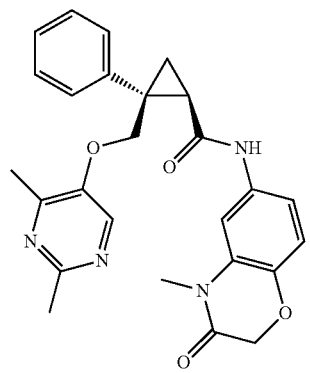 MS [M + H]$^+$ = 459 |
TABLE 13-continued
| Example | Structural formula, MS |
|---|---|
| 23 | 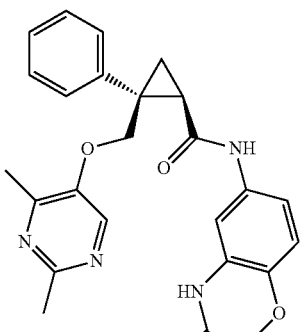 MS [M + H]$^+$ = 445 |
| 24 | 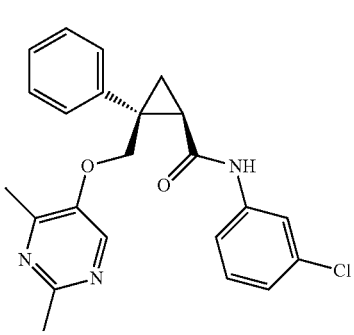 MS [M + H]$^+$ = 408 |
| 25 | 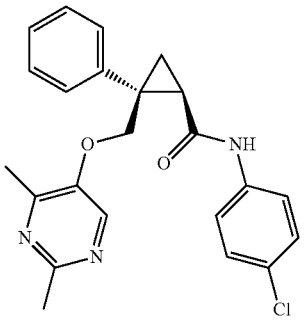 MS [M + H]$^+$ = 408 |

TABLE 13-continued
| Example | Structural formula, MS |
|---|---|
| 26 | 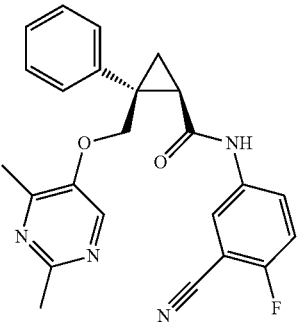  MS [M + H]⁺ = 417 |
| 27 | 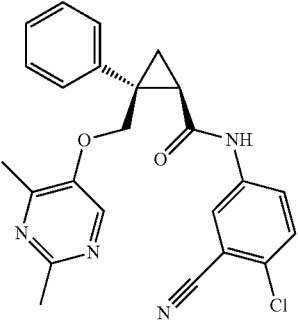  MS [M + H]⁺ = 433 |
| 28 | 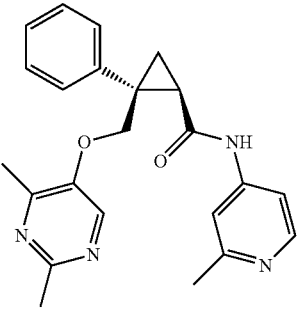  MS [M + H]⁺ = 389 |
| 29 | 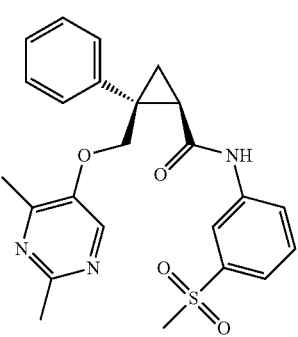  MS [M + H]⁺ = 452 |
| 30 | 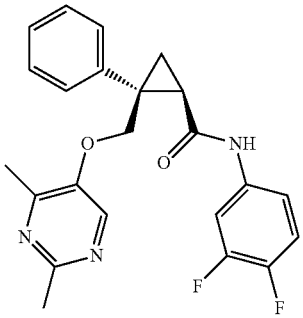  MS [M + H]⁺ = 410 |
TABLE 14
| Example | Structural formula, MS |
|---|---|
| 31 | 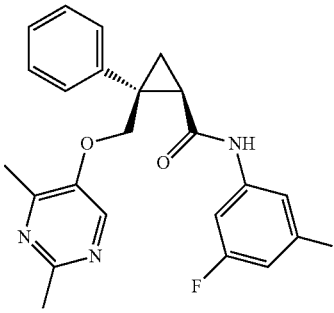  MS [M + H]⁺ = 410 |
| 32 | 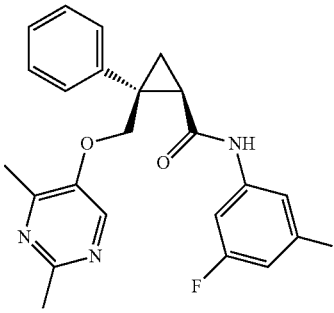  MS [M + H]⁺ = 426 |

TABLE 14-continued

| Example | Structural formula, MS |
|---|---|
| 33 | MS [M + H]⁺ = 409 |
| 34 | MS [M + H]⁺ = 417 |
| 35 | MS [M + H]⁺ = 433 |
| 36 | MS [M + H]⁺ = 404 |
| 37 | MS [M + H]⁺ = 416 |
| 38 | MS [M + H]⁺ = 441 |
| 39 | MS [M + H]⁺ = 413 |

TABLE 14-continued

| Example | Structural formula, MS |
|---|---|
| 40 | 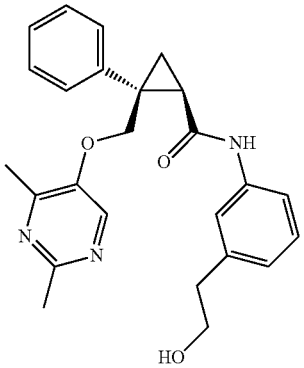 MS [M + H]+ = 418 |
| 41 | 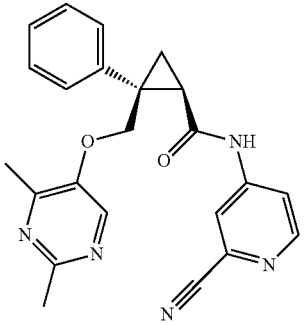 MS [M + H]+ = 400 |
| 42 | 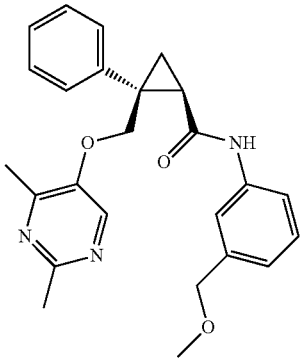 MS [M + H]+ = 418 |
| 43 | 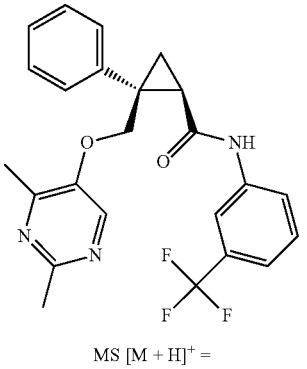 MS [M + H]+ = 442 |
| 44 | 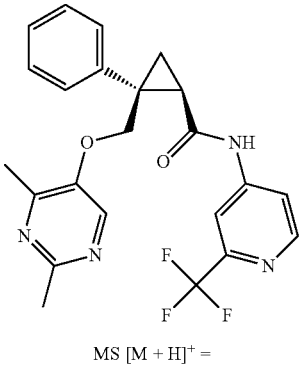 MS [M + H]+ = 443 |

EXAMPLE 45

Synthesis of (1R,2S)-N-(5-chloro-4-methylpyridin-2-yl)-2-{[(2,4-dimethylpyrimidin-5-yl)oxy]methyl}-2-phenylcyclopropanecarboxamide (45)

[Formula 61]

45

The carboxylic acid Prep 13-7 (500 mg) was dissolved in dichloromethane (5 ml), and oxalyl chloride (288 ul) and DMF (several droplets) were then added to the obtained solution. The obtained mixture was stirred at room temperature for 2 hours. Thereafter, the reaction solution was concentrated under reduced pressure, so as to obtain a crude acid chloride. Thereafter, N,N-diisopropylethylamine (664 ul) was added to a 1,4-dioxane solution (4.5 ml) of 2-amino-5-chloro-4-methylpyridine (359 mg), and the temperature of the obtained mixture was then heated to 125° C. A 1,4-dioxane solution (3 ml) of the crude acid chloride was added dropwise to the reaction solution, and while maintaining the temperature, the obtained mixture was stirred for 1 hour. The reaction mixture was cooled to room temperature, and the reaction solution was then stirred for 12 hours. Thereafter, several droplets of water were added to the reaction solution, followed by concentration under reduced pressure. The residue was purified by NH-silica gel column chromatography (n-heptane:ethyl acetate). The obtained product was washed with ether, and then dried, so as to obtain the title compound (95.5 mg).

$^1$H-NMR (400 MHz, CDCl$_3$) δ (ppm): 1.54-1.68 (m, 1H), 1.90 (t, J=5.6 Hz, 1H), 2.07-2.16 (m, 1H), 2.21 (s, 3H), 2.35 (s, 3H), 2.55 (s, 3H), 4.40 (d, J=9.6 Hz, 1H), 4.51 (d, J=9.6 Hz, 1H), 7.20-7.50 (m, 5H), 7.97 (s, 1H), 7.98 (s, 1H), 8.16 (s, 1H), 8.27 (s, 1H).

MS [M+H]$^+$=423

* The compounds of Examples 46 to 50 were synthesized by reacting the carboxylic acid Prep 13-7 with any amine by the same method as that of Example 45. Purification was carried out by LC-MS.

TABLE 15

| Example | Structural formula, MS |
|---|---|
| 46 | MS [M + H]$^+$ = 400 |
| 47 | MS [M + H]$^+$ = 389 |
| 48 | MS [M + H]$^+$ = 406 |
| 49 | MS [M + H]$^+$ = 409 |
| 50 | MS [M + H]$^+$ = 405 |

EXAMPLE 51

Synthesis of (1R,2S)-2-{[(2,4-dimethylpyrimidin-5-yl)oxy]methyl}-N-(5-fluoro-4-methylpyridin-2-yl)-2-phenylcyclopropanecarboxamide (51)

[Formula 62]

The carboxylic acid Prep 13-7 (2.86 g) was dissolved in DMF (57 ml), and 2-amino-5-fluoro-4-picoline (1.45 g) and N,N-diisopropylethylamine (2 ml) were then added to this solution. Thereafter, HATU (4.38 g) was added to the mixed solution under cooling on ice. The mixed solution was stirred in a nitrogen atmosphere at room temperature for 3 hours. Thereafter, 2-amino-5-fluoro-4-picoline (242 mg) was added to the reaction solution, and the obtained mixture was further stirred for 15 hours. Thereafter, 2-amino-5-fluoro-4-picoline (300 mg) was added to the reaction solution, and the obtained mixture was further stirred for 24.5 hours. Subsequently, water was added to the reaction solution, and the mixture was then extracted with ethyl acetate. The organic layer was washed with a saturated sodium chloride aqueous solution, and was then dried over anhydrous magnesium sulfate. The filtrate was concentrated under reduced pressure. The residue was purified by silica gel column chromatography (n-heptane:ethyl acetate). The obtained product of interest was dissolved in ethyl acetate (2 ml) and hexane (24 ml) at 60° C., and while gradually cooling the obtained mixture to room temperature, it was left overnight. Thereafter, the precipitated solid was collected by filtration and was then dried, so as to obtain the title compound (2.4 g).

$^1$H-NMR (400 MHz, CDCl$_3$) δ (ppm): 1.56-1.66 (m, 1H), 1.90 (t, J=4.8 Hz, 1H), 2.10 (dd, J=8.0, 6.0 Hz, 1H), 2.21 (s, 3H), 2.24-230 (m, 3H), 2.55 (s, 3H), 4.41 (d, J=9.6 Hz, 1H), 4.51 (d, J=9.6 Hz, 1H), 7.20-7.54 (m, 5H), 7.90-8.04 (m, 3H), 8.25 (s, 1H).

MS [M+H]$^+$=407

* The compounds of Examples 52 to 72 were synthesized by reacting the carboxylic acid Prep 13-7 with any amine by the same method as that of Example 51.

TABLE 16

| Example | Structural formula | NMR (400 MHz, CDCl$_3$) and/or MS |
|---|---|---|
| 52 | | $^1$H-NMR δ (ppm): 1.61 (dd, J = 8.0, 4.8 Hz), 1.95 (t, J = 5.2 Hz, 1H), 2.19-2.25 (m, 1H), 2.21 (s, 3H), 2.52 (s, 3H), 4.45 (d, J = 9.6 Hz, 1H), 4.53 (d, J = 9.6 Hz, 1H), 7.25-7.70 (m, 6H), 7.62-7.67 (m, 1H), 7.5-7.81 (m, 1H), 7.82-7.94 (m, 1H), 7.99 (s, 1H), 8.11-8.13 (m, 1H), 8.22-8.27 (m, 1H), 8.89-8.04 (brs, 1H). |
| 53 | | $^1$H-NMR δ(ppm): 1.64 (dd, J = 8.0, 5.2 Hz, 1H), 1.91 (t, J = 5.2 Hz, 1H), 2.12 (dd, J = 8.0, 6.0 Hz, 1H), 2.24 (s, 3H), 2.56 (s, 3H), 4.47 (d, J = 9.6 Hz, 1H), 4.53 (d, J = 9.6 Hz, 1H), 6.89 (dd, J = 9.2, 2.8 Hz, 1H), 7.29 (t, J = 7.2 Hz, 1H), 7.35 (t, J = 7.2 Hz, 2H), 7.44 (d, J = 7.2 Hz, 2H), 7.93 (brs, 1H), 7.99 (s, 1H), 8.12-8.17 (m, 2H). |
| 54 | | $^1$H-NMR δ (ppm): 1.64 (dd, J = 8.4, 5.2 Hz, 1H), 1.91 (t, J = 5.2 Hz, 1H), 2.12 (dd, J = 8.4, 6.0 Hz, 1H), 2.23 (s, 3H), 2.56 (s, 3H), 4.46 (d, J = 9.6 Hz, 1H), 4.53 (d, J = 9.6 Hz, 1H), 7.26 (t, J = 8.8 Hz, 1H), 7.29 (t, J = 7.2 Hz, 1H), 7.34 (d, J = 7.2 Hz, 2H), 7.43 (d, J = 7.2 Hz, 2H), 7.99 (s, 1H), 8.10 (dd, J = 8.8, 2.8 Hz, 1H), 8.11 (brs, 1H), 8.34 (d, J = 2.8 Hz, 1H). |

TABLE 16-continued

| Example | Structural formula | NMR (400 MHz, CDCl₃) and/or MS |
|---|---|---|
| 55 | | ¹H-NMR δ (ppm): 1.67 (dd, J = 8.0, 5.2 Hz, 1H), 1.96 (t, J = 5.2 Hz, 1H), 2.19 (dd, J = 8.0, 5.6 Hz, 1H), 2.20 (s, 3H), 2.52 (s, 3H) 4.52 (d, J = 9.6 Hz, 1H) 4.58 (d J = 9.6 Hz, 1H), 7.29 (t, J = 7.2 Hz, 1H), 7.36 (t, J = 7.2 Hz, 2H), 7.47 (d, J = 7.2 Hz, 2H), 7.53 (t, J = 8.0 Hz, 1H), 7.63 (t, J = 8.0 Hz, 1H), 7.75 (d, J = 8.0 Hz, 1H), 8.02 (s, 1H), 8.04 (d, J = 8.0 Hz, 1H), 8.17 (brs, 1H), 8.69 (d, J = 2.0 Hz, 1H), 8.75 (d, J = 2.0 Hz, 1H). |

TABLE 17

| Example | Structural formula | NMR (400 MHz, CDCl₃) and/or MS |
|---|---|---|
| 56 | | ¹H-NMR δ (ppm): 1.63 (dd, J = 8.0, 5.2 Hz, 1H), 1.90 (t, J = 5.2 Hz, 1H), 2.15 (dd, J = 8.0, 5.6 Hz, 1H), 2.21 (s, 3H), 2.55 (s, 3H), 4.04 (s, 3H), 4.46 (d, J = 9.2 Hz, 1H), 4.55 (d, J = 9.2 Hz, 1H), 6.85 (dd, J = 7,6, 4.8 Hz, 1H), 7.30 (t, J = 7.6 Hz, 1H), 7.38 (t, J = 7.6 Hz, 2H), 7.47 (d, J = 7.6 Hz, 2H), 7.85 (d, J = 4.8 Hz, 1H), 7.99 (s, 1H), 8.01 (brs, 1H), 8.43 (d, J = 7.6 Hz, 1H). |
| 57 | | ¹H-NMR δ (ppm): 1.65 (dd, J = 8.0, 5.2 Hz, 1H), 1.90 (t, J = 5.2 Hz, 1H), 2.09 (dd, J = 8.0, 6.0 Hz, 1H), 2.25 (s, 6H), 2.57 (s, 3H), 4.47 (d, J = 9.6 Hz, 1H), 4.53 (d, J = 9.6 Hz, 1H), 7.30 (t, J = 7.2 Hz, 1H), 7.36 (t, J = 7.2 Hz, 2H), 7.45 (d, J = 7.2 Hz, 2H), 7.74 (brs, 1H), 7.93 (s, 1H), 7.97-7.99 (m, 2H). |
| 58 | | ¹H-NMR δ (ppm): 1.64 (dd, J = 8.0, 5.2 Hz, 1H), 1.90 (t, J = 5.2 Hz, 1H), 2.11 (dd, J = 8.0, 5.6 Hz, 1H), 2.23 (s, 3H), 2.34 (s, 3H), 2.56 (s, 3H), 4.46 (d, J = 9.6 Hz, 1H), 4.53 (d, J = 9.6 Hz, 1H), 7.28 (t, J = 7.2 Hz, 1H), 7.34 (t, J = 7.2 Hz, 2H), 7.43 (d, J = 7.2 Hz, 2H), 7.93-8.00 (m, 3H), 8.14 (d, J = 2.8 Hz, 1H). |

TABLE 17-continued

| Example | Structural formula | NMR (400 MHz, CDCl₃) and/or MS |
|---|---|---|
| 59 | 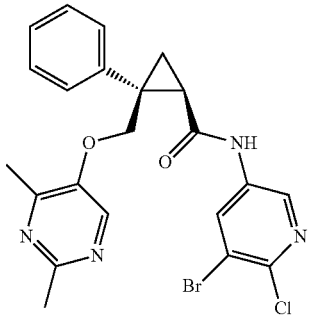 | ¹H-NMR δ (ppm): 1.66 (dd, J = 8.0, 5.2 Hz, 1H), 1.91 (t, J = 5.2 Hz, 1H), 2.10 (dd, J = 8.0, 5.6 Hz, 1H), 2.24 (s, 3H), 2.57 (s, 3H), 4.45 (d, J = 9.6 Hz, 1H), 4.52 (d, J = 9.6 Hz, 1H), 7.29 (t, J = 7.2 Hz, 1H), 7.35 (t, J = 7.2 Hz, 2H), 7.42 (d, J = 7.2 Hz, 2H), 7.99 (s, 1H), 8.04 (brs, 1H), 8.30 (d, J = 2.4 Hz, 1H), 8.47 (d, J = 2.4 Hz, 1H). |
| 60 | 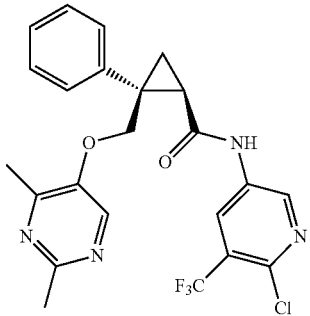 | ¹H-NMR δ (ppm): 1.68 (dd, J = 8.0, 5.2 Hz, 1H), 1.93 (t, J = 5.2 Hz, 1H), 2.12 (dd, J = 8.0, 5.6 Hz, 1H), 2.24 (s, 3H), 2.56 (s, 3H), 4.46 (d, J = 9.6 Hz, 1H), 4.52 (d, J = 9.6 Hz, 1H), 7.30 (t, J = 7.2 Hz, 1H), 7.36 (t, J = 7.2 Hz, 2H), 7.44 (d, J = 7.2 Hz, 2H), 7.99 (s, 1H), 8.01 (brs, 1H), 8.46 (d, J = 2.8 Hz, 1H), 8.57 (d, J = 2.8 Hz, 1H). |

TABLE 18

| Example | Structural formula | NMR (400 MHz, CDCl₃) and/or MS |
|---|---|---|
| 61 | 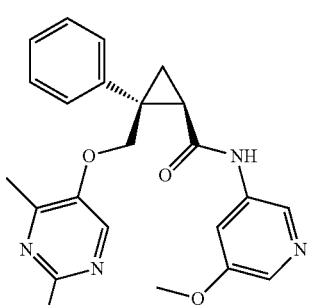 | ¹H-NMR δ (ppm): 1.64 (dd, J = 8.0, 5.2 Hz, 1H), 1.91 (t, J = 5.2 Hz, 1H), 2.14 (dd, J = 8.0, 6.0 Hz, 1H), 2.23 (s, 3H), 2.56 (s, 3H), 3.79 (s, 3H), 4.47 (d, J = 9.6 Hz, 1H), 4.54 (d, J = 9.6 Hz, 1H), 7.29 (t, J = 7.6 Hz, 1H), 7.34 (t, J = 7.6 Hz, 2H), 7.45 (d, J = 7.6 Hz, 2H), 7.85 (brs, 1H), 8.00 (s, 1H), 8.04-8.07 (m, 3H). |
| 62 | 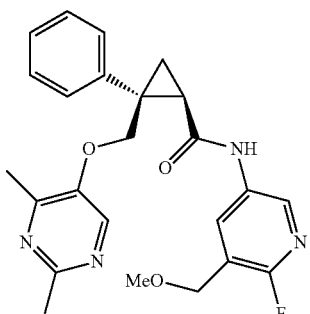 | ¹H-NMR δ (ppm): 1.65 (dd, J = 8.0, 5.2 Hz, 1H), 1.91 (t, J = 5.2 Hz, 1H), 2.09 (dd, J = 8.0, 5.6 Hz, 1H), 2.25 (s, 3H), 2.56 (s, 3H), 3.42 (s, 3H), 4.46 (s, 2H), 4.47 (d, J = 9.6 Hz, 1H), 4.52 (d, J = 9.6 Hz, 1H), 7.30 (t, J = 7.2 Hz, 1H), 7.36 (t, J = 7.2 Hz, 2H), 7.45 (d, J = 7.2 Hz, 2H), 7.65 (brs, 1H), 7.99 (s, 1H), 8.11 (dd, J = 8.4, 2.8 Hz, 1H), 8.15 (d, J = 2.8 Hz, 1H). |

TABLE 18-continued

| Example | Structural formula | NMR (400 MHz, CDCl₃) and/or MS |
|---|---|---|
| 63 | 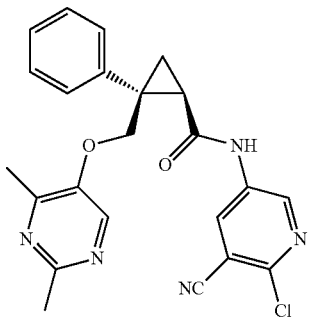 | ¹H-NMR δ (ppm): 1.70 (dd, J = 8.0, 5.2 Hz, 1H), 1.94 (t, J = 5.2 Hz, 1H), 2.11 (dd, J = 8.0, 5.6 Hz, 1H), 2.23 (s, 3H), 2.57 (s, 3H), 4.45 (d, J = 9.2 Hz, 1H), 4.51 (d, J = 9.2 Hz, 1H), 7.31 (t, J = 7.2 Hz, 1H), 7.36 (t, J = 7.2 Hz, 2H), 7.44 (d, J = 7.2 Hz, 2H), 7.93 (brs, 1H), 7.99 (s, 1H), 8.52 (d, J = 2.8 Hz, 1H), 8.55 (d, J = 2.8 Hz, 1H). |
| 64 | 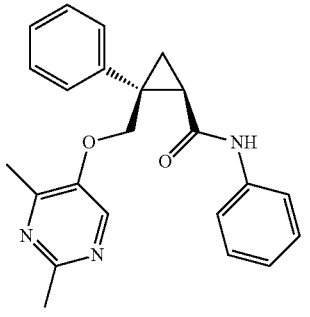 | ¹H-NMR δ (ppm): 1.60 (dd, J = 8.0, 5.6 Hz, 1H), 1.90 (t, J = 5.6 Hz, 1H), 2.06 (dd, J = 8.0, 5.6 Hz, 1H), 2.23 (s, 3H), 2.55 (s, 3H), 4.47 (d, J = 9.4 Hz, 1H), 4.54 (d, J = 9.4 Hz, 1H), 7.08-7.12 (m, 1H), 7.28-7.37 (m, 5H), 7.43-7.46 (m, 4H), 7.58 (brs, 1H), 7.99 (s, 1H).<br>MS [M + H]⁺ = 374 |
| 65 | 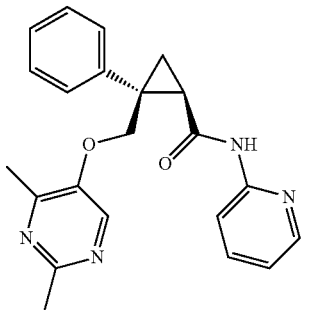 | ¹H-NMR δ (ppm): 1.62 (dd, J = 8.0, 5.2 Hz, 1H), 1.92 (t, J = 5.2 Hz, 1H), 2.15 (brt, 1H), 2.19 (s, 3H), 2.55 (s, 3H), 4.43 (d, J = 9.6 Hz, 1H), 4.54 (d, J = 9.6 Hz, 1H), 6.94-6.98 (m, 1H), 7.27-7.38 (m, 3H), 7.44-7.46 (m, 2H), 7.99 (s, 1H), 8.04 (brd, 1H), 8.20 (brs, 1H), 8.81-8.93 (m, 1H).<br>MS [M + H]⁺ = 375 |
| 66 | 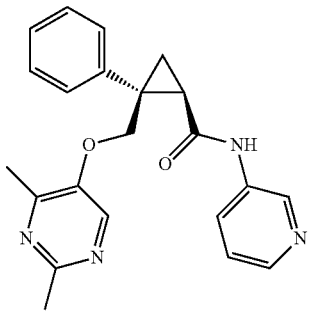 | ¹H-NMR δ (ppm): 1.62 (dd, J = 8.0, 5.6 Hz, 1H), 1.91 (t, J = 5.6 Hz, 1H), 2.14 (dd, J = 8.0, 5.6 Hz, 1H), 2.22 (s, 3H), 2.55 (s, 3H), 4.48 (d, J = 9.6 Hz, 1H), 4.54 (d, J = 9.6 Hz, 1H), 7.21-7.43 (m, 6H), 7.99 (s, 1H), 8.12 (brd, 1H), 8.22-8.45 (m, 2H), 8.52 (d, J = 2.0 Hz, 1H).<br>MS [M + H]⁺ = 375. |

TABLE 19

| Example | Structural formula | NMR (400 MHz, CDCl$_3$) and/or MS |
|---|---|---|
| 67 | | $^1$H-NMR δ (ppm): 1.62-1.65 (m, 1H), 1.92 (t, J = 5.4 Hz, 1H), 2.11-2.15 (m, 1H), 2.21 (s, 3H), 2.56 (s, 3H), 4.45 (d, J = 9.6 Hz, 1H), 4.54 (d, J = 9.6 Hz, 1H), 7.27-7.45 (m, 7H), 8.00 (s, 1H), 8.46 (brs, 2H).<br>MS [M + H]$^+$ = 375 |
| 68 | | $^1$H-NMR δ (ppm): 1.63 (dd, J = 8.0, 5.2 Hz, 1H), 1.91 (t, J = 5.2 Hz, 1H), 2.11 (brt, 1H), 2.21 (s, 3H), 2.55 (s, 3H), 4.39 (d, J = 9.4 Hz, 1H), 4.49 (d, J = 9.4 Hz, 1H ), 6.66 (dd, J = 8.0, 2.6 Hz, 1H), 7.28-7.39 (m, 3H), 7.45-7.47 (m, 2H), 7.74 (q, J = 8.0 Hz, 1H), 7.92 (brd, 1H), 7.96 (s, 1H), 8.17-8.19 (m, 1H).<br>MS [M + H]$^+$ = 393 |
| 69 | | $^1$H-NMR δ (ppm): 1.60 (dd, J = 8.0, 5.2 Hz, 1H), 1.90 (t, J = 5.2 Hz, 1H), 2.11 (brt, 1H), 2.20 (s, 3H), 2.28 (s, 3H), 2.54 (s, 3H), 4.40 (d, J = 9.4 Hz, 1H), 4.51 (d, J = 9.4 Hz, 1H), 7.27-7.38 (m, 3H), 7.45-7.48 (m, 3H), 7.94 (brd, 1H), 7.96 (s, 1H), 8.08 (q, J = 0.8 Hz, 1H), 8.27 (brs, 1H). |
| 70 | | $^1$H-NMR δ (ppm): 1.60 (dd, J = 7.6, 5.2 Hz, 1H), 1.90 (t, J = 5.2 Hz, 1H), 2.13 (brt, 1H), 2.21 (s, 3H), 2.47 (s, 3H), 2.54 (s, 3H), 4.40 (d, J = 9.6 Hz, 1H), 4.50 (d, J = 9.6 Hz, 1H), 6.90 (d, J = 7.2 Hz, 1H), 7.27-7.38 (m, 3H), 7.46-7.48 (m, 2H), 7.55 (brt, 1H), 7.86 (brd, 1H), 7.96 (s, 1H).<br>MS [M + H]$^+$ = 389 |

TABLE 20

| Example | Structural formula | NMR (400 MHz, CDCl₃ and/or MS |
|---|---|---|
| 71 | | ¹H-NMR δ (ppm): 1.62 (dd, J = 8.0, 5.2 Hz, 1H), 1.91 (t, J = 5.2 Hz, 1H), 2.12 (dd, J = 8.0, 5.2 Hz, 1H), 2.21 (s, 3H), 2.55 (s, 3H), 3.41 (s, 3H), 4.41 (d, J = 9.6 Hz, 1H), 4.45-4.54 (m, 3H), 7.30-7.39 (m, 3H), 7.45-7.48 (m, 2H), 7.96 (s, 1H), 8.07 (d, J = 1.2 Hz, 1H), 8.17-8.18 (m, 1H), 8.25 (brs, 1H).<br>MS [M + H]⁺ = 437 |
| 72 | | MS [M + H]⁺ = 405 |

EXAMPLE 73

Synthesis of (1R,2S)-2-{[(2,4-dimethylpyrimidin-5-yl)oxy]methyl}-N-(5-fluoro-4-methoxypyridin-2-yl)-2-phenylcyclopropanecarboxamide (73)

[Formula 63]

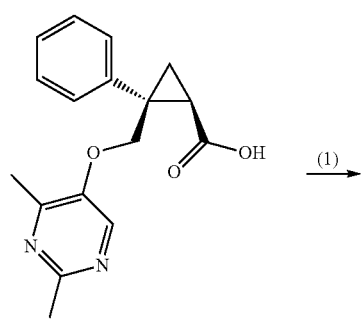

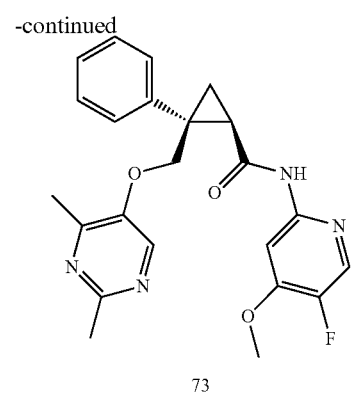

(1) (1R,2S)-2-({[(2,4-dimethylpyrimidin-5-yl)oxy]methyl})-2-phenylcyclopropanecarboxamide (73-1)

N,N-diisopropylethylamine was added to a DMF solution (15 ml) of the carboxylic acid Prep 13-7 (1.0 g), HOBt (679 mg), WSC (963 mg) and ammonium chloride (358 mg) at room temperature, and the obtained mixture was then stirred for 7 days. Thereafter, a saturated sodium bicarbonate aqueous solution was added to the reaction solution, and the obtained mixture was then extracted with ethyl acetate. The organic layer was dried over anhydrous magnesium sulfate and was then filtered. The filtrate was concentrated under reduced pressure, and the residue was then purified by silica gel column chromatography (n-heptane:ethyl acetate=9:1 to 1:4). The obtained crude product was dissolved in ethyl acetate, and n-hexane was then added to the solution. The precipitated solid was collected by filtration and was then dried, so as to obtain compound 74-1 (606 mg).

¹H-NMR (400 MHz, CDCl₃) δ (ppm): 1.53 (dd, J=8.4, 4.8 Hz, 1H), 1.79 (dd, J=6.0, 4.8 Hz, 1H), 1.99 (dd, J=8.4, 6.0 Hz, 1H), 2.35 (s, 3H), 2.58 (s, 3H), 4.45 (s, 2H), 5.40 (brs, 1H), 5.77 (brs, 1H), 7.27-7.36 (m, 3H), 7.42-7.45 (m, 2H), 7.98 (s, 1H).
MS [M+H]$^+$=298

(2) (1R,2S)-2-{[(2,4-dimethylpyrimidin-5-yl)oxy]methyl}-N-(5-fluoro-4-methoxypyridin-2-yl)-2-phenylcyclopropanecarboxamide (73)

The temperature of a 1,4-dioxane solution (20 ml) of the compound 73-1 (300 mg), the 2-chloro-5-fluoro-4-methoxypyridine (245 mg) obtained in Production Example 9-(1), xantphos (351 mg), potassium triphosphate (429 mg) and Pd$_2$DBA$_3$ (185 mg) was heated to 95° C., and the solution was then stirred for 26 hours. Thereafter, water was added to the reaction solution, and the obtained mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate=7:3, to ethyl acetate), and then by NH-silica gel column chromatography (n-heptane:ethyl acetate=4:1 to 2:3). The obtained crude product was dissolved in chloroform, and n-hexane was then added to the solution. The precipitated solid was collected by filtration and was then dried, so as to obtain a title compound (304 mg).
$^1$H-NMR (400 MHz, CDCl$_3$) δ (ppm): 1.63 (dd, J=8.0, 5.6 Hz, 1H), 1.89 (t, J=5.6 Hz, 1H), 2.11 (dd, J=8.0, 5.6 Hz, 1H), 2.23 (s, 3H), 2.55 (s, 3H), 3.88 (s, 3H), 4.41 (d, J=9.6 Hz, 1H), 4.51 (d, J=9.6 Hz, 1H), 7.28-7.39 (m, 3H), 7.45-7.48 (m, 2H), 7.82 (d, J=6.4 Hz, 1H), 7.97 (d, J=2.8 Hz, 1H), 7.98 (s, 1H), 8.30 (brs, 1H).
MS [M+Na]$^+$=445

* The compounds of Examples 74 and 75 were synthesized from the carboxylic acid amide obtained in Example 73-(1) by the same method as that of Example 73-(2).

EXAMPLE 76

Synthesis of (1R,2S)-N-(4,6-difluoropyridin-2-yl)-2-{[(2,4-dimethylpyrimidin-5-yl)oxy]methyl}-2-phenylcyclopropanecarboxamide (76-1) and (1R,2S)-N-(2,6-difluoropyridin-4-yl)-2-{[(2,4-dimethylpyrimidin-5-yl)oxy]methyl}-2-phenylcyclopropanecarboxamide (76-2)

[Formula 64]

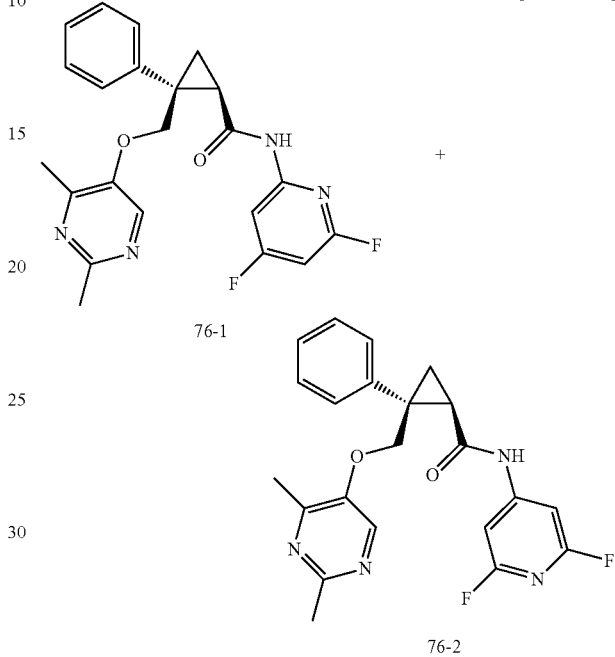

TABLE 21

| Example | Structural formula | NMR (400 MHz, CDCl$_3$) and/or MS |
|---|---|---|
| 74 | | $^1$H-NMR (400 MHz, CDCl$_3$) δ (ppm): 1.67 (dd, J = 8.0, 5.6 Hz, 1H), 1.93 (t, J = 5.6 Hz, 1H), 2.11 (dd, J = 8.0, 5.6 Hz, 1H), 2.23 (s, 3H), 2.56 (s, 3H), 4.46 (d, J = 9.6 Hz, 1H), 4.53 (d, J = 9.6 Hz, 1H), 6.53 (t, J = 72.6 Hz, 1H), 7.28-7.39 (m, 3H), 7.44-7.46 (m, 2H), 7.79 (brs, 1H), 7.99 (s, 1H), 8.06 (brs, 1H), 8.23 (d, J = 2.0 Hz, 1H), 8.37 (d, J = 2.0 Hz, 1H). MS [M + H]$^+$ = 441 |
| 75 | | MS [M + H]$^+$ = 406 |

Sodium hydride (60%, 26.9 mg) was added to a NMP solution (5 ml) of the compound 73-1 (100 mg), and the obtained mixture was stirred at room temperature for 10 minutes. Thereafter, 2,4,6-trifluoropyridine (89.4 mg) was added to the reaction solution. The temperature of the reaction solution was heated to 100° C., and it was then stirred for 4 days. Thereafter, water was added to the reaction solution, and the obtained mixture was then extracted with ethyl acetate. The organic layer was successively washed with water and a saturated sodium chloride aqueous solution, and was then dried over anhydrous magnesium sulfate, followed by filtration. The filtrate was concentrated under reduced pressure, and the residue was then purified by silica gel column chromatography (n-heptane:ethyl acetate=4:1 to 1:9), so as to obtain the title compound 76-1 (11.1 mg) and compound 76-2 (23.4 mg).

76-1

$^1$H-NMR (400 MHz, CDCl$_3$) δ (ppm): 1.64 (dd, J=8.0, 5.6 Hz, 1H), 1.91 (t, J=5.6 Hz, 1H), 2.09 (dd, J=8.0, 5.6 Hz, 1H), 2.22 (s, 3H), 2.55 (s, 3H), 4.37 (d, J=9.8 Hz, 1H), 4.48 (d, J=9.8 Hz, 1H), 6.39 (dt, J=7.6, 1.6 Hz, 1H), 7.28-7.39 (m, 3H), 7.43-7.46 (m, 2H), 7.74 (dd, J=10.0, 1.6 Hz, 1H), 7.95 (s, 1H), 8.21 (brs, 1H).

MS [M+H]$^+$=411

76-2

$^1$H-NMR (400 MHz, CDCl$_3$) δ (ppm): 1.70 (dd, J=8.0, 5.6 Hz, 1H), 1.94 (t, J=5.6 Hz, 1H), 2.07 (dd, J=8.0, 5.6 Hz, 1H), 2.22 (s, 3H), 2.57 (s, 3H), 4.42 (d, J=9.6 Hz, 1H), 4.51 (d, J=9.6 Hz, 1H), 7.00 (s, 2H), 7.31-7.39 (m, 3H), 7.42-7.45 (m, 2H), 7.86 (brs, 1H), 7.98 (s, 1H).

MS [M+H]$^+$=411

EXAMPLE 77

Synthesis of (1R,2S)-2-{[(2,4-dimethylpyrimidin-5-yl)oxy]methyl}-N-(4-fluorophenyl)-2-phenylcyclopropanecarboxamide (77)

[Formula 65]

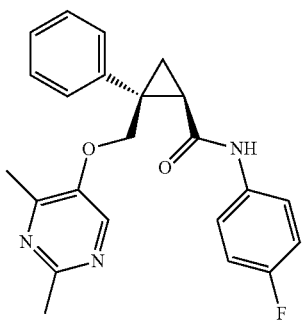

77

The carboxylic acid Prep 13-7 (30 mg) was dissolved in N,N-dimethylformamide (1 ml), and 4-fluoroaniline (33.7 mg), N,N-diisopropylethylamine (176 uX) and HOBt (40.9 mg) were then added to the obtained solution. Then, WSC (58.1 mg) was added thereto at room temperature, and the obtained mixture was stirred for 21 hours. Thereafter, the reaction solution was separated by purification using LC-MS (Waters, column: CAPCELL PAK, C18, ACR, S-5, 20 mm I.D.×50 mm, AGEE01114, mobile phase: methanol-water-TFA), so as to obtain the title compound (10.34 mg).

MS [M+H]=392

* The compounds of Examples 78 to 80 were synthesized by reacting the carboxylic acid Prep 13-7 with any amine by the same method as that of Example 77. Purification was carried out by LC-MS.

TABLE 22

| Example | Structural formula, MS |
|---------|------------------------|
| 78 | MS [M + H]$^+$ = 392 |
| 79 | MS [M + H]$^+$ = 392 |
| 80 | MS [M + H]$^+$ = 399 |

EXAMPLE 81

Synthesis of (1R,2S)-2-[(2,4-dimethyl-1-oxopyrimidin-5-yl)oxymethyl]-N-(6-fluoropyridin-3-yl)-2-phenylcyclopropanecarboxamide (81)

[Formula 66]

53

-continued

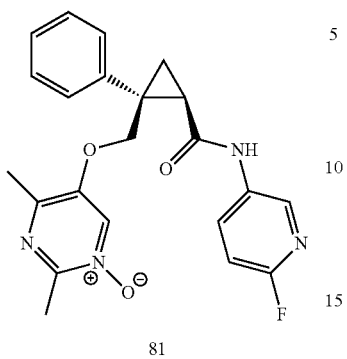

81

The compound 53 (40 mg) was dissolved in dichloromethane (5 ml), and 3-chloroperoxybenzoic acid (26.4 mg) was then added to the solution. The obtained mixture was stirred for 18 hours. Thereafter, potassium carbonate (50 mg) was added to the reaction solution, and the obtained mixture was further stirred for 1 hour. After completion of filtration, the solvent was distilled off under reduced pressure, and the residue was then purified by silica gel column chromatography (n-heptane:ethyl acetate=3:1 to 0:1, and then, ethyl acetate:methanol=8:1), so as to obtain the title compound (25.0 mg).

$^1$H-NMR (400 MHz, CDCl$_3$) δ (ppm): 1.62 (dd, J=8.0, 5.2 Hz, 1H), 1.86 (t, J=5.2 Hz, 1H), 2.23 (dd, J=8.0, 6.0 Hz, 1H), 2.24 (s, 3H), 2.54 (s, 3H), 4.38 (d, J=9.6 Hz, 1H), 4.41 (d, J=9.6 Hz, 1H), 6.89 (dd, J=9.2, 2.8 Hz, 1H), 7.27 (t, J=7.2 Hz, 1H), 7.32 (t, J=7.2 Hz, 2H), 7.42 (d, J=7.2 Hz, 2H), 7.91 (s, 1H), 8.18-8.22 (m, 2H), 8.62 (brs, 1H).

EXAMPLE 82

Synthesis of (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide (82)

[Formula 67]

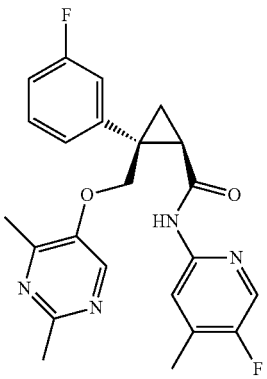

82

N,N-diisopropylethylamine (278 υλ) and HATU (604 mg) were added to a DMF solution (9.7 ml) of the carboxylic acid Prep 14-6 (388 mg) and 2-amino-5-fluoro-4-picoline (154 mg), while stirring at room temperature. The obtained mixture was stirred at room temperature for 6 hours. Thereafter, water was added to the reaction solution, and the obtained mixture was then extracted with ethyl acetate. The organic layer was dried over magnesium sulfate, and was then concentrated under reduced pressure. The residue was purified by silica gel column chromatography (n-heptane:ethyl acetate=9:1 to 2:3). A solid was precipitated with THF-heptane and was then collected by filtration, so as to obtain the title compound (289 mg).

$^1$H-NMR (400 MHz, CDCl$_3$) δ (ppm): 1.55-1.65 (m, 1H), 1.91 (t, J=5.6 Hz, 1H), 2.05-2.13 (m, 1H), 2.22 (s, 3H), 2.27 (s, 3H), 2.56 (s, 3H), 4.41 (d, J=10.0 Hz, 1H), 4.50 (d, J=9.2 Hz, 1H), 6.97-7.04 (m, 1H), 7.14-7.20 (m, 1H), 7.22-7.28 (m, 1H), 7.33 (td, J=8.0, 5.8 Hz, 1H), 7.93 (d, J=5.2 Hz, 1H), 7.99 (s, 1H), 8.00 (s, 1H), 8.24 (brs, 1H).

MS [M+Na]$^+$=447

* The compounds of Examples 83 to 93 were synthesized by reacting the carboxylic acid Prep 14-6 with any amine by the same method as that of Example 82.

TABLE 23

| Example | Structural formula | NMR (400 MHz, CDCl$_3$) and/or MS |
|---|---|---|
| 83 | ![structure] | $^1$H-NMR δ (ppm): 1.62 (dd, J = 8.0, 5.6 Hz, 1H), 1.92 (t, J = 5.6 Hz, 1H), 2.05 (dd, J = 8.0, 5.6 Hz, 1H), 2.23 (s, 3H), 2.57 (s, 3H), 4.46 (d, J = 9.6 Hz, 1H), 4.53 (d, J = 9.6 Hz, 1H), 6.79-6.83 (m, 1H), 6.98-7.02 (m, 1H), 7.09-7.12 (m, 1H), 7.15-7.40 (m, 5H), 7.64 (brs, 1H), 8.01 (s, 1H). MS [M + H]$^+$ = 410 |

TABLE 23-continued
| Example | Structural formula | NMR (400 MHz, CDCl₃) and/or MS |
|---|---|---|
| 84 | 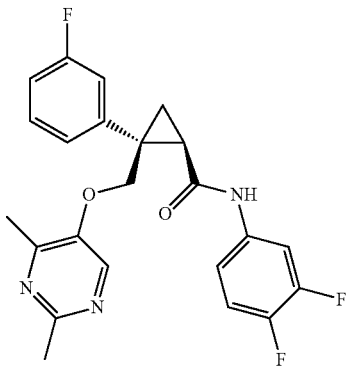 | ¹H-NMR δ (ppm): 1.63 (dd, J = 8.2, 5.6 Hz, 1H), 1.92 (t, J = 5.6 Hz, 1H), 2.03 (dd, J = 8.2, 5.6 Hz, 1H), 2.24 (s, 3H), 2.58 (s, 3H), 4.45 (d, J = 9.6 Hz, 1H), 4.52 (d, J = 9.6 Hz, 1H), 6.98-7.36 (m, 6H), 7.49-7.54 (m, 2H), 8.01 (s, 1H).<br>MS [M + H]⁺ = 428 |
| 85 | 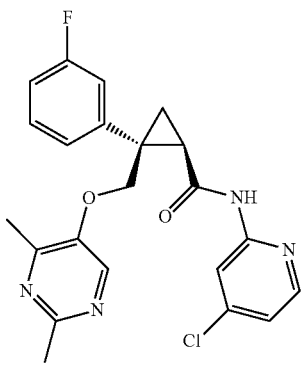 | ¹H-NMR δ (ppm): 1.63 (dd, J = 8.0, 5.6 Hz, 1H), 1.93 (t, J = 5.6 Hz, 1H), 2.13 (dd, J = 8.0, 5.6 Hz, 1H), 2.22 (s, 3H), 2.56 (s, 3H), 4.40 (d, J = 9.8 Hz, 1H), 4.50 (d, J = 9.8 Hz, 1H), 6.98-7.06 (m, 2H), 7.16-7.20 (m, 1H), 7.23-7.36 (m, 2H), 7.98 (s, 1H), 8.13 (brs, 1H), 8.16 (d, J = 5.6 Hz, 1H), 8.42 (brs, 1H).<br>MS [M + H]⁺ = 427 |
| 86 | 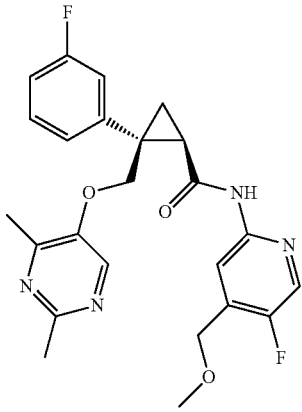 | ¹H-NMR δ (ppm): 1.62 (dd, J = 8.0, 5.2 Hz, 1H), 1.92 (t, J = 5.2 Hz, 1H), 2.09-2.13 (m, 1H), 2.22 (s, 3H), 2.55 (s, 3H), 3.41 (s, 3H), 4.41 (d, J = 9.6 Hz, 1H), 4.45-4.54 (m, 3H), 6.98-7.03 (m, 1H), 7.16-7.19 (m, 1H), 7.23-7.36 (m, 2H), 7.98 (s, 1H), 8.07 (brs, 1H), 8.16-8.17 (m, 1H), 8.26 (brs, 1H).<br>MS [M + H]⁺ = 455 |

TABLE 24

| Example | Structural formula | NMR (400 MHz, CDCl₃) and/or MS |
|---|---|---|
| 87 | | ¹H-NMR δ (ppm): 1.62 (dd, J = 8.0, 5.2 Hz, 1H), 1.93 (t, J = 5.2 Hz, 1H), 2.10-2.19 (m, 1H), 2.21 (s, 3H), 2.56 (s, 3H), 4.41 (d, J = 9.6 Hz, 1H), 4.50 (d, J = 9.6 Hz, 1H), 6.97-7.07 (m, 2H), 7.15-7.21 (m, 1H), 7.23-7.29 (m, 1H), 7.33 (td, J = 8.0, 5.6 Hz, 1H), 7.65-7.71 (m, 1H), 7.98 (s, 1H), 8.06 (brd, J = 8.4 Hz, 1H), 8.24-8.28 (m, 1H), 8.56 (brs, 1H). |
| 88 | | ¹H-NMR δ (ppm): 1.66 (dd, J = 8.4, 5.2 Hz, 1H), 1.93 (t, J = 5.4 Hz, 1H), 2.09 (dd, J = 8.4, 5.6 Hz, 1H), 2.26 (s, 3H), 2.58 (s, 3H), 4.50 (dd, J = 19.8, 9.4 Hz, 2H), 6.87-6.93 (m, 1H), 6.97-7.05 (m, 1H), 7.14-7.37 (m, 3H), 7.65 (brs, 1H), 8.01 (s, 1H), 8.10-8.18 (m, 2H).<br>MS [M + H]⁺ = 411 |
| 89 | | ¹H-NMR δ (ppm): 1.62 (dd, J = 7.8, 5.4 Hz, 1H), 1.92 (t, J = 5.4 Hz, 1H), 2.14 (dd, J = 8.2, 5.8 Hz, 1H), 2.24 (s, 3H), 2.57 (s, 3H), 3.78 (s, 3H), 4.47 (d, J = 9.4 Hz, 1H), 4.53 (d, J = 9.4 Hz, 1H), 6.96-7.02 (m, 1H), 7.12-7.19 (m, 1H), 7.20-7.24 (m, 1H), 7.31 (td, J = 8.0, 6.0 Hz, 1H), 7.85 (brs, 1H), 8.00-8.05 (m, 2H), 8.08 (d, J = 1.6 Hz, 1H), 8.33 (brs, 1H).<br>MS [M + H]⁺ = 423 |
| 90 | | ¹H-NMR δ (ppm): 1.64 (dd, J = 8.2, 5.0 Hz, 1H), 1.94 (t, J = 5.8 Hz, 1H), 2.13 (dd, J = 8.2, 5.8 Hz, 1H), 2.22 (s, 3H), 2.56 (s, 3H), 4.44 (d, J = 10.0 Hz, 1H), 4.52 (d, J = 10.0 Hz, 1H), 6.95-7.02 (m, 1H), 7.11-7.16 (m, 1H), 7.18-7.23 (m, 1H), 7.27-7.34 (m, 1H), 7.43-7.47 (m, 2H), 8.01 (s, 1H), 8.39 (brs, 1H), 8.44-8.49 (m, 2H).<br>MS [M + H]⁺ = 393 |

TABLE 25
| Example | Structural formula | NMR (400 MHz, CDCl₃) and/or MS |
|---|---|---|
| 91 | 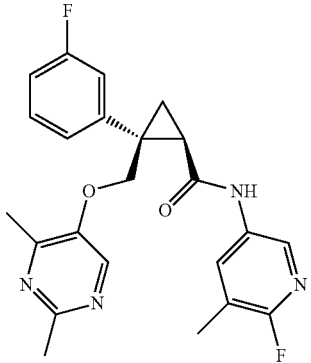 | $^1$H-NMR δ (ppm): 1.63 (dd, J = 8.2, 5.4 Hz, 1H), 1.92 (t, J = 5.4 Hz, 1H), 2.11 (dd, J = 8.2, 5.8 Hz, 1H), 2.24 (s, 3H), 2.26 (s, 3H), 2.58 (s, 3H), 4.47 (d, J = 9.6 Hz, 1H), 4.52 (d, J = 9.6 Hz, 1H), 6.96-7.03 (m, 1H), 7.14-7.20 (m, 1H), 7.20-7.25 (m, 1H), 7.32 (td, J = 8.0, 6.0 Hz, 1H), 7.90-8.04 (m, 4H).<br>MS [M + H]⁺ = 425 |
| 92 | 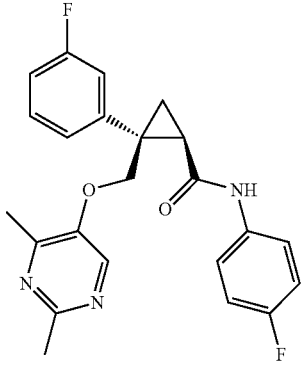 | $^1$H-NMR δ (ppm): 1.55-1.70 (m, 1H), 1.91 (t, J = 5.6 Hz, 1H), 2.05 (dd, J = 7.8, 6.2 Hz, 1H), 2.26 (s, 3H), 2.58 (s, 3H), 4.47 (d, J = 9.6 Hz, 1H), 4.53 (d, J = 9.6 Hz, 1H), 6.94-7.04 (m, 3H), 7.17 (dt, J = 10.4, 2.0 Hz, 1H), 7.21-7.27 (m, 1H), 7.29-7.36 (m, 1H), 7.37-7.44 (m, 2H), 7.56 (brs, 1H), 8.01 (s, 1H).<br>MS [M + H]⁺ = 410 |
| 93 | 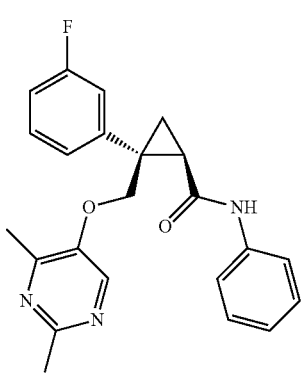 | $^1$H-NMR δ (ppm): 1.55-1.69 (m, 1H), 1.92 (t, J = 5.4 Hz, 1H), 2.06 (dd, J = 8.2, 5.8 Hz, 1H), 2.25 (s, 3H), 2.57 (s, 3H), 4.48 (d, J = 9.2 Hz, 1H), 4.54 (d, J = 9.6 Hz, 1H), 6.96-7.03 (m, 1H), 7.08-7.14 (m, 1H), 7.14-7.20 (m, 1H), 7.20-7.37 (m, 4H), 7.44 (d, J = 7.6 Hz, 2H), 7.56 (brs, 1H), 8.01 (s, 1H).<br>MS [M + H]⁺ = 392 |

EXAMPLE 94

Synthesis of (1R,2S)-2-{[(2,4-dimethylpyrimidin-5-yl)oxy]methyl}-N-(5-fluoro-4-methoxypyridin-2-yl)-2-(3-fluorophenyl)cyclopropanecarboxamide (94)

[Formula 68]

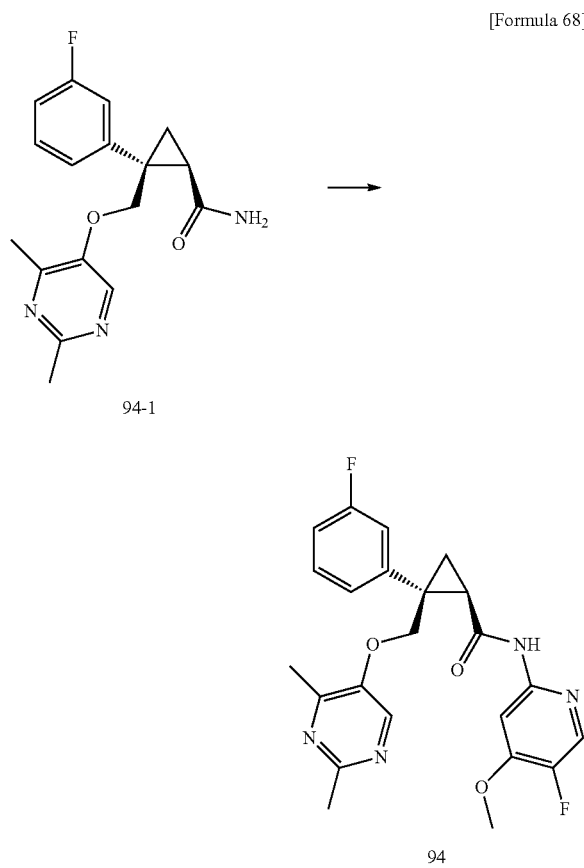

A solution of carboxamide 941(150 mg) prepared from the carboxylic acid Prep 14-6 in accordance with the method of Example 73-(1), 2-chloro-5-fluoro-4-methoxypyridine (Prep 9-1; 115 mg), xantphos (165 mg), potassium triphosphate (202 mg) and Pd$_2$DBA$_3$ (87.2 mg) in 1,4-dioxane (5 ml) was heated to 95° C. and stirred for 18 hours. The reaction solution was cooled to room temperature and filtered by celite. The filtrate was concentrated under reduced pressure, and the obtained residue was purified by silica gel chromatography (n-heptane:ethyl acetate=7:3 to ethyl acetate) and NH-silica gel chromatography (n-heptane:ethyl acetate=4:1 to 2:3). The obtained crude product was dissolved in chloroform, followed by the addition of n-hexane. The precipitated solid was obtained by filtration and dried to obtain the product of the title compound (82.9 mg).

$^1$H-NMR (400 MHz, CDCl$_3$) δ (ppm): 1.63 (dd, J=8.0, 5.6 Hz, 1H), 1.91 (t, J=5.6 Hz, 1H), 2.10 (dd, J=8.0, 5.6 Hz, 1H), 2.23 (s, 3H), 2.56 (s, 3H), 3.87 (s, 3H), 4.41 (d, J=9.6 Hz, 1H), 4.51 (d, J=9.6 Hz, 1H), 6.99-7.03 (m, 1H), 7.16-7.26 (m, 2H), 7.31-7.36 (m, 1H), 7.80 (d, J=6.4 Hz, 1H), 7.98 (d, J=2.8 Hz, 1H), 7.99 (s, 1H), 8.28 (brs, 1H).

MS [M+Na]+=463

EXAMPLE 95

Synthesis of (1R,2S)-2-{[(2,4-dimethylpyrimidin-5-yl)oxy]methyl}-2-(3-fluorophenyl)-N-(5-fluoropyridin-2-yl)cyclopropanecarboxamide (95)

[Formula 69]

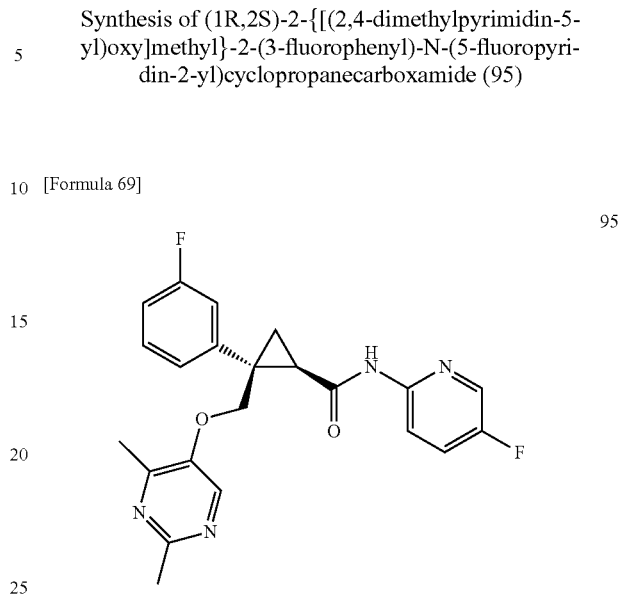

The carboxylic acid Prep 14-6 (226 mg) was dissolved in dichloromethane (10 ml), and oxalyl chloride (122 ul) and DMF (several droplets) were then added to the obtained solution. The obtained mixture was stirred at room temperature for 1 hour. Thereafter, the reaction solution was concentrated under reduced pressure, so as to obtain a crude acid chloride. N,N-diisopropylethylamine (283 ul) was added to a THF solution (10 ml) of 2-amino-5-fluoropyridine (96.1 mg), and the temperature of the solution was then heated to 60° C. A THF solution of the crude acid chloride was added dropwise to the reaction solution, and the obtained mixture was stirred for 1 hour while maintaining the temperature. Thereafter, the reaction mixture was cooled to room temperature, and the reaction solution was then stirred for 1 hour. Thereafter, the reaction solution was concentrated under reduced pressure, and was then partitioned between ethyl acetate and water, so as to separate an organic layer. The organic layer was dried over anhydrous magnesium sulfate, and the filtrate was then concentrated under reduced pressure. The residue was purified by NH-silica gel column chromatography (n-heptane:ethyl acetate=2:1), and diethyl ether was then added to the obtained product of interest. The precipitated solid was collected by filtration and was then dried, so as to obtain the title compound (130 mg).

$^1$H-NMR (400 MHz, d-DMSO) δ (ppm): 1.46-1.50 (m, 1H), 1.68 (t, J=6.0 Hz, 1H), 2.01 (s, 3H), 2.36 (s, 3H), 2.59-2.63 (m, 1H), 4.27 (d, J=10.4 Hz, 1H), 4.66 (d, J=10.4 Hz, 1'-1), 7.06-7.11 (m, 1H), 7.37-7.44 (m, 3H), 7.60-7.65 (m, 1H), 7.85-7.89 (m, 1H), 8.11 (s, 1H), 8.30 (d, J=3.2 Hz, 1H), 11.20 (brs, 1H)

MS [M+H]+=411

* The compounds of Examples 96 to 99 were synthesized by reacting the carboxylic acid Prep 14-6 or a racemic form thereof with any amine by the same method as that of Example 95.

TABLE 26

| Example | Structural formula | NMR. (400 MHz, CDCl₃) and/or MS |
|---|---|---|
| 96 | | ¹H-NMR δ (ppm): 1.68 (dd, J = 8.0, 5.6 Hz, 1H), 1.95 (t, J = 5.6 Hz, 1H), 2.16 (dd, J = 8.0, 6.0 Hz, 1H), 2.21 (s, 3H), 2.56 (s, 3H), 4.39 (d, J = 9.6 Hz, 1H), 4.50 (d, J = 9.6 Hz, 1H), 7.02 (tdd, J = 8.0, 2.4, 1.2 Hz, 1H), 7.17 (dt, J = 10.0, 2.4 Hz, 1H), 7.24 (dt, J = 8.0, 1.2 Hz, 1H), 7.34 (td, J = 8.0, 6.0 Hz, 1H), 7.90 (dd, J = 8.8, 2.4 Hz, 1H), 7.98 (s, 1H), 8.20 (d, J = 8.8 Hz, 1H), 8.48 (brs, 1H), 8.56 (dd, J = 2.4, 0.8 Hz, 1H). |
| 97 | | ¹H-NMR δ (ppm): 1.69 (dd, J = 8.2, 5.4 Hz, 1H), 1.95 (t, J = 5.4 Hz, 1H), 2.07 (dd, J = 7.8, 5.8 Hz, 1H), 2.23 (s, 3H), 2.57 (s, 3H), 4.44 (d, J = 9.6 Hz, 1H), 4.52 (d, J = 9.6 Hz, 1H), 6.98-7.05 (m, 1H), 7.14-7.20 (m, 2H), 7.20-7.31 (m, 2H), 7.31-7.38 (m, 1H), 7.78 (brs, 1H), 8.01 (s, 1H), 8.10 (d, J = 5.2 Hz, 1H).<br>MS [M + H]⁺ = 411 |
| 98 | | MS [M + H]⁺ = 428 |
| 99 | | MS [M + H]⁺ = 393 |

EXAMPLE 100

Synthesis of (1R,2S)-2-{[(2,4-dimethylpyrimidin-5-yl)oxy]methyl}-2-(4-fluorophenyl)-N-(5-fluoropyridin-2-yl)cyclopropanecarboxamide (100)

[Formula 70]

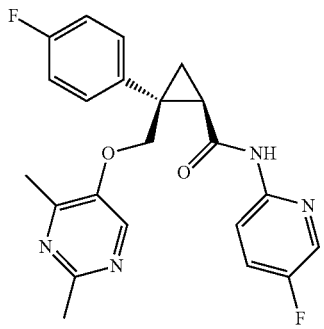

The carboxylic acid Prep 15-5 (200 mg) was dissolved in dichloromethane (10 ml), and oxalyl chloride (108 ul) and DMF (several droplets) were then added to the obtained solution. The obtained mixture was stirred at room temperature for 1 hour. Thereafter, the reaction solution was concentrated under reduced pressure, so as to obtain a crude acid chloride. N,N-diisopropylethylamine (250 ul) was added to a THF solution (10 ml) of 2-amino-5-fluoropyridine (85 mg), and the temperature of the solution was then heated to 60° C. A THF solution of the crude acid chloride was added dropwise to the reaction solution, and the obtained mixture was then stirred for 1 hour while maintaining the temperature. Thereafter, the reaction mixture was cooled to room temperature, and the reaction solution was then stirred for 1 hour. Thereafter, the reaction solution was concentrated under reduced pressure, and was then partitioned between ethyl acetate and water, so as to separate an organic layer. The organic layer was dried over anhydrous magnesium sulfate, and the filtrate was concentrated under reduced pressure. The residue was purified by NH-silica gel column chromatography (n-heptane:ethyl acetate=2:1), and diethyl ether was then added to the obtained product of interest. The precipitated solid was collected by filtration and was then dried, so as to obtain the title compound (102 mg).

$^1$H-NMR (400 MHz, d-DMSO) δ (ppm): 1.43-1.45 (m, 1H), 1.66 (t, J=4.4 Hz, 1H), 2.02 (s, 3H), 2.36 (s, 3H), 2.55-2.58 (m, 1H), 4.26 (d, J=10.4 Hz, 1H), 4.59 (d, J=10.4 Hz, 1H), 7.15-7.20 (m, 2H), 7.57-7.65 (m, 3H), 7.86-7.89 (m, 1H), 8.09 (s, 1H), 8.30 (d, J=3.2 Hz, 1H), 11.18 (brs, 1H)

MS [M+H]$^+$=411

* The compounds of Examples 101 to 103 were synthesized by the same method as that of Example 100, using 2-{[(2,4-dimethylpyrimidin-5-yl)oxy]methyl}-2-(4-fluorophenyl)cyclopropanecarboxylic acid, which can be synthesized using racemic epichlorohydrin in Production Example 15. Purification was carried out by LC-MS.

TABLE 27

| Example | Structural formula, MS |
|---|---|
| 101 | MS[M + H]$^+$ = 418 |
| 102 | MS[M + H]$^+$ = 427 |
| 103 | MS[M + H]$^+$ = 393 |

EXAMPLE 104

Synthesis of 1R,2S)-2-{[(2,4-dimethylpryimidin-5-yl)oxy]methyl}-N-(5-fluoro-4-methoxypyridin-2-yl)-2-(4-fluorophenyl)cyclopropanecarboxamide (104)

[Formula 71]

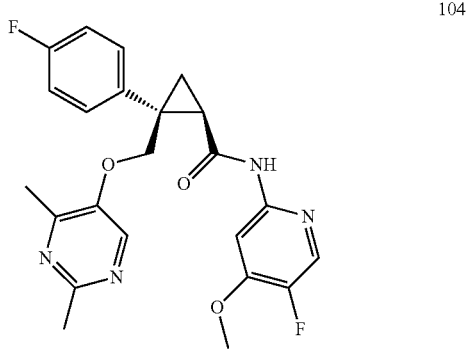

104

A solution of (1R,2S)-2-{[(2,4-dimethylpyrimidin-5-yl)oxy]methyl}-2-(4-fluorophenyl)cyclopropanecarboxamide (150 mg) which has been synthesized by the same method as the Prep73-1, 2-chloro-5-fluoro-4-methoxypyridine (Prep 9-1; 115 mg), xantphos (165 mg), potassium triphosphate (202 mg) and $Pd_2DBA_3$ (87.2 mg) in 1,4-dioxane (5 ml) was heated to 95° C. and stirred for 16 hours. The reaction solution was cooled to room temperature and filtered by celite. The filtrate was concentrated under reduced pressure, and the obtained residue was purified by silica gel chromatography (n-heptane:ethyl acetate=7:3 to ethyl acetate). The obtained crude product was dissolved in chloroform, followed by the addition of n-hexane. The precipitated solid was obtained by filtration and dried to obtain the product of the title compound (35.6 mg), $^1$H-NMR (400 MHz, $CDCl_3$) δ (ppm): 1.60 (dd, J=8.0, 5.2 Hz, 1H), 1.89 (t, J=5.2 Hz, 1H), 2.06 (dd, J=8.0, 5.2 Hz, 1H), 2.23 (s, 3H), 2.55 (s, 3H), 3.88 (s, 3H), 4.40 (d, J=9.4 Hz, 1H), 4.46 (d, J=9.4 Hz, 1H), 7.03-7.08 (m, 2H), 7.42-7.46 (m, 2H), 7.81 (d, J=6.8 Hz, 1H), 7.97-7.98 (m, 2H), 8.24 (brs, 1H).

MS[M+H]$^+$=441

EXAMPLE 105

Synthesis of (1R,2S)-N,2-bis(4-fluorophenyl)-2-{[(2,4-dimethylpyrimidin-5-yl)oxy]methyl}-N,2-bis(4-fluorophenyl)cyclopropanecarboxamide (105)

[Formula 72]

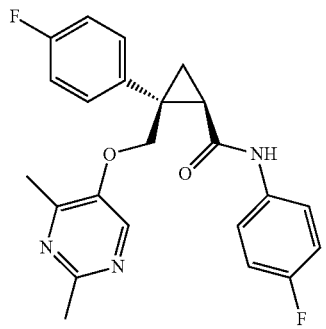

105

The carboxylic acid Prep 15-5 (33 mg) was dissolved in DMF (2 ml), and 4-fluoroaniline (15 mg), N,N-diisopropylethylamine(23.5 ul) and HATU (51.3 mg) were then added to the solution. The obtained mixture was stirred at room temperature for 20 hours. Thereafter, water was added to the reaction solution, and the obtained mixture was then extracted with ethyl acetate. The organic layer was concentrated. The residue was purified by silica gel column chromatography (n-heptane:ethyl acetate=9:1 to 2:3), so as to obtain the title compound (22.1 mg).

$^1$H-NMR (400 MHz, $CDCl_3$) δ (ppm): 1.53-1.62 (m, 1H), 1.89 (t, J=5.4 Hz, 1H), 2.01 (dd, J=8.2, 5.8 Hz, 1H), 2.25 (s, 3H), 2.57 (s, 3H), 4.47 (dd, J=12.4, 9.6 Hz, 2H), 6.97-7.08 (m, 4H), 7.37-7.46 (m, 4H), 7.50 (brs, 1H), 7.99 (s, 1H).

\* The compounds of Examples 106 to 112 were synthesized by reacting the carboxylic acid Prep 15-5 with any amine by the same method as that of Example 105.

TABLE 28

| Example | Structural formula | NMR and/or MS |
|---|---|---|
| 106 | | $^1$H-NMR (400 MHz, $CDCl_3$) δ (ppm): 1.58 (dd, J = 8.0, 5.2 Hz, 1H), 1.89 (t, J = 5.2 Hz, 1H), 2.00 (dd, J = 8.0, 6.0 Hz, 1H), 2.24 (s, 3H), 2.57 (s, 3H), 4.44 (d, J = 9.6 Hz, 1H), 4.48 (d, J = 9.6 Hz, 1H), 7.01-7.12 (m, 4H), 7.39-7.36 (m, 2H), 7.48-7.55 (m, 1H), 7.68 (brs, 1H), 7.99 (s, 1H). |

TABLE 28-continued

| Example | Structural formula | NMR and/or MS |
|---|---|---|
| 107 | | ¹H-NMR (400 MHz, CDCl₃) δ (ppm): 1.58 (dd, J = 8.0, 5.2 Hz, 1H), 1.89 (t, J = 5.2 Hz, 1H), 2.02 (dd, J = 8.6, 6.0 Hz, 1H), 2.23 (s, 3H), 2.56 (s, 3H), 4.44 (d, J = 9.6 Hz, 1H), 4.48 (d, J = 9.6 Hz, 1H), 6.76-6.84 (m, 1H), 7.01-7.12 (m, 3H), 7.21-7.28 (m, 2H), 7.36-7.45 (m, 1H), 7.79 (br, 1H), 7.99 (s, 1H). |
| 108 | | MS [M + H]⁺ = 428 |
| 109 | | ¹H-NMR (400 MHz, CDCl₃) δ (ppm): 1.59 (dd, J = 8.0, 5.6 Hz, 1H), 1.91 (t, J = 5.6 Hz, 1H), 2.08 (dd, J = 8.0, 5.6 Hz, 1H), 2.22 (s, 3H), 2.55 (s, 3H), 3.41 (s, 3H), 4.40 (d, J = 9.6 Hz, 1H), 4.45 (d, J = 9.6 Hz, 1H), 4.48 (d, J = 13.6 Hz, 1H), 4.52 (d, J = 13.6 Hz, 1H), 7.02-7.08 (m, 2H), 7.42-7.46 (m, 2H), 7.97 (s, 1H), 8.07 (d, J = 1.2 Hz, 1H), 8.18 (brd, J = 5.2 Hz, 1H), 8.26 (brs, 1H). MS [M + H]⁺ = 455 |
| 110 | | ¹H-NMR (400 MHz, CDCl₃) δ (ppm): 1.58 (dd, J = 8.2, 5.0 Hz, 1H), 1.91 (t, J = 5.4 Hz, 1H), 2.06-2.13 (m, 1H), 2.20 (s, 3H), 2.55 (s, 3H), 4.40 (d, J = 9.2 Hz, 1H), 4.46 (d, J = 9.6 Hz, 1H), 7.00-7.08 (m, 3H), 7.41-7.48 (m, 2H), 7.66 (td, J = 7.8, 1.8 Hz, 1H), 7.97 (s, 1H), 8.05 (brd, J = 10.4 Hz, 1H), 8.26 (dq, J = 4.4, 0.8 Hz, 1H), 8.41 (brs, 1H) |

TABLE 28-continued

| Example | Structural formula | NMR and/or MS |
|---|---|---|
| 111 | | ¹H-NMR (400 MHz, CDCl₃) δ (ppm): 1.58 (dd, J = 7.6, 5.2 Hz, 1H), 1.89 (t, J = 5.6 Hz, 1H), 2.03-2.09 (m, 1H), 2.22 (s, 3H), 2.28 (s, 3H), 2.56 (s, 3H), 4.40 (d, J = 9.2 Hz, 1H), 4.46 (d, J = 9.6 Hz, 1H), 7.01-7.12 (m, 2H), 7.40-7.47 (m, 2H), 7.94 (brd, J = 6.0 Hz, 1H), 7.97 (s, 1H), 8.00 (d, J = 1.2 Hz, 1H), 8.28 (brs, 1H) |
| 112 | | ¹H-NMR (400 MHz, CDCl₃) δ (ppm): 1.62 (dd, J = 8.4, 5.2 Hz, 1H), 1.90 (t, J = 5.6 Hz, 1H), 2.06-2.14 (m, 1H), 2.24 (s, 3H), 2.56 (s, 3H), 3.79 (s, 3H), 4.47 (dd, J = 13.6, 9.6 Hz, 2H), 7.01-7.08 (m, 2H), 7.41-7.48 (m, 2H), 7.86 (brs, 1H), 8.00 (s, 2H), 8.03-8.11 (m, 2H). |

EXAMPLE 113

Synthesis of (1R,2R)-2-{[(2,4-dimethylpyrimidin-5-yl)oxy]methyl}-N-(5-fluoropyridin-2-yl)-1-methyl-2-phenylcyclopropanecarboxamide (113)

[Formula 73]

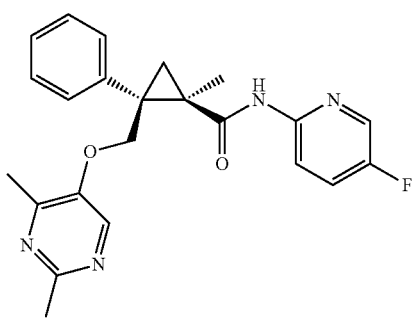

113

Oxalyl chloride (22.8 ul) was added to a dichloromethane solution (1.5 ml) of the carboxylic acid Prep 20-6 (41.5 mg), while the solution was stirred under cooling on ice. The obtained mixture was stirred at room temperature for 2 hours, and the reaction solution was then concentrated under reduced pressure. The residue was dissolved in dichloromethane (1 ml). Then, a dichloromethane solution (1 ml) of 2-amino-5-fluoropyridine (22.3 mg) and N,N-diisopropylethylamine (69.4 ul) were added to the obtained solution, while the solution was stirred under cooling on ice. The obtained mixture was stirred at room temperature for 4 hours. Thereafter, water was added to the reaction solution, and the obtained mixture was then extracted with ethyl acetate. The organic layer was washed with a saturated sodium chloride aqueous solution, was dried over magnesium sulfate, and was then concentrated under reduced pressure. The residue was purified by silica gel column chromatography (n-heptane:ethyl acetate), so as to obtain the title compound (8.0 mg).

¹H-NMR (400 MHz, CDCl₃) δ (ppm): 1.25 (s, 3H), 1.34 (d, J=5.6 Hz, 1H), 2.08 (d, J=5.2 Hz, 1H), 2.25 (s, 3H), 2.53 (s, 3H), 4.29 (dd, J=15.6, 9.6 Hz, 2H), 7.28-7.42 (m, 4H), 7.42-7.48 (m, 2H), 7.87 (s, 1H), 8.07-8.13 (m, 2H), 8.32 (brs, 1H).

EXAMPLE 114

Synthesis of (1R,2R)-N-(5-cyanopyridin-2-yl)-2-{[(2,4-dimethylpyrimidin-5-yl)oxy]methyl}-1-methyl-2-phenylcyclopropanecarboxamide (114)

[Formula 74]

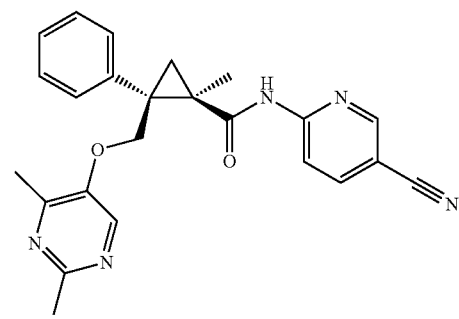

114

Oxalyl chloride (24.7 ul) was added to a dichloromethane solution (1.5 ml) of the carboxylic acid Prep 20-6 (45 mg), while the solution was stirred under cooling on ice. The obtained mixture was stirred at room temperature for 2 hours, and the reaction solution was then concentrated under reduced pressure. The residue was dissolved in dichloromethane (1.5 ml), and thereafter, a THF solution (1 ml) of 2-amino-5-cyanopyridine (22.3 mg) and N,N-diisopropylethylamine (75.3 ul) were added to the solution, while the solution was stirred under cooling on ice. The obtained mixture was stirred at room temperature for 3 hours. Thereafter, water was added to the reaction solution, and the obtained mixture was then extracted with ethyl acetate. The organic layer was washed with a saturated sodium chloride aqueous solution, dried over magnesium sulfate, and concentrated under reduced pressure. The residue was purified by silica gel column chromatography (n-heptane:ethyl acetate=1:0 to 0:1), so as to obtain the title compound (28.2 mg).

$^1$H-NMR (400 MHz, CDCl$_3$) δ (ppm): 1.26 (s, 3H), 1.38 (d, J=5.2 Hz, 1H), 2.12 (d, J=5.2 Hz, 1H), 2.25 (s, 3H), 2.53 (s, 3H), 4.25 (d, J=9.6 Hz, 1H), 4.32 (d, J=9.6 Hz, 1H), 7.30-7.42 (m, 3H), 7.43-7.48 (m, 2H), 7.85-7.91 (m, 2H), 8.23 (dd, J=8.6, 1.0 Hz, 1H), 8.50 (brs, 1H), 8.53-8.56 (m, 1H).

EXAMPLE 115

Synthesis of 1R,2S)-2-(3-cyanophenyl)-2-{[2,4-dimethylprimidin-5-yl)oxy]methyl}-N-4-fluorophenyl) cyclopropanecarboxamide (115)

[Formula 75]

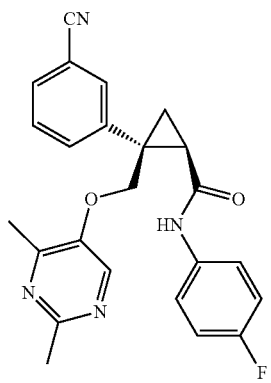

(115)

N,N-diisopropylethylamine (28.5 ul) and HATU (62.2 mg) were added to a DMF solution (1 ml) of the carboxylic acid Prep 18-4 (40 mg) and 4-fluoroaniline (18.2 mg), while the solution was stirred at room temperature. The obtained mixture was stirred at room temperature for 8 hours. Thereafter, water was added to the reaction solution, and the mixture was then extracted with ethyl acetate. The organic layer was concentrated under reduced pressure. The residue was purified by silica gel column chromatography (n-heptane:ethyl acetate=9:1 to 2:3). Subsequently, the resultant product was subjected to chiral resolution using HPLC (Daicel Chiral pak IA column, n-hexane:ethanol 30%), so as to obtain the title compound (13.1 mg).

$^1$H-NMR (400 MHz, CDCl$_3$) δ (ppm): 1.59 (dd, J=8.0, 5.2 Hz, 1H), 1.96 (t, J=5.4 Hz, 1H), 2.08 (dd, J=8.0, 6.0 Hz, 1H), 2.25 (s, 3H), 2.57 (s, 3H), 4.49 (s, 2H), 6.96-7.04 (m, 2H), 7.40-7.46 (m, 2H), 7.49 (t, J=7.8 Hz, 1H), 7.61 (brd, J=7.6 Hz, 1H), 7.72 (brd, J=7.6 Hz, 1H), 7.84 (brd, J=8.0 Hz, 2H), 8.00 (s, 1H).

\* The compounds of Examples 116 and 117 were synthesized by reacting the carboxylic acid Prep 18-4 and any amine by the same method as that of Example 115.

TABLE 29

| Example | Structural formula | NMR |
| --- | --- | --- |
| 116 | | $^1$H-NMR (400 MHz, CDCl$_3$) δ (ppm): 1.60-1.70 (m, 1H), 1.97 (t, J = 5.5 Hz, 1H), 2.08-2.16 (m, 1H), 2.21 (s, 3H), 2.57 (s, 3H), 4.47 (dd, J = 17.2, 9.8 Hz, 2H), 7.37-7.44 (m, 1H), 7.50 (t, J = 7.8 Hz, 1H), 7.62 (dt, J = 7.8, 1.6 Hz, 1H), 7.71-7.75 (m, 1H), 7.78 (brs, 1H), 7.99 (s, 1H), 8.04-8.11 (m, 1H), 8.13 (d, J = 3.1 Hz, 1H), 8.43 (brs, 1H). |
| 117 | | $^1$H-NMR (400 MHz, CDCl$_3$) δ (ppm): 1.60-1.70 (m, 1H), 1.96 (t, J = 7.4 Hz, 1H), 2.07-2.15 (m, 1H), 2.22 (s, 3H), 2.28 (s, 3H), 2.56 (s, 3H), 4.44 (d, J = 9.2 Hz, 1H), 4.49 (d, J = 10.0 Hz, 1H), 7.50 (t, J = 8.0 Hz, 1H), 7.62 (dt, J = 8.0, 1.2 Hz, 1H), 7.73 (dt, J = 7.6, 1.6 Hz, 1H), 7.77 (brs, 1H), 7.93 (brd, J = 4.8 Hz, 1H), 7.99 (s, 1H), 8.01 (brs, 1H), 8.36 (brs, 1H). |

EXAMPLE 118

Synthesis of (1R,2S)-2-{[(4-ethyl-2-methylpyrimidin-5-yl)oxy]methyl}-2-phenyl-N-(pyridin-2-yl)cyclopropanecarboxamide (118)

[Formula 76]

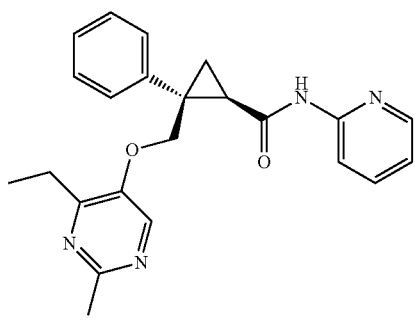

N,N-diisopropylethylamine (21.4 ul) and HATU (46.8 mg) were added to a DMF solution (0.75 ml) of the carboxylic acid Prep 19-3 (30 mg) and 2-aminopyridine (8.9 mg), while the solution was stirred at room temperature. The obtained mixture was stirred at room temperature for 3 hours. Thereafter, water was added to the reaction solution, and the mixture was then extracted with ethyl acetate. The organic layer was concentrated. The residue was purified by silica gel column chromatography (n-heptane:ethyl acetate=9:1 to 2:3), so as to obtain the title compound (32.1 mg).

$^1$H-NMR (400 MHz, CDCl$_3$) δ (ppm): 0.97 (t, J=7.6 Hz, 3H), 1.62 (dd, J=8.2, 5.0 Hz, 1H), 1.91 (t, J=5.4 Hz, 1H), 2.10-2.18 (m, 1H), 2.50-2.65 (m, 2H), 2.56 (s, 3H), 4.44 (d, J=9.2 Hz, 1H), 4.51 (d, J=9.2 Hz, 1H), 6.96-7.02 (m, 1H), 7.25-7.39 (m, 3H), 7.43-7.48 (m, 2H), 7.62-7.68 (m, 1H), 7.99 (s, 1H), 8.07 (brd, J=8.8 Hz, 1H), 8.23 (dq, J=4.8, 0.8 Hz, 1H), 8.65 (brs, 1H), \* The compounds of Examples 119 to 121 were synthesized by reacting the carboxylic acid Prep 19-3 and any amine by the same method as that of Example 1.

TABLE 30

| Example | Structural formula | NMR and/or MS |
|---|---|---|
| 119 | | $^1$H-NMR (400 MHz, CDCl$_3$) δ (ppm): 0.985 (t, J = 7.6 Hz, 3H), 1.60-1.63 (m, 1H), 1.90 (t, J = 5.2 Hz, 1H), 2.11 (brt, 1H), 2.51-2.62 (m, 5H), 4.42 (d, J = 9.2 Hz, 1H), 4.48 (d, J = 9.2 Hz, 1H), 7.27-7.51 (m, 6H), 7.91 (s, 1H), 8.08 (m, 2H), 8.26 (brs, 1H). MS [M + H]$^+$ = 407 |
| 120 | | $^1$H-NMR (400 MHz, CDCl$_3$) δ (ppm): 0.97 (t, J = 8.0 Hz, 3H), 1.67 (dd, J = 8.4 Hz, 5.2 Hz, 1H), 1.93 (t, J = 5.2 Hz, 1H), 2.16 (dd, J = 8.0 Hz, 5.6 Hz, 1H), 2.50-2.60 (m, 5H), 4.40 (d, J = 9.6 Hz, 1H), 4.48 (d, J = 9.6 Hz, 1H), 7.29-7.46 (m, 5H), 7.89 (dd, J = 2.4 Hz, 8.8 Hz, 1H), 7.97 (s, 1H), 8.23 (d, J = 8.8 Hz, 1H), 8.53-8.55 (m, 2H). MS [M + H]$^+$ = 414 |
| 121 | | $^1$H-NMR (400 MHz, CDCl$_3$) δ (ppm): 0.99 (t, J = 7.6 Hz, 3H), 1.63 (dd, J = 8.0 Hz, 5.2 Hz, 1H), 1.93 (t, J = 5.6 Hz, 1H), 2.12 (brt, J = 8.0 Hz, 1H), 2.51-2.60 (m, 5H), 4.41 (d, J = 9.2 Hz, 1H), 4.48 (d, J = 9.6 Hz, 1H), 7.26-7.47 (m, 5H), 7.61 (dd, J = 2.8 Hz, 9.2 Hz, 1H), 7.97 (s, 1H), 8.06 (d, J = 9.2 Hz, 1H), 8.22 (d, J = 2.8 Hz, 1H) 8.29 (brs, 1H). MS [M + H]$^+$ = 423 |

\* The compounds of Examples 122 to 124 were synthesized by reacting the carboxylic acid Prep 19-3 with any amine by the same method as that of Example 51.

TABLE 31

| Example | Structural formula | NMR and/or MS |
|---|---|---|
| 122 | 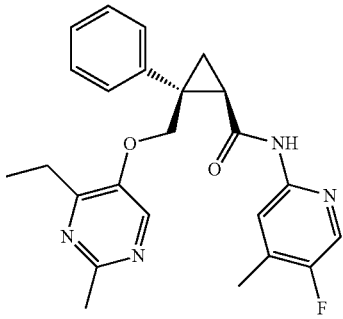 | $^1$H-NMR (400 MHz, CDCl$_3$) δ (ppm): 0.99 (t, J = 7.4 Hz, 3H), 1.62 (dd, J = 7.8, 5.0 Hz, 1H), 1.89 (t, J = 5.6 Hz, 1H), 2.11 (dd, J = 7.8, 5.8 Hz, 1H), 2.27 (s, 3H), 2.50-2.65 (m, 2H), 2.57 (s, 3H), 4.43 (d, J = 9.2 Hz, 1H), 4.50 (d, J = 9.2 Hz, 1H), 7.25-7.32 (m, 1H), 7.33-7.39 (m, 2H), 7.43-7.47 (m, 2H), 7.96 (brd, J = 6.0 Hz, 1H), 7.97-8.01 (m, 2H), 8.40 (brs, 1H). |
| 123 | 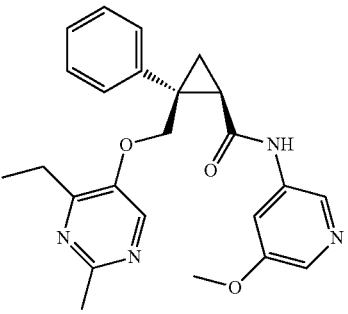 | $^1$H-NMR (400 MHz, CDCl$_3$) δ (ppm): 1.02 (t, J = 7.2 Hz, 3H), 1.63 (dd, J = 7.6, 5.2 Hz, 1H), 1.91 (t, J = 5.4 Hz, 1H), 2.14 (dd, J = 8.0, 6.0 Hz, 1H), 2.54-2.67 (m, 2H), 2.57 (s, 3H), 3.78 (s, 3H), 4.50 (dd, J = 19.2, 9.6 Hz, 2H), 7.25-7.31 (m, 1H), 7.31-7.38 (m, 2H), 7.41-7.47 (m, 2H), 7.86 (t, J = 2.2 Hz, 1H), 7.98-8.08 (m, 3H), 8.20 (brs, 1H). |
| 124 | 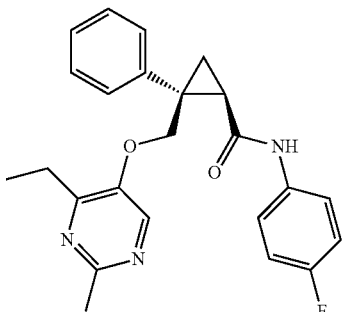 | $^1$H-NMR (400 MHz, CDCl$_3$) δ (ppm): 1.04 (t, J = 7.8 Hz, 3H), 1.58-1.67 (m, 1H), 1.89 (t, J = 5.6 Hz, 1H), 2.03-2.09 (m, 1H), 2.55-2.66 (m, 2H), 2.58 (s, 3H), 4.50 (dd, J = 14.6, 9.4 Hz, 2H), 6.95-7.03 (m, 2H), 7.26-7.32 (m, 1H), 7.33-7.48 (m, 6H), 7.57 (brs, 1H), 8.00 (s, 1H). |

\* The compounds of Examples 125 and 126 were synthesized by reacting the carboxylic acid Prep 17-4 with any amine by the same method as that of Example 1.

TABLE 32

| Example | Structural formula | NMR and/or MS |
|---|---|---|
| 125 | | $^1$H-NMR (400 MHz, CDCl$_3$) δ (ppm): 1.47 (dd, J = 8.0, 5.2 Hz, 1H), 1.83 (dd, J = 6.4, 5.2 Hz, 1H), 2.12 (dd, J = 8.0, 6.4 Hz, 1H), 2.23 (s, 3H), 2.54 (s, 3H), 4.03 (s, 3H), 4.21 (d, J = 9.4 Hz, 1H), 4.27 (d, J = 9.4 Hz, 1H), 6.93-6.99 (m, 2H), 7.28-7.45 (m, 3H), 7.87 (s, 1H), 8.14 (d, J = 3.2 Hz, 1H), 8.17 (dd, J = 4.4, 9.6 Hz, 1H), 8.60 (brs, 1H). |
| 126 | | $^1$H-NMR (400 MHz, CDCl$_3$) δ (ppm): 1.49 (dd, J = 8.0, 5.6 Hz, 1H), 1.85 (dd, J = 6.2, 5.6 Hz, 1H), 2.12 (dd, J = 8.0, 6.2 Hz, 1H), 2.22 (s, 3H), 2.54 (s, 3H), 3.98 (s, 3H), 4.27 (d, J = 9.6 Hz, 1H), 4.32 (d, J = 9.6 Hz, 1H), 6.93-7.00 (m, 2H), 7.29-7.33 (m, 2H), 7.38-7.40 (m, 1H), 7.89 (s, 1H), 7.96 (brs, 1H), 8.24 (brd, 1H), 8.36 (dd, J = 4.6, 1.4 Hz, 1H), 8.57 (d, J = 2.0 Hz, 1H). MS [M + H]$^+$ = 405 |

EXAMPLE 127

Synthesis of (1R,2S)-N-(5-cyanopyridin-2-yl)-2-{[(2-methoxy-4-methylpyrimidin-5-yl)oxy]methyl}-2-phenylcyclopropanecarboxamide (127)

[Formula 77]

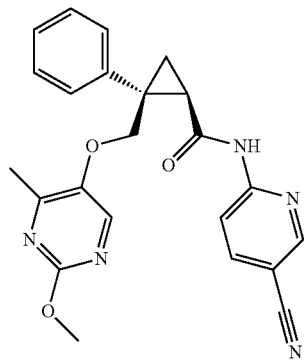

127

The title compound was synthesized by amidation of the carboxylic acid Prep 21 by the same method as that of Example 1.

MS [M+H]$^+$=416

EXAMPLE 128

Synthesis of (1R,2S)-N-(5-chloropyridin-2-yl)-2-{[(2-ethyl-4-methylpyrimidin-5-yl)oxy]methyl}-2-phenylcyclopropanecarboxamide (128)

[Formula 78]

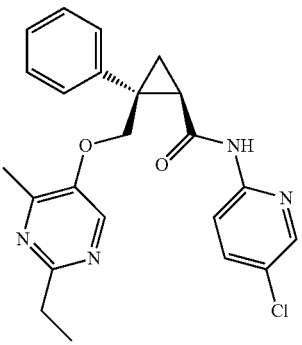

128

The title compound was synthesized by amidation of the carboxylic acid Prep 22 of Production Example 22 by the same method as that of Example 1.

MS [M+H]$^+$=423

EXAMPLE 129

Synthesis of (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide (129)

[Formula 79]

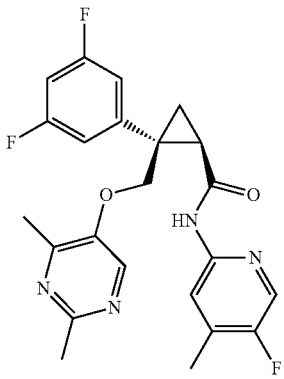

2-Amino-5-fluoro-4-picoline (415 mg), HATU (1.71 g) and N,N-diisopropylethylamine (1.56 ml) were added to a DMF solution (20 ml) of the carboxylic acid Prep 16-7 (1.0 g). The obtained mixture was stirred at room temperature for 2 days. Thereafter, water was added to the reaction solution, and the obtained mixture was then extracted with diethyl ether. The organic layer was dried over anhydrous magnesium sulfate and was then filtered. The filtrate was concentrated under reduced pressure, and the residue was then purified by NH-silica gel column chromatography (n-heptane: ethyl acetate=4:1 to 1:2), so as to obtain the title compound (880 mg).

$^1$H-NMR (400 MHz, CDCl$_3$) δ (ppm): 1.60-1.63 (m, 1H), 1.92 (t, J=5.6 Hz, 1H), 2.07 (brt, J=8.0 Hz, 1H), 2.22 (s, 3H), 2.27 (s, 3H), 2.56 (s, 3H), 4.41 (d, J=9.2 Hz, 1H), 4.49 (d, J=9.6 Hz, 1H), 6.76 (t, J=8.8 Hz, 1H), 6.97-6.99 (brd, 2H), 7.90 (d, J=6.4 Hz, 1H), 7.99 (s, 2H), 8.27 (brs, 1H).

* The compounds of Examples 130 to 138 were synthesized by reacting the carboxylic acid Prep 16-7 with any amine by the same method as that of Example 51.

TABLE 33

| Example | Structural formula | NMR (400 MHz, CDCl$_3$) and/or MS |
|---|---|---|
| 130 | | $^1$H-NMR δ (ppm): 1.60 (dd, J = 8.0, 5.2 Hz, 1H), 1.92 (t, J = 5.6 Hz, 1H), 2.03 (brt, J = 7.6 Hz, 1H), 2.25 (s, 3H), 2.57 (s, 3H), 4.46 (d, J = 9.6 Hz, 1H), 4.51 (d, J = 10.0 Hz, 1H), 6.75 (t, J = 6.8 Hz, 1H), 6.97-7.01 (m, 4H), 7.38-7.40 (m, 2H), 7.62 (s, 1H), 8.01 (s, 1H). MS [M + H]$^+$ = 428 |
| 131 | | $^1$H-NMR δ (ppm): 1.59-1.62 (m, 1H), 1.94 (t, J = 5.2 Hz, 1H), 2.11 (brt, J = 8.0 Hz, 1H), 2.21 (s, 3H), 2.56 (s, 3H), 4.41 (d, J = 9.6 Hz, 1H), 4.50 (d, J = 9.6 Hz, 1H), 6.76 (t, J = 6.8 Hz, 1H), 6.98-7.04 (m, 3H), 7.65 (t, J = 7.6 Hz, 1H), 7.99-8.03 (m, 2H), 8.26 (d, J = 4.0 Hz, 1H), 8.47 (s, MS [M + H]$^+$ = 411 |

TABLE 33-continued

| Example | Structural formula | NMR (400 MHz, CDCl$_3$) and/or MS |
|---|---|---|
| 132 | | $^1$H-NMR δ (ppm): 1.62 (dd, J = 8.4, 5.6 Hz, 1H), 1.93 (t, J = 5.2 Hz, 1H), 2.10 (brdt, J = 7.6 Hz, 1H), 2.22 (s, 3H), 2.56 (s, 3H), 4.40 (d, J = 10.0 Hz, 1H), 4.49 (d, J = 9.2 Hz, 1H), 6.76 (t, J = 8.8 Hz, 1H), 6.96-7.00 (m, 2H), 7.61 (dd, J = 2.8 Hz, 9.2 Hz, 1H), 7.99-8.02 (m, 2H), 8.21 (d, J = 2.0 Hz, 1H), 8.45 (s, 1H).<br>MS [M + H]$^+$ = 445 |
| 133 | | $^1$H-NMR δ (ppm): 1.61-1.64 (m, 1H), 1.93 (t, J = 5.2 Hz, 1H), 2.09 (brt, J = 8.0 Hz, 1H), 2.22 (s, 3H), 2.56 (s, 3H), 4.40 (d, J = 9.6 Hz, 1H), 4.49 (d, J = 9.6 Hz, 1H), 6.74-6.79 (m, 1H), 6.98 (d, J = 6.0 Hz, 2H), 7.36-7.41 (m, 1H), 7.99 (s, 1H), 8.05 (dd, J = 3.6 Hz, 9.2 Hz, 1H), 8.11 (d, J = 2.8 Hz, 1H), 8.35 (brt, 1H).<br>MS [M + H]$^+$ = 429 |
| 134 | | $^1$H-NMR δ (ppm): 1.61-1.63 (m, 1H), 1.92 (t, J = 5.6 Hz, 1H), 2.02 (dd, J = 8.4, 5.6 Hz, 1H), 2.25 (s, 3H), 2.58 (s, 3H), 4.45 (d, J = 9.6 Hz, 1H), 4.51 (d, J = 9.6 Hz, 1H), 6.75 (t, J = 8.8 Hz, 1H), 6.96-7.12 (m, 4H), 7.47-7.53 (m, 1H), 7.62 (s, 1H), 8.01 (s, 1H).<br>MS [M + H]$^+$ = 446 |

TABLE 34

| Example | Structural formula | NMR and/or MS |
|---|---|---|
| 135 | | $^1$H-NMR (400 MHz, CDCl$_3$) δ (ppm): 1.63 (dd, J = 8.4, 5.6 Hz, 1H), 1.93 (t, J = 5.2 Hz, 1H), 2.09 (dd, J = 8.0, 5.6 Hz, 1H), 2.26 (s, 3H), 2.57 (s, 3H), 4.44 (d, J = 9.2 Hz, 1H), 4.50 (d, J = 9.6 Hz, 1H), 6.74-7.01 (m, 5H), 7.59 (brs, 1H), 8.00-8.07 (m, 2H).<br>MS [M + H]$^+$ = 446 |

TABLE 34-continued

| Example | Structural formula | NMR and/or MS |
|---|---|---|
| 136 | 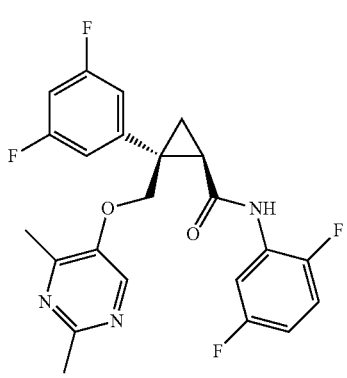 | ¹H-NMR (400 MHz, CDCl₃) δ (ppm): 1.65 (dd, J = 8.4, 5.2 Hz, 1H), 1.94 (t, J = 5.2 Hz, 1H), 2.10 (dd, J = 8.0, 5.6 Hz, 1H), 2.24 (s, 3H), 2.57 (s, 3H), 4.43 (d, J = 10.0 Hz, 1H), 4.51 (d, J = 10.0 Hz, 1H), 6.70-6.79 (m, 2H), 6.96-7.08 (m, 3H), 7.73 (brs, 1H), 7.96-8.01 (m, 2H). MS [M + H]⁺ = 446 |
| 137 | 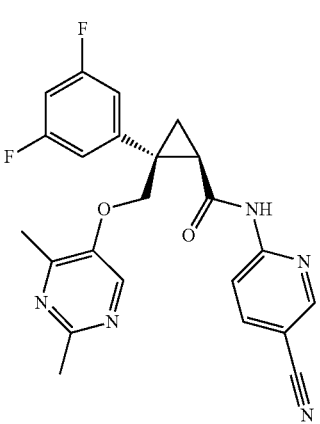 | ¹H-NMR (400 MHz, CDCl₃) δ (ppm): 1.67 (dd, J = 8.4, 5.2 Hz, 1H), 1.96 (t, J = 5.6 Hz, 1H), 2.15 (brt, J = 7.2 Hz, 1H), 2.21 (s, 3H), 2.56 (s, 3H), 4.39 (d, J = 10.0 Hz, 1H), 4.48 (d, J = 10.0 Hz, 1H), 6.77 (t, J = 8.4 Hz, 1H), 6.80-7.02 (m, 2H), 7.89 (dd, J = 8.8, 2.0 Hz, 1H), 7.99 (s, 1H), 8.18 (d, J = 9.2 Hz, 1H), 8.55-8.58 (m, 2H). MS [M + H]⁺ = 436 |
| 138 | 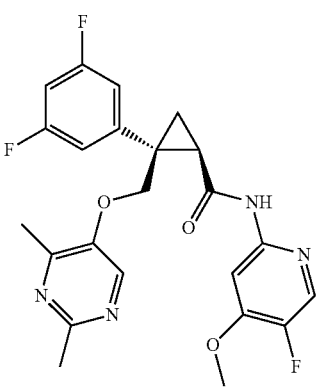 | ¹H-NMR (400 MHz, CDCl₃) δ (ppm): 1.63 (dd, J = 8.0, 5.8 Hz, 1H), 1.92 (t, J = 5.8 Hz, 1H), 2.08 (dd, J = 8.0, 5.8 Hz, 1H), 2.24 (s, 3H), 2.56 (s, 3H), 3.87 (s, 3H), 4.41 (d, J = 9.8 Hz, 1H), 4.50 (d, J = 9.8 Hz, 1H), 6.77 (tt, J = 8.8, 2.4H, 1H), 6.97-7.02 (m, 2H), 7.78 (d, J = 6.8 Hz, 1H), 7.97 (d, J = 2.4 Hz, 1H), 8.00 (s, 1H), 8.28 (brs, 1H). MS [M + H]⁺ = 459 |

\* The compounds of Examples 139 to 142 were synthesized by reacting the carboxylic acid Prep 23 with any amine by the same method as that of Example 1.

TABLE 35

| Example | Structural formula | NMR and/or MS |
|---|---|---|
| 139 | | ¹H-NMR (400 MHz, CDCl₃) δ (ppm): 1.64 (dd, J = 8.0 Hz, 5.2 Hz, 1H), 1.91 (t, J = 5.2 Hz, 1H), 2.12 (brt, J = 8.0 Hz, 1H), 2.62 (s, 3H), 3.28 (s, 3H), 4.27-4.55 (m, 4H), 7.26-7.46 (m, 6H), 7.62 (dd, J = 2.4 Hz, 8.8 Hz, 1H), 8.05-8.08 (m, 2H), 8.23 (d, J = 2.4 Hz, 1H), 8.29 (brs, 1H).<br>MS [M + Na]⁺ = 461 |
| 140 | | MS [M + Na]⁺ = 452 |
| 141 | | ¹H-NMR (400 MHz, CDCl₃) δ (ppm): 1.62-1.64 (m, 1H), 1.90 (t, J = 5.2 Hz, 1H), 2.12 (brt, J = 7.6 Hz, 1H), 2.62 (s, 3H), 3.27 (s, 3H), 4.27-4.55 (m, 4H), 7.30-7.46 (m, 6H), 8.08-8.12 (m, 3H), 8.37 (brs, 1H).<br>MS [M + H]⁺ = 423 |
| 142 | | MS [M + H]⁺ = 425 |

\* The compounds of Examples 143 to 150 were synthesized by reacting the carboxylic acid Prep 23 with any amine by the same method as that of Example 51.

TABLE 36

| Example | Structural formula, MS |
|---|---|
| 143 | [M + H]⁺ = 439 |
| 144 | [M + H]⁺ = 473 |
| 145 | [M + H]⁺ = 437 |
| 146 | [M + H]⁺ = 440 |

TABLE 36-continued

| Example | Structural formula, MS |
|---|---|
| 147 | [M + H]⁺ = 440 |
| 148 | [M + H]⁺ = 422 |
| 149 | [M + H]⁺ = 422 |
| 150 | [M + H]⁺ = 440 |

\* The compounds of Examples 151 to 153 were synthesized by reacting the carboxylic acid Prep 24 with any amine by the same method as that of Example 1.

TABLE 37
| Example | Structural formula, MS |
|---|---|
| 151 | 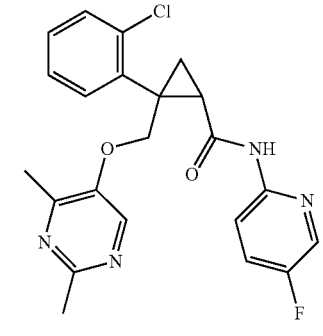 [M + H]⁺ = 427 |
| 152 | 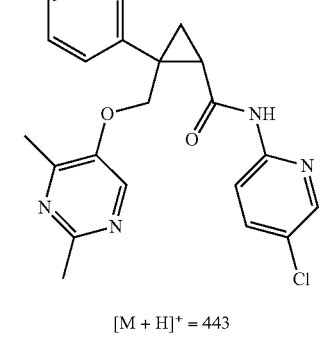 [M + H]⁺ = 443 |
| 153 | 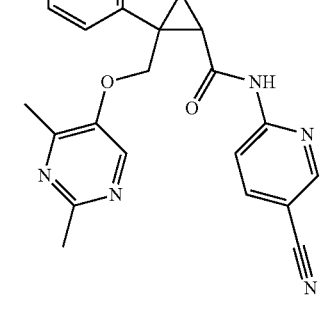 [M + H]⁺ = 434 |
TABLE 38
| Example | Structural formula, MS |
|---|---|
| 154 | 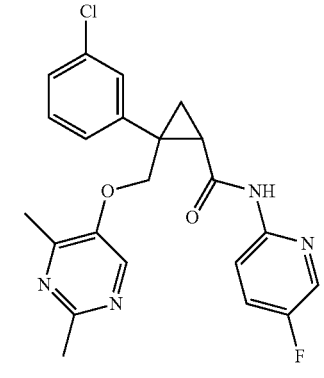 [M + H]⁺ = 427 |
| 155 | 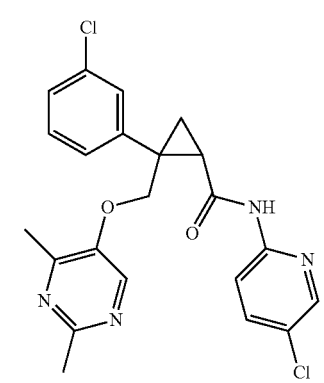 [M + H]⁺ = 443 |
| 156 | 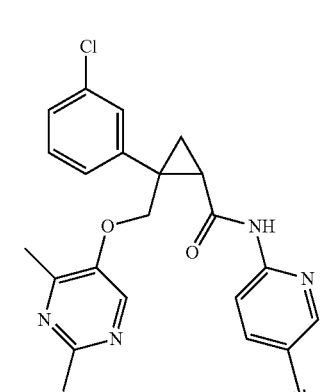 [M + H]⁺ = 434 |
\* The compounds of Examples 154 to 157 were synthesized by reacting the carboxylic acid Prep 25 with any amine by the same method as that of Example 1.

TABLE 38-continued

| Example | Structural formula, MS |
|---|---|
| 157 | (structure shown)<br>[M + H]⁺ = 409 |

\* The compounds of Examples 158 to 161 were synthesized by reacting the carboxylic acid Prep 26 and any amine by the same method as that of Example 1. The compound of Example 161 was obtained by performing chiral resolution on racemic products (Chiral pak-IA (hexane:ethanol=70:30, 15 mL/min, 254 nm, rt) 10.5 mM ((+)-form), 13.0 min ((−)-form, target compound).

TABLE 39

| Example | Structural formula, MS |
|---|---|
| 158 | (structure shown)<br>[M + H]⁺ = 443 |
| 159 | (structure shown)<br>[M + H]⁺ = 434 |

| Example | Structural formula, MS |
|---|---|
| 160 | 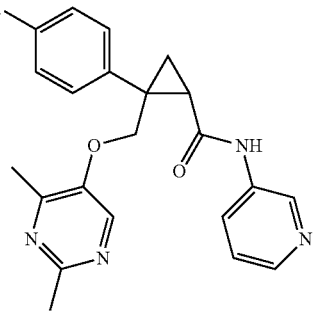<br>[M + H]⁺ = 409 |
| 161 | 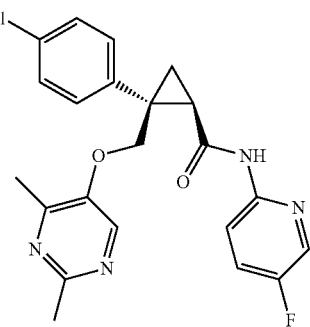<br>¹H-NMR (400 MHz, CDCl₃) δ (ppm): 1.59 (dd, J = 8.0, 5.2 Hz, 1H), 1.91 (t, J = 5.2 Hz, 1H), 2.07 (dd, J = 8.0, 6.0 Hz, 1H), 2.21 (s, 3H), 2.56 (s, 3H), 4.40 (d, J = 9.6 Hz, 1H), 4.47 (d, J = 9.6 Hz, 1H), 7.34-7.72 (m, 5H), 7.97 (s, 1H), 8.07 (dd, J = 9.2, 4.0 Hz, 1H), 8.12 (d, J = 2.8 Hz, 1H), 8.36 (brs, 1H). |

EXAMPLE 162

Synthesis of 2-(2,3-difluorophenyl)-2-{[(2,4-dimethylpyrimidin-5-yl)oxy]methyl}-N-(5-fluoropyridin-2-yl)cyclopropanecarboxamide (162)

[Formula 80]

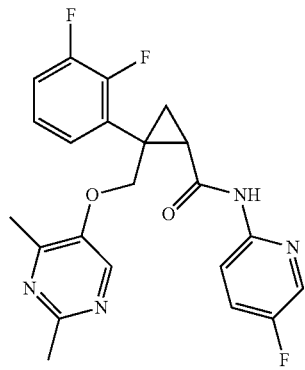

162

The title compound was synthesized by amidating the carboxylic acid Prep 27 by the same method as that of Example 51, ¹H-NMR (400 MHz, CDCl₃) δ (ppm): 1.53 (dd, J=8.0, 5.2 Hz, 1H), 1.94 (t, J=5.2 Hz, 1H), 2.16-2.22 (m, 4H), 2.54 (s, 3H), 4.34 (d, J=9.6 Hz, 1H), 4.42 (d, J=9.6 Hz, 1H), 7.06-7.42 (m, 4H), 7.93 (s, 1H), 8.09-8.14 (m, 2H), 8.34 (brs, 1H).

MS [M+H]⁺=429

EXAMPLE 163

Synthesis of 2-(2,5-difluorophenyl)-2-{[(2,4-dimethylpyrimidin-5-yl)oxy]methyl}-N-(5-fluoropyridin-2-yl)cyclopropanecarboxamide (163)

[Formula 81]

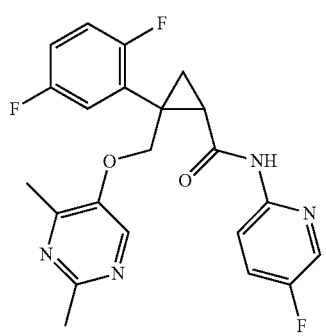

163

The title compound was synthesized by amidating the carboxylic acid Prep 28 by the same method as that of Example 51.

¹H-NMR (400 MHz, CDCl₃) δ (ppm): 1.53 (dd, J=8.0, 5.2 Hz, 1H), 1.94 (t, J=5.2 Hz, 1H), 2.17 (brt, J=7.6 Hz, 1H), 2.22 (s, 3H), 2.54 (s, 3H), 4.32 (d, J=9.6 Hz, 1H), 4.40 (d, J=9.6 Hz, 1H), 6.97-7.43 (m, 4H), 7.93 (s, 1H), 8.10-8.14 (m, 2H), 8.34 (brs, 1H).

MS [M+H]=429

* The compounds of Examples 164 to 172 were synthesized by reacting the carboxylic acid (Prep 29) and any amine by the same method as that of Example 52.

TABLE 40
| Example | Structural formula | NMR and/or MS |
|---|---|---|
| 164 | 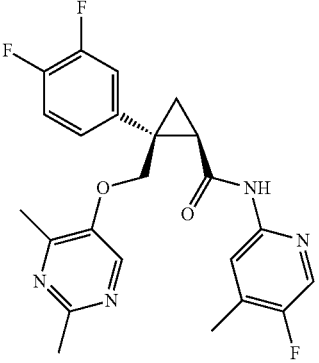 | $^1$H-NMR (400 MHz, CDCl$_3$) δ (ppm): 1.58 (dd, J = 8.4, 5.2 Hz, 1H), 1.91 (t, J = 5.2 Hz, 1H), 2.05 (brt, J = 8.0 Hz, 1H), 2.21 (s, 3H), 2.26 (s, 3H), 2.55 (s, 3H), 4.40 (d, J = 10.0 Hz, 1H), 4.46 (d, J = 9.6 Hz, 1H), 7.10-7.23 (m, 3H), 7.91 (d, J = 5.2 Hz, 1H), 7.96-7.98 (m, 2H), 8.49 (brs, 1H).<br>MS [M + H]$^+$ = 443 |
| 165 | 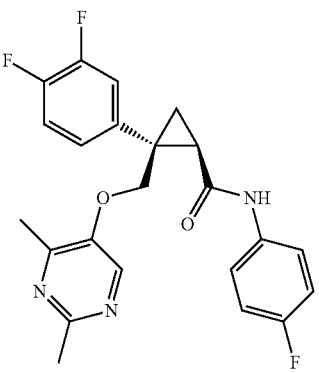 | $^1$H-NMR (400 MHz, CDCl$_3$) δ (ppm): 1.57 (dd, J = 8.0, 5.2 Hz, 1H), 1.90 (t, J = 4.8 Hz, 1H), 2.00 (brt, J = 8.0 Hz, 1H), 2.25 (s, 3H), 2.57 (s, 3H), 4.45 (d, J = 9.6 Hz, 1H), 4.48 (d, J = 10.0 Hz, 1H), 6.97-7.41 (m, 7H), 7.58 (s, 1H), 7.80 (s, 1H).<br>MS [M + H]$^+$ = 428 |
| 166 | 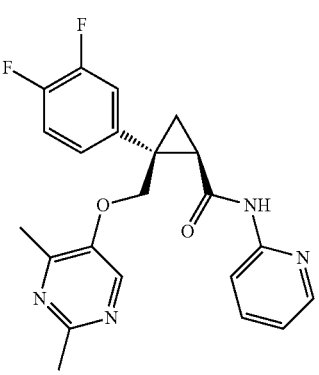 | $^1$H-NMR (400 MHz, CDCl$_3$) δ (ppm): 1.58 (dd, J = 8.4, 5.2 Hz, 1H), 1.91 (t, J = 5.2 Hz, 1H), 2.08 (brt, J = 5.2 Hz, 1H), 2.21 (s, 3H), 2.55 (s, 3H), 4.40 (d, J = 9.6 Hz, 1H), 4.46 (d, J = 9.2 Hz, 1H), 7.01-7.32 (m, 5H), 7.63-7.67 (m, 1H), 7.98 (s, 1H), 8.03 (d, J = 8.4 Hz, 1H), 8.26 (d, J = 4.0 Hz, 1H), 8.44 (s, 1H).<br>MS [M + H]$^+$ = 411 |

TABLE 41

| Example | Structural formula | NMR and/or MS |
|---|---|---|
| 167 | | ¹H-NMR (400 MHz, CDCl₃) δ (ppm): 1.63-1.68 (m, 1H), 1.94 (t, J = 5.2 Hz, 1H), 2.12 (brt, J = 7.6 Hz, 1H), 2.21 (s, 3H), 2.58 (s, 3H), 4.38 (d, J = 9.6 Hz, 1H), 4.44 (d, J = 9.6 Hz, 1H), 7.13-7.32 (m, 4H), 7.90 (dd, J = 2.4 Hz, 9.2 Hz, 1H), 7.97 (s, 1H), 8.19 (s, 1H), 8.51 (s, 1H), 8.56 (d, J = 2.0 Hz, 1H).<br>MS [M + H]⁺ = 436 |
| 168 | | ¹H-NMR (400 MHz, CDCl₃) δ (ppm): 1.58-1.61 (m, 1H), 1.91 (t, J = 5.6 Hz, 1H), 2.07 (brt, J = 6.0 Hz, 1H), 2.22 (s, 3H), 2.56 (s, 3H), 4.38 (d, J = 9.2 Hz, 1H), 4.45 (d, J = 9.2 Hz, 1H), 7.12-7.31 (m, 3H), 7.62 (dd, J = 8.8, 2.4 Hz, 1H), 7.97 (s, 1H), 8.03 (d, J = 8.8 Hz, 1H), 8.22 (d, J = 2.8 Hz, 1H), 833 (s, 1H).<br>MS [M + H]⁺ = 445 |
| 169 | | ¹H-NMR (400 MHz, CDCl₃) δ (ppm): 1.58-1.61 (m, 1H), 1.91 (t, J = 5.2 Hz, 1H), 2.07 (brt, J = 8.0 Hz, 1H), 2.21 (s, 3H), 2.56 (s, 3H), 4.39 (d, J = 9.6 Hz, 1H), 4.45 (d, J = 9.6 Hz, 1H), 7.12-7.41 (m, 4H), 7.97 (s, 1H), 8.04-8.08 (m, 1H), 8.12 (d, J = 2.4 Hz, 1H), 8.30 (brs, 1H).<br>MS [M + H]⁺ = 429 |
| 170 | | ¹H-NMR (400 MHz, CDCl₃) δ (ppm): 1.58-1.61 (m, 1H), 1.90 (t, J = 5.6 Hz, 1H), 1.91 (dd, J = 8.4, 6.0 Hz, 1H), 2.25 (s, 3H), 2.57 (s, 3H), 4.44 (d, J = 10 Hz, 1H), 4.47 (d, J = 9.6 Hz, 1H), 7.04-7.31 (m, 5H), 7.48-7.53 (m, 1H), 7.57 (s, 1H), 8.00 (s, 1H).<br>MS [M + H]⁺ = 446 |

TABLE 41-continued

| Example | Structural formula | NMR and/or MS |
|---|---|---|
| 171 | | $^1$H-NMR (400 MHz, CDCl$_3$) δ (ppm): 1.58-1.62 (m, 1H), 1.91 (t, J = 5.6 Hz, 1H), 2.06 (dd, J = 8.0, 6.0 Hz, 1H), 2.26 (s, 3H), 2.57 (s, 3H), 4.43 (d, J = 9.2 Hz, 1H), 4.47 (d, J = 9.2 Hz, 1H), 6.81-6.91 (m, 2H), 7.11-7.32 (m, 3H), 7.59 (brs, 1H), 7.99-8.08 (m, 2H). MS [M + H]$^+$ = 446 |
| 172 | | $^1$H-NMR (400 MHz, CDCl$_3$) δ (ppm): 1.62 (dd, J = 8.4, 5.6 Hz, 1H), 1.92 (t, J = 5.6 Hz, 1H), 2.08 (dd, J = 8.4, 5.6 Hz, 1H), 2.24 (s, 3H), 2.57 (s, 3H), 4.42 (d, J = 9.6 Hz, 1H), 4.47 (d, J = 10.0 Hz, 1H), 6.71-6.75 (m, 1H), 7.02-7.32 (m, 4H), 7.73 (brs, 1H), 7.60-8.20 (m, 2H). MS [M + H]$^+$ = 446 |

EXAMPLE 173

Synthesis of (1R,2S)-2-(3,4-difluorophenyl)-2-{[(2,4-dimethylpyrimidin-5-yl)oxy]methyl}-N-(5-fluoro-4-methoxypyridin-2-yl)cyclopropanecarboxamide (173)

[Formula 82]

173

The title compound was synthesized from Prep 29 according to Example 73. $^1$H-NMR (400 MHz, CDCl$_3$) δ (ppm): 1.60 (dd, J=8.0, 5.6 Hz, 1H), 1.90 (t, J=5.6 Hz, 1H), 2.06 (dd, J=8.0, 5.6 Hz, 1H), 2.24 (s, 3H), 2.56 (s, 3H), 3.88 (s, 3H), 4.40 (d, J=9.6 Hz, 1H), 4.46 (d, J=9.6 Hz, 1H), 7.12-7.32 (m, 3H), 7.79 (d, J=6.8 Hz, 1H), 7.98-7.99 (m, 2H), 8.25 (brs, 1H).

MS [M+H]$^+$=459

* The compounds of Examples 174 and 175 were synthesized by reacting the carboxylic acid Prep 30 and any amine by the same method as that of Example 45.

TABLE 42

| Example | Structural formula, MS |
|---|---|
| 174 | 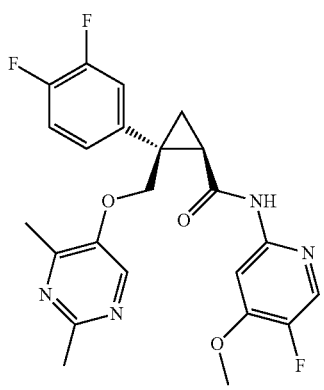 MS [M + H]$^+$ = 407 |

TABLE 42-continued

| Example | Structural formula, MS |
|---------|------------------------|
| 175 | 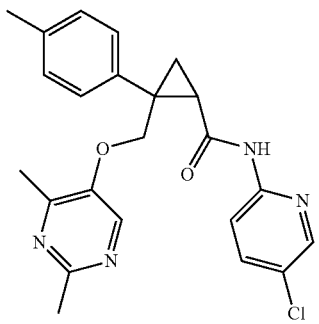 MS [M + H]⁺ = 423 |

\* The compounds of Examples 176 and 177 were synthesized by reacting the carboxylic acid Prep 31 of Production Example 31 and any amine by the same method as that of Example 1.

TABLE 43

| Example | Structural formula, MS |
|---------|------------------------|
| 176 | 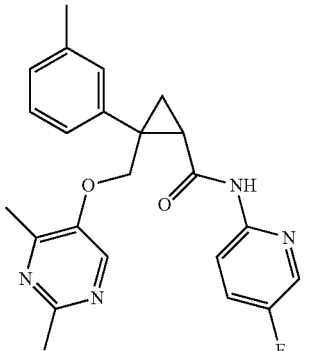 MS [M + H]⁺ = 407 |
| 177 | 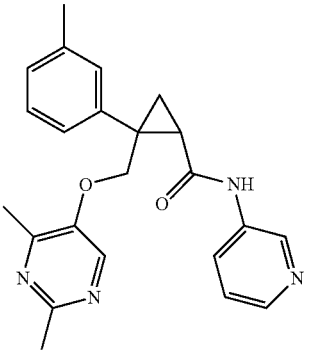 MS [M + H]⁺ = 389 |

\* The compounds of Examples 178 to 180 were synthesized by reacting the carboxylic acid Prep 32 of Production Example 32 and any amine by the same method as that of Example 1.

TABLE 44

| Example | Structural formula, MS |
|---------|------------------------|
| 178 | 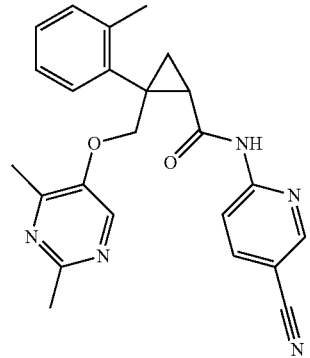 MS [M + H]⁺ = 414 |
| 179 | 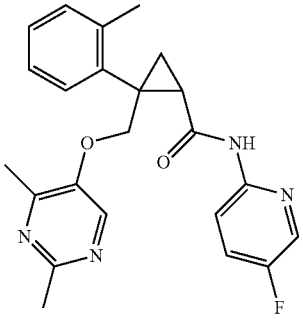 MS [M + H]⁺ = 407 |
| 180 | 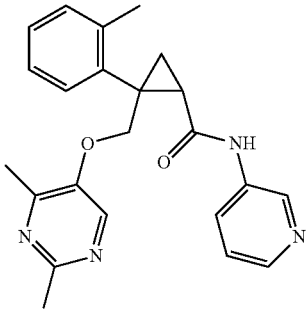 ¹H-NMR(400MHz, CDCl₃)δ(ppm): 1.49-1.55(m, 1 H), 1.97(t, J = 5.2 Hz, 1 H), 2.16 (dd, J = 8.2, 5.8 Hz, 1 H), 2.21(s, 3 H), 2.53 (s, 3 H), 2.55(s, 3 H), 4.45(dd, J = 11.0, 9.4 Hz, 2 H), 7.17-7.31(m, 4 H), 7.42-7.48(m, 1 H), 7.82(brs, 1 H), 7.93(s, 1 H), 8.14(brd, J = 8.8 Hz, 1 H), 8.36(d, J = 3.6 Hz, 1 H), 8.58(d, J = 2.4 Hz, 1 H). |

\* The compounds of Examples 181 and 182 were synthesized by reacting the carboxylic acid Prep 33 of Production Example 33 and any amine by the same method as that of Example 45.

TABLE 45

| Example | Structural formula, MS |
|---|---|
| 181 | 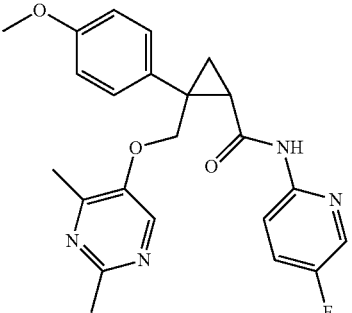<br>MS [M + H]$^+$ = 423 |

TABLE 45-continued

| Example | Structural formula, MS |
|---|---|
| 182 | 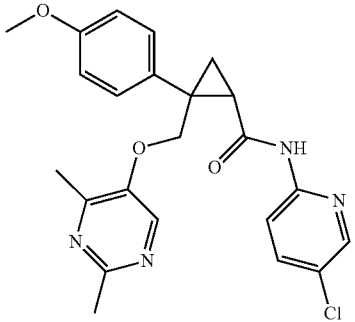<br>MS [M + H]$^+$ = 439 |

\* The compounds of Examples 183 to 190 were synthesized by reacting the carboxylic acid Prep 34 of Production Example 34 and any amine by the same method as that of Example 1. The compounds of Examples 186 to 190 were obtained by performing chiral resolution.

TABLE 46-1

| Example | Structural formula | NMR and/or MS |
|---|---|---|
| 183 | 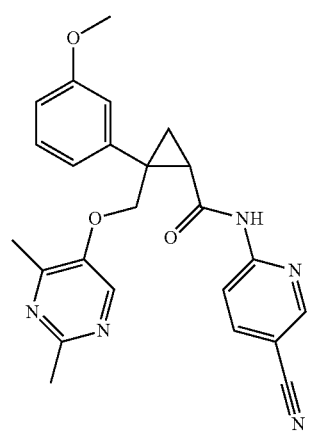 | $^1$H-NMR (400 MHz, CDCl$_3$) δ (ppm): 1.68 (dd, J = 8.0, 5.6 Hz, 1 H), 1.92 (t, J = 5.6 Hz, 1 H), 2.16 (dd, J = 5.6, 8.0 Hz, 1 H), 2.21 (s, 3 H), 2.55 (s, 3 H), 3.83 (s, 3 H), 4.37 (d, J = 9.6 Hz, 1 H), 4.50 (d, J = 9.6 Hz, 1 H), 6.85 (ddd, J = 8.0, 2.6, 0.8 Hz, 1 H), 7.00-7.05 (m, 2 H), 7.29 (t, J = 8.0 Hz, 1 H), 7.89 (dd, J = 8.8, 2.2 Hz, 1 H), 7.96 (s, 1 H), 8.21 (d, J = 8.8 Hz, 1 H), 8.48 (brs, 1 H), 8.56 (dd, J = 2.2, 0.8 Hz, 1 H).<br>MS [M + H]$^+$ = 430 |
| 184 | 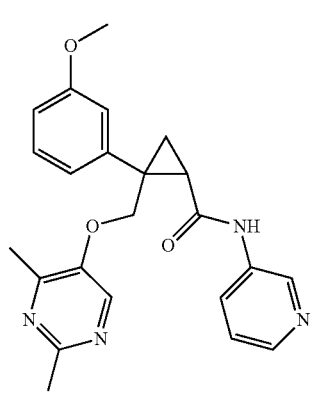 | $^1$H-NMR (400 MHz, CDCl$_3$) δ (ppm): 1.63 (dd, J = 8.0, 5.6 Hz, 1 H), 1.90 (t, J = 5.6 Hz, 1 H), 2.12 (dd, J = 8.0, 5.6 Hz, 1 H), 2.24 (s, 3 H), 2.56 (s, 3 H), 3.81 (s, 3 H), 4.45 (d, J = 9.6 Hz, 1 H), 4.54 (d, J = 9.6 Hz, 1 H), 6.83 (dd, J = 8.4, 2.0 Hz, 1 H), 7.01-7.04 (m, 2 H), 7.23-7.30 (m, 2 H), 7.87 (brs, 1 H), 7.99 (s, 1 H), 8.10 (brd, 1 H), 8.34 (d, J = 4.4 Hz, 1 H), 8.53 (d, J = 2.0 Hz, 1 H).<br>MS [M + H]$^+$ = 405 |

TABLE 46-1-continued

| Example | Structural formula | NMR and/or MS |
|---|---|---|
| 185 | | ¹H-NMR (400 MHz, CDCl₃) δ (ppm): 1.63 (dd, J = 8.0, 5.6 Hz, 1 H), 1.89 (t, J = 5.6 Hz, 1 H), 2.13 (dd, J = 8.0, 5.6 Hz, 1 H), 2.22 (s, 3 H), 2.55 (s, 3 H), 3.82 (s, 3 H), 4.38 (d, J = 9.6 Hz, 1 H), 4.51 (d, J = 9.6 Hz, 1 H), 6.84 (ddd, J = 8.4, 2.4, 0.8 Hz, 1 H), 7.01-7.06 (m, 2 H), 7.26-7.30 (m, 1 H), 7.61 (dd, J = 8.8, 2.4 Hz, 1 H), 7.96 (s, 1 H), 8.04 (d, J = 8.8 Hz, 1 H), 8.22 (dd, J = 0.8, 2.4 Hz, 1 H), 8.32 (brs, 1 H). MS [M + H]⁺ = 439 |
| 186 | | ¹H-NMR (400 MHz, CDCl₃) δ (ppm): 1.62 (dd, J = 8.0, 5.6 Hz, 1 H), 1.89 (t, J = 5.6 Hz, 1 H), 2.12 (dd, J = 8.0, 5.6 Hz, 1 H), 2.22 (s, 3 H), 2.55 (s, 3 H), 3.82 (s, 3 H), 4.39 (d, J = 9.6 Hz, 1 H), 4.51 (d, J = 9.6 Hz, 1 H), 6.84 (ddd, J = 8.0, 2.6, 0.8 Hz, 1 H), 7.01-7.06 (m, 2 H), 7.29 (d, J = 8.0 Hz, 1 H), 7.38 (ddd, J = 9.2, 7.6, 2.8 Hz, 1 H), 7.97 (s, 1 H), 8.07 (dd, J = 9.2, 4.0 Hz, 1 H), 8.12 (d, J = 2.8 Hz, 1 H), 8.28 (brs, 1 H). MS [M + H]⁺ = 423 |
| 187 | | ¹H-NMR (400 MHz, CDCl₃) δ (ppm): 1.56 (dd, J = 8.2, 5.2 Hz, 1 H), 1.85 (t, J = 5.6 Hz, 1 H), 2.06 (dd, J = 8.0, 6.0 Hz, 1 H), 2.25 (s, 3 H), 2.55 (s, 3 H), 3.80 (s, 3 H), 4.44 (d, J = 9.6 Hz, 1 H), 4.53 (d, J = 9.6 Hz, 1 H), 6.80-6.83 (m, 1 H), 6.93-7.02 (m, 4 H), 7.23-7.27 (m, 1 H), 7.35-7.41 (m, 2 H) 7.99 (s, 1 H), 7.94-8.00 (m, 1 H). |
| 188 | | ¹H-NMR (400 MHz, CDCl₃) δ (ppm): 1.61 (dd, J = 8.2, 5.2 Hz, 1 H) 1.90 (t, J = 5.2 Hz, 1 H), 2.12-2.16 (m, 1 H), 2.21 (s, 3 H), 2.55 (s, 3 H), 3.81 (s, 3 H), 4.41 (d, J = 9.6 Hz, 1 H), 4.54 (d, J = 9.6 Hz, 1 H), 6.82-6.85 (m, 1 H), 6.94-7.05 (m, 3 H), 7.24-7.29 (m, 1 H), 7.61-7.65 (m, 1 H) 7.99 (s, 1 H), 8.02-8.05 (m, 1 H), 8.19-8.21 (m, 1 H), 8.88 (brs, 1 H). |

TABLE 46-1-continued

| Example | Structural formula | NMR and/or MS |
|---|---|---|
| 189 | 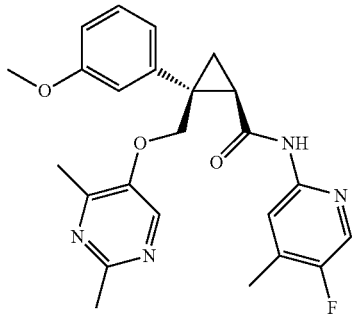 | ¹H-NMR (400 MHz, CDCl₃) δ (ppm): 1.61 (dd, J = 8.2, 5.2 Hz, 1 H) 1.88 (t, J = 5.6 Hz, 1 H), 2.12 (dd, J = 8.0, 6.0 Hz, 1 H), 2.22 (s, 3 H), 2.26 (s, 3 H), 2.55 (s, 3 H), 3.81 (s, 3 H), 4.41 (d, J = 9.2 Hz, 1 H), 4.53 (d, J = 9.6 Hz, 1 H), 6.81-6.85 (m, 1 H), 6.99-7.04 (m, 2 H), 7.25-7.29 (m, 1 H), 7.91-7.95 (m, 2 H), 7.99 (s, 1 H), 8.70 (brs, 1 H). |
| 190 | 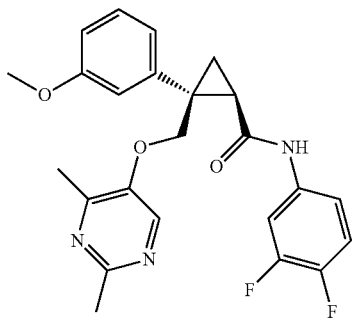 | ¹H-NMR (400 MHz, CDCl₃) δ (ppm): 1.59-1.62 (m, 1 H), 1.88 (t, J = 5.6 Hz, 1 H), 2.04 (dd, J = 8.2, 5.6 Hz, 1 H), 2.24 (s, 3 H), 2.57 (s, 3 H), 3.82 (s, 3 H), 4.43 (d, J = 9.6 Hz, 1 H), 4.53 (d, J = 9.6 Hz, 1 H), 6.81-6.85 (m, 1 H), 6.99-7.12 (m, 4 H), 7.25-7.30 (m, 1 H), 7.48-7.54 (m, 1 H), 7.60 (brs, 1 H), 7.99 (s, 1 H). |

* The compounds of Examples 191 to 201 were synthesized by reacting the carboxylic acid Prep 35 and any amine. It is to be noted that, with regard to condensation methods, the compounds of Examples 193 to 197 were condensed according to the method of Example 51 and the compounds of Examples 198 and 201 were condensed by the method of Example 1.

TABLE 47-1

| Example | Structural formula | NMR and/or MS |
|---|---|---|
| 191 | 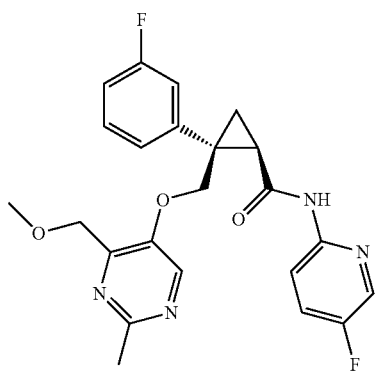 | ¹H-NMR (400 MHz, CDCl₃) δ (ppm): 1.63 (dd, J = 8.0, 5.2 Hz, 1 H), 1.92 (t, J = 5.2 Hz, 1 H), 2.12 (dd, J = 8.0, 6.0 Hz, 1 H), 2.63 (s, 3 H), 3.30 (s, 3 H), 4.29 (d, J = 13.6 Hz, 1 H), 4.44 (d, J = 13.6 Hz, 1 H), 4.46 (d, J = 9.6 Hz, 1 H), 4.53 (d, J = 9.6 Hz, 1 H), 7.01 (tdd, J = 8.0, 2.4, 1.2 Hz, 1 H), 7.18-7.24 (m, 2 H), 7.34 (dd, J = 8.0, 6.0 Hz, 1 H), 7.40 (ddd, J = 10.4, 9.2, 2.8 Hz, 1 H), 8.08 (dd, J = 9.2, 4.0 Hz, 1 H), 8.11 (s, 1 H), 8.13 (d, J = 2.4 Hz, 1 H), 8.38 (brs, 1 H). |

TABLE 47-1-continued

| Example | Structural formula | NMR and/or MS |
|---|---|---|
| 192 | | ¹H-NMR (400 MHz, CDCl₃) δ (ppm): 1.59 (dd, J = 8.0, 5.2 Hz, 1 H), 1.90 (t, J = 5.2 Hz, 1 H), 2.06 (dd, J = 8.0, 6.0 Hz, 1 H), 2.61 (s, 3 H), 3.30 (s, 3 H), 4.34 (d, J = 13.2 Hz, 1 H), 4.41 (d, J = 13.2 Hz, 1 H), 4.48 (d, J = 9.6 Hz, 1 H), 4.57 (d, J = 9.6 Hz, 1 H), 6.97-7.01 (m, 3 H), 7.18-7.24 (m, 2 H), 7.31 (td, J = 8.0, 6.0 Hz, 1 H), 7.39-7.43 (m, 2 H), 7.65 (brs, 1 H), 8.12 (s, 1 H). |
| 193 | | ¹H-NMR (400 MHz, CDCl₃) δ (ppm): 1.63 (dd, J = 8.0, 5.2 Hz, 1 H), 1.93 (t, J = 5.2 Hz, 1 H), 2.14 (brs, 1 H), 2.63 (s, 3 H), 3.26 (s, 3 H), 4.27 (d, J = 13.6 Hz, 1 H), 4.43 (d, J = 13.6 Hz, 1 H), 4.48 (d, J = 9.6 Hz, 1 H), 4.56 (d, J = 9.6 Hz, 1 H), 6.98-7.03 (m, 2 H), 7.19 (d, J = 10.0 Hz, 1 H), 7.22 (d, J = 8.0 Hz, 1 H), 7.33 (td, J = 8.0, 6.0 Hz, 1 H), 7.65 (td, J = 8.0, 2.0 Hz, 1 H), 8.05 (d, J = 8.0 Hz, 1 H), 8.12 (s, 1 H), 8.22 (dd, J = 4.8, 1.2 Hz, 1 H), 8.81 (s, 1 H). |
| 194 | | ¹H-NMR (400 MHz, CDCl₃) δ (ppm): 1.59 (dd, J = 8.0, 5.2 Hz, 1 H), 1.90 (t, J = 5.2 Hz, 1 H), 2.06 (dd, J = 8.0, 6.0 Hz, 1 H), 2.61 (s, 3 H), 3.31 (s, 3 H), 4.35 (d, J = 12.8 Hz, 1 H), 4.40 (d, J = 12.8 Hz, 1 H), 4.46 (d, J = 9.6 Hz, 1 H), 4.57 (d, J = 9.6 Hz, 1 H), 7.00 (td, J = 8.4, 2.0 Hz, 1 H), 7.04-7.11 (m, 2 H), 7.18-7.22 (m, 2 H), 7.32 (td, J = 8.4, 6.0 Hz, 1 H), 7.52 (dd, J = 10.8, 6.8 Hz, 1 H), 7.80 (brs, 1 H), 8.12 (s, 1 H). |

TABLE 48-1

| Example | Structural formula | NMR and/or MS |
|---|---|---|
| 195 | | ¹H-NMR (400 MHz, CDCl₃) δ (ppm): 1.59 (dd, J = 8.0, 5.6 Hz, 1 H), 1.95 (t, J = 5.6 Hz, 1 H), 2.09 (dd, J = 8.0, 5.6 Hz, 1 H), 2.63 (s, 3 H), 3.29 (s, 3 H), 4.32 (d, J = 13.2 Hz, 1 H), 4.42 (d, J = 13.2 Hz, 1 H), 4.48 (d, J = 10.0 Hz, 1 H), 4.58 (d, J = 10.0 Hz, 1 H), 6.80 (t, J = 7.6 Hz, 1 H), 7.00 (tdd, J = 8.0, 2.4, 1.2 Hz, 1 H), 7.13 (dt, J = 9.6, 2.4 Hz, 1 H), 7.14-7.27 (m, 3 H), 7.33 (td, J = 8.0, 6.0 Hz, 1 H), 7.41 (t, J = 10.8 Hz, 1 H), 7.85 (brs, 1 H), 8.12 (s, 1 H). |

TABLE 48-1-continued

| Example | Structural formula | NMR and/or MS |
|---|---|---|
| 196 | 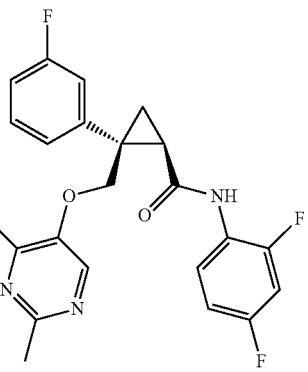 | $^1$H-NMR (400 MHz, CDCl$_3$) δ (ppm): 1.64 (dd, J = 5.2 Hz, 8.0 Hz, 1 H), 1.91 (t, J = 5.2 Hz, 1 H), 2.11 (dd, J = 6.0 Hz, 8.0 Hz, 1 H), 2.63 (s, 3 H), 3.33 (s, 3 H), 4.32-4.56 (m, 4 H), 6.81-6.90 (m, 2 H), 7.01 (t, J = 8.8 Hz, 1 H), 7.21-7.36 (m, 3 H), 7.62 (brs, 1 H), 8.05-8.12 (m, 2 H).<br>MS [M + H]$^+$ = 458 |
| 197 | 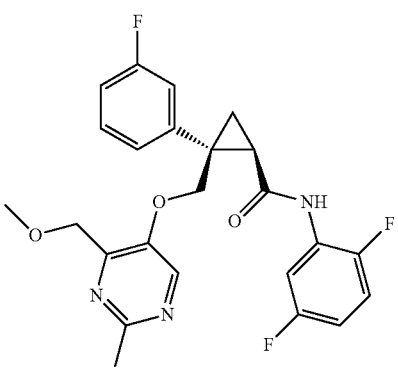 | $^1$H-NMR (400 MHz, CDCl$_3$) δ (ppm): 1.65 (dd, J = 5.2 Hz, 8.0 Hz, 1 H), 1.93 (t, J = 5.2 Hz, 1 H), 2.11 (dd, J = 6.0 Hz, 8.4 Hz, 1 H), 2.63 (s, 3 H), 3.31 (s, 3 H), 4.29-4.57 (m, 4 H), 6.70-6.76 (m, 1 H), 6.99-7.08 (m, 2 H), 7.17-7.37 (m, 3 H), 7.77 (brs, 1 H), 8.02-8.12 (m, 2 H).<br>MS [M + H]$^+$ = 458 |
| 198 | 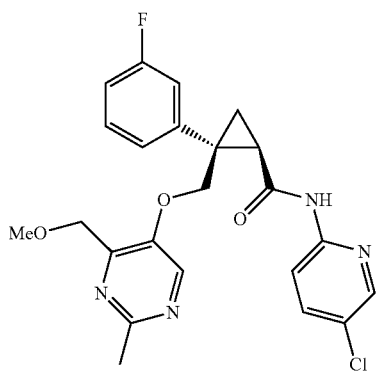 | $^1$H-NMR (400 MHz, CDCl$_3$) δ (ppm): 1.61 (dd, J = 8.2, 5.2 Hz, 1 H) 1.88 (t, J = 5.6 Hz, 1 H), 2.12 (dd, J = 8.0, 6.0 Hz, 1 H), 2.22 (s, 3 H), 2.26 (s, 3 H), 2.55 (s, 3 H), 3.81 (s, 3 H), 4.41 (d, J = 9.2 Hz, 1 H), 4.53 (d, J = 9.6 Hz, 1 H), 6.81-6.85 (m, 1 H), 6.99-7.04 (m, 2 H), 7.25-7.29 (m, 1 H), 7.91-7.95 (m, 2 H), 7.99 (s, 1 H), 8.70 (brs, 1 H). |
| 199 | 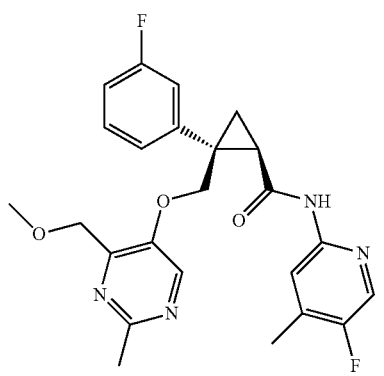 | $^1$H-NMR (400 MHz, CDCl$_3$) δ (ppm): 1.62 (dd, J = 8.0, 5.2 Hz, 1 H), 1.90 (d, J = 5.2 Hz, 1 H), 2.10 (dd, J = 8.0, 6.0 Hz, 1 H), 2.27 (s, 3 H), 2.63 (s, 3 H), 3.31 (s, 3 H), 4.29 (d, J = 13.2 Hz, 1 H), 4.42 (d, J = 13.2 Hz, 1 H), 4.45 (d, J = 9.6 Hz, 1 H), 4.53 (d, J = 9.6 Hz, 1 H), 7.00 (tdd, J = 8.0, 2.4, 1.2 Hz, 1 H), 7.19 (dt, J = 10.0, 2.4 Hz, 1 H), 7.22 (dt, J = 8.0, 1.2 Hz, 1 H), 7.33 (td, J = 6.0, 6.0 Hz, 1 H), 7.95 (brs, 1 H), 8.01 (s, 1 H), 8.10 (s, 1 H), 8.25 (s, 1 H). |

TABLE 49

| Example | Structural formula | NMR (400 MHz, CDCl₃) |
|---|---|---|
| 200 | | ¹H-NMR δ (ppm): 1.69 (dd, J = 8.0, 5.2 Hz, 1 H), 1.95 (t, J = 5.2 Hz, 1 H), 2.16 (dd, J = 8.0, 6.0 Hz, 1 H), 2.62 (s, 3 H), 3.29 (s, 3 H), 4.30 (d, J = 13.2 Hz, 1 H), 4.38 (d, J = 13.2 Hz, 1 H), 4.45 (d, J = 9.6 Hz, 1 H), 4.53 (d, J = 9.6 Hz, 1 H), 7.02 (dd, J = 8.8, 2.0 Hz, 1 H), 7.19-7.25 (m, 2 H), 7.35 (td, J = 8.0, 6.0 Hz, 1 H), 7.90 (dd, J = 8.8, 2.4 Hz, 1 H), 8.11 (s, 1 H), 8.22 (dd, J = 8.8, 1.2 Hz, 1 H), 8.55 (brs, 1 H), 8.57 (dd, J = 2.4, 1.2 Hz, 1 H). |
| 201 | | ¹H-NMR δ (ppm): 1.66 (dd, J = 8.0, 5.2 Hz, 1 H), 1.94 (t, J = 5.2 Hz, 1 H), 2.16 (dd, J = 8.0, 6.0 Hz, 1 H), 2.61 (s, 3 H), 3.27 (s, 3 H), 4.29 (d, J = 13.2 Hz, 1 H), 4.40 (d, J = 13.2 Hz, 1 H), 4.45 (d, J = 9.6 Hz, 1 H), 4.53 (d, J = 9.6 Hz, 1 H), 7.01 (tdd, J = 8.4, 2.8, 1.2 Hz, 1 H), 7.19 (dt, J = 10.0, 2.8 Hz, 1 H), 7.23 (dt, J = 8.4, 1.2 Hz, 1 H), 7.34 (td, J = 8.4, 6.0 Hz, 1 H), 7.88 (dd, J = 8.8, 2.4 Hz, 1 H), 8.11 (s, 1 H), 8.21 (d, J = 8.8 Hz, 1 H), 8.54 (d, J = 2.4 Hz, 1 H), 8.57 (brs, 1 H). |

\* The compounds of Examples 202 to 210 were synthesized by reacting the carboxylic acid Prep 36 and any amine by the same method as that of Example 51.

TABLE 50-1

| Example | Structural formula | NMR (400 MHz, CDCl₃) and/or MS |
|---|---|---|
| 202 | | ¹H-NMR δ (ppm): 1.60 (dd, J = 8.0, 5.2 Hz, 1 H), 1.90 (t, J = 5.2 Hz, 1 H), 2.07 (dd, J = 8.0, 6.0 Hz, 1 H), 2.62 (s, 3 H), 3.29 (s, 3 H), 4.29 (d, J = 13.2 Hz, 1 H), 4.40 (d, J = 13.2 Hz, 1 H), 4.44 (d, J = 9.6 Hz, 1 H), 4.49 (d, J = 9.6 Hz, 1 H), 7.05 (tt, J = 8.8, 1.6 Hz, 2 H), 7.37-7.46 (m, 3 H), 8.09-8.13 (m, 3 H), 8.32 (brs, 1 H). |
| 203 | | ¹H-NMR δ (ppm): 1.56 (dd, J = 8.0, 5.2 Hz, 1 H), 1.88 (t, J = 5.2 Hz, 1 H), 2.05 (dd, J = 8.0, 6.0 Hz, 1 H), 2.61 (s, 3 H), 3.29 (s, 3 H), 4.34 (d, J = 12.8 Hz, 1 H), 4.39 (d, J = 12.8 Hz, 1 H), 4.48 (d, J = 9.6 Hz, 1 H), 4.53 (d, J = 9.6 Hz, 1 H), 6.99 (t, J = 8.4 Hz, 2 H), 7.04 (t, J = 8.4 Hz, 2 H), 7.40-7.45 (m, 4 H), 7.63 (brs, 1 H), 8.11 (s, 1 H). |

TABLE 50-1-continued

| Example | Structural formula | NMR (400 MHz, CDCl₃) and/or MS |
|---|---|---|
| 204 | 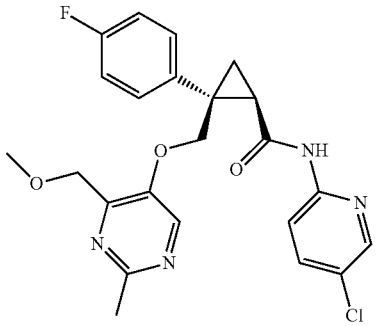 | ¹H-NMR δ (ppm): 1.60 (dd, J = 8.0, 5.2 Hz, 1 H), 1.90 (t, J = 5.2 Hz, 1 H), 2.08 (dd, J = 8.0, 6.0 Hz, 1 H), 2.62 (s, 3 H), 3.28 (s, 3 H), 4.29 (d, J = 13.6 Hz, 1 H), 4.40 (d, J = 13.6 Hz, 1 H), 4.43 (d, J = 9.6 Hz, 1 H), 4.49 (d, J = 9.6 Hz, 1 H), 7.05 (t, J = 8.4 Hz, 2 H), 7.44 (dd, J = 8.4, 4.8 Hz, 2 H), 7.62 (dd, J = 8.8, 2.4 Hz, 1 H), 8.06 (d, J = 8.8 Hz, 1 H), 8.08 (s, 1 H), 8.23 (d, J = 2.4 Hz, 1 H), 8.32 (brs, 1 H). |
| 205 | 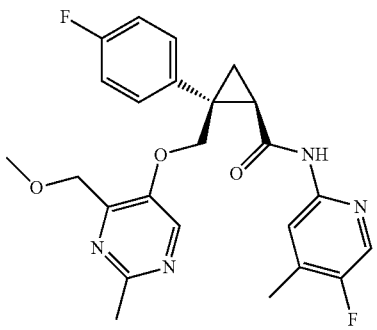 | ¹H-NMR δ (ppm): 1.59 (dd, J = 8.0, 5.6 Hz, 1 H), 1.89 (t, J = 5.6 Hz, 1 H), 2.06 (dd, J = 8.0, 6.0 Hz, 1 H), 2.28 (s, 3 H), 2.62 (s, 3 H), 3.30 (s, 3 H), 4.29 (d, J = 13.6 Hz, 1 H), 4.41 (d, J = 13.6 Hz, 1 H), 4.44 (d, J = 9.2 Hz, 1 H), 4.49 (d, J = 9.2 Hz, 1 H), 7.05 (t, J = 8.8 Hz, 2 H), 7.43 (dd, J = 8.8, 4.8 Hz, 2 H), 7.95 (d, J = 5.2 Hz, 1 H), 8.00 (s, 1 H), 8.09 (s, 1 H), 8.26 (brs, 1 H). |
| 206 | 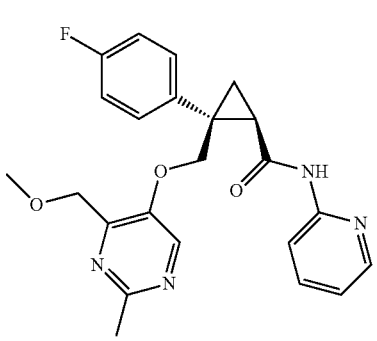 | ¹H-NMR δ (ppm): 1.59 (dd, J = 8.0, 5.2 Hz, 1 H), 1.91 (t, J = 5.2 Hz, 1 H), 2.10 (dd, J = 8.0, 6.0 Hz, 1 H), 2.62 (s, 3 H), 3.26 (s, 3 H), 4.28 (d, J = 13.6 Hz, 1 H), 4.44 (d, J = 13.6 Hz, 1 H), 4.41 (d, J = 9.6 Hz, 1 H), 4.50 (d, J = 9.6 Hz, 1 H), 7.02-7.08 (m, 3 H), 7.44 (dd, J = 8.8, 4.8 Hz, 2 H), 7.66 (td, J = 7.2, 2.0 Hz, 1 H), 8.06 (d, J = 7.2 Hz, 1 H), 8.09 (s, 1 H), 8.27 (dd, J = 4.8, 2.0 Hz, 1 H), 8.36 (brs, 1 H). |
| 207 | 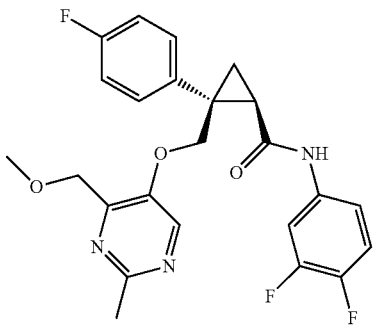 | ¹H-NMR δ (ppm): 1.57 (dd, J = 8.0, 5.2 Hz, 1 H), 1.88 (t, J = 5.2 Hz, 1 H), 2.02 (dd, J = 8.0, 6.0 Hz, 1 H), 2.61 (s, 3 H), 3.30 (s, 3 H), 4.34 (d, J = 12.8 Hz, 1 H), 4.39 (d, J = 12.8 Hz, 1 H), 4.45 (d, J = 9.6 Hz, 1 H), 4.52 (d, J = 9.6 Hz, 1 H), 7.01-7.11 (m, 4 H), 7.43 (dd, J = 8.4, 4.8 Hz, 2 H), 7.52 (dd, J = 10.8, 6.0 Hz, 1 H), 7.74 (brs, 1 H), 8.11 (s, 1 H). |

TABLE 50-1-continued

| Example | Structural formula | NMR (400 MHz, CDCl₃) and/or MS |
|---|---|---|
| 208 | 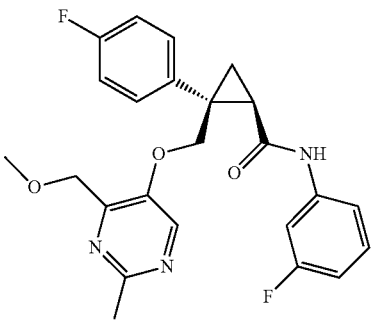 | ¹H-NMR δ (ppm): 1.56 (dd, J = 8.0, 5.6 Hz, 1 H), 1.89 (t, J = 5.6 Hz, 1 H), 2.04 (dd, J = 8.0, 5.6 Hz, 1 H), 2.61 (s, 3 H), 3.27 (s, 3 H), 4.32 (d, J = 13.2 Hz, 1 H), 4.40 (d, J = 13.2 Hz, 1 H), 4.46 (d, J = 9.2 Hz, 1 H), 4.53 (d, J = 9.2 Hz, 1 H), 6.80 (t, J = 8.0 Hz, 1 H), 7.04 (t, J = 8.8 Hz, 2 H), 7.12 (d, J = 8.0 Hz, 1 H), 7.24 (dd, J = 14.4, 8.0 Hz, 1 H), 7.40-7.44 (m, 3 H), 7.77 (brs, 1 H), 8.10 (s, 1 H). |

TABLE 51

| Example | Structural formula | NMR (400 MHz, CDCl₃) and/or MS |
|---|---|---|
| 209 | 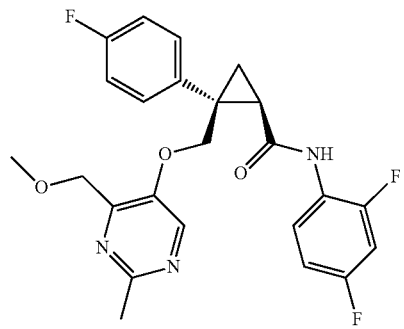 | ¹H-NMR δ (ppm): 1.60 (dd, J = 8.4, 5.2 Hz, 1 H), 1.89 (t, J = 5.2 Hz, 1 H), 2.08 (dd, J = 8.0, 5.6 Hz, 1 H), 2.63 (s, 3 H), 3.32 (s, 3 H), 4.31-4.52 (m, 4 H), 6.82-6.91 (m, 2 H), 7.05 (t, J = 8.8 Hz, 2 H), 7.42-7.45 (m, 2 H), 7.61 (brs, 1 H), 8.08-8.11 (m, 2 H).<br>MS [M + H]⁺ = 458 |
| 210 | 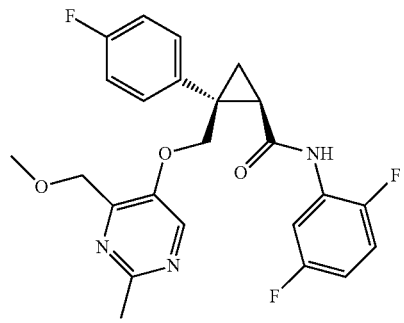 | ¹H-NMR δ (ppm): 1.62 (dd, J = 8.0, 5.2 Hz, 1 H), 1.91 (t, J = 5.6 Hz, 1 H), 2.08 (dd, J = 8.4, 6.0 Hz, 1 H), 2.63 (s, 3 H), 3.30 (s, 3 H), 4.29-4.52 (m, 4 H), 6.70-6.76 (m, 2 H), 7.02-7.08 (m, 3 H), 7.42-7.45 (m, 2 H), 7.52 (brs, 1 H), 8.03 (brds, 1 H), 8.10 (s, 1 H).<br>MS [M + H]⁺ = 458. |

\* The compounds of Examples 211 to 217 were synthesized by reacting the carboxylic acid Prep 37 and any amine by the same method as that of Example 51.

TABLE 52

| Example | Structural formula | NMR (400 MHz, CDCl$_3$) and/or MS |
|---|---|---|
| 211 | | $^1$H-NMR (400 MHz, CDCl$_3$) δ (ppm): 1.57-1.61 (m, 1 H), 1.91 (t, J = 5.6 Hz, 1 H), 2.04-2.09 (m, 1 H), 2.62 (s, 3 H), 3.28 (s, 3 H), 4.25-4.50 (m, 4 H), 7.03-7.36 (m, 4 H), 7.66 (t, J = 8.0 Hz, 1 H), 8.03-8.05 (m, J = 8.0 Hz, 1 H), 8.10 (s, 1 H), 8.27 (d, J = 3.6 Hz, 1 H), 8.38 (brds, 1 H). MS [M + H]$^+$ = 441 |
| 212 | | $^1$H-NMR δ (ppm): 1.58-1.61 (m, 1 H), 1.90 (t, J = 5.6 Hz, 1 H), 2.06 (brt, J = 5.6 Hz, 1 H), 2.27 (s, 3 H), 2.63 (s, 3 H), 3.32 (s, 3 H), 4.27-4.50 (m, 4 H), 7.13-7.19 (m, 2 H), 7.33 (t, J = 9.2 Hz, 1 H), 7.93 (d, J = 5.6 Hz, 1 H), 8.00 (s, 1 H), 8.10 (s, 1 H), 8.29 (s, 1 H). MS [M + H]$^+$ = 473 |
| 213 | | $^1$H-NMR δ (ppm): 1.55-1.57 (m, 1 H), 1.90 (t, J = 5.6 Hz, 1 H), 2.02 (dd, J = 8.0, 6.0 Hz, 1 H), 2.62 (s, 3 H), 3.32 (s, 3 H), 4.32-4.54 (m, 4 H), 6.99 (t, J = 8.8 Hz, 2 H), 7.13-7.42 (m, 5 H), 7.60 (s, 1 H), 8.12 (s, 1 H). MS [M + H]$^+$ = 458 |

TABLE 53

| Example | Structural formula | NMR (400 MHz, CDCl$_3$) and/or MS |
|---|---|---|
| 214 | | $^1$H-NMR δ (ppm): 1.55-1.58 (m, 1 H), 1.90 (t, J = 5.2 Hz, 1 H), 2.02 (dd, J = 8.4, 6.0 Hz, 1 H), 2.61 (s, 3 H), 3.33 (s, 3 H), 4.34-4.53 (m, 4 H), 7.05-7.17 (m, 4 H), 7.35 (t, J = 9.2 Hz, 1 H), 7.52 (t, J = 8.4 Hz, 1 H), 7.73 (s, 1 H), 8.12 (s, 1 H). MS [M + H]$^+$ = 476 |

TABLE 53-continued

| Example | Structural formula | NMR (400 MHz, CDCl₃) and/or MS |
|---|---|---|
| 215 | 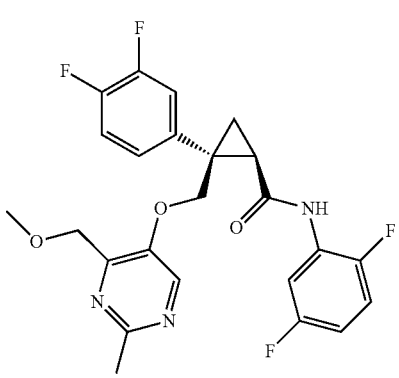 | $^1$H-NMR δ (ppm): 1.62 (dd, J = 8.8, 5.6 Hz, 1 H), 1.92 (t, J = 5.2 Hz, 1 H), 2.08 (dd, J = 8.4, 6.0 Hz, 1 H), 2.63 (s, 3 H), 3.32 (s, 3 H), 4.30-4.52 (m, 4 H), 6.71-6.75 (m, 1 H), 7.02-7.36 (m, 4 H), 7.79 (brds, 1 H), 8.00 (m, 1 H), 8.12 (s, 1 H).<br>MS [M + H]⁺ = 476 |
| 216 | 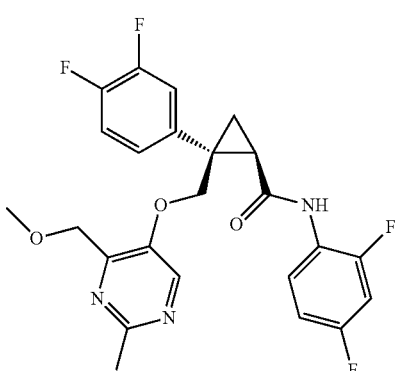 | $^1$H-NMR δ (ppm): 1.58-1.62 (m, 1 H), 1.90 (t, J = 5.6 Hz, 1 H), 2.07 (dd, J = 8.0, 6.0 Hz, 1 H), 2.63 (s, 3 H), 3.34 (s, 3 H), 4.32-4.52 (m, 4 H), 6.81-6.91 (m, 2 H), 7.12-7.18 (m, 2 H), 7.34 (t, J = 8.8 Hz, 1 H ), 7.65 (brs, 1 H), 8.03-8.12 (m, 2 H).<br>MS [M + H]⁺ = 476 |
| 217 | 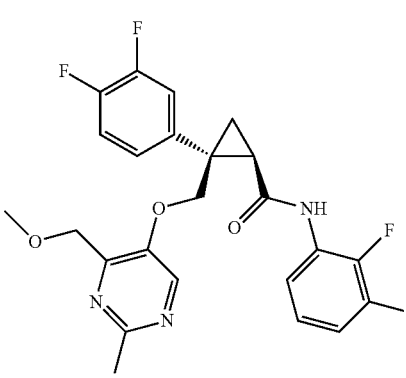 | $^1$H-NMR δ (ppm): 1.61 (dd, J = 8.4, 5.2 Hz, 1 H), 1.92 (t, J = 5.6 Hz, 1 H), 2.10 (dd, J = 8.0, 6.0 Hz, 1 H), 2.62 (s, 3 H), 3.33 (s, 3 H), 4.30-4.52 (m, 4 H), 6.90-7.37 (m, 5 H), 7.77 (brs, 1 H), 7.90 (brs, 1 H), 8.12 (s, 1 H).<br>MS [M + H]⁺ = 476 |

\* The compounds of Examples 218 to 221 were synthesized by reacting the carboxylic acid Prep 38 and any amine by the same method as that of Example 51,

TABLE 54

| Example | Structural formula | NMR (400 MHz, CDCl₃) and/or MS |
|---|---|---|
| 218 | 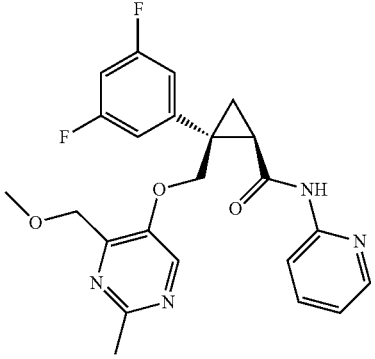 | ¹H-NMR δ (ppm): 1.62 (dd, J = 8.0, 5.6 Hz, 1 H), 1.93 (t, J = 5.2 Hz, 1 H), 2.11 (brt, 1 H), 2.62 (s, 3 H), 3.28 (s, 3 H), 4.25-4.54 (m, 4 H), 6.76 (t, J = 7.2 Hz, 1 H), 7.00-7.03 (m, 3 H), 7.65 (t, J = 8.0 Hz, 1 H), 8.02 (d, J = 7.6 Hz, 1 H), 8.12 (s, 1 H), 8.25 (d, J = 8.4 Hz, 1 H), 8.59 (s, 1 H).<br>MS [M + Na]⁺ = 464 |
| 219 | 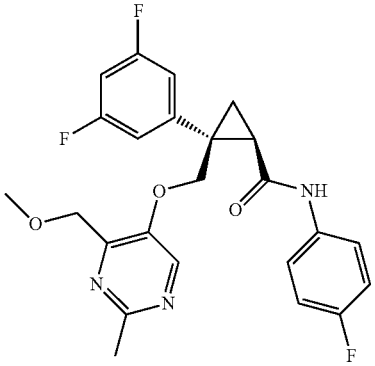 | ¹H-NMR δ (ppm): 1.58-1.60 (m, 1 H), 1.92 (t, J = 5.6 Hz, 1 H), 2.05 (dd, J = 8.0, 5.6 Hz, 1 H), 2.61 (s, 3 H), 3.32 (s, 3 H), 4.33-4.58 (m, 4 H), 6.76 (t, J = 8.8 Hz, 1 H), 6.97-7.02 (m, 4 H), 7.38-7.42 (m, 2 H), 7.62 (s, 1 H), 8.14 (s, 1 H).<br>MS [M + H]⁺ = 459 |
| 220 | 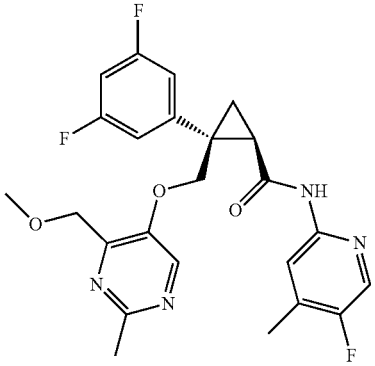 | ¹H-NMR δ (ppm): 1.60-1.64 (m, 1 H), 1.92 (t, J = 5.6 Hz, 1 H), 2.08 (brt, J = 8.0 Hz, 1 H), 2.27 (s, 3 H), 2.63 (s, 3 H), 3.33 (s, 3 H), 4.27-4.53 (m, 4 H), 6.76 (t, J = 8.8 Hz, 1 H), 6.99-7.02 (m, 2 H), 7.92 (d, J = 6.4 Hz, 1 H), 8.01 (s, 1 H), 8.12 (s, 1 H), 8.27 (s, 1 H).<br>MS [M + Na]⁺ = 496 |
| 221 | 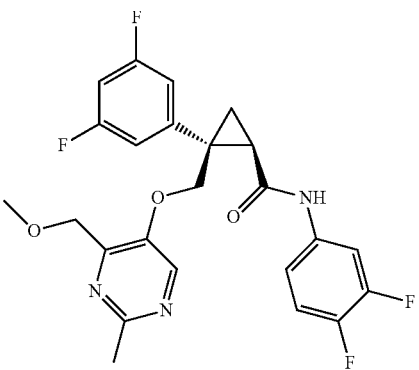 | ¹H-NMR δ (ppm): 1.57-1.61 (m, 1 H), 1.92 (t, J = 5.6 Hz, 1 H), 2.05 (dd, J = 8.0, 5.6 Hz, 1 H), 2.61 (s, 3 H), 3.33 (s, 3 H), 4.33-4.57 (m, 4 H), 6.76 (t, J = 8.8 Hz, 1 H), 7.00-7.09 (m, 4 H), 7.52 (brt, J = 7.2 Hz, 1 H), 7.78 (s, 1 H), 8.13 (s, 1 H).<br>MS [M + Na]⁺ = 498 |

* The compounds of Examples 222 to 227 were synthesized by reacting the carboxylic acid Prep 39 and any amine. It is to be noted that, with regard to condensation methods, the compounds of Examples 222 to 226 were condensed according to the method of Example 51 and the compound of Example 227 was condensed by the method of Example 1. In addition, the compounds of Examples 225 and 226 were obtained by performing chiral resolution on racemic products.

TABLE 55-1

| Example | Structural formula | NMR (400 MHz, CDCl$_3$) and/or MS |
|---|---|---|
| 222 | | $^1$H-NMR δ (ppm): 1.61 (dd, J = 8.0, 5.2 Hz, 1 H), 1.91 (t, J = 5.2 Hz, 1 H), 2.11 (dd, J = 8.0, 6.0 Hz, 1 H), 2.62 (s, 3 H), 3.31 (s, 3 H), 4.31 (d, J = 13.2 Hz, 1 H), 4.41 (d, J = 13.2 Hz, 1 H), 4.46 (d, J = 9.6 Hz, 1 H), 4.49 (d, J = 9.6 Hz, 1 H), 7.28-7.42 (m, 4 H), 7.48 (s, 1 H), 8.08 (dd, J = 9.2, 4.0 Hz, 1 H), 8.09 (s, 1 H), 8.12 (q, J = 2.8 Hz, 1 H), 8.39 (brs, 1 H). |
| 223 | | $^1$H-NMR δ (ppm): 1.62 (dd, J = 8.0, 5.6 Hz, 1 H), 1.91 (t, J = 5.6 Hz, 1 H), 2.11 (dd, J = 8.0, 5.6 Hz, 1 H), 2.62 (s, 3 H), 3.31 (s, 3 H), 4.30 (d, J = 13.6 Hz, 1 H), 4.41 (d, J = 13.6 Hz, 1 H), 4.44 (d, J = 9.6 Hz, 1 H), 4.49 (d, J = 9.6 Hz, 1 H), 7.25-7.35 (m, 3 H), 7.48 (s, 1 H), 7.62 (dd, J = 8.8, 2.8 Hz, 1 H), 8.05 (d, J = 8.8 Hz, 1 H), 8.09 (s, 1 H), 8.23 (d, J = 2.8 Hz, 1 H), 8.42 (brs, 1 H). |
| 224 | | $^1$H-NMR δ (ppm): 1.59 (dd, J = 8.0, 5.2 Hz, 1 H), 1.89 (t, J = 5.2 Hz, 1 H), 2.06 (dd, J = 8.0, 5.6 Hz, 1 H), 2.62 (s, 3 H), 3.22 (s, 3 H), 4.35 (d, J = 13.2 Hz, 1 H), 4.42 (d, J = 13.2 Hz, 1 H), 4.48 (d, J = 9.6 Hz, 1 H), 4.54 (d, J = 9.6 Hz, 1 H), 6.99 (t, J = 8.8 Hz, 2 H), 7.24-7.32 (m, 3 H), 7.42 (dd, J = 8.8, 4.8 Hz, 2 H), 7.49 (s, 1 H), 7.66 (brs, 1 H), 8.12 (s, 1 H). |
| 225 | | $^1$H-NMR δ (ppm): 1.61 (dd, J = 8.0, 5.2 Hz, 1 H), 1.92 (t, J = 5.2 Hz, 1 H), 2.12 (dd, J = 8.0, 6.0 Hz, 1 H), 2.62 (s, 3 H), 3.29 (s, 3 H), 4.29 (d, J = 13.6 Hz, 1 H), 4.43 (d, J = 13.6 Hz, 1 H), 4.46 (d, J = 9.6 Hz, 1 H), 4.51 (d, J = 9.6 Hz, 1 H), 7.03 (dd, J = 7.2, 4.8 Hz, 1 H), 7.26-7.35 (m, 3 H), 7.49 (s, 1 H), 7.66 (td, J = 7.2, 2.0 Hz, 1 H), 8.06 (d, J = 7.2 Hz, 1 H), 8.10 (s, 1 H), 8.27 (d, J = 4.8 Hz, 1 H), 8.50 (brs, 1 H). |

TABLE 55-1-continued

| Example | Structural formula | NMR (400 MHz, CDCl₃) and/or MS |
|---|---|---|
| 226 | 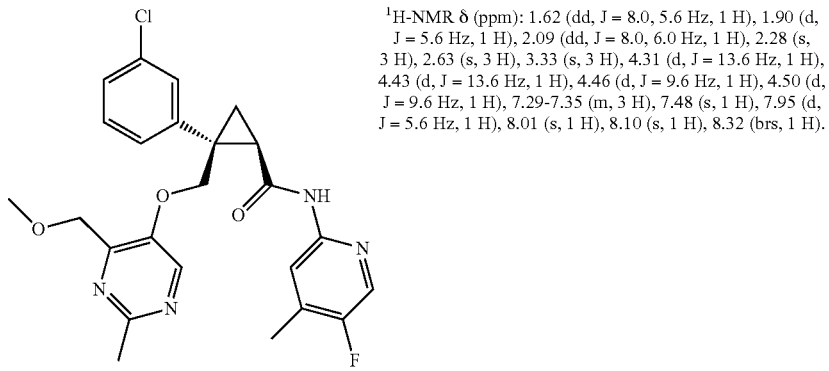 | ¹H-NMR δ (ppm): 1.62 (dd, J = 8.0, 5.6 Hz, 1 H), 1.90 (d, J = 5.6 Hz, 1 H), 2.09 (dd, J = 8.0, 6.0 Hz, 1 H), 2.28 (s, 3 H), 2.63 (s, 3 H), 3.33 (s, 3 H), 4.31 (d, J = 13.6 Hz, 1 H), 4.43 (d, J = 13.6 Hz, 1 H), 4.46 (d, J = 9.6 Hz, 1 H), 4.50 (d, J = 9.6 Hz, 1 H), 7.29-7.35 (m, 3 H), 7.48 (s, 1 H), 7.95 (d, J = 5.6 Hz, 1 H), 8.01 (s, 1 H), 8.10 (s, 1 H), 8.32 (brs, 1 H). |
| 227 | 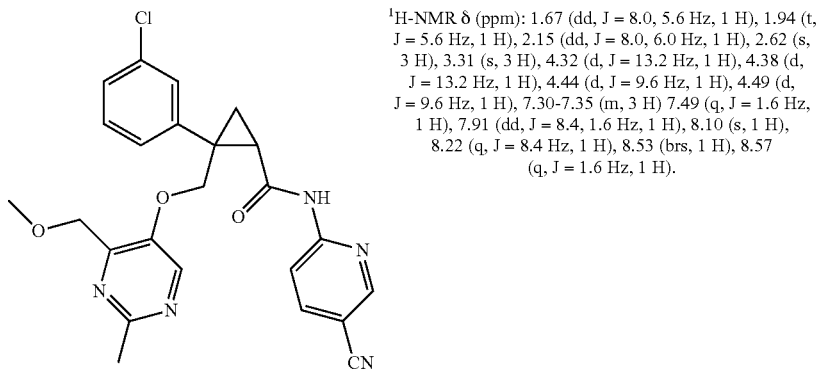 | ¹H-NMR δ (ppm): 1.67 (dd, J = 8.0, 5.6 Hz, 1 H), 1.94 (t, J = 5.6 Hz, 1 H), 2.15 (dd, J = 8.0, 6.0 Hz, 1 H), 2.62 (s, 3 H), 3.31 (s, 3 H), 4.32 (d, J = 13.2 Hz, 1 H), 4.38 (d, J = 13.2 Hz, 1 H), 4.44 (d, J = 9.6 Hz, 1 H), 4.49 (d, J = 9.6 Hz, 1 H), 7.30-7.35 (m, 3 H) 7.49 (q, J = 1.6 Hz, 1 H), 7.91 (dd, J = 8.4, 1.6 Hz, 1 H), 8.10 (s, 1 H), 8.22 (q, J = 8.4 Hz, 1 H), 8.53 (brs, 1 H), 8.57 (q, J = 1.6 Hz, 1 H). |

\* The compounds of Examples 228 to 230 were synthesized by reacting the carboxylic acid Prep 40 and any amine by the same method as that of Example 51.

TABLE 56

| Example | Structural formula | NMR (400 MHz, CDCl₃) and/or MS |
|---|---|---|
| 228 | | ¹H-NMR δ (ppm): 1.60 (dd, J = 8.0, 5.6 Hz, 1 H), 1.92 (t, J = 5.6 Hz, 1 H), 2.14 (dd, J = 8.0, 5.6 Hz, 1 H), 2.56 (s, 3 H), 2.77 (qui, J = 6.8 Hz, 1 H), 2.92 (qui, J = 6.8 Hz, 1 H), 3.18 (s, 3 H), 3.48-3.57 (m, 2 H), 4.44 (d, J = 9.6 Hz, 1 H), 4.51 (d, J = 9.6 Hz, 1 H), 6.97-7.04 (m, 2 H), 7.19 (dt, J = 8.0, 1.2 Hz, 1 H), 7.24 (dt, J = 8.0, 1.2 Hz, 1 H), 7.32 (dt, J = 8.0, 6.0 Hz, 1 H), 7.65 (td, J = 7.6, 2.0 Hz, 1 H), 8.02 (s, 1 H), 8.05 (d, J = 7.6 Hz, 1 H), 8.26 (d, J = 4.8 Hz, 1 H), 8.52 (brs, 1 H). |

TABLE 56-continued

| Example | Structural formula | NMR (400 MHz, CDCl₃) and/or MS |
|---|---|---|
| 229 | 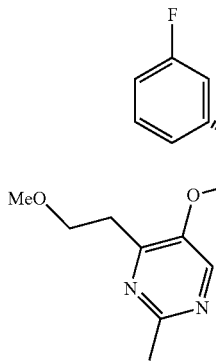 | ¹H-NMR δ (ppm): 1.60 (dd, J = 8.0, 5.2 Hz, 1 H), 1.90 (t, J = 5.2 Hz, 1 H), 2.11 (dd, J = 8.0, 5.6 Hz, 1 H), 2.27 (s, 3 H), 2.56 (s, 3 H), 2.77 (qui, J = 6.8 Hz, 1 H), 2.93 (qui, J = 6.8 Hz, 1 H), 3.21 (s, 3 H), 3.51-3.57 (m, 2 H), 4.43 (d, J = 9.6 Hz, 1 H), 4.51 (d, J = 9.6 Hz, 1 H), 6.99 (td, J = 8.0, 2.4 Hz, 1 H), 7.18 (dt, J = 8.8, 2.0 Hz, 1 H), 7.23 (d, J = 8.0 Hz, 1 H), 7.32 (td, J = 8.0, 6.0 Hz, 1 H), 7.94 (d, J = 6.0 Hz, 1 H), 8.00 (s, 1 H), 8.02 (s, 1 H), 8.43 (brs, 1 H). |
| 230 | 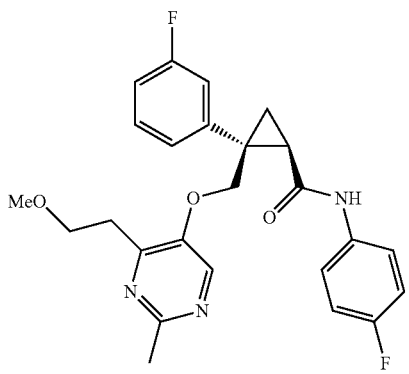 | ¹H-NMR δ (ppm): 1.56 (dd, J = 8.0, 5.6 Hz, 1 H), 1.91 (t, J = 5.6 Hz, 1 H), 2.08 (dd, J = 8.0, 5.6 Hz, 1 H), 2.55 (s, 3 H), 2.82-2.97 (m, 2 H), 3.23 (s, 3 H), 3.52-3.61 (m, 2 H), 4.45 (d, J = 9.6 Hz, 1 H), 4.55 (d, J = 9.6 Hz, 1 H), 6.96-7.01 (m, 3 H), 7.19-7.24 (m, 2 H), 7.31 (td, J = 8.4, 6.0 Hz, 1 H), 7.40 (dd, J = 8.8, 4.8 Hz, 1 H), 7.79 (brs, 1 H), 8.03 (s, 1 H). |

\* The compounds of Examples 231 to 236 were synthesized by reacting the carboxylic acid Prep 41 and any amine by the same method as that of Example 51.

TABLE 57-1

| Example | Structural formula | NMR (400 MHz, CDCl₃) and/or MS |
|---|---|---|
| 231 |  | ¹H-NMR δ (ppm): 1.56 (dd, J = 8.0, 5.2 Hz, 1 H), 1.87 (t, J = 5.2 Hz, 1 H), 2.07 (dd, J = 8.0, 6.0 Hz, 1 H), 2.62 (s, 3 H), 3.30 (s, 3 H), 3.80 (s, 3 H), 4.35 (d, J = 13.2 Hz, 1 H), 4.44 (d, J = 13.2 Hz, 1 H), 4.46 (d, J = 9.6 Hz, 1 H), 4.56 (d, J = 9.6 Hz, 1 H), 6.54 (dt, J = 10.8, 2.0 Hz, 1 H), 6.77-6.79 (m, 2 H), 6.98 (t, J = 8.8 Hz, 2 H), 7.41 (dd, J = 8.8, 4.8 Hz, 2 H), 7.85 (brs, 1 H), 8.12 (s, 1 H). |

TABLE 57-1-continued

| Example | Structural formula | NMR (400 MHz, CDCl₃) and/or MS |
|---|---|---|
| 232 | | ¹H-NMR δ (ppm): 1.56 (dd, J = 8.0, 5.2 Hz, 1 H), 1.87 (t, J = 5.2 Hz, 1 H), 2.07 (dd, J = 8.0, 6.0 Hz, 1 H), 2.61 (s, 3 H), 3.32 (s, 3 H), 3.79 (s, 3 H), 4.36 (d, J = 13.2 Hz, 1 H), 4.43 (d, J = 13.2 Hz, 1 H), 4.44 (d, J = 9.6 Hz, 1 H), 4.55 (d, J = 9.6 Hz, 1 H), 6.54 (dt, J = 10.8, 2.4 Hz, 1 H), 6.76-6.78 (m, 2 H), 7.02-7.10 (m, 2 H), 7.53 (dd, J = 10.8, 6.8 Hz, 1 H), 8.03 (brs, 1 H), 8.12 (s, 1 H). |
| 233 | | ¹H-NMR δ (ppm): 1.61 (dd, J = 8.0, 5.2 Hz, 1 H), 1.89 (t, J = 5.2 Hz, 1 H), 2.11 (dd, J = 8.0, 6.0 Hz, 1 H), 2.63 (s, 3 H), 3.30 (s, 3 H), 3.81 (s, 3 H), 4.30 (d, J = 13.2 Hz, 1 H), 4.43 (d, J = 13.2 Hz, 1 H), 4.45 (d, J = 9.6 Hz, 1 H), 4.53 (d, J = 9.6 Hz, 1 H), 6.56 (dt, J = 10.8, 2.4 Hz, 1 H), 6.76-6.80 (m, 2 H), 7.39 (ddd, J = 10.4, 9.2, 2.8 Hz, 1 H), 8.07 (dd, J = 9.2, 4.0 Hz, 1 H), 8.10 (s, 1 H), 8.11 (d, J = 2.4 Hz, 1 H), 8.49 (brs, 1 H). |
| 234 | | ¹H-NMR δ (ppm): 1.61 (dd, J = 8.0, 5.2 Hz, 1 H), 1.88 (t, J = 5.2 Hz, 1 H), 2.09 (dd, J = 8.0, 6.0 Hz, 1 H), 2.27 (s, 3 H), 2.63 (s, 3 H), 3.31 (s, 3 H), 3.80 (s, 3 H), 4.30 (d, J = 13.6 Hz, 1 H), 4.44 (d, J = 13.6 Hz, 1 H), 4.44 (d, J = 9.2 Hz, 1 H), 4.53 (d, J = 9.2 Hz, 1 H), 6.56 (dt, J = 10.4, 2.4 Hz, 1 H), 6.75-6.79 (m, 2 H), 7.94 (d, J = 5.6 Hz, 1 H), 7.98 (s, 1 H), 8.11 (s, 1 H), 8.49 (brs, 1 H). |
| 235 | | ¹H-NMR δ (ppm): 1.59 (dd, J = 8.0, 5.2 Hz, 1 H), 1.89 (t, J = 5.2 Hz, 1 H), 2.12 (dd, J = 8.0, 5.6 Hz, 1 H), 2.62 (s, 3 H), 3.26 (s, 3 H), 3.80 (s, 3 H), 4.28 (d, J = 13.6 Hz, 1 H), 4.43 (d, J = 13.6 Hz, 1 H), 4.48 (d, J = 9.6 Hz, 1 H), 4.53 (d, J = 9.6 Hz, 1 H), 6.55 (dt, J = 10.8, 2.4 Hz, 1 H), 6.76-6.79 (m, 2 H), 7.00 (dd, J = 7.6, 4.8 Hz, 1 H), 7.65 (td, J = 7.6, 2.0 Hz, 1 H), 8.03 (d, J = 7.6 Hz, 1 H), 8.10 (s, 1 H), 8.24 (d, J = 4.8 Hz, 1 H), 8.67 (brs, 1 H). |

TABLE 57-1-continued

| Example | Structural formula | NMR (400 MHz, CDCl₃) and/or MS |
|---------|-------------------|-------------------------------|
| 236 | | $^1$H-NMR δ (ppm): 1.57 (dd, J = 8.0, 5.6 Hz, 1 H), 1.88 (t, J = 5.6 Hz, 1 H), 2.07 (dd, J = 8.0, 6.0 Hz, 1 H), 2.61 (s, 3 H), 3.29 (s, 3 H), 3.80 (s, 3 H), 4.33 (d, J = 13.2 Hz, 1 H), 4.43 (d, J = 13.2 Hz, 1 H), 4.45 (d, J = 9.6 Hz, 1 H), 4.56 (d, J = 9.6 Hz, 1 H), 6.54 (dt, J = 10.4, 2.4 Hz, 1 H), 6.76-6.81 (m, 3 H), 7.11 (dd, J = 8.0, 2.0 Hz, 1 H), 7.23 (dd, J = 14.8, 2.0 Hz, 1 H), 7.40 (d, J = 11.2 Hz, 1 H), 7.82 (brs, 1 H), 8.11 (s, 1 H). |

\* The compounds of Examples 237 to 239 were synthesized by reacting the carboxylic acid Prep 42 and any amine by the same method as that of Example 51.

TABLE 58

| Example | Structural formula | NMR (400 MHz, CDCl₃) and/or MS |
|---------|-------------------|-------------------------------|
| 237 | | $^1$H-NMR δ (ppm): 1.59 (dd, J = 8.0, 5.6 Hz, 1H), 1.87 (t, J = 5.6 Hz, 1H), 2.04 (dd, J = 8.0, 5.6 Hz, 1H), 2.63 (s, 3H), 3.28 (s, 3H), 3.92 (s, 3H), 4.34 (d, J = 13.2 Hz, 1H), 4.42 (d, J = 13.2 Hz, 1H), 4.49 (d, J = 9.2 Hz, 1H), 4.55 (d, J = 9.2 Hz, 1H), 6.98-7.08 (m, 5H), 7.39-7.43 (m, 2H), 7.55 (brs, 1H), 8.13 (s, 1H). MS [M + Na]$^+$ = 492 |
| 238 | | $^1$H-NMR δ (ppm): 1.59 (dd, J = 8.2, 5.6 Hz, 1H), 1.87 (t, J = 5.6 Hz, 1H), 2.03 (dd, J = 8.2, 5.6 Hz, 1H), 2.63 (s, 3H), 3.30 (s, 3H), 3.91 (s, 3H), 4.35 (d, J = 13.0 Hz, 1H), 4.41 (d, J = 13.0 Hz, 1H), 4.47 (d, J = 9.6 Hz, 1H), 4.55 (d, J = 9.6 Hz, 1H), 6.97-7.12 (m, 5H), 7.50-7.55 (m, 1H), 7.67 (brs, 1H), 8.13 (s, 1H). MS [M + H]$^+$ = 488 |

TABLE 58-continued

| Example | Structural formula | NMR (400 MHz, CDCl₃) and/or MS |
|---|---|---|
| 239 | 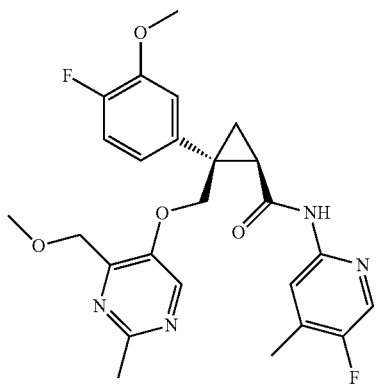 | ¹H-NMR δ (ppm): 1.60 (dd, J = 8.0, 5.2 Hz, 1H), 1.88 (t, J = 5.2 Hz, 1H), 2.07 (dd, J = 8.0, 5.2 Hz, 1H), 2.28 (m, 3H), 2.63 (s, 3H), 3.29 (s, 3H), 3.92 (s, 3H), 4.29 (d, J = 13.4 Hz, 1H), 4.42 (d, J = 13.4 Hz, 1H), 4.45 (d, J = 9.6 Hz, 1H), 4.51 (d, J = 9.6 Hz, 1H), 6.97-7.09 (m, 3H), 7.96 (d, J = 5.6 Hz, 1H), 8.02 (d, J = 1.2 Hz, 1H), 8.10 (s, 1H), 8.21 (brs, 1H). MS [M + Na]⁺ = 507. |

\* The compounds of Examples 240 to 244 were synthesized by reacting the carboxylic acid Prep 43 and any amine by the same method as that of Example 1.

TABLE 59

| Example | Structural formula, MS |
|---|---|
| 240 | 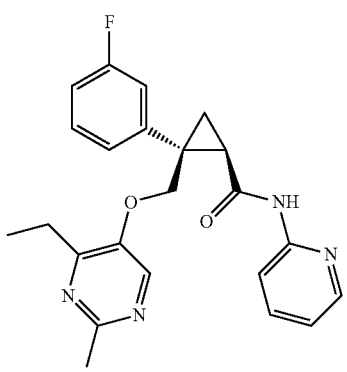<br>MS [M + H]⁺ = 407 |
| 241 | 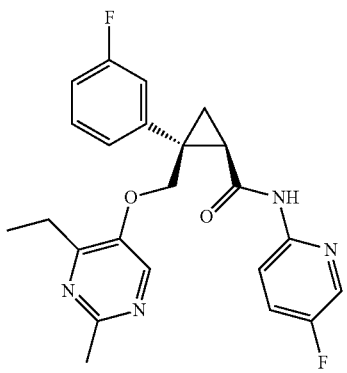<br>MS [M + H]⁺ = 425 |

TABLE 59-continued

| Example | Structural formula, MS |
|---|---|
| 242 | 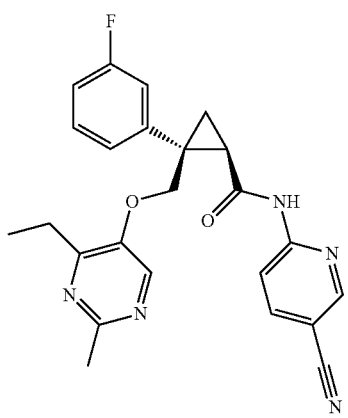<br>MS [M + H]⁺ = 432 |
| 243 | 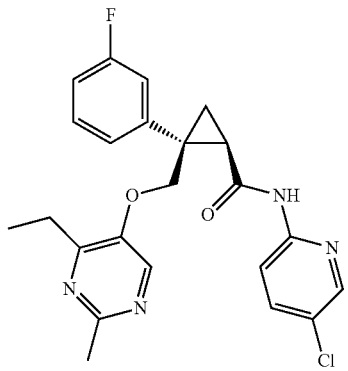<br>MS [M + H]⁺ = 441 |

TABLE 59-continued

| Example | Structural formula, MS |
|---|---|
| 244 | 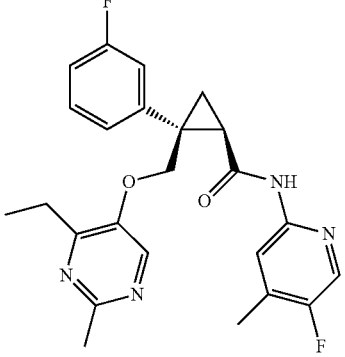 MS [M + H]⁺ = 439 |

\* The compounds of Examples 245 to 250 were synthesized by reacting the carboxylic acid Prep 44 and any amine by the same method as that of Example 1.

TABLE 60

| Example | Structural formula, MS |
|---|---|
| 245 | MS [M + H]⁺ = 407 |
| 246 | MS [M + H]⁺ = 425 |
| 247 | MS [M + H]⁺ = 441 |
| 248 | MS [M + H]⁺ = 439 |
| 249 | MS [M + H]⁺ = 424 |
| 250 | MS [M + H]⁺ = 424 |

\* The compounds of Examples 251 to 256 were synthesized by reacting the carboxylic acid Prep 45 or the corresponding racemic form and any amine. It is to be noted that the compounds of Examples 251 to 253 were condensed according to the method of Example 51, and that the compounds of Examples 254 to 256 were condensed by the method of Example 1, followed by chiral resolution,

TABLE 61

| Example | Structural formula | NMR (400 MHz, CDCl₃) and/or MS |
| --- | --- | --- |
| 251 |  | ¹H-NMR δ (ppm): 1.59 (dd, J = 8.2, 4.8 Hz, 1H), 1.91 (t, J = 5.2 Hz, 1H), 2.12-2.18 (m, 1H), 2.21 (s, 3H), 2.55 (s, 3H), 3.79 (s, 3H), 4.41 (d, J = 9.6 Hz, 1H), 4.52 (d, J = 9.6 Hz, 1H), 6.54 (dt, J = 10.4, 2.0 Hz, 1H), 6.73-6.79 (m, 2H), 6.95-6.99 (m, 1H), 7.61-7.67 (m, 1H), 8.00 (s, 1H), 7.99-8.05 (m, 1H), 8.19-8.21 (m, 1H), 9.25 (brs, 1H). |
| 252 |  | ¹H-NMR δ (ppm): 1.56 (dd, J = 8.2, 5.2 Hz, 1H), 1.87 (t, J = 5.6 Hz, 1H), 2.03-2.07 (m, 1H), 2.26 (s, 3H), 2.57 (s, 3H), 3.79 (s, 3H), 4.43 (d, J = 9.6 Hz, 1H), 4.51 (d, J = 9.6 Hz, 1H), 6.53 (dt, J = 10.4, 2.4 Hz, 1H), 6.74-6.78 (m, 2H), 6.95-7.00 (m, 2H), 7.36-7.41 (m, 2H), 7.90 (brs, 1H) 7.99 (s, 1H). |
| 253 |  | ¹H-NMR δ (ppm): 1.66 (dd, J = 8.0, 5.2 Hz, 1H), 1.92 (t, J = 5.2 Hz, 1H), 2.16 (t, J = 9.0 Hz, 1H), 2.22 (s, 3H), 2.56 (s, 3H), 3.81 (s, 3H) 4.37 (d, J = 9.6 Hz, 1H), 4.48 (d, J = 9.6 Hz, 1H), 6.50-6.58 (m, 1H) 6.75-6.81 (m, 2H), 7.87-7.91 (m, 1H), 7.98 (s, 1H), 8.17-8.21 (m, 1H), 8.55-8.57 (m, 1H), 8.63 (brs, 1H). |
| 254 |  | ¹H-NMR δ (ppm): 1.56 (dd, J = 8.0, 5.2 Hz, 1H), 1.88 (t, J = 5.2 Hz, 1H), 2.10-2.16 (m, 1H), 2.20 (s, 3H), 2.53 (s, 3H), 3.77 (s, 3H) 4.38 (d, J = 9.6 Hz, 1H), 4.49 (d, J = 9.6 Hz, 1H), 6.52 (dt, J = 10.8, 1.6 Hz, 1H) 6.73-6.79 (m, 2H), 7.32-7.38 (m, 1H), 7.97 (s, 1H), 8.00-8.08 (m, 2H), 9.02 (brs, 1H). |

TABLE 61-continued

| Example | Structural formula | NMR (400 MHz, CDCl₃) and/or MS |
|---|---|---|
| 255 | | ¹H-NMR δ (ppm): 1.61 (dd, J = 8.0, 5.2 Hz, 1H), 1.90 (t, J = 5.2 Hz, 1H), 2.12 (brs, 1H), 2.23 (s, 3H), 2.56 (s, 3H), 3.80 (s, 3H) 4.38 (d, J = 9.6 Hz, 1H), 4.50 (d, J = 9.6 Hz, 1H), 6.55 (dt, J = 10.8, 1.6 Hz, 1H), 6.72-6.82 (m, 2H), 7.56-7.64 (m, 1H), 7.99 (s, 1H), 7.78-8.08 (m, 1H), 8.16-8.24 (m, 1H), 8.62 (brs, 1H). |
| 256 | | ¹H-NMR δ (ppm): 1.60 (dd, J = 8.0, 5.2 Hz, 1H), 1.89 (t, J = 5.6 Hz, 1H), 2.09 (dd, J = 7.8, 6.4 Hz, 1H), 2.23 (s, 3H), 2.26 (s, 3H), 2.56 (s, 3H), 3.79 (s, 3H), 4.40 (d, J = 9.6 Hz, 1H), 4.52 (d, J = 9.6 Hz, 1H), 6.55 (dt, J = 10.4, 2.0 Hz, 1H), 6.75 (dt, J = 8.8, 2.0 Hz, 1H), 6.77-6.79 (m, 1H), 7.89-7.95 (m, 2H), 8.00 (s, 1H), 8.68 (brs, 1H). |

\* The compounds of Examples 257 to 259 were synthesized by reacting the carboxylic acid Prep 46 and any amine by the same method as that of Example 51.

TABLE 62

| Example | Structural formula | NMR (400 MHz, CDCl₃) and/or MS |
|---|---|---|
| 257 | | ¹H-NMR δ (ppm): 1.61 (dd, J = 8.0, 5.2 Hz, 1H), 1.90 (t, J = 5.2 Hz, 1H), 2.12 (t, J = 6.0 Hz, 1H), 2.23 (s, 3H), 2.56 (s, 3H), 3.91 (s, 3H), 4.39 (d, J = 9.6 Hz, 1H), 4.48 (d, J = 9.6 Hz, 1H), 6.96-7.10 (m, 3H), 7.60-7.64 (m, 1H), 7.98 (s, 1H), 8.03-8.06 (m, 1H), 8.21-8.22 (m, 1H), 8.47 (brs, 1H). |
| 258 | | ¹H-NMR δ (ppm): 1.59 (dd, J = 8.0, 5.2 Hz, 1H), 1.89 (t, J = 5.2 Hz, 1H), 2.04-2.12 (m, 1H), 2.23 (s, 3H), 2.27 (s, 3H), 2.56 (s, 3H), 3.90 (s, 3H), 4.41 (d, J = 9.2 Hz, 1H), 4.48 (d, J = 9.2 Hz, 1H), 6.95-7.27 (m, 3H), 7.93-8.01 (m, 2H) 7.99 (s, 1H), 8.63 (brs, 1H). |

TABLE 62-continued

| Example | Structural formula | NMR (400 MHz, CDCl₃) and/or MS |
|---|---|---|
| 259 | | $^1$H-NMR δ (ppm): 1.59 (dd, J = 8.0, 5.2 Hz, 1H), 1.90 (t, J = 4.8 Hz, 1H), 2.10-2.14 (m, 1H), 2.22 (s, 3H), 2.55 (s, 3H), 3.90 (s, 3H) 4.41 (d, J = 9.6 Hz, 1H), 4.48 (d, J = 9.6 Hz, 1H), 6.96-7.10 (m, 4H), 7.62-7.68 (m, 1H), 7.99 (s, 1H), 8.02-8.07 (m, 1H), 8.22-8.25 (m, 1H), 8.72 (brs, 1H). |

EXAMPLE 260

Synthesis of N-(5-chloropyridin-2-yl)-2-{[(2,4-dimethylpyrimidin-5-yl)oxy]methyl}-2-pyridin-3-ylcyclopropanecarboxamide (260)

[Formula 83]

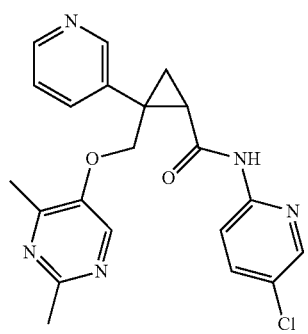

The title compound was synthesized by amidating the carboxylic acid Prep 47 according to the method of Example 51.

$^1$H-NMR (400 MHz, CDCl₃) δ (ppm): 1.63 (dd, J=8.0, 5.2 Hz, 1H), 1.96 (t, J=4.8 Hz, 1H), 2.14-2.22 (m, 1H), 2.22 (s, 3H), 2.56 (s, 3H), 4.44 (d, J=9.6 Hz, 1H), 4.49 (d, J=9.6 Hz, 1H), 7.29-7.33 (m, 1H), 7.61-7.64 (m, 1H), 7.79 (dt, J=7.6, 1.9 Hz, 1H), 7.99 (s, 1H), 8.04-8.07 (m, 1H), 8.20-8.22 (m, 1H), 8.56-8.59 (m, 1H), 8.77-8.78 (m, 1H), 8.89-8.95 (brs, 1H).

* The compounds of Examples 261 to 281 were synthesized according to the methods described in the production examples and the examples.

TABLE 63

| Example | Structural formula, MS |
|---|---|
| 261 | MS[M + H]⁺ = 418 |
| 262 | MS[M + H]⁺ = 427 |
| 263 | MS[M + H]⁺ = 411 |

TABLE 63-continued
| Example | Structural formula, MS |
|---|---|
| 264 | 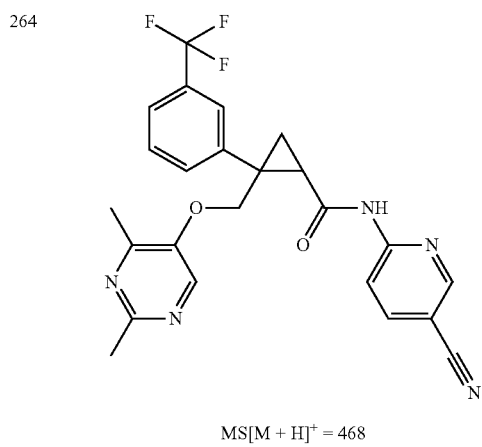 MS[M + H]⁺ = 468 |
| 265 | 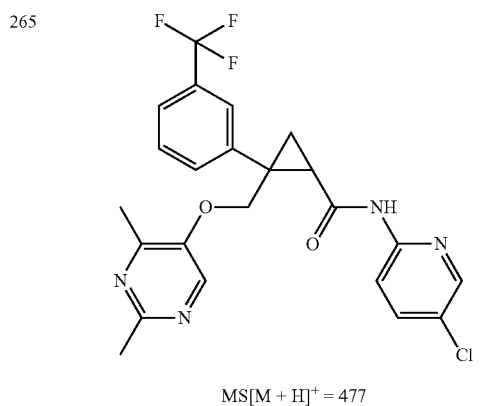 MS[M + H]⁺ = 477 |
| 266 | 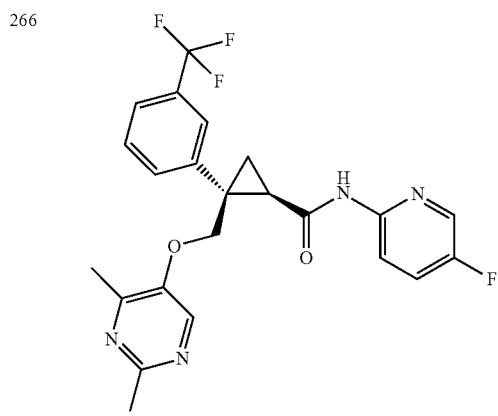 MS[M + H]⁺ = 461 |
TABLE 63-continued
| Example | Structural formula, MS |
|---|---|
| 267 | 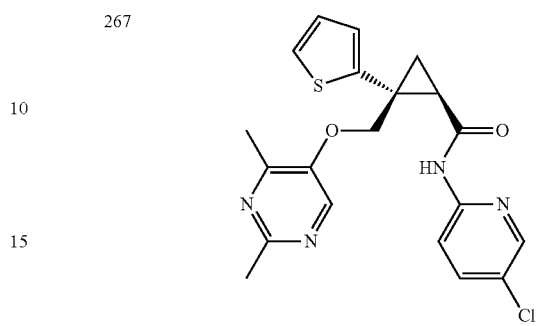 MS[M + H]⁺ = 415 |
| 268 | 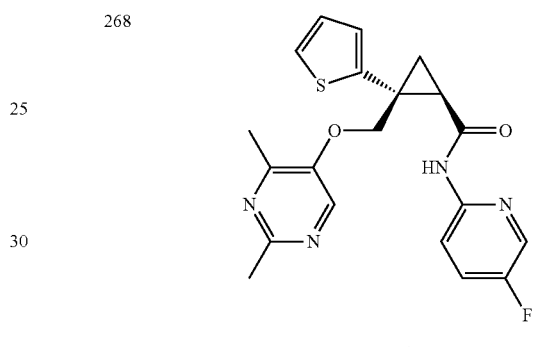 MS[M + H]⁺ = 399 |
| 269 | 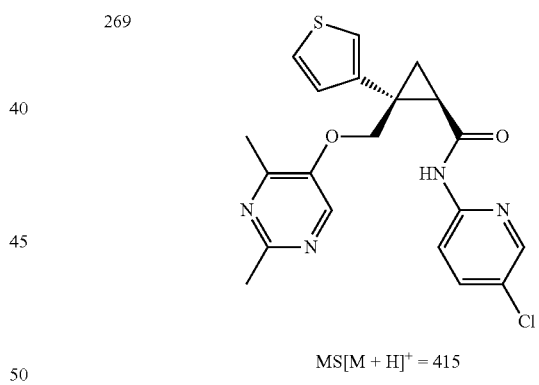 MS[M + H]⁺ = 415 |
| 270 | 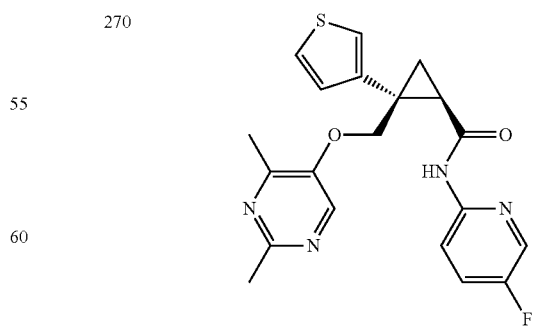 MS[M + H]⁺ = 399 |

TABLE 63-continued
| Example | Structural formula, MS |
|---|---|
| 271 | 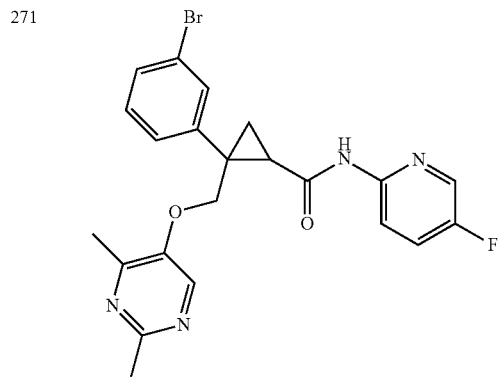<br>MS[M + H]⁺ = 472 |
| 272 | 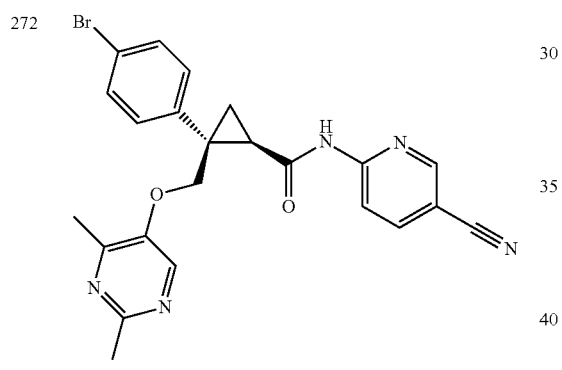<br>MS[M + H]⁺ = 478 |
| 273 | 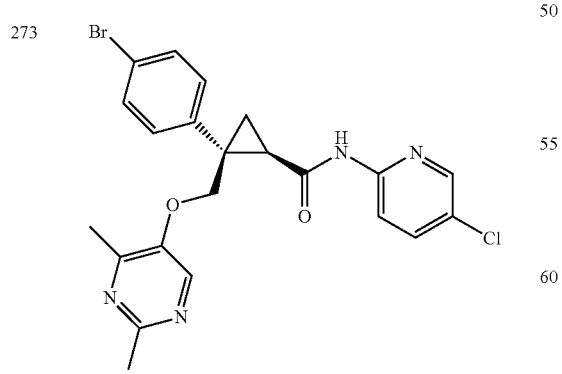<br>MS[M + H]⁺ = 488 |
TABLE 63-continued
| Example | Structural formula, MS |
|---|---|
| 274 | 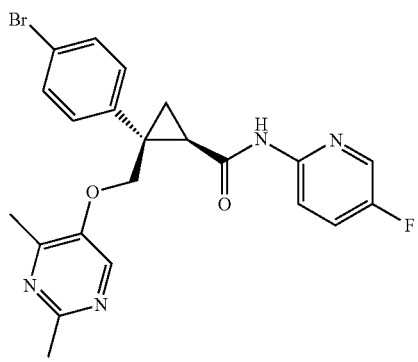<br>MS[M + H]⁺ = 472 |
| 275 | 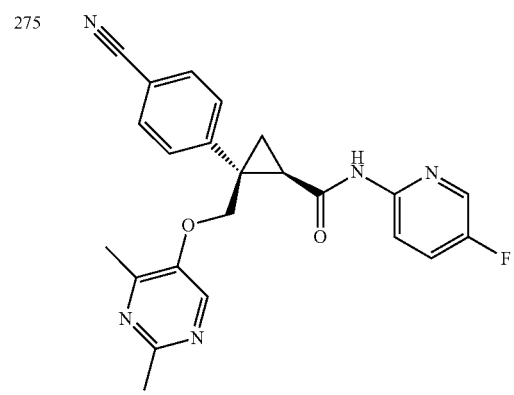<br>MS[M + H]⁺ = 418 |
| 276 | 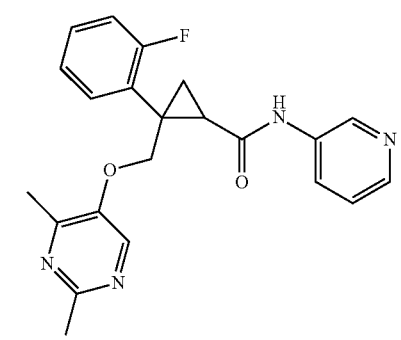<br>MS[M + H]⁺ = 393 |

TABLE 63-continued
| Example | Structural formula, MS |
|---------|------------------------|
| 277 | 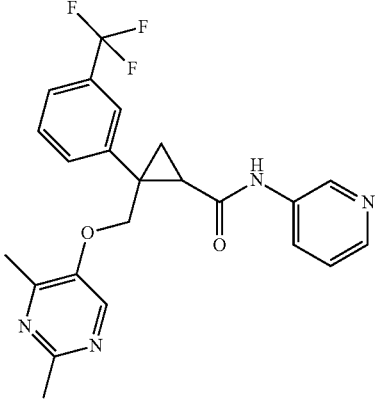 MS[M + H]⁺ = 443 |
TABLE 64
| Example | Structural formula | NMR (400 MHz, CDCl₃) and/or MS |
|---------|-------------------|-------------------------------|
| 278 | 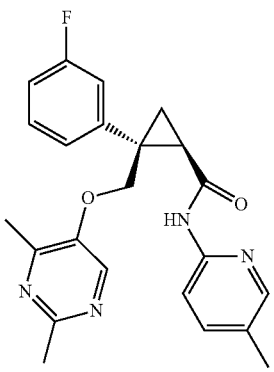 | $^1$H-NMR (400 MHz, CDCl₃) δ (ppm): 1.55-1.65 (m, 1H), 1.91 (t, J = 5.6 Hz, 1H), 2.07-2.14 (m, 1H), 2.21 (s, 3H), 2.28 (s, 3H), 2.55 (s, 3H), 4.41 (d, J = 9.6 Hz, 1H), 4.50 (d, J = 9.6 Hz, 1H), 6.96-7.04 (m, 1H), 7.14-7.20 (m, 1H), 7.22-7.28 (m, 1H), 7.33 (td, J = 8.0, 5.8 Hz, 1H), 7.44-7.48 (m, 1H), 7.93 (brd, J = 3.6 Hz, 1H), 7.97 (s, 1H), 8.06-8.12 (m, 1H), 8.31 (brs, 1H).<br>MS [M + H]⁺ = 407, MS [M + Na]⁺ = 429 |
| 279 | 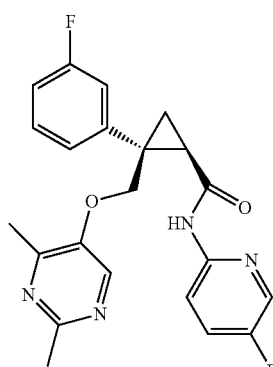 | $^1$H-NMR (400 MHz, CDCl₃) δ (ppm): 1.60-1,66 (m, 1H), 1.92 (t, J = 5.6 Hz, 1H), 2.07-2.15 (m, 1H), 2.21 (s, 3H), 2.26 (s, 3H), 4.39 (d, J = 9.6 Hz, 1H), 4.49 (d, J = 9.6 Hz, 1H), 6.97-7.04 (m, 1H), 7.13-7.20 (m, 1H), 7.22-7.28 (m, 1H), 7.33 (td, J = 8.0, 6.0 Hz, 1H), 7.75 (dd, J = 8.4, 6.0 Hz, 1H), 7.96-8.03 (m, 1H), 7.97 (s, 1H), 8.23 (brs, 1H), 8.31-8.33 (m, 1H).<br>MS [M + Na]⁺ = 493 |

TABLE 64-continued

| Example | Structural formula | NMR (400 MHz, CDCl₃) and/or MS |
|---|---|---|
| 280 | | ¹H-NMR (400 MHz, CDCl₃) δ (ppm): 1.55-1.65 (m, 1H), 1.91 (t, J = 5.6 Hz, 1H), 2.05-2.15 (m, 1H), 2.21 (s, 3H), 2.56 (s, 3H), 4.38 (d, J = 9.2 Hz, 1H), 4.49 (d, J = 9.6 Hz, 1H), 6.97-7.04 (m, 1H), 7.14-7.20 (m, 1H), 7.21-7.28 (m, 1H), 7.29-7.37 (m, 1H), 7.86-7.94 (m, 2H), 7.97 (s, 1H), 8.35 (brs, 1H), 8.46 (brs, 1H). MS [M + Na]⁺ = 541 |
| 281 | | ¹H-NMR (400 MHz, CDCl₃) δ (ppm): 1.65 (dd, J = 8.4, 5.2 Hz, 1H), 1.94 (t, J = 5.2 Hz, 1H), 2.12-2.18 (m, 1H), 2.19 (s, 3H), 2.55 (s, 3H), 3.93 (s, 3H), 4.39 (d, J = 10.0 Hz, 1H), 4.50 (d, J = 9.6 Hz, 1H), 6.98-7.04 (m, 1H), 7.16-7.20 (m, 1H), 7.22-7.28 (m, 1H), 7.34 (td, J = 8.0, 6.0 Hz, 1H), 7.98 (s, 1H), 8.12 (brd, J = 9.2 Hz, 1H), 8.23-8.27 (m, 1H), 8.49 (brs, 1H), 8.91 (dd, J = 2.0, 0.8 Hz, 1H). MS [M + H]⁺ = 451, MS [M + Na]⁺ = 473 |

EXAMPLE 282

Synthesis of (1R,2S)-2-{[(2,4-dimethylpryimidin-5-yl)oxy]methyl}-N-5-fluoromethylpyridin-2-yl)-2-(3-fluorophenyl)cyclopropanecarboxamide (282)

[Formula 84]

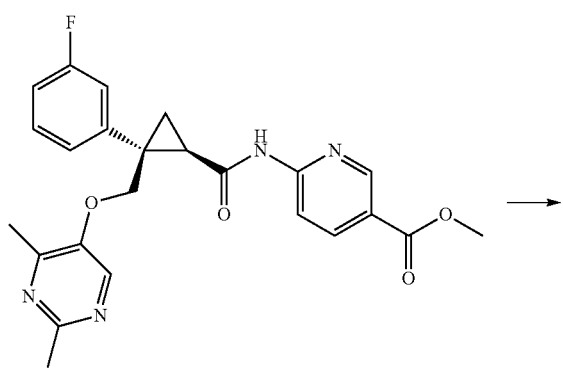

281

→

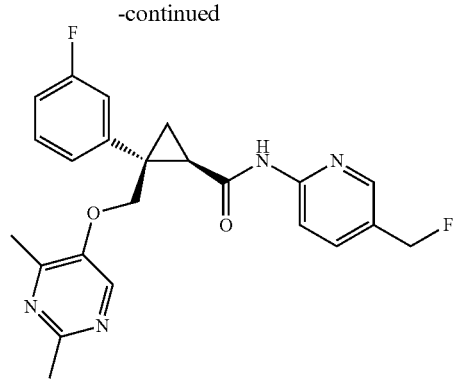

282

The compound 281 (51.6 mg) was dissolved in THF (5 ml), and lithium aluminum hydride (8.73 mg) was then added to the obtained solution under cooling in an ice water bath. The obtained mixture was stirred for 30 minutes, and the reaction solution was then transferred into ice chilled water. Thereafter, ethyl acetate was added thereto to carry out liquid separation. The organic layer was washed with a saturated sodium chloride aqueous solution. The resultant organic layer was dried over magnesium sulfate, and the solvent was then concentrated under reduced pressure. The residue was purified by silica gel column chromatography (ethyl acetate:methanol=1:0 to 9:1), so as to obtain an alcohol intermediate (20 mg). The obtained alcohol intermediate (20 mg) was dissolved in dichloromethane (3 ml), and [bis(2-methoxyethyl)amino]sulfa trifluoride (34.9 υλ) was then added to the obtained solution under cooling in an ice water bath. The obtained mixture was stirred for 0.5 hours, and it was then stirred at room temperature for 3 hours. Thereafter, a saturated sodium bicarbonate aqueous solution was added to the reaction solution, and liquid separation was then carried out with ethyl acetate. The organic layer was successively washed with water and a saturated sodium chloride aqueous solution. The resultant organic layer was dried over magnesium sulfate, and the solvent was then concentrated under reduced pressure. The residue was purified by silica gel column chromatography (n-heptane:ethyl acetate=7:3 to 1:1), so as to obtain the title compound (5.0 mg).

$^1$H-NMR (400 MHz, CDCl$_3$) δ (ppm): 1.55-1.65 (m, 1H), 1.93 (t, J=5.6 Hz, 1H), 2.10-2.18 (m, 1H), 2.21 (s, 3H), 2.55 (s, 3H), 4.40 (d, J=9.6 Hz, 1H), 4.50 (d, J=9.6 Hz, 1H), 5.34 (d, J=48.0 Hz, 2H), 6.97-7.04 (m, 1H), 7.14-7.21 (m, 1H), 7.22-7.28 (m, 1H), 7.33 (td, J=8.0 Hz, 6.0 Hz, 1H), 7.70 (td, J=8.8 Hz, 2.0 Hz, 1H), 8.09 (d, J=8.0 Hz, 1H), 8.30 (d, J=2.0 Hz, 1H), 8.32 (t, J=2.0 Hz, 1H), 8.40 (brs, 1H).

MS [M+Na]$^+$=447

The compound of Example 283 was synthesized from the carboxylic acid Prep 56 obtained in Production Example 56 by the same method as that of Example 82. The compounds of Examples 284 and 285 were synthesized by the same method as that of Example 81.

TABLE 65

| Example | Structural formula | NMR and/or MS |
|---------|-------------------|---------------|
| 283 | 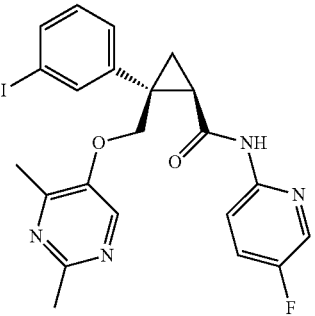 | $^1$H-NMR (400 MHz, CDCl$_3$) δ (ppm): 1.59-1.62 (m, 1H), 1.90 (t, J = 5.8 Hz, 1H), 2.03-2.13 (m, 1H), 2.24 (s, 3H), 2.56 (s, 3H), 4.42 (q, J = 12.0 Hz, 2H), 7.10 (t, J = 7.8 Hz, 1H), 7.36-7.45 (m, 2H), 7.62-7.67 (m, 1H), 7.85 (s, 1H), 7.97 (s, 1H), 8.04-8.11 (m, 1H), 8.14 (d, J = 2.4 Hz, 1H), 8.28 (s, 1H)<br>MS [M + H]$^+$ = 519 |
| 284 | 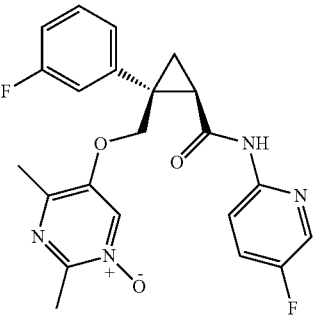 | $^1$H-NMR (600 MHz, CD$_3$OD) δ (ppm): 1.58 (t, J = 6.0 Hz, 1H), 1.88 (t, J = 6.0 Hz, 1H), 2.19 (s, 3H), 2.49 (s, 3H), 2.52 (t, J = 9,0 Hz, 1H), 4.42 (d, J = 12.0 Hz, 1H), 4.65 (d, J = 12.0 Hz, 1H), 7.00-7.04 (m, 1H), 7.33-7.38 (m, 3H), 7.46-7.50 (m, 1H), 7.96 (dd, J = 0.08, 0.04 Hz, 1H), 8.17 (d, J = 0.3 Hz, 1H), 8.19 (s, 1H)<br>MS [M + H]$^+$ = 427 |
| 285 | 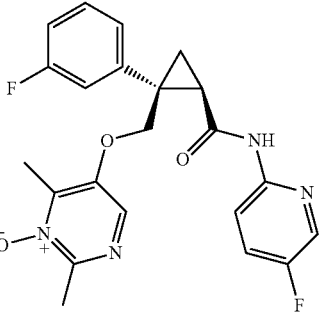 | $^1$H-NMR (400 MHz, CD$_3$OD) δ (ppm): 1.58 (dd, J = 8.0, 5.2 Hz, 1H), 1.89 (dd, J = 6.0, 5.2 Hz, 1H), 2.21 (s, 3H), 2.50-2.56 (m, 1H), 2.52 (s, 3H), 4.52 (d, J = 10.0 Hz, 1H), 4.76 (d, J = 10.0 Hz, 1H), 6.98-7.06 (m, 1H), 7.32-7.41 (m, 3H), 7.47 (ddd, J = 9.2, 8.0, 3.2 Hz, 1H), 7.94 (dd, J = 9.4, 4.2 Hz, 1H), 7.98 (s, 1H), 8.18 (d, J = 3.2 Hz, 1H)<br>MS [M + H]$^+$ = 427 |

EXAMPLE 286

Synthesis of (1R,2S)-2-(3-fluorophenyl)-N-(5-fluoropyridin-2-yl)-2-{[(4-hydroxymethyl-2-methylpyrimidin-5-yl)oxy]methyl}-2-(3-fluorophenyl)cyclopropanecarboxamide (286)

[Formula 85]

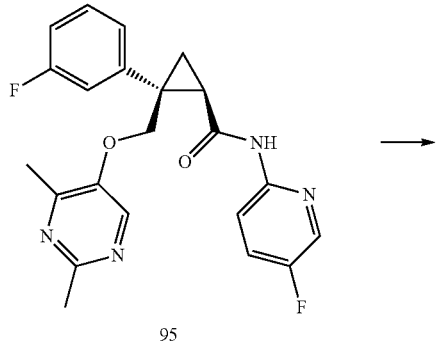

95

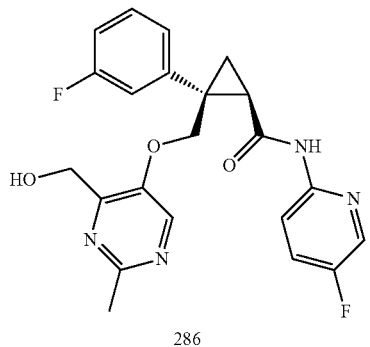

286

To a THF solution (10 ml) of the compound 95 (200 mg), n-BuLi (2.76 M n-hexane solution: 0.371 ml) was added while stirring at −78° C., and the obtained solution was then stirred for 1 hour. Thereafter, a THF solution (3 ml) of (2-benzenesulfonyl-3-phenyloxaziridine) (Davis, F. A., J. Org. Chem. 1982, 47, 1774) (135 mg) was added to the reaction solution at −78° C. While the temperature of the reaction solution was warmed to room temperature, it was stirred for 14 hours. Thereafter, a saturated ammonium chloride aqueous solution was added to the reaction solution, followed by extraction with ethyl acetate. The organic layer was washed with a saturated sodium chloride aqueous solution, dried over magnesium sulfate, and concentrated under reduced pressure. The obtained residue was purified by silica gel column chromatography (n-heptane:ethyl acetate=9:1 to 0:1). The resultant product was purified by HPLC again, so as to obtain the title compound (1.19 mg).

$^1$H-NMR (600 MHz, CD$_3$OD) δ (ppm): 1.56 (t, J=6.0 Hz, 1H), 1.85 (t, J=6.0 Hz, 1H), 2.49 (t, J=6.0 Hz, 1H), 2.53 (s, 3H), 4.41 (d, J=12.0 Hz, 1H), 4.49 (d, J=12.0 Hz, 1H), 4.57 (d, J=12.0 Hz, 1H), 4.66 (d, J=12.0 Hz, 1H), 6.98-7.04 (m, 1H), 7.32-7.36 (m, 1H), 7.36-7.39 (m, 2H), 7.44-7.50 (m, 1H), 7.90-7.95 (m, 1H), 8.13 (s, 1H), 8.17 (brs, 1H).

MS [M+Na]$^+$=449

The compounds of Examples 287 to 290 were synthesized from the carboxylic acid Prep 48-5 according to the examples.

TABLE 66

| Example | Structural formula | NMR (400 MHz, CDCl$_3$) and/or MS |
|---|---|---|
| 287 | | MS [M + H]$^+$ = 421 |
| 288 | | $^1$H-NMR (400 MHz, CDCl$_3$) δ (ppm): 1.06 (s, 3H), 1.56 (s, 3H), 1.94 (s, 1H), 2.26 (s, 3H), 2.57 (s, 3H), 4.67 (d, J = 9.6 Hz, 1H), 4.74 (d, J = 9.6 Hz, 1H), 7.23-7.41 (m, 6H), 7.86-8.06 (m, 2H), 8.20 (brd, J = 8.8 Hz, 1H), 8.35 (dd, J = 4.8, 1.2 Hz, 1H), 8.54 (d, J = 1.2 Hz, 1H). |

TABLE 66-continued

| Example | Structural formula | NMR (400 MHz, CDCl$_3$) and/or MS |
|---|---|---|
| 289 | | MS [M + H]$^+$ = 402 |
| 290 | | MS [M + H]$^+$ = 433 |

EXAMPLE 291

Synthesis of (1R,2S)-2-(3,5-difluorophenyl)-N-(5-fluoropyridin-2-yl)-2-{[(2-oxo-4-trifluoromethyl-1,2-dihydropyrimidin-5-yl)oxy]methyl}cyclopropanecarboxamide (291)

[Formula 86]

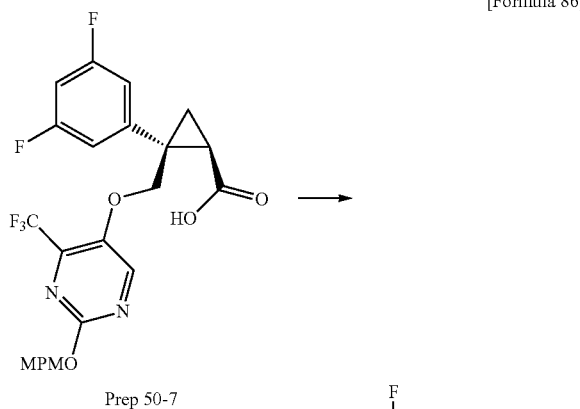

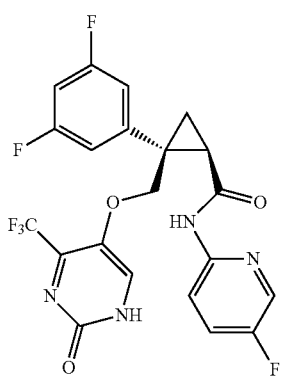

2-Amino-5-fluoropyridine (26.4 mg), HAUT (89.4 mg) and N,N-diisopropylethylamine (40.7 ul) were added to a DMF solution (2 ml) of the compound Prep 50-7 (100 mg). The obtained mixture was stirred at room temperature overnight. Thereafter, water was added to the reaction solution, and the obtained mixture was then extracted with diethyl ether. The organic layer was washed with a saturated sodium chloride aqueous solution, was then dried over anhydrous magnesium sulfate, and was then filtered. The filtrate was concentrated under reduced pressure. To the residue, 4 N hydrochloric acid/ethyl acetate (2 ml) was added, and the obtained mixture was then stirred at room temperature for 1 hour. Thereafter, the reaction mixture was concentrated under reduced pressure. To the residue, a saturated sodium bicarbonate aqueous solution and ethyl acetate were added, and the obtained mixture was then subjected to liquid separation and extraction. The obtained organic layer was dried over magnesium sulfate. The resultant organic layer was concentrated under reduced pressure, and the obtained residue was then purified by silica gel column chromatography (n-heptane:ethyl acetate=2:1 to 0:1), so as to obtain the title compound (30 mg).

$^1$H-NMR (400 MHz, CDCl$_3$) δ (ppm): 1.59-1.63 (m, 1H), 1.86 (t, J=6.0 Hz, 1H), 2.17 (brt, J=6.0 Hz, 1H), 4.41 (t, J=10.8 Hz, 2H), 6.70-6.76 (m, 1H), 6.97 (d, J=6.0 Hz, 2H) 7.38-7.43 (m, 1H), 7.91 (s, 1H), 8.06-8.09 (m, 2H), 9.13 (s, 1H).

MS [M+Na]$^+$=485.

EXAMPLE 292

Synthesis of (1R,2R)-2-[2-(2,4-dimethylpyrimidin-5-yl)ethyl]-N-(5-fluoro-4-methylpyridin-2-yl)-2-phenylcyclopropanecarboxamide (292)

[Formula 87]

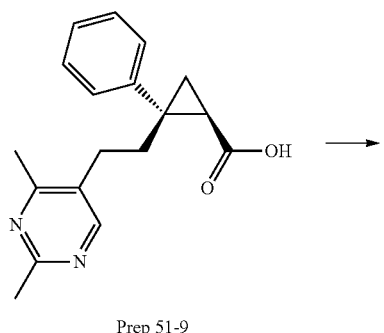

Prep 51-9

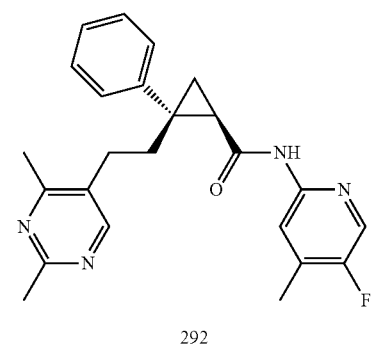

292

The compound Prep 51-9 was treated in the same manner as that of Example 291, so as to obtain the title compound.
MS [M+H]$^+$=405

EXAMPLE 293

Synthesis of (1R,2S)-2-[N-2,4-dimethylpryimidin-5-yl)methylaminomethyl]-N-(5-fluoropyridin-2-yl)-2-(3-fluorophenyl)cyclopropanecarboxamide (293)

[Formula 88]

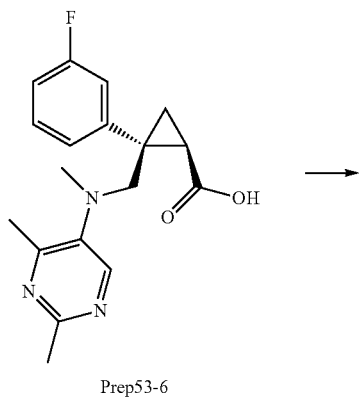

Prep53-6

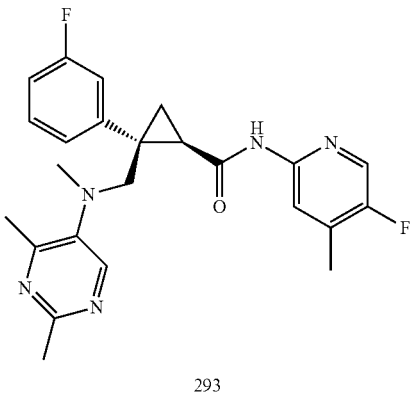

293

The compound Prep 53-6 (50 mg) was dissolved in DMF (15.6 ml), and thereafter, HATU (116 mg), N,N-diisopropylethylamine (79.4 ul) and 2-amino-5-fluoro-4-picoline (57.5 mg) were added to the solution. The obtained mixture was stirred at room temperature for 1 hour. Thereafter, water was added to the reaction solution, and the reaction solution was then concentrated under reduced pressure. The residue was purified by silica gel column chromatography (n-heptane:ethyl acetate=7:3 to 3:7), so as to obtain the title compound (26.8 mg).

$^1$H-NMR (400 MHz, CDCl$_3$) δ (ppm): $^1$H-NMR (400 MHz, CDCl$_3$) δ (ppm): 1.54 (dd, J=9.6, 4.8 Hz, 1H), 1.69 (t, J=5.2 Hz, 1H), 1.86-1.90 (m, 1H), 2.04 (s, 3H), 2, 32 (s, 1H), 2.52 (s, 3H), 2.63 (s, 3H), 3, 54 (d, J=13.6 Hz, 1H), 3.59 (d, J=13.6 Hz, 1H), 6.89-7.05 (m, 3H), 7.20-7.26 (m, 2H), 7.97 (s, 1H), 8.05-8.10 (m, 2H), 8.10 (s, 1H), 8.55 (brs, 1H).

The compounds of Examples 294 to 296 were synthesized by reacting the carboxylic acid Prep 53-6 with any amine according to the method of Example 293.

TABLE 67

| Example | Structural formula, MS |
|---|---|
| 294 | MS [M + H]$^+$ = 423 |

TABLE 67-continued
| Example | Structural formula, MS |
|---|---|
| 295 | 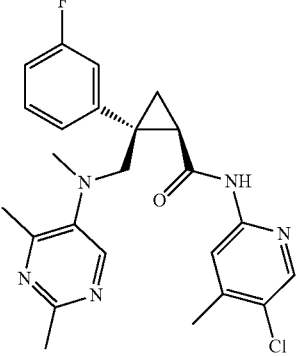<br>MS [M + H]⁺ = 454 |
| 296 | 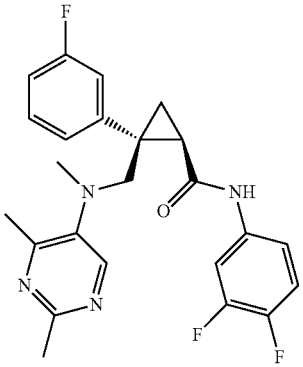<br>MS [M + H]⁺ = 441 |
The compounds of Examples 297 to 301 were synthesized from the carboxylic acid Prep 54 according to the method of Example 293.
TABLE 68
| Example | Structural formula, MS |
|---|---|
| 297 | 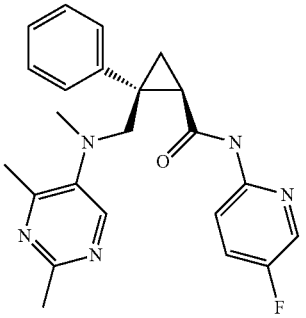<br>MS [M + H]⁺ = 405 |
TABLE 68-continued
| Example | Structural formula, MS |
|---|---|
| 298 | 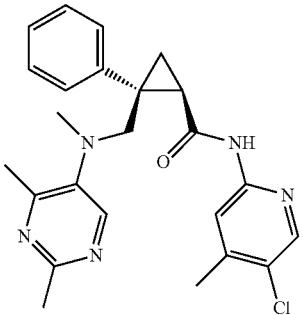<br>MS [M + H]⁺ = 423 |
| 299 | 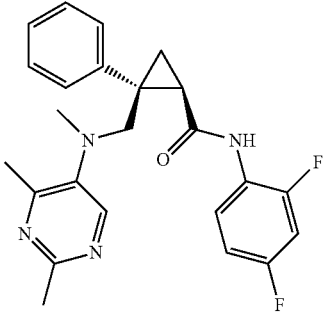<br>MS [M + H]⁺ = 420 |
| 300 | 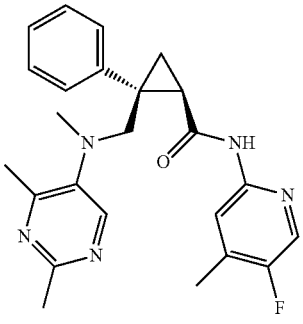<br>MS [M + H]⁺ = 405 |
| 301 | 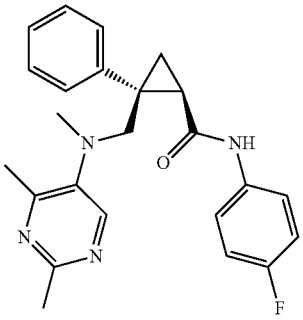<br>MS [M+ H]⁺ = 436 |

EXAMPLE 302

Synthesis of (1R,2S)-2-(3-fluorophenyl)-N-(5-fluoropyridin-2-yl)-2-[N-(2-methyl-4-trifluoromethylpyrimidin-5-yl)aminomethyl]cyclopropanecarboxamide (302)

[Formula 89]

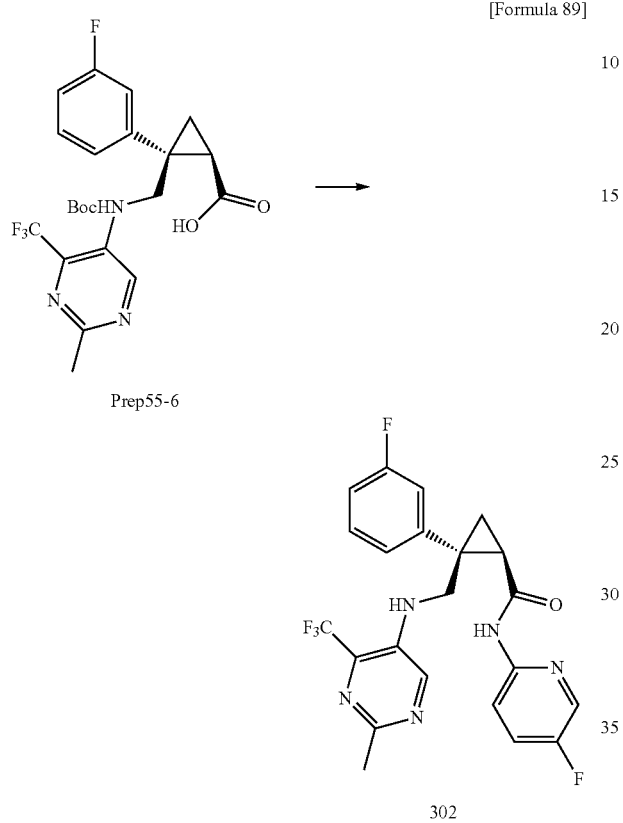

2-Amino-5-fluoropyridine (8.6 mg), HATU (29.2 mg) and N,N-diisopropylethylamine (13.3 ul) were added to a DMF solution (1 ml) of the compound Prep 55-6 (30 mg). The obtained mixture was stirred at room temperature overnight. Thereafter, water was added to the reaction solution, and the obtained mixture was then extracted with diethyl ether. The organic layer was washed with sodium chloride aqueous solution, was then dried over anhydrous magnesium sulfate, and was then filtered. The filtrate was concentrated under reduced pressure. To the residue, 4 N hydrochloric acid/ethyl acetate (3 ml) was added, and the obtained mixture was then stirred at room temperature for 1 hour. Thereafter, the reaction mixture was concentrated under reduced pressure. To the residue, a saturated sodium bicarbonate aqueous solution and ethyl acetate were added, and the obtained mixture was then subjected to liquid separation and extraction. The obtained organic layer was dried over magnesium sulfate. The resultant organic layer was concentrated under reduced pressure, and the obtained residue was then purified by silica gel column chromatography (n-heptane:ethyl acetate=9:1 to 1:1), so as to obtain the title compound (8.6 mg).

$^1$H-NMR (400 MHz, CDCl$_3$) δ (ppm): 1.53-1.56 (m, 1H), 1.81 (t, J=5.2 Hz, 1H), 2.02 (brt, J=7.6 Hz, 1H), 2.57 (s, 3H), 3.77 (dd, J=14.0, 5.6 Hz, 1H), 3.89 (dd, J=13.6, 5.6 Hz, 1H), 4.45 (brs, 1H), 6.98-7.15 (m, 3H), 7.30-7.47 (m, 2H), 8.13-8.17 (m, 3H), 8.32 (s, 1H).

MS [M+Na]$^+$=486.

EXAMPLE 303

Synthesis of 2-{(1R,2S)-2-{[(2,4-dimethylpyrimidin-5-yl)oxy]methyl}-2-phenylcyclopropyl}-5-fluoro-1H-benzimidazole (303)

[Formula 90]

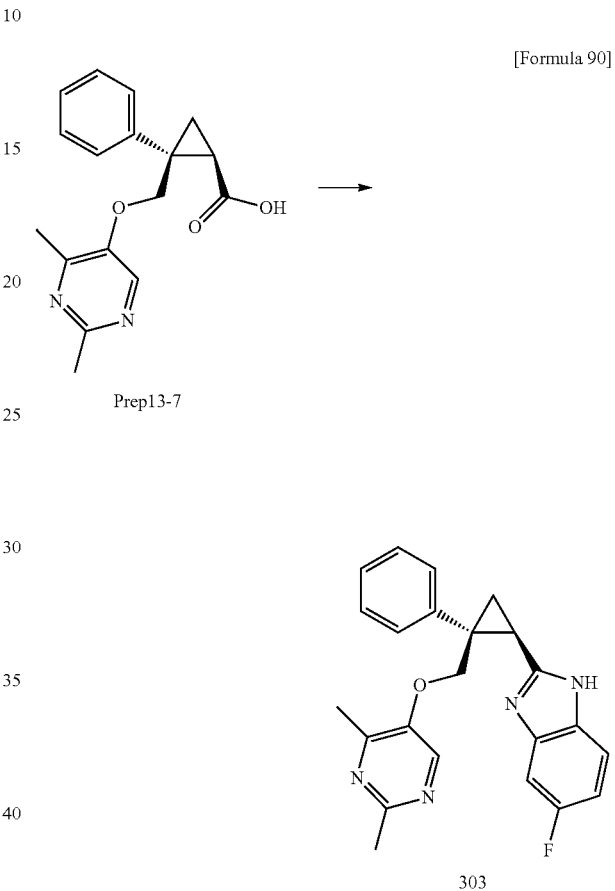

HATU (153 mg), N,N-diisopropylethylamine (104 ul) and 3,4-diamino-5-fluorobenzene (45.3 mg) were added to a DMF solution (3 ml) of the compound Prep 13-7(100 mg), and the obtained mixture was then stirred at room temperature overnight. Thereafter, water was added to the reaction mixture, and liquid separation and extraction were then carried out with ethyl acetate. The obtained organic layer was dried over magnesium sulfate, and the resultant organic layer was then concentrated under reduced pressure. The obtained residue was dissolved in acetic acid (3 ml), and the obtained solution was then stirred at 90° C. for 5 hours. Thereafter, the reaction mixture was concentrated under reduced pressure, and the resultant product was filtered with a NH-silica gel pad. The filtrate was concentrated under reduced pressure. The residue was purified by silica gel column chromatography (n-heptane:ethyl acetate=5:1 to ethyl acetate), so as to obtain the title compound (15 mg).

MS [M+H]$^+$=389.

The compounds of Examples 304 and 305 were synthesized by the same method as that of Example 303.

TABLE 69

| Example | Structural formula, MS |
|---|---|
| 304 |  MS[M + H]$^+$ = 372 |
| 305 | MS[M + H]$^+$ = 372 |

EXAMPLE 306

Synthesis of 2-{(1R,2S)-2-(3,5-difluorophenyl)-2-{[(2,4-dimethylpyrimidin-5-yl)oxy]methyl}cyclopropyl}-6-fluoro-1H-imidazo[4,5-b]pyridine (306)

[Formula 91]

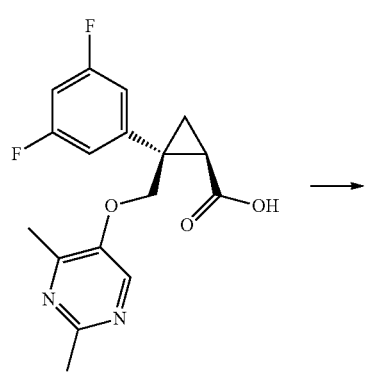

Prep16-7

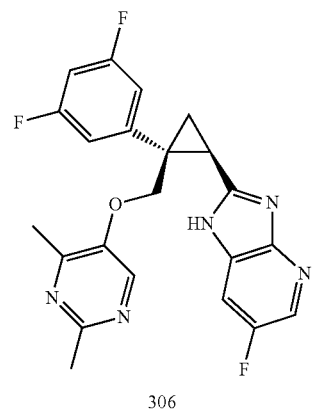

306

HATU (45.9 mg), N,N-diisopropylethylamine (31.2 ul) and 2,3-diamino-5-fluorobenzene (15.5 mg) were added to a DMF solution (900 ul) of the compound Prep 16-7 (30 mg), and the obtained mixture was then stirred at room temperature for 2 hours. Thereafter, a saturated sodium bicarbonate aqueous solution was added to the reaction mixture, and liquid separation and extraction were then carried out with ethyl acetate. The obtained organic layer was dried over magnesium sulfate, and the resultant organic layer was then concentrated under reduced pressure. The obtained residue was dissolved in acetic acid (900 ul), and the obtained solution was then stirred with INITIATOR MICROWAVE SYNTHESIZER (Biotage) at 150° C. for 11 hours. Thereafter, the reaction mixture was concentrated under reduced pressure, and ethyl acetate and a sodium bicarbonate aqueous solution were added to the residue to carry out liquid separation and extraction. The obtained organic layer was dried over magnesium sulfate, and the resultant organic layer was then concentrated under reduced pressure. The obtained residue was purified by silica gel column chromatography (n-heptane:ethyl acetate=5:1 to 0:1), so as to obtain the title compound (9.3 mg).

MS [M+H]$^+$=426.

EXAMPLE 307

Synthesis of 6-chloro-2-[((1R,2S)-2-(3,5-difluorophenyl)-2-{[(2,4-dimethylpyrimidin-5-yl)oxy]methyl}cyclopropyl]-1H-imidazo[4,5-b]pyridine (307)

[Formula 92]

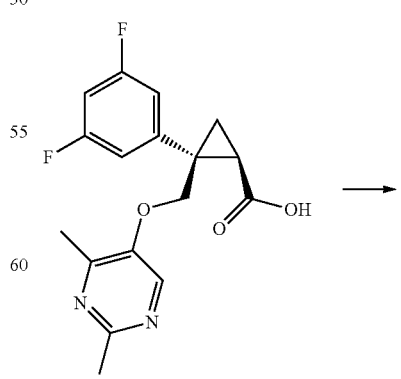

Prep16-7

EXAMPLE 310

Synthesis of 2-[(1R,2S)-2-{{[(2,4-dimethylpyrimidin-5-yl)oxy]methyl}-2-(3-fluorophenyl)cyclopropyl]quinazolin-4(1H)-one (310)

[Formula 93]

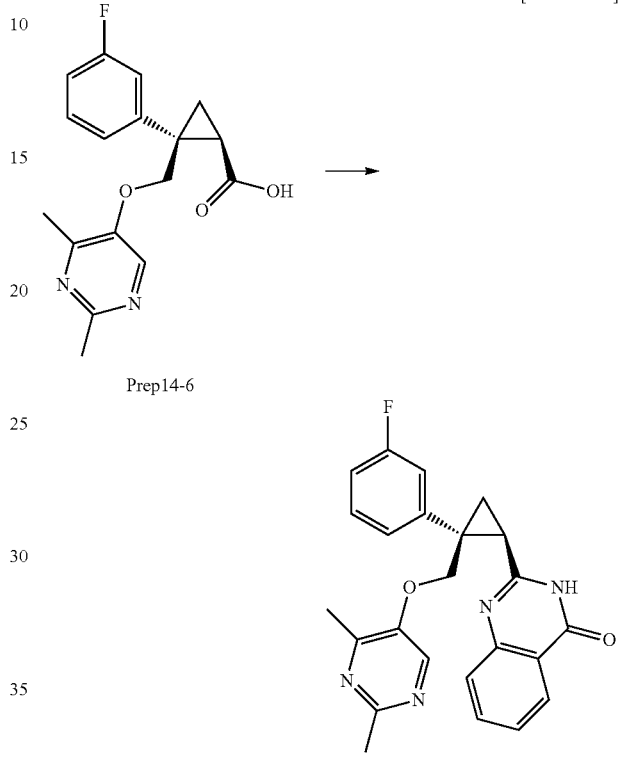

The compound Prep 14-6 (50 mg), 2-aminobenzamide (23.7 mg) and HATU (66.1 mg) were dissolved in MIT (0.24 ml), and thereafter, N,N-diisopropylethylamine (22.9 ul) was added to the solution. The obtained mixture was stirred at room temperature for 24 hours. Thereafter, water was added to the reaction solution, and the obtained mixture was then extracted with ethyl acetate. The organic layer was successively washed with water and a saturated sodium chloride aqueous solution, and was then dried over anhydrous sodium sulfate. The solvent was distilled off under reduced pressure, and the residue was dissolved in isopropylalcohol (3 ml). Potassium tert-butoxide (35.5 mg) was added to the solution, and the obtained mixture was then stirred under heating at 100° C. for 2 hours. Thereafter, the reaction solution was cooled to room temperature. A droplet of water was added to the reaction solution, and the obtained mixture was then concentrated under reduced pressure. The residue was purified by NH-silica gel column chromatography (n-heptane:ethyl acetate=9:1 to 0:1), so as to obtain the title compound (20.6 mg).

$^1$H-NMR (400 MHz, CDCl$_3$) δ (ppm): 1.65 (dd, J=8.0, 5.2 Hz, 1H), 2.14 (s, 3H), 2.33 (t, J=5.2 Hz, 1H), 2.44 (s, 3H), 2.75-2.79 (m, 1H), 4.43 (d, J=9.6, 1H), 4.45 (d, J=9.6 Hz, 1H), 7.07 (tdd, J=8.0, 2.0, 1.2 Hz, 1H), 7.39 (td, J=8.0, 6.0 Hz, 1H), 7.46-7.52 (m, 2H), 7.62-7.65 (m, 2H), 7.75 (t, J=6.8 Hz, 1H), 7.79 (s, 1H), 8.33 (d, J=8.0 Hz, 1H), 13.1 (brs, 1H).

MS[M+H]$^+$: 417

---

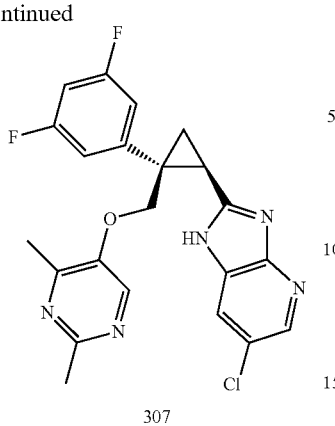

307

The title compound was synthesized by the same method as that of Example 306. $^1$H-NMR (400 MHz, CDCl$_3$) δ (ppm): 1.87 (dd, J=8.8, 5.6 Hz, 1H), 2.11 (s, 3H), 2.50 (s, 3H), 2.21 (t, J=6.0 Hz, 1H), 2.68 (dd, J=8.8, 6.4 Hz, 1H), 4.41 (d, J=10.0 Hz, 1H), 4.45 (d, J=9.6 Hz, 1H), 6.77-6.82 (m, 1H), 6.99-7.09 (m, 2H), 7.82 (s, 1H), 7.88 (d, J=2.4 Hz, 1H), 8.22 (d, J=2.0 Hz, 1H), 11.5 (s, 1H).

The following compounds were synthesized by the same method as that of Example 306.

TABLE 70

| Example | Structural formula, MS |
|---|---|
| 308 | MS[M + H]$^+$ = 408 |
| 309 | MS[M + H]$^+$ = 404 |

TABLE 71

| Example | Structural formula | NMR(400 MHz, CDCl₃)and/or MS |
|---|---|---|
| 311 | | ¹H-NMR(400 MHz, CDCl₃)δ(ppm): 1.68(dd, J = 8.0, 5.2 Hz, 1H), 2.11(s, 3H), 2.31(t, J = 5.2 Hz, 1H), 2.45(s, 3H), 2.76(dd, J = 8.0, 6.0 Hz, 1H), 4.40(d, J = 10.0, 1H), 4.45(d, J = 10.0 Hz, 1H), 7.10(td, J = 8.8, 2.0 Hz, 1H), 7.43(td, J = 8.8, 6.0 Hz, 1H), 7.52(d, J = 8.8 Hz, 1H), 7.56 (d, J = 8.8 Hz, 1H), 7.61(d, J = 8.8 Hz, 1H), 7.68(dd, J = 8.8, 2.4 Hz, 1H), 7.78(s, 1H), 8.27(d, J = 2.4 Hz, 1H), 13.4(s, 1H).<br>MS[M + H]⁺ = 451 |
| 312 | | MS[M + H]⁺ = 418 |

The following compounds were synthesized by reacting the carboxylic acid described in Production Examples with any amine by the same method as that of Example 51.

TABLE 72

| Example | Structural Formula, MS |
|---|---|
| 313 | MS[M + H]⁺ = 407 |

TABLE 72-continued

| Example | Structural Formula, MS |
|---|---|
| 314 | MS[M + H]⁺ = 441 |
| 315 | MS[M + H]⁺ = 440 |

TABLE 72-continued

| Example | Structural Formula, MS |
|---|---|
| 316 | 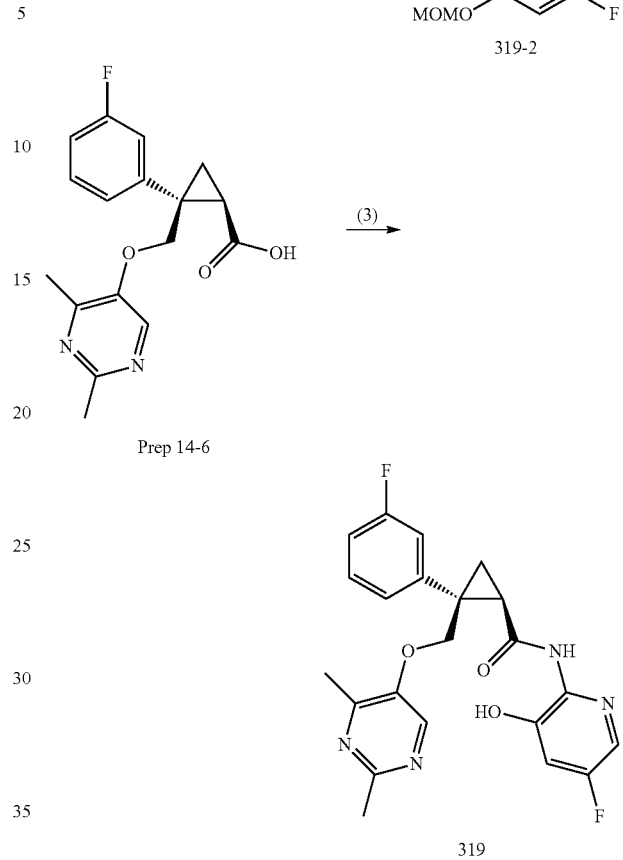  MS[M + H]⁺ = 424 |
| 317 | MS[M + H]⁺ = 407 |
| 318 | MS[M + H]⁺ = 423 |

EXAMPLE 319

Synthesis of (1R,2S)-2-{{[(2,4-dimethylpyrimidin-5-yl)oxy]methyl}}-N-(5-fluoro-3-hydroxypyridin-2-yl)-2-(3-fluorophenyl)cyclopropanecarboxamide (319)

[Formula 94]

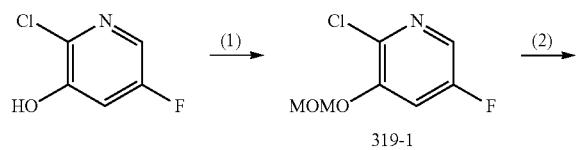

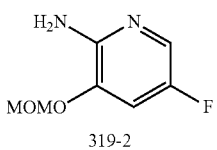

(1) 2-chloro-5-fluoro-3-(methoxymethoxy)pyridine (319-1)

A DMF (10 ml) solution of 2-chloro-5-fluoro-3-hydroxy-pyridine (500 mg) was cooled to 0° C. Sodium hydroxide (60% oil dispersion: 149 mg) was added to the reaction solution, and the obtained mixture was stirred at 0° C. for 15 minutes. Chloromethyl methyl ether (293 ul) was added to the reaction solution at the same temperature as described above, and the obtained mixture was heated to room temperature and stirred for 1 hour. Diethyl ether and water were added to the reaction solution, and the organic layer was successively washed with water and a saturated sodium chloride aqueous solution. The organic layer was dried over anhydrous magnesium sulfate and then filtered. The filtrate was concentrated under reduced pressure, and the residue was purified by silica gel column chromatography (n-heptane:ethyl acetate=19:1 to 7:3), so as to obtain the title compound (598 mg).

¹H-NMR (400 MHz, CDCl3) δ (ppm): 3.52 (s, 3H), 5.28 (s, 2H), 7.32 (dd, J=9.2, 2.8 Hz, 1H), 7.95 (dd, J=2.8, 0.8 Hz, 1H).

(2) 5-fluoro-3-(methoxymethoxy)pyridine-2-amine (319-2)

Benzophenoneimine (55.3 ul), 2,2-bis(diphenylphos-phino)-1,1-binaphthyl (29.3 mg), sodium tert-butoxide (22.6 mg) and Pd₂DBA₃ (15.3 mg) were added to a toluene (0.5 ml) solution of the compound 319-1 (30 mg). The reaction solution was heated to 100° C. and stirred for 3 hours. Diethyl ether was added to the reaction solution, and the obtained mixture was filtered with Celite. The filtrate was concentrated under reduced pressure. 2 M hydrochloric acid (78.5 ul) was added to a THF (1 ml) solution of the residue, and the obtained mixture was stirred at room temperature for 12 hours. A saturated sodium bicarbonate aqueous solution was added to the reaction solution, and the mixture was extracted with dichloromethane. The organic layer was dried over anhydrous magnesium sulfate and then filtered. The filtrate was concentrated under reduced pressure, and the residue was purified by silica gel column chromatography (n-heptane: ethyl acetate=9:1 to ethyl acetate), so as to obtain the title compound (17 mg).

¹H-NMR (400 MHz, CDCl3) δ (ppm): 3.49 (s, 3H), 4.52 (brs, 2H), 5.20 (s, 2H), 7.09 (dd, J=9.6, 2.6 Hz, 1H), 7.63 (d, J=2.6 Hz, 1H).

MS [M+H]+=173

(3) Synthesis of (1R,2S)-2-{[(2,4-dimethylpyrimidin-5-yl)oxy]methyl}1-N-(5-fluoro-3-hydroxypyridin-2-yl)-2-(3-fluorophenyl)cyclopropanecarboxamide (319)

Prep 14-6 (30 mg) was dissolved in DMF (0.6 ml). 5-fluoro-3-(methoxymethoxy)pyridine-2-amine (compound 319-2: 17 mg), HATU (39.7 mg) and N,N-diisopropylethylamine (15 ul) were added to the solution, and the obtained mixture was stirred at room temperature for 5 hours. Thereafter, it was heated to 40° C. and further stirred for 22 hours. Water was added to the reaction solution, and the mixture was extracted with ethyl acetate. The organic layer was successively washed with water and a saturated sodium chloride aqueous solution, dried over anhydrous magnesium sulfate, and then filtered. The filtrate was concentrated under reduced pressure, and the residue was filtered through NH silica gel pad. The filtrate was concentrated under reduced pressure. Thereafter, the residue was dissolved in a THF (0.5 ml)-methanol (0.5 ml) mixed solvent, and 5 M hydrochloric acid (0.5 ml) was added to the solution. The reaction solution was heated to 90° C. and stirred for 30 minutes. A saturated sodium bicarbonate aqueous solution was added to the reaction solution, and the mixture was extracted with chloroform. The organic layer was dried over anhydrous magnesium sulfate and then filtered. The filtrate was concentrated under reduced pressure, and the residue was purified by silica gel column chromatography (n-heptane:ethyl acetate=9:1 to 1:9), so as to obtain the title compound (8.2 mg).

1H-NMR (400 MHz, CDCl3) δ (ppm): 1.74 (dd, J=8.0, 5.6 Hz, 1H), 1.97 (t, J=5.6 Hz, 1H), 2.22 (dd, J=8.0, 5.6 Hz, 1H), 2.27 (s, 3H), 2.58 (s, 3H), 4.42 (d, J=9.6 Hz, 1H), 4.51 (d, J=9.6 Hz, 1H), 7.00-7.05 (m, 2H), 7.18 (dt, J=9.6, 2.4 Hz, 1H), 7.24 (dt, J=8.0, 1.2 Hz, 1H), 7.34 (dt, J=6.6, 5.6 Hz, 1H), 7.73 (d, J=2.4 Hz, 1H), 7.97 (s, 1H), 8.56 (brs, 1H), 10.43 (s, 1H).

MS[M+H]+=427

EXAMPLE 320

Synthesis of (1R,2S)-2-{[(4-fluoromethyl-2-methylpyrimidin-5-yl)oxy]methyl}-2-(3-fluorophenyl)-N-(5-fluoropyridin-2-yl)cyclopropanecarboxamide (320)

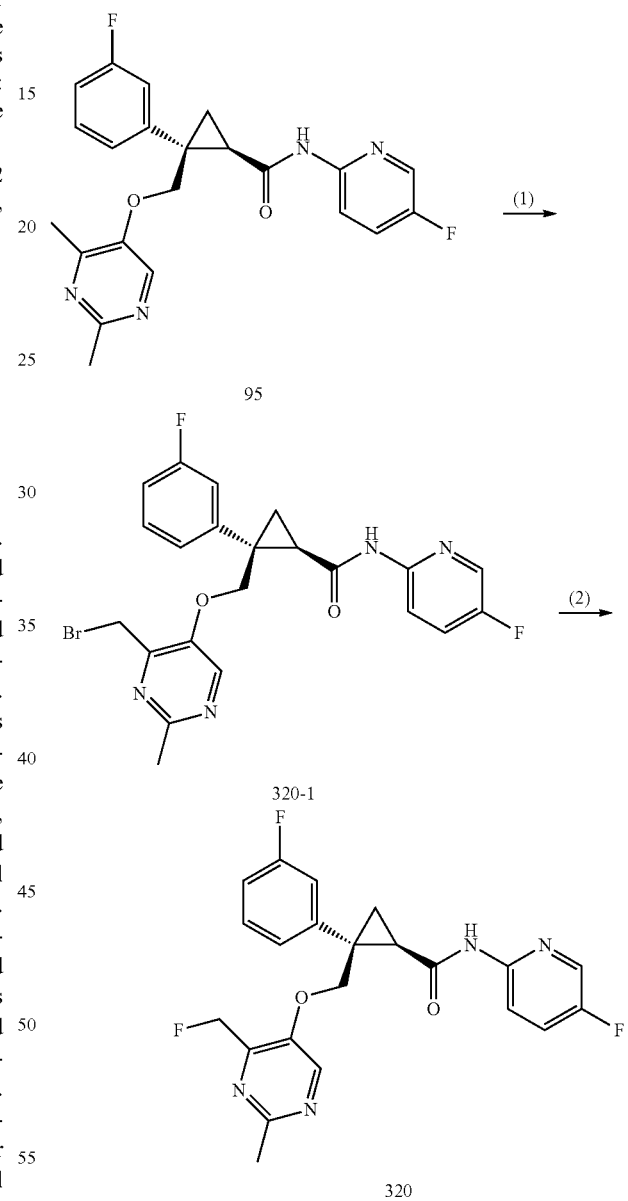

[Formula 95]

(1) Synthesis of (1R,2S)-2-{[(4-bromomethyl-2-methylpyrimidin-5-yl)oxy]methyl}-2-(3-fluorophenyl)-N-(5-fluoropyridin-2-yl)cyclopropanecarboxamide (320-1)

Bromine (65.5 ul) was added to a chloroform (15 ml) solution of the compound 95 (500 mg), while the solution was stirred under cooling on ice. The obtained mixture was stirred at room temperature for 14 hours. A saturated sodium thiosulfate aqueous solution was added to the reaction solution, and the mixture was extracted with ethyl acetate. The obtained organic layer was washed with a saturated sodium chloride aqueous solution, then dried over magnesium sulfate, and concentrated under reduced pressure. The obtained residue was purified by silica gel column chromatography (n-heptane:ethyl acetate=1:0 to 7:3), so as to obtain a compound 317-1 (153 mg).

1H-NMR (400 MHz, CDCl3) δ (ppm): 1.61-1.68 (m, 1H), 1.90-1.97 (m, 1H), 2.11-2.18 (m, 1H), 2.59 (s, 3H), 4.24 (t, J=11.8 Hz, 2H), 4.56 (s, 2H), 6.97-7.05 (m, 1H), 7.19-7.41 (m, 4H), 8.03-8.10 (m, 1H), 8.12 (s, 1H), 8.15 (s, 1H), 8.35 (brs, 1H).

(2)(1R,2S)-2-{[(4-(fluoromethyl-2-methylpyrimidin-5-yl)oxy)methyl]-2-(3-fluorophenyl)-N-(5-fluoropyridin-2-yl)cyclopropanecarboxamide (320)

Potassium fluoride (17.8 mg) and 18-crown-6 (80.9 mg) were added to an acetonitrile (10 ml) solution of the compound 320-1 (50 mg), and the obtained mixture was stirred at 60° C. for 8 hours. The temperature of the reaction solution was returned to room temperature. Water was added to the reaction solution, and the mixture was extracted with ethyl acetate. The obtained organic layer was washed with a saturated sodium chloride aqueous solution, then dried over magnesium sulfate, and concentrated under reduced pressure. The obtained residue was purified by silica gel column chromatography (n-heptane:ethyl acetate=19:1 to 1:1), so as to obtain the title compound (3.03 mg).

1H-NMR (400 MHz, CDCl3) δ (ppm): 1.60-1.65 (m, 1H), 1.92 (t, J=5.4 Hz, 1H), 2.09-2.16 (m, 1H), 2.63 (s, 3H), 4.50 (d, J=9.4 Hz, 1H), 4.56 (d, J=9.4 Hz, 1H), 5.20 (dd, J=22.8, 12.0 Hz, 1H), 5.31 (dd, J=22.8, 12.0 Hz, 1H), 6.98-7.05 (m, 1H), 7.13-7.19 (m, 1H), 7.22-7.28 (m, 1H), 7.30-7.43 (m, 2H), 8.02-8.10 (m, 1H), 8.14 (d, J=2.8 Hz, 1H), 8.18 (s, 1H), 8.36 (brs, 1H).

EXAMPLE 321

Synthesis of (1R,2S)-2-{[(2,4-dimethylpyrimidin-5-yl)oxy]methyl}-2-(3-fluoro-4-hydroxyphenyl)-N-(5-fluoropyridin-2-yl)cyclopropanecarboxamide (321)

[Formula 96]

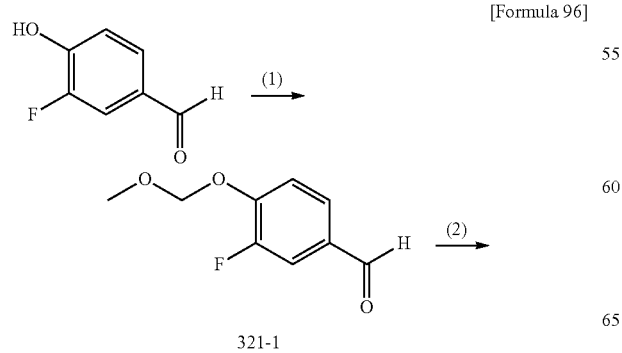

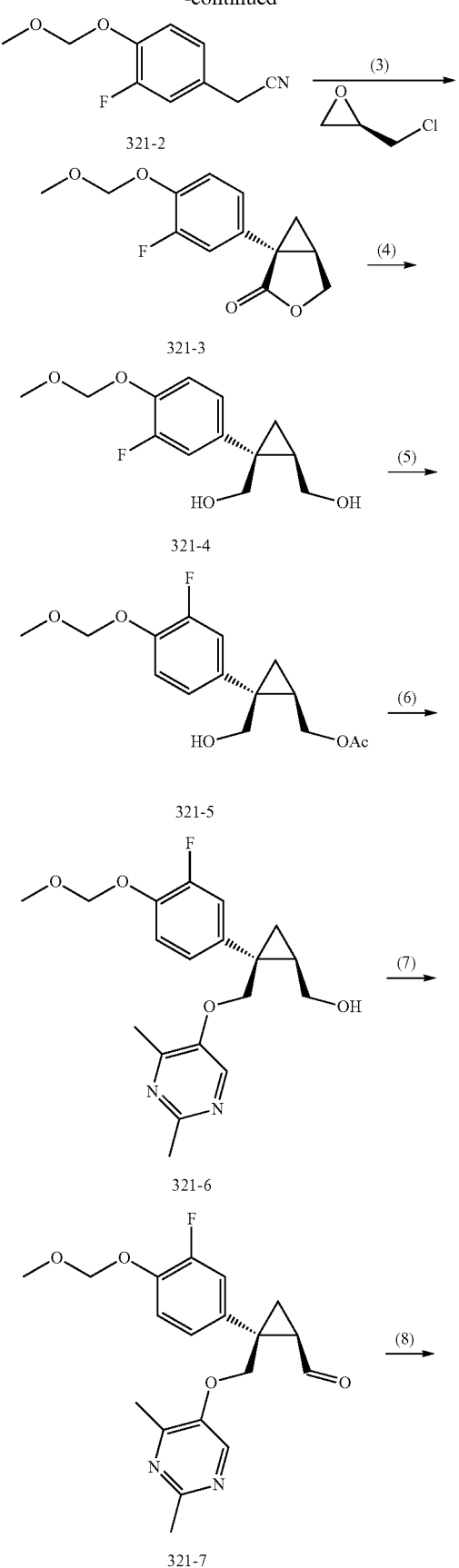

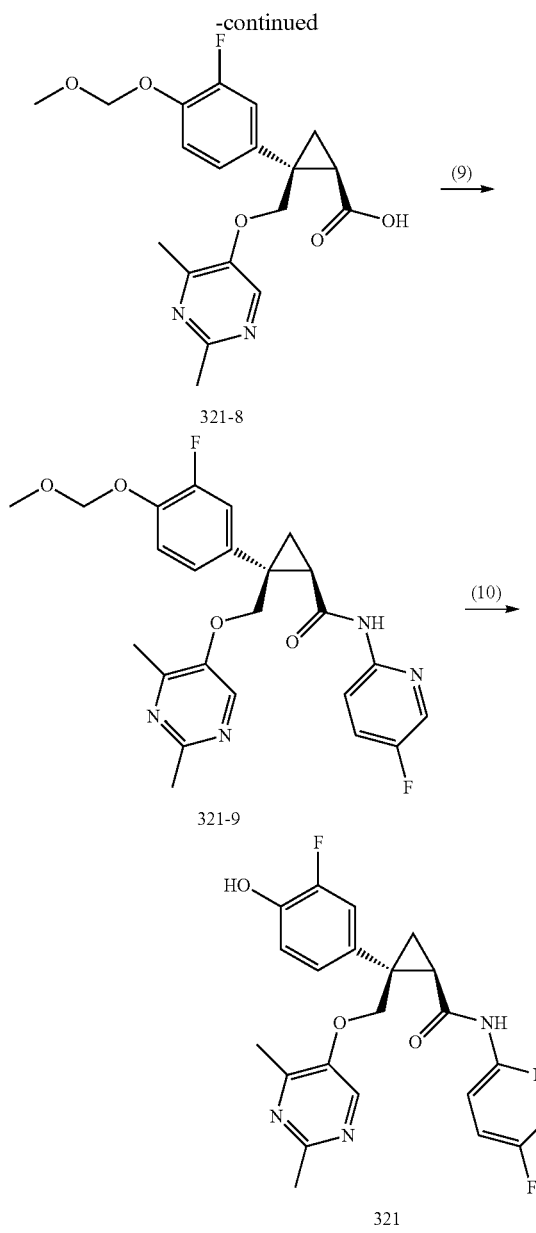

(1) 3-fluoro-4-(methoxymethoxy)benzaldehyde (321-1)

N,N-diisopropylethylamine (23.7 ml) and chloromethyl methyl ether (7.76 ml) were added to a dichloromethane (130 ml) solution of 3-fluoro-4-hydroxybenzaldehyde (13 g) under cooling on ice, and the obtained mixture was stirred at room temperature for 11 hours. Water was added to the reaction solution, and the mixture was extracted with dichloromethane. The obtained organic layer was dried over magnesium sulfate and concentrated under reduced pressure. The obtained residue was purified by silica gel column chromatography (n-heptane:ethyl acetate=19:1 to 7:3), so as to obtain the title compound (17.4 g).

1H-NMR (400 MHz, CDCl3) δ (ppm): 3.54 (s, 3H), 5.32 (s, 2H), 7.31-7.36 (m, 1H), 7.60-7.65 (m, 2H), 9.88 (d, J=2.4 Hz, 1H)

(2) 2-[3-fluoro-4-(methoxymethoxy)phenyl]acetonitrile (321-2)

Sodium borohydride (2.15 g) was added to a methanol-THF (20 ml-100 ml) solution of the compound 321-1 (17.4 g), while the solution was stirred under cooling on ice. The obtained mixture was stirred at room temperature for 1 hour. A saturated ammonium chloride aqueous solution was added to the reaction solution, and the mixture was extracted with ethyl acetate. The obtained organic layer was dried over magnesium sulfate and then concentrated under reduced pressure. The obtained residue was dissolved in dichloromethane (100 ml). Triethylamine (19.8 ml) and methanesulfonyl chloride (8.05 ml) were added to the solution, while the solution was stirred under cooling on ice. The obtained mixture was stirred at room temperature for 14 hours. Water was added to the reaction solution, and the mixture was extracted with ethyl acetate. The obtained organic layer was dried over magnesium sulfate and then concentrated under reduced pressure. The obtained residue was dissolved in acetonitrile (100 ml). Sodium iodide (2.83 g) and sodium cyanide (6.95 g) were added to the solution, and the obtained mixture was stirred at 80° C. for 3 hours. Thereafter, sodium cyanide (9.27 g) and dimethyl sulfoxide (30 ml) were added to the reaction solution, and the obtained mixture was stirred at 100° C. for 5 hours. The reaction solution was concentrated under reduced pressure. Water was added to the residue, and the mixture was then extracted with ethyl acetate. The obtained organic layer was washed with a saturated sodium chloride aqueous solution, then dried over magnesium sulfate, and concentrated under reduced pressure. The obtained residue was purified by silica gel column chromatography (n-heptane:ethyl acetate=1:0 to 1:1), so as to obtain the title compound (11.5 g).

1H-NMR (400 MHz, CDCl3) δ (ppm): 3.52 (s, 3H), 3.70 (s, 2H), 5.22 (s, 2H), 7.01-7.06 (m, 1H), 7.09 (dd, J=11.4, 2.2 Hz, 1H), 7.20 (t, J=8.8 Hz, 1H)

(3) (1S,5R)-1-[3-fluoro-4-methoxymethoxy)phenyl]-3-oxabicyclo[3.1.0]hexan-2-one (321-3)

NaHMS (63.6 ml, 1.9 M) was added to a THF (60 ml) solution of the compound 321-2 (11.5 g), while the solution was stirred at −15° C. The obtained mixture was stirred at −15° C. for 30 minutes, and (R)-(−)-epichlorohydrin (4.61 ml) was then added to the reaction mixture. The obtained mixture was stirred at −15° C. for 1 hour and then stirred at room temperature overnight. A small amount of water was added to the reaction solution, and the obtained mixture was concentrated under reduced pressure. Ethanol (90 ml) and a 1 N potassium hydroxide aqueous solution (118 ml) were added to the obtained residue, and the mixture was stirred at 110° C. for 5 hours. The temperature of the reaction solution was returned to room temperature. Thereafter, 5 N hydrochloric acid (82.5 ml) was added to the reaction solution, and the obtained mixture was stirred at 50° C. for 3 hours. The temperature of the reaction solution was returned to room temperature. Water was added to the reaction solution, and the mixture was extracted with ethyl acetate. The obtained organic layer was washed with a saturated sodium chloride aqueous solution, then dried over magnesium sulfate, and concentrated under reduced pressure. The obtained residue was washed with t-butyl methyl ether and then collected by filtration. The obtained solid (5.58 g) was dissolved in dichloromethane (60 ml). N,N-diisopropylethylamine (7 ml) and chloromethyl methyl ether (2.24 ml) were added to the solution, while the solution was stirred under cooling on ice. The obtained mixture was stirred at room temperature for 14 hours. Water was added to the reaction solution, and the mixture was extracted with ethyl acetate. The obtained organic layer was washed with a saturated sodium chloride aqueous solution, then dried over magnesium sulfate, and concentrated under reduced pressure, so as to obtain the title compound (7.09 g).

1H-NMR (400 MHz, CDCl3) δ (ppm): 1.37 (t, J=5.0 Hz, 1H), 1.57-1.63 (m, 1H), 2.50-2.57 (m, 1H), 3.51 (s, 3H), 4.29 (d, J=9.2 Hz, 1H), 4.46 (dd, J=9.2, 4.4 Hz, 1H), 5.21 (s, 2H), 7.08-7.12 (m, 1H), 7.13-7.24 (m, 2H)

(4) (1S,2R)-1-[3-fluoro-4-(methoxymethoxy)phenyl]cyclopropane-1,2-dimethanol (321-4)

Lithium borohydride (918 mg) was added to a THF-MeOH (100 ml-20 ml) solution of the compound 321-3 (7.09 g), while the solution was stirred at −30° C. The obtained mixture was stirred at room temperature for 15 hours. Water was added to the reaction solution. Thereafter, a saturated ammonium chloride aqueous solution was added to the mixture, and the obtained mixture was extracted with ethyl acetate. The obtained organic layer was dried over magnesium sulfate and then concentrated under reduced pressure. The obtained residue was purified by silica gel column chromatography (n-heptane/ethyl acetate=9:1 to 3:7), so as to obtain the title compound (6.94 g).

1H-NMR (400 MHz, CDCl3) δ (ppm): 0.77 (t, J=5.2 Hz, 1H), 1.06 (dd, J=8.6, 5.0 Hz, 1H), 1.60-1.68 (m, 1H), 2.60-2.65 (m, 1H), 2.88-2.96 (m, 1H), 3.35-3.45 (m, 1H), 3.52 (s, 3H), 3.52-3.59 (m, 1H), 4.10-4.24 (m, 2H), 5.19 (s, 2H), 7.06-7.18 (m, 3H)

(5) {(1R,2S)-2-[3-fluoro-4-(methoxymethoxy)phenyl]-2-(hydroxymethyl)cyclopropyl}methyl acetate (321-5)

Vinyl acetate (3.75 ml) and Lipase acrylic resin from *candida antarctica* (SIGMA, 0.35 g) were added to a THF (20 ml) solution of the compound 321-4 (6.94 g), and the obtained mixture was stirred at room temperature for 15 hours. The reaction solution was filtered, and the filtrate was concentrated under reduced pressure, so as to obtain the title compound (7.57 g).

1H-NMR (400 MHz, CDCl3) δ (ppm): 0.79 (t, J=5.4 Hz, 1H), 1.12 (dd, J=9.0, 5.0 Hz, 1H), 1.52-1.67 (m, 1H), 2.14 (s, 3H), 3.51 (s, 3H), 3.65 (d, J=12.2 Hz, 1H), 3.95 (d, J=12.2 Hz, 1H), 4.02 (dd, J=12.0, 10.0 Hz, 1H), 4.56 (dd, J=12.0, 5.6 Hz, 1H), 5.19 (s, 2H), 7.00-7.16 (m, 3H)

(6) {(1R,2S)-2-{[(2,4-dimethylpyrimidin-5-yl)oxy]methyl}-2-[3-fluoro-4-(methoxymethoxy)phenyl]cyclopropyl}methanol (321-6)

Diisopropyl dicarboxylate (6.04 ml) was added dropwise to a THF (100 ml) solution of the compound 321-5 (7.57 g), triphenylphosphine (7.99 g) and 2,4-dimethyl-pyrimidin-5-ol (3.15 g), while the solution was stirred under cooling on ice. The obtained mixture was stirred at room temperature for 14.5 hours. The reaction solution was concentrated under reduced pressure. Thereafter, n-heptane/ethyl acetate (5/1) was added to the residue, and the obtained mixture was stirred at room temperature for 2 hours. The formed solid was filtered off, and the filtrate was concentrated under reduced pressure. The residue was purified by NH-silica gel column chromatography (n-heptane:ethyl acetate=1:0 to 1:1). The obtained compound was dissolved in ethanol (50 ml). A 1 N NaOH aqueous solution (50 ml) was added to the solution, and the obtained mixture was stirred at room temperature for 2 hours. The solvent was distilled off under reduced pressure. Thereafter, water was added to the residue, and the mixture was extracted with ethyl acetate. The obtained organic layer was washed with a saturated sodium chloride aqueous solution, then dried over magnesium sulfate, and concentrated under reduced pressure. The obtained residue was purified by NH-silica gel column chromatography (n-heptane:ethyl acetate=9:1 to 0:1), so as to obtain the title compound (7.4 g).

1H-NMR (400 MHz, CDCl3) δ (ppm): 0.95 (t, J=5.8 Hz, 1H), 1.15-1.30 (m, 1H), 1.72-1.83 (m, 1H), 2.16 (dd, J=5.2, 3.2 Hz, 1H), 2.40 (s, 3H), 2.61 (s, 3H), 3.50-3.59 (m, 1H), 3.51 (s, 3H), 4.02-4.10 (m, 2H), 4.39 (d, J=9.6 Hz, 1H), 5.19 (s, 2H), 7.08-7.22 (m, 3H), 8.00 (s, 1H)

(7) (1R,2S)-2-{[(2,4-dimethylpyrimidin-5-yl)oxy]methyl}-2-[3-fluoro-4-(methoxymethoxy)phenyl]cyclopropanecarbaldehyde (321-7)

A dichloromethane (20 ml) solution of dimethyl sulfoxide (5.8 ml) was added dropwise to a dichloromethane (100 ml) solution of oxalyl chloride (3.45 ml), while the solution was stirred at −78° C. The obtained mixture was stirred at −78° C. for 10 minutes, and a dichloromethane (30 ml) solution of the compound 321-6 (7.4 g) was then added dropwise to the reaction mixture. The obtained mixture was stirred at −78° C. for 30 minutes. Thereafter, triethylamine (17.1 ml) was added to the reaction mixture, and the obtained mixture was stirred for 2 hours, while it was heated to 0° C. Water was added to the reaction solution, and the mixture was extracted with dichloromethane. The obtained organic layer was dried over magnesium sulfate and then concentrated under reduced pressure, so as to obtain the title compound (7.8 g).

1H-NMR (400 MHz, CDCl3) δ (ppm): 1.50-1.70 (m, 1H), 1.95 (t, J=5.6 Hz, 1H), 2.38 (s, 3H), 2.42-2.50 (m, 1H), 2.60 (s, 3H), 3.51 (s, 3H), 4.16 (d, J=9.8 Hz, 1H), 4.40 (d, J=9.8 Hz, 1H), 5.21 (s, 2H), 7.10-7.24 (m, 3H), 7.94 (s, 1H), 9.85 (d, J=3.2 Hz, 1H)

(8) (1R,2S)-2-{[(2,4-dimethylpyrimidin-5-yl)oxy]methyl}-2-[3-fluoro-4-(methoxymethoxy)phenyl]cyclopropanecarboxylic acid (321-8)

2-methyl-2-butene (11.5 ml) and sodium dihydrogen phosphate (3.89 g) were added to an acetone-water (100 ml-25 ml) solution of the compound 321-7 (7.8 g). The reaction solution was cooled on ice. Sodium chlorite (3.91 g) was added to the reaction mixture, and the obtained mixture was stirred at room temperature for 15 hours. Water was added to the reaction solution, and the mixture was extracted with ethyl acetate. The obtained organic layer was dried over magnesium sulfate and concentrated under reduced pressure. The obtained residue was purified by silica gel column chromatography (n-heptane:ethyl acetate=9:1 to 0:1), so as to obtain the title compound (4.57 g).

1H-NMR (400 MHz, CDCl3) δ (ppm): 1.49-1.55 (m, 1H), 1.70-1.76 (m, 1H), 2.18-2.25 (m, 1H), 2.36 (s, 3H), 2.56 (s, 3H), 3.52 (s, 3H), 4.40-4.50 (m, 2H), 5.21 (s, 2H), 7.13-7.29 (m, 3H), 8.18 (s, 1H)

(9) (1R,2S)-2-{[(2,4-dimethylpyrimidin-5-yl)oxy]methyl}-2-[3-fluoro-4-(methoxymethoxy)phenyl]-N-(5-fluoropyridin-2-yl)cyclopropanecarboxamide (321-9)

The title compound 321-9 (1.01 g) was obtained by reacting the compound 321-8 (1.00 g) and 2-amino-5-fluoropyridine (328 m g) by the same method as that of Example 51 (with HATU as a reacting agent).

1H-NMR (400 MHz, CDCl3) δ (ppm): 1.57-1.64 (m, 1H), 1.86-1.92 (m, 1H), 2.05-2.10 (m, 1H), 2.23 (s, 3H), 2.56 (s, 3H), 3.52 (s, 3H), 4.38 (d, J=9.2 Hz, 1H), 4.46 (d, J=9.2 Hz, 1H), 5.21 (s, 2H), 7.12-7.28 (m, 3H), 7.35-7.43 (m, 1H), 7.97 (s, 1H), 8.03-8.09 (m, 1H), 8.12 (s, 1H), 8.35 (s, 1H)

MS[M+H]+=471

(10) 1R,2S)-2-{[(2,4-dimethylpyrimidin-5-yl)oxy]methyl}-2-(3-fluoro-4-hydroxphenyl)-N-5-fluoropyridin-2-yl)cyclopropanecarboxamide (321)

5 N hydrochloric acid (15 ml) was added to a THF (15 ml) solution of the compound 321-9 (1.01 g), and the obtained mixture was stirred at room temperature for 2 hours. A 5 N sodium hydroxide aqueous solution was added to the reaction solution under cooling on ice for neutralization, and the mixture was then extracted with ethyl acetate. The obtained organic layer was washed with a saturated sodium chloride aqueous solution, then dried over magnesium sulfate, and concentrated under reduced pressure. The obtained residue was washed with ethyl acetate and collected by filtration, so as to obtain the title compound 321 (721 mg).

1H-NMR (400 MHz, CD3OD) δ (ppm): 1.47-1.55 (m, 1H), 1.78-1.85 (m, 1H), 2.20 (s, 3H), 2.40-2.47 (m, 1H), 2.46 (s, 3H), 4.40 (d, J=9.8 Hz, 1H), 4.59 (d, J=9.8 Hz, 1H), 6.85-6.93 (m, 1H), 7.15-7.22 (m, 1H), 7.27-7.34 (m, 1H), 7.43-7.52 (m, 1H), 7.89-7.97 (m, 1H), 8.06 (s, 1H), 8.17 (d, J=3.2 Hz, 1H)

MS [M+H]+=427

EXAMPLE 322

Synthesis of (1R,2S)-2-{[(2,4-dimethylpyrimidin-5-yl)oxy]methyl}-2-(3-fluoro-4-methoxyphenyl)-N-(5-fluoropyridin-2-yl)cyclopropanecarboxamide (322)

[Formula 97]

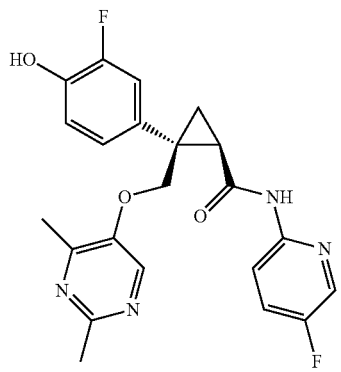

-continued

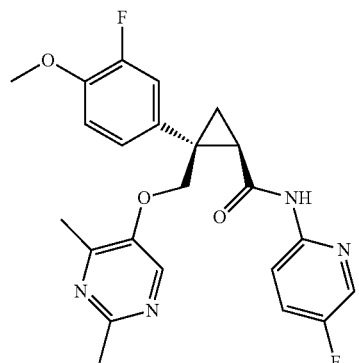

322

Cesium carbonate (172 mg) and methyl iodide (26.8 ul) were added to a DMF (5 ml) solution of the compound 321 (150 mg), and the obtained mixture was stirred at room temperature for 2 hours. Water was added to the reaction solution, and the mixture was extracted with ethyl acetate. The obtained organic layer was washed with a saturated sodium chloride aqueous solution, dried over magnesium sulfate, and then concentrated under reduced pressure. The obtained residue was purified by silica gel column chromatography (n-heptane:ethyl acetate=9:1 to 2:3), so as to obtain the title compound (70 mg).

1H-NMR (400 MHz, CDCl3) δ (ppm): 1.58 (dd, J=7.8, 5.4 Hz, 1H), 1.88 (t, J=5.4 Hz, 1H), 2.03-2.10 (m, 1H), 2.23 (s, 3H), 2.56 (s, 3H), 4.89 (s, 3H), 4.38 (d, J=9.2 Hz, 1H), 4.46 (d, J=9.2 Hz, 1H), 6.93 (t, J=8.4 Hz, 1H), 7.13-7.23 (m, 2H), 7.35-7.42 (m, 1H), 7.98 (s, 1H), 8.06 (dd, J=9.6, 3.8 Hz, 1H), 8.10 (d, J=2.8 Hz, 1H), 8.49 (brs, 1H)

EXAMPLE 323

Synthesis of (1R,2S)-2-(3-fluorophenyl)-N-(5-fluoropyridin-2-yl)-2-{[(2-hydroxymethyl-4-methylpyrimidin-5-yl)oxy]methyl}cyclopropanecarboxamide (323)

[Formula 98]

-continued

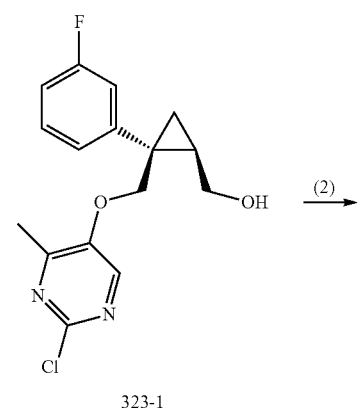

323-1

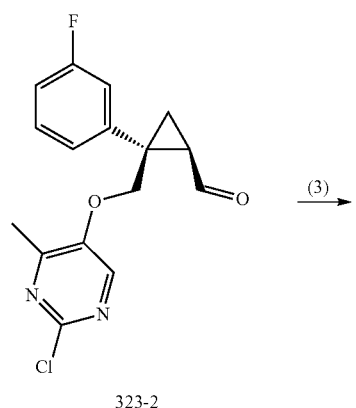

323-2

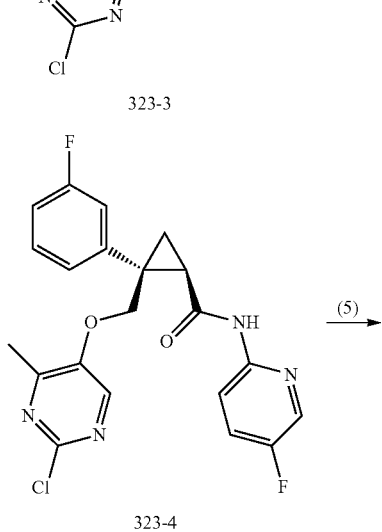

323-3

323-4

-continued

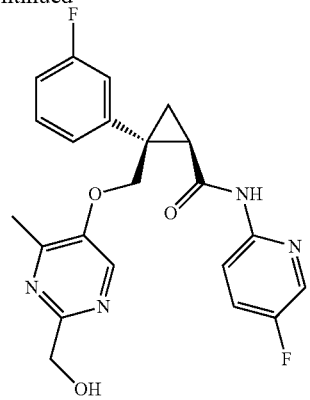

323

(1) {(1R,2S)-2-{[(2-chloro-4-methylpyrimidin-5-yl)oxy]methyl}-2-(3-fluorophenyl)cyclopropyl}methanol (323-1)

Diisopropyl azodicarboxylate (5.39 ml) was added to a THF (45 ml) solution of Prep 49 (5.58 g), Prep 1-2 (2.81 g) and triphenylphosphine (6.14 g), while the solution was stirred under cooling on ice. The obtained mixture was stirred at room temperature for 14 hours. A small amount of water was added to the reaction solution, and the obtained mixture was concentrated under reduced pressure. n-Heptane/ethyl acetate (5/1) was added to the obtained residue, and the mixture was stirred at room temperature for 1 hour. The formed solid was filtered off, and the filtrate was concentrated under reduced pressure. The obtained residue was dissolved in ethanol-THF (45 ml-45 ml). A 1 N sodium hydroxide aqueous solution was added to the solution, and the obtained mixture was stirred at room temperature for 2 hours. The solvent was distilled off under reduced pressure. Thereafter, water was added to the residue, and the mixture was extracted with ethyl acetate. The obtained organic layer was washed with a saturated sodium chloride aqueous solution, then dried over magnesium sulfate, and concentrated under reduced pressure. The obtained residue was purified by silica gel column chromatography (n-heptane:ethyl acetate=9:1 to 2:3), so as to obtain the title compound (5.67 g).

1H-NMR (400 MHz, CDCl3) δ (ppm): 0.99-1.05 (m, 1H), 1.25-1.33 (m, 1H), 1.76-1.87 (m, 1H), 1.88-1.94 (m, 1H), 2.42 (s, 3H), 3.55-3.65 (m, 1H), 4.02-4.12 (m, 1H), 4.12-4.20 (m, 1H), 4.42 (dd, J=9.6, 3.6 Hz, 1H), 6.92-6.99 (m, 1H), 7.09-7.15 (m, 1H), 716-7.22 (m, 1H), 7.24-7.33 (m, 1H), 7.93 (s, 0.5H), 7.97 (s, 0.5)

(2) (1R,2S)-2-{[(2-chloro-4-methylpyrimidin-5-yl)oxy]methyl}-2-(3-fluorophenyl)cyclopropanecarbaldehyde (323-2)

A dichloromethane (25 ml) solution of dimethyl sulfoxide (5 ml) was added dropwise to a dichloromethane (100 ml) solution of oxalyl chloride (2.98 ml), while the solution was stirred at −78° C. The obtained mixture was stirred at −78° C. for 10 minutes, and a dichloromethane (25 ml) solution of the compound 323-1 (5.67 g) was then added dropwise to the reaction mixture. The obtained mixture was stirred at −78° C. for 30 minutes. Thereafter, triethylamine (14.7 ml) was added to the reaction mixture, and the obtained mixture was stirred for 2 hours, while it was heated to 0° C. Water was added to the reaction solution, and the mixture was extracted with dichloromethane. The obtained organic layer was dried over magnesium sulfate and then concentrated under reduced pressure, so as to obtain the title compound (7.12 g).

1H-NMR (400 MHz, CDCl3) δ (ppm): 1.69 (dd, J=8.4, 5.2 Hz, 1H), 1.95-2.01 (m, 1H), 2.39 (s, 1H), 2.53-2.60 (m, 1H), 4.24 (dd, J=10.0, 3.2 Hz, 1H), 4.44 (dd, J=9.8, 3.4 Hz, 1H), 6.99-7.06 (m, 1H), 7.12-7.18 (m, 1H), 7.19-7.25 (m, 1H), 7.30-7.38 (m, 1H), 7.89 (s, 0.5H), 7.93 (s, 0.5H), 9.94 (s, 1H)

(3) (1R,2S)-2-{[(2-chloro-4-methylpyrimidin-5-yl)oxy]methyl}-2-(3-fluorophenyl)cyclopropanecarboxylic acid (323-3)

2-methyl-2-butene (11.7 ml) and sodium dihydrogen phosphate (3.98 g) were added to an acetone-water (80 ml-20 ml) solution of the compound 323-2 (7.1 g). The reaction solution was cooled on ice. Sodium chlorite (4 g) was added to the reaction solution, and the obtained mixture was stirred at room temperature for 18 hours. Water was added to the reaction solution, and the mixture was extracted with ethyl acetate. The obtained organic layer was dried over magnesium sulfate and concentrated under reduced pressure. The obtained residue was purified by silica gel column chromatography (n-heptane:ethyl acetate=9:1 to 3:7), so as to obtain the title compound (5.77 g).

1H-NMR (400 MHz, CDCl3) δ (ppm): 1.62-1.69 (m, 1H), 1.72-1.80 (m, 1H), 2.21-2.29 (m, 1H), 2.40 (s, 1H), 4.37-4.47 (m, 1H), 4.47-4.54 (m, 1H), 6.97-7.05 (m, 1H), 7.13-7.20 (m, 1H), 7.21-7.26 (m, 1H), 7.33 (td, J=8.0, 6.0 Hz, 1H), 7.98 (s, 0.5H), 8.02 (s, 0.5H)
MS[M+H]+=337

(4) (1R,2S)-2-{([(2-chloro-4-methylpyrimidin-5-yl)oxy]methyl}-2-(3-fluorophenyl)-N-(5-fluoropyridin-2-yl)cyclopropanecarboxamide (323-4)

The title compound was synthesized by reacting the carboxylic acid 323-3 and 2-amino-5-fluoropyridine by the same method as that of Example 51.

1H-NMR (400 MHz, CDCl3) δ (ppm): 1.61-1.69 (m, 1H), 1.88-1.95 (m, 1H), 2.08-2.17 (m, 1H), 2.25 (s, 3H), 4.40-4.50 (m, 1H), 4.50-4.57 (m, 1H), 6.98-7.06 (m, 1H), 7.11-7.18 (m, 1H), 7.21-7.25 (m, 1H), 7.30-7.38 (m, 1H), 7.38-7.45 (m, 1H), 7.92 (s, 0.5H), 7.96 (s, 0.5H), 8.02-8.09 (m, 1H), 8.13 (d, J=3.2 Hz, 1H), 8.33 (brs, 1H)

(5) 1R,2S)-2-(3-fluorophenyl)-N-(5-fluoropyridin-2-yl)-2-{[(2-hydroxymethyl-4-methylpyrimidin-5-yl)oxy]methyl}cyclopropanecarboxamide (323)

(Tert-butyldimethylsilyloxymethyl)tri-n-butyltin (Tetrahedron Vol. 45, No. 4, 993-1006: 121 mg) and tetrakistriphenylphosphinepalladium (13.4 mg) were added to a N-methylpyrrolidone (2.5 ml) solution of the compound 323-4 (100 mg), and the obtained mixture was stirred at 140° C. for 6 hours. The temperature of the reaction solution was returned to room temperature. Thereafter, THF (2 ml) and tetrabutyl ammonium fluoride (1 M THF solution: 232 ul) were added to the reaction solution, and the obtained mixture was stirred at room temperature for 14 hours. Water was added to the reaction solution, and the mixture was extracted with ethyl acetate. The obtained organic layer was washed with a saturated sodium chloride aqueous solution, dried over magnesium sulfate, and then concentrated under reduced pressure. The obtained residue was purified by silica gel column chromatography (n-heptane:ethyl acetate=19:1 to 1:1), so as to obtain the title compound (26.6 mg).

1H-NMR (400 MHz, CDCl3) δ (ppm): 1.65 (dd, J=8.4, 5.6 Hz, 1H), 1.93 (t, J=5.6 Hz, 1H), 2.08-2.18 (m, 1H), 2.27 (s, 3H), 4.46 (d, J=9.2 Hz, 1H), 4.54 (d, J=9.2 Hz, 1H), 4.66 (2H, s), 6.98-7.05 (m, 1H), 7.14-7.30 (m, 2H), 7.32-7.43 (m, 2H), 8.03-8.09 (m, 1H), 8.07 (s, 1H), 8.14 (d, J=2.8 Hz, 1H), 8.30 (brs, 1H)

EXAMPLE 324

Synthesis of (1R,2S)-2-{[(2,4-dimethylpyrimidin-5-yl)oxy]methyl}-2-(5-fluoro-2-hydroxyphenyl]-N-(5-fluoropyridin-2-yl)cyclopropanecarboxamide (324)

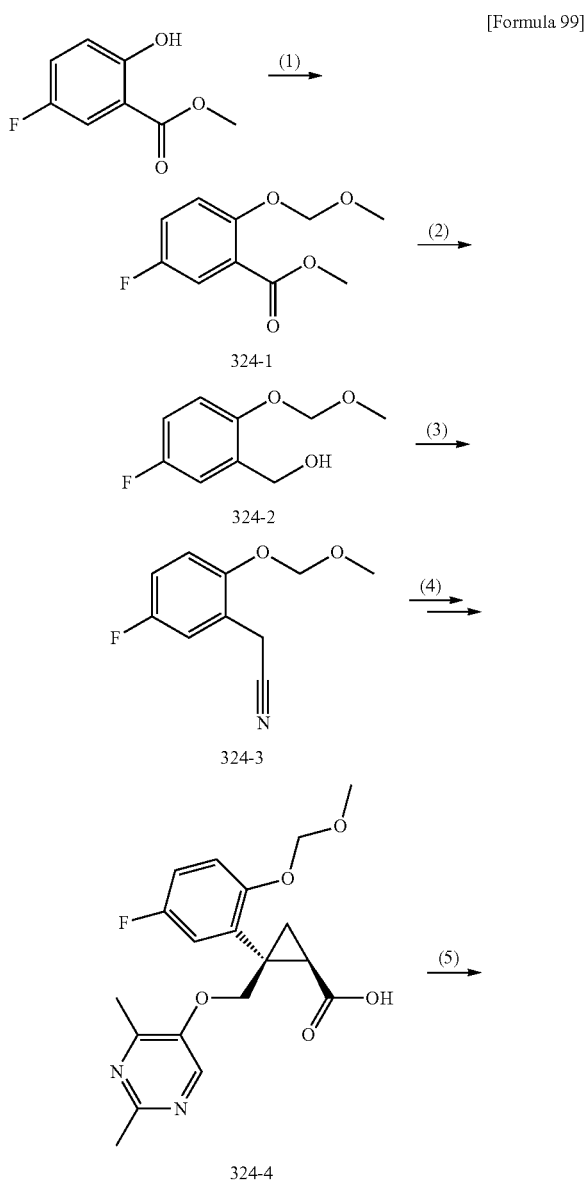

[Formula 99]

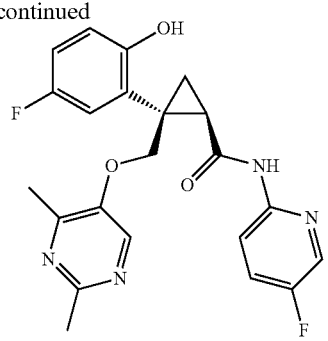

324

(1) Methyl 5-fluoro-2-(methoxymethoxy)benzoate (324-1)

N,N-diisopropylethylamine (15.4 ml) and chloromethyl methyl ether (4.91 ml) were added to a dichloromethane (100 ml) solution of methyl 5-fluoro-2-hydroxybenzoate (10 g), while the solution was stirred under cooling on ice. The obtained mixture was stirred at room temperature for 14 hours. Water was added to the reaction solution, and the mixture was extracted with dichloromethane. The obtained organic layer was dried over magnesium sulfate and then concentrated under reduced pressure, so as to obtain the title compound (12.4 g).

1H-NMR (400 MHz, CDCl3) δ (ppm): 3.52 (s, 3H), 3.90 (s, 3H), 5.20 (s, 2H), 7.11-7.22 (m, 2H), 7.47-7.52 (m, 1H)

(2) [5-fluoro-2-(methoxymethoxy)phenyl]methanol (324-2)

Lithium aluminum hydride (2.2 g) was added to a THF (200 ml) solution of the compound 324-1 (12.4 g), while the solution was stirred under cooling on ice. The obtained mixture was stirred at room temperature for 3 hours. Ice was added by portions to the reaction solution, and thereby excessive lithium aluminum hydride was decomposed. Thereafter, a small amount of 27% ammonium aqueous solution and Celite were added to the residue, and the obtained mixture was stirred at room temperature for 20 minutes. Magnesium sulfate was added to the reaction solution, and the mixture was filtered. The filtrate was concentrated under reduced pressure. The obtained residue was purified by silica gel column chromatography (n-heptane/ethyl acetate=1:0 to 3:1), so as to obtain the title compound (5.23 g).

1H-NMR (400 MHz, CDCl3) δ (ppm): 3.48 (s, 3H), 4.68 (d, J=6.4 Hz, 2H), 5.18 (s, 2H), 6.92 (td, J=8.8, 2.8 Hz, 1H), 7.03-7.10 (m, 2H)

(3) 2-[5-fluoro-2-(methoxymethoxy)phenyl]acetonitrile (324-3)

Triethylamine (5.95 ml) and methanesulfonyl chloride (2.42 ml) were added to a dichloromethane (60 ml) solution of the compound 324-2 (5.23 g), while the solution was stirred under cooling on ice. The obtained mixture was stirred at room temperature for 1 hour. A saturated sodium chloride aqueous solution was added to the reaction solution, and the mixture was extracted with ethyl acetate. The obtained organic layer was dried over magnesium sulfate and then concentrated under reduced pressure. The obtained residue was dissolved in dimethyl sulfoxide (30 ml). Sodium cyanide (2.09 g) and sodium iodide (851 mg) were added to the solution, and the obtained mixture was stirred at 90° C. for 3 hours. The temperature of the reaction solution was returned to room temperature. Thereafter, water was added to the reaction solution, and the mixture was extracted with diethyl ether. The obtained organic layer was dried over magnesium sulfate and concentrated under reduced pressure. The obtained residue was purified by silica gel column chromatography (n-heptane:ethyl acetate=1:0 to 4:1), so as to obtain the title compound (4.33 g).

1H-NMR (400 MHz, CDCl3) δ (ppm): 3.49 (s, 3H), 3.70 (s, 2H), 5.21 (s, 2H), 6.95-7.02 (m, 1H), 7.08-7.13 (m, 2H)

(4) (1R,2S)-2-{[(2,4-dimethylpyrimidin-5-yl)oxy]methyl}-2-[3-fluoro-6-(methoxymethoxy)phenyl]cyclopropanecarboxylic acid (324-4)

The title compound was synthesized from the compound 324-3 according to the method of Production Example 321 (3)-(8).

1H-NMR (400 MHz, CDCl3) δ (ppm): 1.47 (dd, J=8.2, 5.0 Hz, 1H), 1.77 (dd, J=6.2, 5.4 Hz, 1H), 2.18 (dd, J=8.4, 6.4 Hz, 1H), 2.30 (s, 3H), 2.57 (s, 3H), 3.50 (s, 3H), 4.41 (d, J=9.6 Hz, 1H), 4.53 (d, J=9.6 Hz, 1H), 5.23 (q, J=6.8 Hz, 2H), 6.95 (ddd, J=8.8, 7.6, 3.2 Hz, 1H), 7.06 (dd, J=8.8, 4.8 Hz, 1H), 7.18 (dd, J=8.8, 3.0 Hz, 1H), 8.16 (s, 1H) (5) (1R,2S)-2-{[(2,4-dimethylpyrimidin-5-yl)oxy]methyl}-2-[5-fluoro-2-hydroxyphenyl]-N-(5-fluoropyridin-2-yl)cyclopropanecarboxamide (324)

The title compound was synthesized from the carboxylic acid 328-4 according to the method of Example 3 (1)-(2).

1H-NMR (400 MHz, CDCl3) (ppm): 1.55-1.66 (m, 1H), 1.92-1.97 (m, 1H), 2.07-2.16 (m, 1H), 2.25 (s, 3H), 2.58 (s, 3H), 4.46 (dd, J=11.6, 9.2 Hz, 2H), 6.86-7.06 (m, 4H), 7.36-7.45 (m, 1H), 8.02 (s, 1H), 8.06-8.15 (m, 1H), 8.14 (d, J=2.8 Hz, 1H), 8.62 (brs, 1H)

MS[M+Na]+=448

EXAMPLE 325

Synthesis of (1R,2S)-2-{[(2,4-dimethylpyrimidin-5-yl)oxy]methyl}-N-(5-fluoro-6-hydroxypyridin-2-yl)-2-(3-fluorophenyl)cyclopropanecarboxamide (325)

[Formula 100]

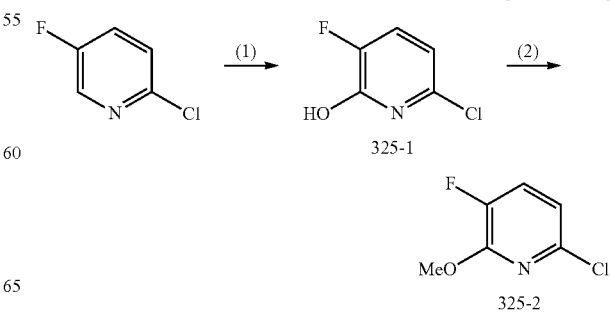

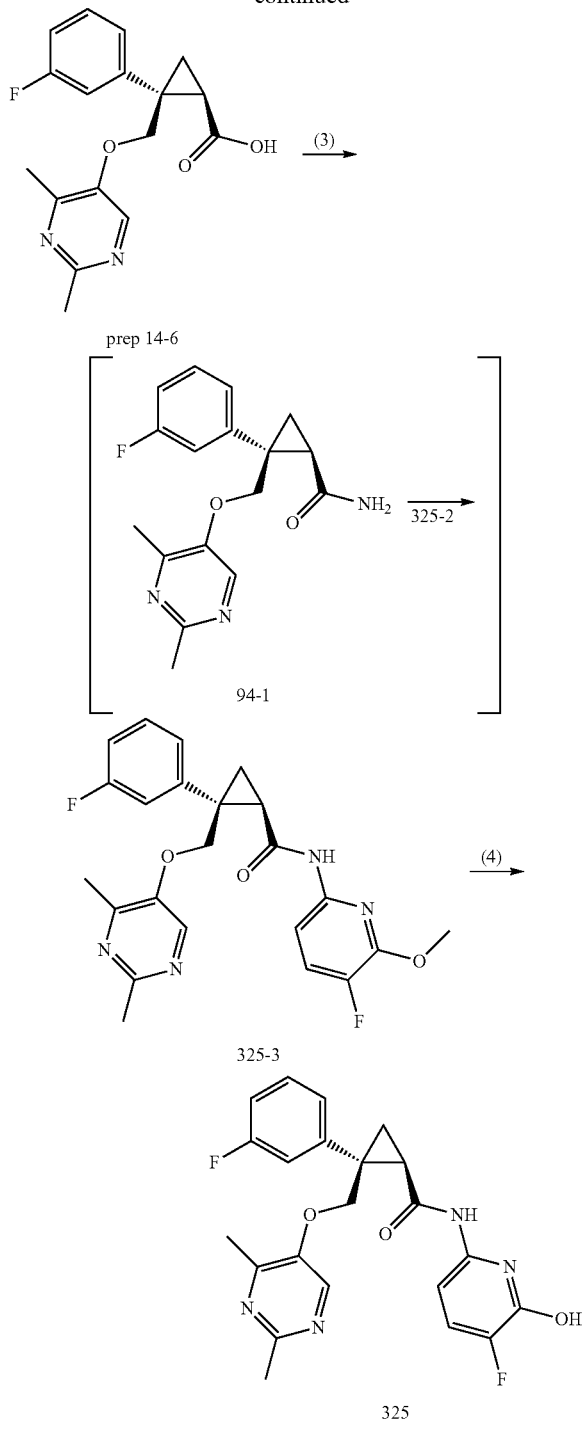

prep 14-6

94-1

325-3

325

(1) 6-chloro-3-fluoropyridin-2-ol (325-1)

3-chloroperoxybenzoic acid (21 g) was added to a dichloromethane (200 ml) solution of 2-chloro-3-fluoropyridine (10 g), and the obtained mixture was stirred at 65° C. for 8 hours. The reaction solution was cooled on ice. A saturated sodium thio sulfate aqueous solution was added to the reaction solution, and the obtained mixture was stirred for 20 minutes. A saturated sodium bicarbonate aqueous solution was added to the reaction solution, and the mixture was extracted with chloroform. The obtained organic layer was dried over magnesium sulfate and then concentrated under reduced pressure. The residue was washed with t-butyl methyl ether/n-heptane (1/1), and the solid was collected by filtration. The obtained solid was dissolved in THF (150 ml). Triethylamine (13.2 ml) and trifluoroacetic acid anhydride (33.2 ml) were added to the solution, while the solution was stirred under cooling on ice. The obtained mixture was stirred at room temperature for 5 hours. A small amount of water was added to the reaction solution. Thereafter, a 5 N sodium hydroxide aqueous solution was added to the mixture, while the solution was stirred under cooling on ice. The obtained mixture was stirred at room temperature for 1 hour. The reaction solution was converted to the mild acidic range by addition of acetic acid, and it was then extracted with ethyl acetate. The obtained organic layer was washed with a saturated sodium chloride aqueous solution, then dried over magnesium sulfate, and concentrated under reduced pressure. The obtained residue was purified by silica gel column chromatography (n-heptane:ethyl acetate=19:1 to 1:1). The obtained solid was washed with t-butyl methyl ether/n-heptane (1/1) and then collected by filtration, so as to obtain the title compound (2.6 g).

1H-NMR (400 MHz, CDCl3) δ (ppm): 6.50 (d, J=8.0 Hz, 1H), 7.24-7.33 (m, 1H)

(2) 6-chloro-3-fluoro-2-methoxypyridine (325-2)

Methyl iodide (262 ul) and silver carbonate (1.12 g) were added to a chloroform (3 ml) solution of the compound 325-1 (300 mg), and the obtained mixture was stirred at 40° C. for 5 hours. The temperature of the reaction solution was cooled to room temperature. The reaction solution was filtered, and the filtrate was concentrated under reduced pressure. The obtained residue was purified by silica gel column chromatography (n-heptane:ethyl acetate=1:0 to 1:1), so as to obtain the title compound (86 mg).

1H-NMR (400 MHz, CDCl3) δ (ppm): 4.03 (s, 3H), 6.86 (dd, J=8.0, 2.4 Hz, 1H), 7.30 (dd, J=9.6, 8.0 Hz, 1H)

(3) (1R,2S)-2-{[(2,4-dimethylpyrimidin-5-yl)oxy]methyl}-N-(5-fluoro-6-methoxypyridin-2-yl)-2-(3-fluorophenyl)cyclopropanecarboxamide (325-3)

The title compound was synthesized from the compound 94-1 and the compound 325-2 by the same method as that of Example 73.

1H-NMR (400 MHz, CDCl3) δ (ppm): 1.61-1.67 (m, 1H), 1.92 (t, J=5.4 Hz, 1H), 2.05-2.16 (m, 1H), 2.24 (s, 3H), 2.56 (s, 3H), 3.96 (s, 3H), 4.42 (d, J=9.4 Hz, 1H), 4.53 (d, J=9.4 Hz, 1H), 6.97-7.05 (m, 1H), 7.16-7.22 (m, 1H), 7.23-7.40 (m, 3H), 7.55 (dd, J=8.6, 2.2 Hz, 1H), 7.94-8.03 (m, 1H)

MS[M+Na]+=441

(4) (1R,2S)-2-{[(2,4-dimethylpyrimidin-5-yl)oxy]methyl}-N-(5-fluoro-6-hydroxypyridin-2-yl)-2-(3-fluorophenyl)cyclopropanecarboxamide (325)

A mixture of the compound 325-3 (70 mg) and pyridine hydrochloride (367 mg) was stirred at 115° C. for 2.5 hours. The temperature of the reaction solution was returned to room temperature. Thereafter, water was added to the reaction solution, and the obtained mixture was extracted with ethyl acetate. The solvent was distilled off. The obtained residue was purified by silica gel column chromatography (n-heptane:ethyl acetate (19:1 to 0:1) to ethyl acetate:methanol (9:1)). The obtained purified product was further repurified by preparative silica gel TLC (ethyl acetate:methanol=19:1), so as to obtain the title compound (30 mg).

1H-NMR (400 MHz, CDCl3) δ (ppm): 1.60-1.67 (m, 1H), 1.89 (t, J=5.6 Hz, 1H), 2.28 (s, 3H), 2.35 (dd, J=8.4, 6.0 Hz, 1H), 2.57 (s, 3H), 4.46 (dd, J=21.6, 9.6 Hz, 2H), 6.89-7.01 (m, 2H), 7.12-7.32 (m, 4H), 8.00 (s, 1H), 10.6 (brs, 1H)
MS[M+Na]+=427
EXAMPLE 326
Synthesis of (1R,2S)-2-{[(2,4-dimethyl-6-oxo-1,6-dihydropyrimidin-5-yl)oxy]methyl}-2-(3-fluorophenyl)-N-(5-fluoropyridin-2-yl)cyclopropanecarboxamide (326)
[Formula 101]
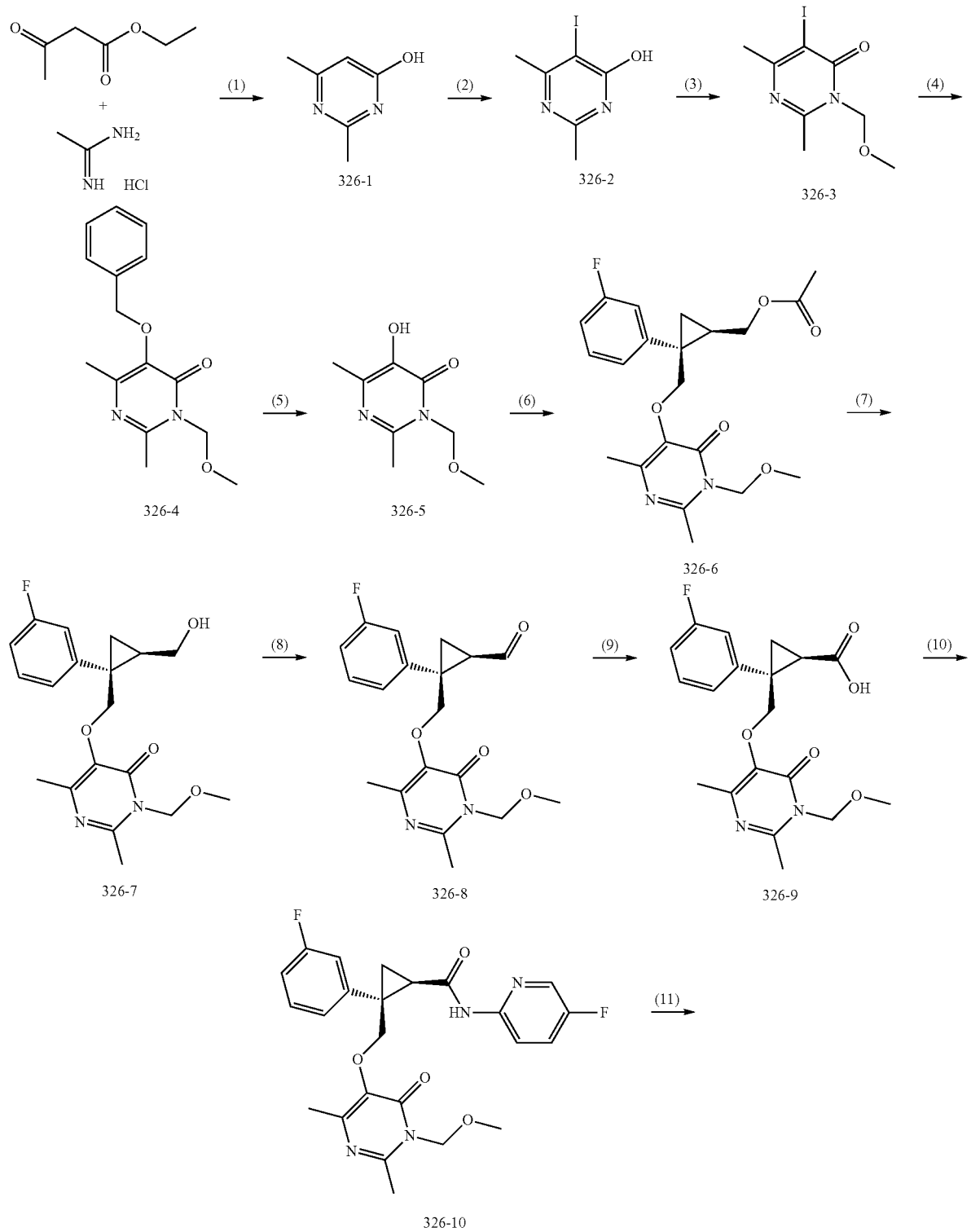

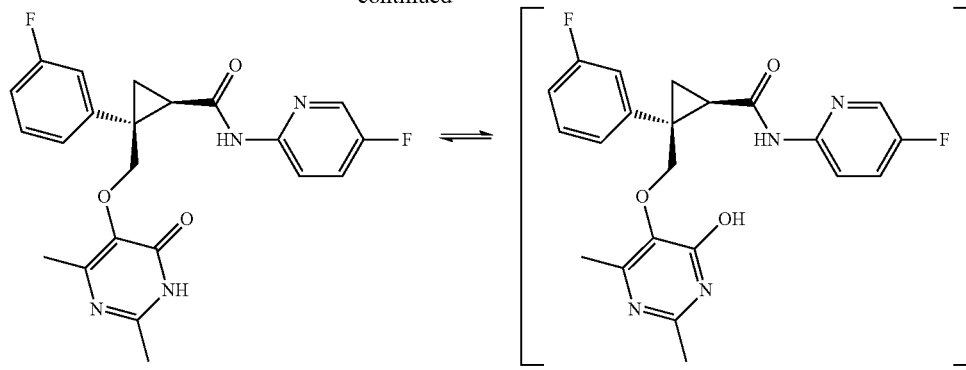

326

(1) 2,6-dimethylpyrimidin-4-ol (326-1)

Sodium (3.6 g) was added by portions to ethanol (92 ml) over 2 hours, while the solution was stirred at room temperature. Thereafter, ethyl acetoacetate (10 ml) and acetamidine hydrochloride (7.42 g) were added to the reaction solution, and the obtained mixture was stirred at 70° C. for 16 hours. Thereafter, the reaction mixture was stirred at 100° C. for 9 hours, and the temperature of the reaction solution was returned to room temperature. Concentrated hydrochloric acid was added to the reaction solution, so that the pH value was adjusted to around 5. The obtained mixture was concentrated under reduced pressure, so as to obtain a crude title compound (25.6 g).

1H-NMR (400 MHz, CDCl3) δ (ppm): 2.30 (s, 3H), 2.46 (s, 3H), 6.17 (s, 1H)

(2) 5-iodo-2,6-dimethylpyrimidin-4-ol (326-2)

The crude compound 326-1 (25.6 g) was dissolved in a 1.25 N sodium hydroxide aqueous solution (140 ml). Iodine (19.9 g) was added to the solution, and the obtained mixture was then stirred at 120° C. for 2 hours. The temperature of the reaction solution was returned to room temperature, and the reaction solution was then extracted with chloroform. The obtained organic layer was dried over magnesium sulfate and then concentrated under reduced pressure, so as to obtain the title compound (14.5 g).

1H-NMR (400 MHz, CDCl3) δ (ppm): 2.49 (s, 3H), 2.60 (s, 3H), 12.8 (brs, 1H)

(3) 5-iodo-3-(methoxymethyl)-2,6-dimethylpyrimidin-4(3H)-one (326-3)

N,N-diisopropylethylamine (13.1 ml) was added to a dichloromethane (100 ml) solution of the compound 326-2 (14.5 g). Chloromethyl methyl ether (4.85 ml) was added to the reaction solution, while the solution was stirred at −40° C. The obtained mixture was stirred at room temperature for 15 hours. Water was added to the reaction solution, and the mixture was extracted with dichloromethane. The obtained organic layer was dried over magnesium sulfate and then concentrated under reduced pressure. The obtained residue was purified by silica gel column chromatography (n-heptane:ethyl acetate=19:1 to 0:1), so as to obtain the title compound (10.6 g) and 5-iodo-4-(methoxymethoxy)-2,6-dimethylpyrimidine (2.55 g).

1H-NMR (400 MHz, CDCl3) δ (ppm): 2.54 (s, 3H), 2.57 (s, 3H), 3.44 (s, 3H), 5.52 (s, 2H)

(4) 5-(benzyloxy)-3-(methoxymethyl)-2,6-dimethylpyrimidin-4(3H)-one (326-4)

The compound 326-3 (4.78 g) was dissolved in toluene (130 ml). Cesium carbonate (10.6 g), 1,10-phenanthroline (4.41 g) and copper iodide (3.1 g) were added to the solution, and the obtained mixture was stirred for 5 minutes. Thereafter, benzyl alcohol (5.28 ml) was added to the reaction mixture. The obtained mixture was stirred at 110° C. for 5 days. The reaction mixture was diluted with ethyl acetate and filtered. The filtrate was concentrated under reduced pressure, and the obtained residue was purified by silica gel column chromatography (n-heptane:ethyl acetate=19:1 to 1:2), so as to obtain the title compound (1.42 g).

MS [M+H]+=275.

(5) 5-hydroxy-3-(methoxymethyl)-2,6-dimethylpyrimidin-4(3H)-one (326-5)

The compound 326-4 (1.42 g) was dissolved in ethyl acetate (30 ml). Palladium-carbon (700 mg) was added to the solution, and the obtained mixture was stirred in a hydrogen atmosphere for 1 hour. The reaction mixture was filtered with Celite, and the filtrate was concentrated under reduced pressure, so as to obtain the crude title compound (954 mg).

1H-NMR (400 MHz, CDCl3) δ (ppm): 2.27 (s, 3H), 2.53 (s, 3H), 3.41 (s, 3H), 5.47 (s, 2H), 6.07 (brs, 1H).

(6) [(1R,2S)-2-(3-fluorophenyl)-2-({[1-(methoxymethyl)-2,4-dimethyl-6-oxo-1,6-dihydropyrimidin-5-yl]oxy}methyl)cyclopropyl]methyl acetate (326-6)

A THF solution (5 ml) of Prep 49 (1.36 g) was added to a THF solution (15 ml) of the compound 326-5 (954 mg). Thereafter, triphenylphosphine (1.63 g) was added to the mixture, and diisopropyl azodicarboxylate (1.9 M, 3.27 ml,) was added dropwise to the mixture under cooling on ice. The obtained mixture was stirred at the same temperature as described above for 2 hours, then heated to room temperature, and stirred overnight. The reaction mixture was concentrated under reduced pressure, and the obtained residue was purified by silica gel column chromatography (n-heptane:ethyl acetate=9:1 to 0:1), so as to obtain the title compound (1.0 g).

MS[M+Na]+=427.

(7) 5-{[(1R,2S)-2-(3-fluorophenyl)-2-(hydroxymethyl)cyclopropyl]methoxy}-3-(methoxymethyl)-2,6-dimethylpyrimidin-4(3H)-one (326-7)

A 2 N sodium hydroxide aqueous solution (1.36 ml) was added to an ethanol solution (10 ml) of the compound 326-6 (1.0 g). The obtained mixture was stirred at room temperature for 30 minutes. Thereafter, water was added the reaction solution, and chloroform was added to the obtained mixture to carry out liquid separation and extraction. The obtained organic layer was dried over magnesium sulfate. It was concentrated under reduced pressure, and the obtained residue was purified by silica gel column chromatography (n-heptane:ethyl acetate=2:1 to 0:1), so as to obtain the title compound (895 mg).

MS[M+Na]+=385.

(8) (1R,2S)-2-(3-fluorophenyl)-2-({[1-(methoxymethyl)-2,4-dimethyl-6-oxo-1,6-dihydropyrimidin-5-yl]oxy}methyl)cyclopropanecarbaldehyde (326-8)

A Dess-Martin reagent was added to a dichloromethane (15 ml) solution of the compound 326-7 (895 mg) under cooling on ice. The obtained mixture was stirred at room temperature for 1 hour, and a mixed solution of a sodium bicarbonate aqueous solution-sodium sulfite aqueous solution was then added to the reaction mixture under cooling on ice. The obtained mixture was stirred in this state for 30 minutes, and dichloromethane was then added to the reaction mixture to carry out liquid separation and extraction. The obtained organic layer was dried over magnesium sulfate and concentrated under reduced pressure. The residue was purified by silica gel column chromatography (n-heptane:ethyl acetate=3:1 to 0:1), so as to obtain the title compound (779.5 mg).

MS [M+H]+=361.

(9) (1R,2S)-2-(3-fluorophenyl)-2-({[1-(methoxymethyl)-2,4-dimethyl-6-oxo-1,6-dihydropyrimidin-5-yl]oxy}methyl)cyclopropanecarboxylic acid (326-9)

2-methyl 2-butene (1.14 ml), sodium dihydrogen phosphate (389 mg) and sodium chlorite (305 mg) were added to an acetone-water mixed solvent (8 ml-2 ml) of the compound 326-8 (779 mg). The obtained mixture was stirred at room temperature for 1 hour. Thereafter, water was added to the reaction solution, and chloroform was added to the reaction solution to carry out liquid separation and extraction. A small amount of 1 N hydrochloric acid was added to the obtained extract, and chloroform was further added to the reaction solution to carry out liquid separation and extraction. The obtained organic layer was dried over magnesium sulfate. The organic layer was dried over anhydrous magnesium sulfate and concentrated under reduced pressure, so as to obtain a crude product of the title carboxylic acid (814 mg).

MS[M+H]+=377.

(10) (1R,2S)-2-(3-fluorophenyl)-N-(5-fluoropyridin-2-3/1)-2-({[1-(methoxymethyl)-2,4-dimethyl-6-oxo-1,6-dihydropyrimidin-5-yl]oxy}methyl)cyclopropanecarboxamide (326-10)

2-amino-5-fluoropyridine (17.9 mg), HATU (60.7 mg) and N,N-diisopropylethylamine (27.7 ul) were added to a dichloromethane (1.3 ml)-DMF (2.6 ml) mixed solution of the compound 326-9 (50 mg). The obtained mixture was stirred at room temperature overnight, and the reaction was then checked by LC-MS. 2-amino-5-fluoropyridine was further added in an amount of 2 equivalents (30 mg), and the obtained mixture was stirred at 90° C. for 5 hours. The reaction mixture was cooled to room temperature. Water was added to the reaction solution, and diethyl ether was added to the obtained mixture to carry out liquid separation and extraction. The obtained organic layer was dried over anhydrous magnesium sulfate and concentrated under reduced pressure. The obtained residue was purified by silica gel column chromatography (n-heptane:ethyl acetate=9:1 to 1:2), so as to obtain the title compound (41 mg).

MS[M+Na]+=493.

(11) (1R,2S)-2-{[(2,4-dimethyl-6-oxo-1,6-dihydropyrimidin-5-yl)oxy]methyl}-2-(3-fluorophenyl)-N-(5-fluoropyridin-2-yl)cyclopropanecarboxamide (326)

An ethanol (3 ml)-concentrated hydrochloric acid (1 ml) mixed solution of the compound 330-10 (150 mg) was stirred at 90° C. for 30 minutes. The reaction mixture was cooled to room temperature, and a 1 N sodium hydroxide aqueous solution was added dropwise to the reaction solution. The precipitated crystal was filtered, washed with water, and then washed with a t-butyl methyl ether-heptane (1:1) solution. The crystal that had been collected by filtration was dried under reduced pressure, so as to obtain the title compound (62 mg).

1H-NMR (400 MHz, CDCl3) (ppm): 1.33 (dd, J=8.0, 4.8 Hz, 1H), 1.52 (t, J=4.4 Hz, 1H), 1.74 (s, 3H), 2.02 (s, 3H), 2.62 (t, J=7.6 Hz, 1H), 4.22 (d, J=10.8 Hz, 1H), 4.80 (d, J=11.2 Hz, 1H), 7.03-7.08 (m, 1H), 7.33-7.40 (m, 2H), 7.49-7.50 (m, 1H), 7.52-7.72 (m, 1H), 8.03-8.06 (m, 1H), 8.31 (d, J=3.2 Hz, 1H), 11.1 (s, 1H), 12.2 (brs, 1H).

MS[M+Na]+=449.

EXAMPLE 327

Synthesis of (1R,2S)-2-{[(2,4-dimethylpyrimidin-5-yl)oxy]methyl}-N-(6-fluoro-5-methoxypyridin-3-yl)-2-phenylcyclopropanecarboxamide (327)

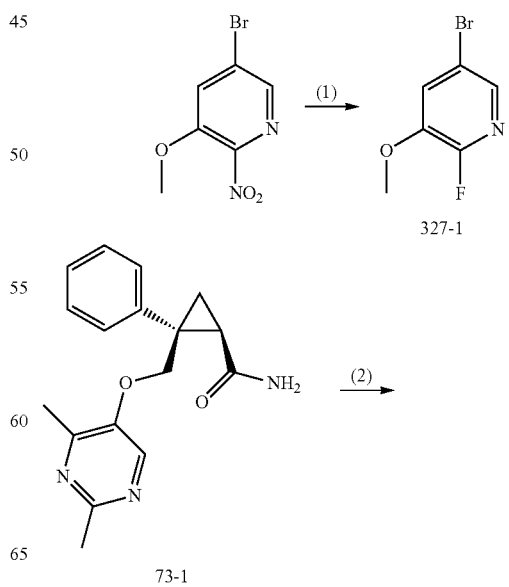

[Formula 102]

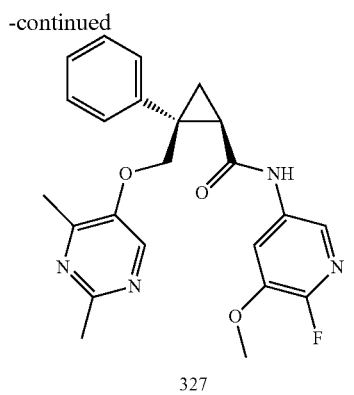

327

(1) Synthesis of
3-bromo-6-fluoro-5-methoxypyridine (327-1)

Tetrabutyl ammonium fluoride (1.0 M THF solution: 3.9 ml) was added to a DMF (5 ml) solution of 5-bromo-3-methoxy-2-nitropyridine (CAS No. 152684-26-9) (450 mg), and the obtained mixture was stirred at 70° C. for 72 hours. The reaction solution was cooled to room temperature. Water was added to the reaction solution, and the mixture was extracted with ethyl acetate. The organic layer was dried over sodium sulfate and then filtered. The filtrate was concentrated under reduced pressure, and the residue was purified by silica gel column chromatography (n-heptane:ethyl acetate=10:1 to 2:1), so as to obtain the title compound (258 mg).

1H-NMR (400 MHz, CDCl3) δ (ppm): 3.91 (s, 3H), 7.39 (dd, J=8.8, 2.4 Hz, 1H), 7.80 (t, J=2.4 Hz, 1H).

(2) Synthesis of (1R,2S)-2-{[(2,4-dimethylpyrimidin-5-yl)oxy]methyl}-N-(6-fluoro-5-methoxypyridin-3-yl)-2-phenylcyclopropanecarboxamide (327)

A 1,4-dioxane (3 ml) solution of the carboxamide73-1 (50 mg), the compound 327-1 (48 mg), xantphos (29 mg), potassium triphosphate (71 mg) and Pd$_2$DBA$_3$ (15 mg) was heated to 100° C. and stirred for 15 hours. Water was added to the reaction solution, and the obtained mixture was extracted with ethyl acetate. The organic layer was successively washed with water and a saturated sodium chloride aqueous solution, then dried over anhydrous sodium sulfate, and filtered. The filtrate was concentrated under reduced pressure, and the residue was purified by silica gel column chromatography (n-heptane to n-heptane:ethyl acetate=1:2), so as to obtain the title compound (5.9 mg).

1H-NMR (400 MHz, CDCl3) δ (ppm): 1.65 (dd, J=8.0, 5.6 Hz, 1H), 1.91 (t, J=5.6 Hz, 1H), 2.10 (dd, J=8.0, 5.6 Hz, 1H), 2.25 (s, 3H), 2.56 (s, 3H), 3.81 (s, 3H), 4.47 (d, J=9.6 Hz, 1H), 4.54 (d, J=9.6 Hz, 1H), 7.30 (t, J=7.2 Hz, 1H), 7.37 (t, J=7.2 Hz, 2H), 7.46 (d, J=7.2 Hz, 2H), 7.54 (t, J=2.4 Hz, 1H), 7.71 (brs, 1H), 7.93 (dd, J=9.2, 2.4 Hz, 1H), 8.01 (s, 1H).

MS [M+Na]+=423

TEST EXAMPLE

1. Measurement of Orexin Receptor-Binding Ability

The assay was carried out using a 96-well Wheat Germ Agglutinin Flash Plate (PerkinElmer). The volume in a single assay well was 100 ul, and the composition of the reaction solution was as follows:

25 mM HEPES (pH 7.5), 1 mM CaCl$_2$, 4.5 mM MgCl$_2$, 0.5% BSA (bovine serum albumin), 0.1% sodium azide, 0.05% Tween-20, and 0.2% DMSO.

Cell membranes were prepared from recombinant CHO cells that expressed OX2 or OX1. The cell membranes were used in an amount of 5 μg protein/assay. Test compound in various concentrations, and 0.2 nM [$^{125}$I]-OX-A as tracer were added to the cell membranes, and then allowed to react at room temperature for 30 minutes. After completion of the reaction, the reaction solution as a whole was discarded, and the wells were then washed once with 200 ul of wash buffer (25 mM HEPES (pH 7.5), 1 mM CaCl$_2$, 5 mM MgCl$_2$, 0.5% BSA, 0.1% sodium azide, 0.05% Tween-20, and 525 mM sodium chloride). Finally, the radioactivity of each well was measured using a scintillation counter (TopCount, PerkinElmer). The obtained results are shown in terms of I050 values (nM) in the following table.

TABLE 73

| Example No. | OX1 (IC50) nM | OX2 (IC50) nM |
|---|---|---|
| 1 | 139 | 6.8 |
| 2 | 296 | 19 |
| 4 | 55 | 38 |
| 5 | 145 | 38 |
| 10 | 228 | 31 |
| 11 | 279 | 53 |
| 12 | 247 | 53 |
| 13 | 1235 | 71 |
| 14 | 302 | 16 |
| 15 | 213 | 41 |
| 16 | 40 | 1.9 |
| 17 | 294 | 38 |
| 18 | 344 | 33 |
| 19 | 93 | 10 |
| 22 | 273 | 17 |
| 23 | 1697 | 67 |
| 24 | 28 | 7.0 |
| 25 | 927 | 59 |
| 26 | 20 | 3.7 |
| 27 | 169 | 15 |
| 28 | 1702 | 101 |
| 29 | 459 | 55 |
| 30 | 78 | 12 |
| 31 | 222 | 26 |
| 32 | 15 | 3.5 |
| 33 | 209 | 15 |
| 34 | 430 | 18 |
| 35 | 558 | 43 |
| 36 | 9 | 3.0 |
| 37 | 41 | 8.0 |
| 38 | 518 | 29 |
| 39 | 354 | 6.0 |
| 40 | 172 | 9.0 |
| 41 | 125 | 8.0 |
| 42 | 374 | 12 |
| 43 | 86 | 7.0 |
| 44 | | 26 |
| 45 | 13.9 | 6.2 |
| 46 | 423 | 43 |
| 47 | 228 | 29 |
| 49 | 65 | 23 |
| 50 | 12 | 13 |
| 51 | 6.4 | 3.9 |
| 52 | 37 | 28 |
| 53 | 261 | 18 |
| 57 | 532 | 35 |
| 58 | 1928 | 89 |
| 59 | 1407 | 51 |
| 60 | >2000 | 105 |
| 61 | 874 | 16 |
| 64 | 74 | 15 |
| 65 | 1034 | 81 |
| 66 | 398 | 50 |
| 68 | 140 | 56 |

TABLE 73-continued

| Example No. | OX1 (IC50) nM | OX2 (IC50) nM |
|---|---|---|
| 69 | 126 | 34 |
| 70 | 704 | 41 |
| 71 | 52 | 5.1 |
| 72 | 202 | 31 |
| 73 | 3.4 | 5.7 |
| 74 |  | 60 |
| 76-1 | 489 | 61 |
| 76-2 | 914 | 47 |
| 77 | 41 | 24 |
| 78 | 662 | 94 |
| 79 | 90 | 26 |
| 80 | 54 | 16 |
| 81 | 2592 | 63 |
| 82 | 2.4 | 3.7 |
| 83 |  | 14 |
| 84 | 6 | 3.0 |
| 85 | 4 | 5.0 |
| 86 | 6.3 | 6.1 |
| 87 | 43 | 10 |
| 88 | 267 | 13 |
| 89 | 161 | 14 |
| 90 | 2058 | 95 |
| 91 | 215 | 22 |
| 92 | 23 | 8.0 |
| 93 | 54 | 9.0 |
| 94 | 2.8 | 2.3 |
| 95 | 13.4 | 5.2 |
| 96 | 32 | 5.0 |
| 97 | 105 | 21 |
| 98 | 18 | 10 |
| 99 | 644 | 58 |
| 100 | 40 | 7.6 |
| 101 | 290 | 84 |
| 102 | 50 | 23 |
| 103 | 2943 | 96 |
| 104 | 4 | 4.3 |
| 105 | 195 | 18 |
| 106 |  | 19 |
| 107 |  | 41 |
| 108 |  | 73 |
| 109 | 12 | 5.8 |
| 110 | 340 | 110 |
| 111 | 34 | 6.0 |
| 112 | 1022 | 18 |
| 115 |  | 21 |
| 116 |  | 14 |
| 117 | 19 | 4.0 |
| 118 | 342 | 24 |
| 119 | 21 | 5.2 |
| 120 | 123 | 7.0 |
| 121 | 10 | 3.1 |
| 122 | <20 | 7.0 |
| 123 |  | 29 |
| 124 |  | 31 |
| 125 | 1045 | 84 |
| 126 | 100 | 107 |
| 127 | 1099 | 80 |
| 128 | 231 | 75 |
| 129 | 1.0 | 1.5 |
| 130 | 22 | 4.0 |
| 131 | 89 | 5.0 |
| 132 | 18 | 4.0 |
| 133 | 7 | 3.0 |
| 134 | <2 | 4.0 |
| 135 | 14 | 8.0 |
| 136 |  | 15.0 |
| 137 | 97 | 4.0 |
| 138 | 2.6 | 2.4 |
| 139 | 22 | 3.3 |
| 140 | 44 | 8.9 |
| 141 | 9 | 1.3 |
| 142 | 331 | 36 |
| 143 |  | 14 |
| 144 |  | 12 |
| 145 |  | 9 |
| 146 |  | 37 |
| 147 |  | 69 |
| 148 |  | 20 |
| 149 |  | 10 |
| 150 |  | 10 |
| 151 | 102 | 25 |
| 152 | 58 | 36 |
| 153 | 447 | 32 |
| 154 | 6 | 7.0 |
| 155 | 10 | 6.0 |
| 156 | 42 | 13 |
| 157 | 397 | 69 |
| 158 | 180 | 27 |
| 159 | 624 | 62 |
| 160 | 389 | 28 |
| 161 | 50 | 12 |
| 162 | 65 | 13 |
| 163 | <20 | 10 |
| 164 | 3 | 6.0 |
| 165 | 29 | 7.0 |
| 166 | 50 | 7.0 |
| 167 | 38 | 10 |
| 168 | 15 | 4.0 |
| 169 | 14 | 4.0 |
| 170 |  | 7.0 |
| 171 | 43 | 11 |
| 172 |  | 28 |
| 173 | 3.6 | 3.3 |
| 174 | 33 | 55 |
| 175 | 62 | 35 |
| 176 | 137 | 26 |
| 177 | 334 | 84 |
| 178 | 769 | 60 |
| 179 | 167 | 29 |
| 180 | 231 | 33 |
| 181 | 118 | 100 |
| 182 | 99 | 21 |
| 183 | 337 | 42 |
| 184 | 784 | 21 |
| 185 | 24 | 7.0 |
| 186 | 22 | 7.0 |
| 187 |  | 16 |
| 188 |  | 61 |
| 189 | 7 | 4.1 |
| 190 | 11 | 5.0 |
| 191 | 1 | 1.0 |
| 192 | 12 | 5.0 |
| 193 | 36 | 8.0 |
| 194 | 7 | 3.0 |
| 195 | 6 | 3.0 |
| 196 | 9 | 4.0 |
| 197 |  | 7.0 |
| 198 | 5 | 4.0 |
| 199 | 2 | 2.0 |
| 200 | 67 | 12 |
| 201 | 5 | 4.0 |
| 202 | 14 | 2.0 |
| 203 | 215 | 8.0 |
| 204 | 22 | 5.0 |
| 205 | 9 | 6.0 |
| 206 |  | 27 |
| 207 | 110 | 9.0 |
| 208 |  | 11 |
| 209 |  | 48 |
| 210 |  | >60 |
| 211 | 20 | 4.0 |
| 212 | 4 | 7.0 |
| 213 | 14 | 11 |
| 214 |  | 7.0 |
| 215 |  | 12 |
| 216 |  | 7.0 |
| 217 |  | 21 |
| 218 | 10 | 3.0 |
| 219 | 10 | 3.0 |
| 220 |  | 21.0 |
| 221 | <2 | 3.0 |
| 222 |  | 68.0 |
| 223 |  | 34 |
| 224 |  | 27 |

TABLE 73-continued

| Example No. | OX1 (IC50) nM | OX2 (IC50) nM |
|---|---|---|
| 225 | 6 | 3.0 |
| 226 |  | 7.0 |
| 227 |  | 14 |
| 228 |  | 45 |
| 229 | 19 | 4.0 |
| 230 |  | 16 |
| 231 |  | 7.0 |
| 232 | 1 | 3.0 |
| 233 |  | 6.0 |
| 234 | <2 | 4.0 |
| 235 |  | 6.0 |
| 236 | 21 | 5.0 |
| 237 |  | 31 |
| 238 |  | 15 |
| 239 |  | 7.0 |
| 240 | 8.7 | 2.9 |
| 241 | 2 | 2.2 |
| 242 | 6 | 4.0 |
| 243 | 2 | 3.3 |
| 244 | 3 | 5.3 |
| 245 | 64 | 10 |
| 246 | 16 | 4.0 |
| 247 | 22 | 3.0 |
| 248 | 10 | 3.0 |
| 249 |  | 17 |
| 250 |  | 14 |
| 251 |  | 30 |
| 252 |  | 18 |
| 253 |  | 41 |
| 254 | 109 | 11 |
| 255 |  | 27 |
| 256 | 12 | 5.0 |
| 257 |  | 84 |
| 258 |  | >60 |
| 259 |  | >60 |
| 260 | >2000 | 70 |
| 262 | 85 | 51 |
| 263 | 82 | 17 |
| 264 | 792 | 23 |
| 265 | 43 | 10 |
| 266 | 30 | 2.7 |
| 267 | 118 | 64 |
| 268 | 164 | 36 |
| 269 | 264 | 23 |
| 270 | 264 | 58 |
| 271 | 18 | 5.0 |
| 273 | 69 | 10 |
| 274 | 59 | 19 |
| 276 | 3213 | 76 |
| 277 | 2214 | 104 |
| 278 | 76 | 10 |
| 279 | 24 | 3.2 |
| 280 | 24 | 21 |
| 282 | 21 | 2.4 |
| 283 | 172 | 9.0 |
| 284 | 112 | 6.0 |
| 285 | 77 | 16 |
| 286 | >200 | 4.5 |
| 291 | >200 | 49 |
| 292 | 240 | 34 |
| 293 | 79 | 9.0 |
| 294 | >200 | 14 |
| 295 | 5 | 6.0 |
| 296 | >200 | 8.0 |
| 299 | 304 | 46 |
| 300 | 495 | 34 |
| 301 | 175 | 28 |
| 302 | 8 | 3.0 |
| 303 | 75 | 3.0 |
| 304 |  | 90 |
| 306 | 15 | 8.0 |
| 307 |  | 33 |
| 308 |  | 31 |
| 309 |  | 10 |
| 310 | 40 | 13 |
| 311 | 23 | 3.1 |
| 312 | 136 | 62 |
| 313 | 224 | 107 |
| 314 |  | 173 |
| 315 |  | 208 |
| 316 | 7 | 1.1 |
| 317 | 451 | 20 |
| 318 | 135 | 11 |
| 319 | >200 | 128 |
| 320 | 12.3 | 2.3 |
| 321 | 20 | 7.0 |
| 322 | 30 | 7.0 |
| 323 | 32.6 | 2.6 |
| 324 | 113 | 5.9 |
| 325 | 158 | 20 |
| 326 | 123 | 6.0 |
| 327 | 192 | 3.0 |

2. Measurement of Antagonism (PLAP Assay)

The antagonistic function of the compound of the present invention to prevent the activation of OX2 and OX1 by orexin-A (OX-A), which is a natural peptide agonist, was measured using a cell-based reporter assay. A HEK-293 cell line expressing genetically recombinant human OX2 (accession No. NM_001526.3) or a HEK-293 cell line expressing genetically recombinant human OX1 (accession No. NM_001525.2), which had pBabeCLIH as expression vector, was used. The cells were plated at a density of 10,000 cells/well onto a non-coated 96-well plate in Dulbecco's modified Eagle medium (Sigma Cat No. D6046:10% v/v heat-inactivated fetal bovine serum was contained). The cells were cultured at 37° C. overnight, so that they could adhere to the plate. On the following day, cells were incubated with a compound of the present invention dissolved in Dulbecco's modified Eagle medium (Sigma Cat No. A8806:0.1% w/v bovine serum albumin was contained), and added to the cell plate to reach a final concentration of 0.1% dimethyl sulfoxide.

The thus obtained mixture was incubated at room temperature for 1 hour. Thereafter, human OX-A and forskolin were dissolved in the same medium as described above, which contained fetal bovine serum albumin, and the medium was then added to the cells, resulting in a final concentration of 300 nM forskolin. Subsequently, the cells were cultured at 37° C. for approximately 18 to 24 hours. During the culture, as a result of activation of the orexin receptor and subsequent dose-dependent increase in intracellular calcium concentration, a reporter enzyme, placental alkaline phosphatase (PLAP), was expressed under the control of a CRE×4+VIP promoter in a pBabeCLcre4vPdNN vector and secreted into the culture medium supernatant. On the following day, reporter enzyme activity was detected by mixing 5 ul of the culture medium supernatant with 20 ul of detection buffer (containing 1.34 g/L, sodium bicarbonate, 1.27 g/L sodium carbonate and 0.2 g/L magnesium sulfate heptahydrate in water) and 25 ul of Lumi-Phos530 reagent (Wako Pure Chemical Industries Ltd.), followed by incubating the obtained mixture light-protected at room temperature for 2 hours, before performing luminescence measurement (ARVO Reader, PerkinElmer). The Kd value of human OX-A with respect to each receptor was measured by titration from 0 to 300 nM. Then, the IC50 value of the compound of the present invention with respect to the activity of 1 nM human OX-A was converted into a Ki value (nM) using the Cheng-Prusoff equation. The obtained Ki values (nM) are shown in the following table.

TABLE 74

| Example No. | OX1 (Ki) nM | OX2 (Ki) nM |
| --- | --- | --- |
| 1 | 157 | 10 |
| 16 | 80 | 5.4 |
| 26 | 27 | 0.4 |
| 45 | 19 | 0.45 |
| 51 | 29 | 1.2 |
| 61 | >667 | 26 |
| 64 | 133 | 6.3 |
| 65 | >667 | 60. |
| 66 | >667 | 34 |
| 67 | >667 | 57 |
| 82 | 0.96 | 0.085 |
| 95 | 9.9 | 0.69 |
| 100 | 147 | 9.4 |
| 119 | 21 | 0.6 |
| 120 | 273 | 5.7 |
| 121 | 26 | 0.3 |
| 129 | 0.97 | 0.06 |
| 139 | 113 | 1.7 |
| 161 | 32 | 2.9 |
| 164 | 0.93 | 0.087 |
| 186 | 87 | 3.4 |
| 240 | 18 | 0.91 |
| 263 | 193 | 8.6 |

3. Sleep Experiment

As a method for measuring the influence of the present compound on sleep time, electroencephalogram (EEG) and electromyogram (EMG) measurements were carried out in mice (C57BL/6NCrlCrLj).

In order to measure brain waves and muscle signals, EEG and EMG electrode implantation was performed on individual mice, and the mice were then housed in a state in which they could freely move and habituate in individual recording cages for 1 week or longer. Thereafter, amplified EEG and EMG signals were digitally recorded.

Mice received either oral administration of vehicle or test compound in vehicle, after which sleep/wake behavior of mice was recorded for 3 hours.

For sleep analysis, automatic analysis software from Kissei Comtec Co., Ltd. was used to analyze EEG frequency and EMG activity signals in detail and to determine sleep and wake states. Thereafter, accumulated sleeping time over 3 hours was calculated.

The effect of the compound to increase sleep time was evaluated as the difference between sleeping time on the vehicle-administration day and the sleep time on the subsequent drug-administration day. The obtained results are shown in the following table.

TABLE 75

| Example No. | Sleep extended time 10 mg/kg (min/3 hrs) |
| --- | --- |
| 1 | 18.3 |
| 16 | 19.0 |
| 45 | 15.2 |
| 51 | 23.6 |
| 73 | 22.7 |
| 82 | 33.5 |
| 95 | 39.8 |
| 96 | 12.1 |
| 100 | 23.8 |
| 105 | 14.3 |
| 119 | 16.0 |
| 120 | 11.5 |
| 121 | 26.7 |
| 129 | 30.0 |
| 130 | 24.2 |
| 141 | 28.7 |
| 161 | 10.0 |
| 164 | 48.4 |
| 186 | 14.7 |
| 191 | 41.8 |
| 199 | 36.2 |
| 240 | 7.7 |
| 263 | 27.3 |

Furthermore, among the above compounds, the compounds of Examples 1, 51, 82, 95, 129 and 240 were orally administered into mice at a dose of 0.3, 1, 3, 10, 30 or 100 mg/kg, and the prolongation of sleep time of each compound was measured (refer to the following graph). The minimum effective dose (MED; mg/kg) was obtained from accumulated sleep time of mice with three hours after the administration. The obtained results were 30, 3, 1-3, ≦1, 1-3 and 10 mg/kg for the compounds of Examples 1, 51, 82, 95, 129 and 240, respectively.

As described in detail above, the cyclopropane compounds of the present invention, a pharmaceutically acceptable salt thereof or a solvate thereof has orexin receptor antagonism, promote sleep time increase, and therefore has the potential to be useful for the treatement of sleep disturbance, for example, insomnia, via orexin receptor antagonism.

The invention claimed is:

1. A compound represented by the following formula (A) or a pharmaceutically acceptable salt thereof:

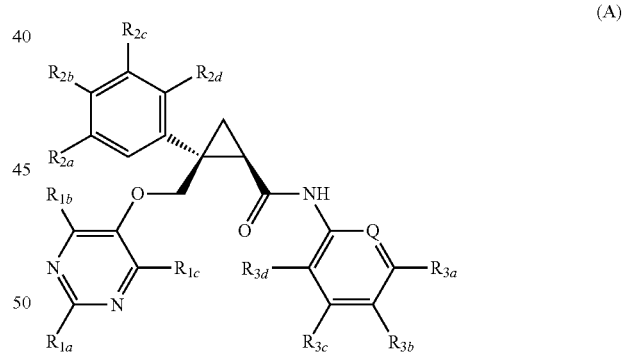

(A)

wherein
Q represents —CH— or a nitrogen atom,
when Q represents —CH—,
$R_{1a}$ and $R_{1b}$ each independently represent a $C_{1-6}$ alkyl group, a halo-$C_{1-6}$ alkyl group or a $C_{1-6}$ alkoxy-$C_{1-6}$ alkyl group,
$R_{1c}$ represents a hydrogen atom,
$R_{2a}$, $R_{2b}$, $R_{2c}$ and $R_{2d}$ each independently represent a hydrogen atom, a halogen atom, a $C_{1-6}$ alkyl group, a $C_{1-6}$ alkoxy group or a halo-$C_{1-6}$ alkyl group,
$R_{3a}$ and $R_{3c}$ each independently represent a hydrogen atom, a halogen atom, a $C_{1-6}$ alkyl group, a halo-$C_{1-6}$ alkyl group, a $C_{1-6}$ alkoxy group, a $C_{1-6}$ alkoxy-$C_{1-6}$ alkyl group, a cyano group or a cyano-$C_{1-6}$ alkyl group, $R_{3b}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom or a fluorine atom, or when Q represents a nitrogen atom, $R_{1a}$ and $R_{1b}$ each independently represent a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group, $R_{1c}$ represents a hydrogen atom or a hydroxyl group, $R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group or a halo-$C_{1-6}$ alkyl group, $R_{3a}$ represents a hydrogen atom, a halogen atom, a $C_{1-6}$ alkyl group, a $C_{1-6}$ alkoxy group or a $C_{1-6}$ alkoxy-$C_{1-6}$ alkyl group, $R_{3b}$ represents a hydrogen atom, a halogen atom, a $C_{1-6}$ alkyl group or a halo-$C_{1-6}$ alkyl group, $R_{3c}$ represents a hydrogen atom, a halogen atom, a $C_{1-6}$ alkyl group, a halo-$C_{1-6}$ alkyl group, a $C_{1-6}$ alkoxy group, or a $C_{1-6}$ alkoxy-$C_{1-6}$ alkyl group, and $R_{3d}$ represents a hydrogen atom.

2. The compound according to claim 1, which is represented by the following formula (B), or a pharmaceutically acceptable salt thereof:

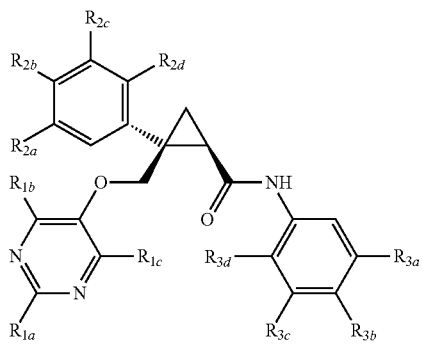

(B)

wherein $R_{1a}$ and $R_{1b}$ each independently represent a $C_{1-6}$ alkyl group, a halo-$C_{1-6}$ alkyl group or a $C_{1-6}$ alkoxy-$C_{1-6}$ alkyl group, $R_{1c}$ represents a hydrogen atom, $R_{2a}$, $R_{2b}$, $R_{2c}$ and $R_{2d}$ each independently represent a hydrogen atom, a halogen atom, a $C_{1-6}$ alkyl group, a $C_{1-6}$ alkoxy group or a halo-$C_{1-6}$ alkyl group, $R_{3a}$ and $R_{3c}$ each independently represent a hydrogen atom, a halogen atom, a $C_{1-6}$ alkyl group, a halo-$C_{1-6}$ alkyl group, a $C_{1-6}$ alkoxy group, a $C_{1-6}$ alkoxy-$C_{1-6}$ alkyl group, a cyano group or a cyano-$C_{1-6}$ alkyl group, $R_{3b}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom or a fluorine atom.

3. The compound according to claim 1, which is represented by the following formula (C), or a pharmaceutically acceptable salt thereof:

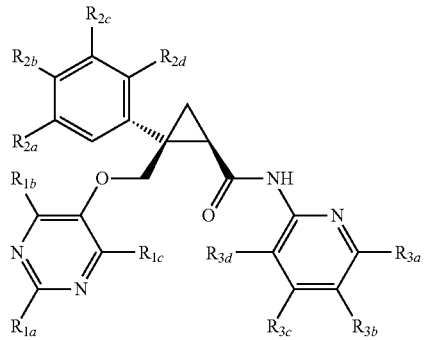

(C)

wherein $R_{1a}$ represents a $C_{1-6}$ alkyl group or a hydroxy-$C_{1-6}$ alkyl group, $R_{1b}$ represents a $C_{1-6}$ alkyl group, a halo-$C_{1-6}$ alkyl group, a hydroxy-$C_{1-6}$ alkyl group or a $C_{1-6}$ alkoxy-$C_{1-6}$ alkyl group, $R_{1c}$ represents a hydrogen atom or a hydroxyl group, $R_{2a}$, $R_{2b}$, $R_{2c}$ and $R_{2d}$ each independently represent a hydrogen atom, a halogen atom, a hydroxyl group, a $C_{1-6}$ alkyl group, a $C_{1-6}$ alkoxy group or a halo-$C_{1-6}$ alkyl group, $R_{3a}$ represents a substituent selected from a hydrogen atom, a halogen atom, a $C_{1-6}$ alkyl group, a $C_{1-6}$ alkoxy group and a $C_{1-6}$ alkoxy-$C_{1-6}$ alkyl group, $R_{3b}$ represents a hydrogen atom, a halogen atom, a $C_{1-6}$ alkyl group or a halo-$C_{1-6}$ alkyl group, $R_{3c}$ represents a hydrogen atom, a halogen atom, a $C_{1-6}$ alkyl group, a halo-$C_{1-6}$ alkyl group, a $C_{1-6}$ alkoxy group or a $C_{1-6}$ alkoxy-$C_{1-6}$ alkyl group, and $R_{3d}$ represents a hydrogen atom.

4. The compound according to claim 3, or a pharmaceutically acceptable salt thereof, wherein $R_{1a}$ represents a methyl group, $R_{1b}$ represents a methyl group, an ethyl group, a hydroxymethyl group, a methoxymethyl group or a methoxyethyl group, and $R_{1c}$ represents a hydrogen atom.

5. A compound, which is selected from the following compounds, or a pharmaceutically acceptable salt thereof:
1) (1R,2S)-2-{[(2,4-dimethylpyrimidin-5-yl)oxy]methyl}-N-(5-fluoropyridin-2-yl)-2-phenylcyclopropanecarboxamide,
2) (1R,2S)-N-(5-chloropyridin-2-yl)-2-{[(2,4-dimethylpyrimidin-5-yl)oxy]methyl}-2-phenylcyclopropanecarboxamide,
3) (1R,2S)-N-[3-(dimethylamino)phenyl]-2-{[(2,4-dimethylpyrimidin-5-yl)oxy]methyl}-2-phenylcyclopropanecarboxamide,
4) (1R,2S)-N-(3-chlorophenyl)-2-{[(2,4-dimethylpyrimidin-5-yl)oxy]methyl}-2phenylcyclopropanecarboxamide,
5) (1R,2S)-N-(3-cyano-4-fluorophenyl)-2-{[(2,4-dimethylpyrimidin-5-yl)oxy]methyl}-2-phenylcyclopropanecarboxamide,
6) (1R,2S)-N-(3-chloro-4-fluorophenyl)-2-{[(2,4-dimethylpyrimidin-5-yl)oxy]methyl}-2-phenylcyclopropanecarboxamide,
7) (1R,2S)-2-{[(2,4-dimethylpyrimidin-5-yl)oxy]methyl}-N-(3-methoxyphenyl)-2-phenylcyclopropanecarboxamide,
8) (1R,2S)-N-[3-(cyanomethyl)phenyl]-2-{[(2,4-dimethylpyrimidin-5-yl)oxy]methyl}-2-phenylcyclopropanecarboxamide, 9) (1R,2S)-2-{[(2,4-dimethylpyrimidin-5-yl)oxy]methyl}-2-phenyl-N-[3-(trifluoromethyl)phenyl]cyclopropanecarboxamide,
10) (1R,2S)-N-(5-chloro-4-methylpyridin-2-yl)-2-{[(2,4-dimethylpyrimidin-5-yl)oxy]methyl}-2-phenylcyclopropanecarboxamide,
11) (1R,2S)-2-{[(2,4-dimethylpyrimidin-5-yl)oxy]methyl}-N-(5-fluoro-4-methylpyridin-2-yl)-2-phenylcyclopropanecarboxamide,
12) (1R,2S)-2-{[(2,4-dimethylpyrimidin-5-yl)oxy]methyl}-N-[5-fluoro-4-(methoxymethyl)pyridin-2-yl]-2-phenylcyclopropanecarboxamide,
13) (1R,2S)-2-{[(2,4-dimethylpyrimidin-5-yl)oxy]methyl}-N-(5-fluoro-4-methoxypyridin-2-yl)-2-phenylcyclopropanecarboxamide,
14) (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide,
15) (1R,2S)-N-(3,4-difluorophenyl)-2-{[(2,4-dimethylpyrimidin-5-yl)oxy]methyl}-2-(3-fluorophenyl)cyclopropanecarboxamide,
16) (1R,2S)-N-(4-chloropyridin-2-yl)-2-{[(2,4-dimethylpyrimidin-5-yl)oxy]methyl}-2-(3-fluorophenyl)cyclopropanecarboxamide,
17) (1R,2S)-2-{[(2,4-dimethylpyrimidin-5-yl)oxy]methyl}-N-(5-fluoro-4-methoxymethylpyridin-2-yl)-2-(3-fluorophenyl)cyclopropanecarboxamide,
18) (1R,2S)-2-{[(2,4-dimethylpyrimidin-5-yl)oxy]methyl}-2-(3-fluorophenyl)-N-(4-fluorophenyl)cyclopropanecarboxamide,
19) (1R,2S)-2-{[(2,4-dimethylpyrimidin-5-yl)oxy]methyl}-2-(3-fluorophenyl)-N-phenylcyclopropanecarboxamide,
20) (1R,2S)-2-{[(2,4-dimethylpyrimidin-5-yl)oxy]methyl}-N-(5-fluoro-4-methoxypyridin-2-yl)-2-(3-fluorophenyl)cyclopropanecarboxamide,
21) (1R,2S)-2-{[(2,4-dimethylpyrimidin-5-yl)oxy]methyl}-2-(3-fluorophenyl)-N-(5-fluoropyridin-2-yl)cyclopropanecarboxamide,
22) (1R,2S)-N-(5-cyanopyridin-2-yl)-2-{[(2,4-dimethylpyrimidin-5-yl)oxy]methyl}-2-(3-fluorophenyl)cyclopropanecarboxamide,
23) (1R,2S)-2-{[(2,4-dimethylpyrimidin-5-yl)oxy]methyl}-2-(4-fluorophenyl)-N-(5-fluoropyridin-2-yl)cyclopropanecarboxamide,
24) (1R,2S)-2-{[(2,4-dimethylpyrimidin-5-yl)oxy]methyl}-N-(5-fluoro-4-methoxypyridin-2-yl)-2-(4-fluorophenyl)cyclopropanecarboxamide,
25) (1R,2S)-2-{[(2,4-dimethylpyrimidin-5-yl)oxy]methyl}-N-(5-fluoro-4-methoxymethylpyridin-2-yl)-2-(4-fluorophenyl)cyclopropanecarboxamide,
26) (1R,2S)-2-{[(2,4-dimethylpyrimidin-5-yl)oxy]methyl}-N-(5-fluoro-4-methylpyridin-2-yl)-2-(4-fluorophenyl)cyclopropanecarboxamide,
27) (1R,2S)-2-(3-cyanophenyl)-2-{[(2,4-dimethylpyrimidin-5-yl)oxy]methyl}-N-(5-fluoro-4-methylpyridin-2-yl)cyclopropanecarboxamide,
28) (1R,2S)-2-{[(4-ethyl-2-methylpyrimidin-5-yl)oxy]methyl}-N-(5-fluoropyridin-2-yl)-2-phenylcyclopropanecarboxamide,
29) (1R,2S)-N-(5-cyanopyridin-2-yl)-2-{[(4-ethyl-2-methylpyrimidin-5-yl)oxy]methyl}-2-phenylcyclopropanecarboxamide,
30) (1R,2S)-N-(5-chloropyridin-2-yl)-2-{[(4-ethyl-2-methylpyrimidin-5-yl)oxy]methyl}-2-phenylcyclopropanecarboxamide,
31) (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide,
32) (1R,2S)-2-(3,5-difluorophenyl)-2-{[(2,4-dimethylpyrimidin-5-yl)oxy]methyl}-N-(4-fluorophenyl)cyclopropanecarboxamide,
33) (1R,2S)-2-(3,5-difluorophenyl)-2-{[(2,4-dimethylpyrimidin-5-yl)oxy]methyl}-N-(pyridin-2-yl)cyclopropanecarboxamide,
34) (1R,2S)-N-(5-chloropyridin-2-yl)-2-(3,5-difluorophenyl)-2-{[(2,4-dimethylpyrimidin-5-yl)oxy]methyl}cyclopropanecarboxamide,
35) (1R,2S)-2-(3,5-difluorophenyl)-2-{[(2,4-dimethylpyrimidin-5-yl)oxy]methyl}-N-(5-fluoropyridin-2-yl)cyclopropanecarboxamide,
36) (1R,2S)-N-(3,4-difluorophenyl)-2-(3,5-difluorophenyl)-2-{[(2,4-dimethylpyrimidin-5-yl)oxy]methyl}cyclopropanecarboxamide,
37) (1R,2S)-N-(2,4-difluorophenyl)-2-(3,5-difluorophenyl)-2-{[(2,4-dimethylpyrimidin-5-yl)oxy]methyl}cyclopropanecarboxamide,
38) (1R,2S)-N-(5-cyanopyridin-2-yl)-2-(3,5-difluorophenyl)-2-{[(2,4-dimethylpyrimidin-5-yl)oxy]methyl}cyclopropanecarboxamide,
39) (1R,2S)-2-(3,5-difluorophenyl)-2-{[(2,4-dimethylpyrimidin-5-yl)oxy]methyl}-N-(5-fluoro-4-methoxypyridin-2-yl)cyclopropanecarboxamide,
40) (1R,2S)-N-(5-chloropyridin-2-yl)-2-{[(4-(methoxymethyl)-2-methylpyrimidin-5-yl)oxy]methyl}-2-phenylcyclopropanecarboxamide,
41) (1R,2S)-N-(5-cyanopyridin-2-yl)-2-{[(4-(methoxymethyl)-2-methylpyrimidin-5-yl)oxy]methyl}-2-phenylcyclopropanecarboxamide,
42) (1R,2S)-N-(5-fluoropyridin-2-yl)-2-{[(4-(methoxymethyl)-2-methylpyrimidin-5-yl)oxy]methyl}-2-phenylcyclopropanecarboxamide,
43) (1R,2S)-N-(5-fluoro-4-methylpyridin-2-yl)-2-{[(4-methoxymethyl-2-methylpyrimidin-5-yl)oxy]methyl}-2-phenylcyclopropanecarboxamide,
44) (1R,2S)-N-(4-fluorophenyl)-2-{[(4-methoxymethyl-2-methylpyrimidin-5-yl)oxy]methyl}-2-phenylcyclopropanecarboxamide,
45) (1R,2S)-N-(3,4-difluorophenyl)-2-{[(4-methoxymethyl-2-methylpyrimidin-5-yl)oxy]methyl}-2-phenylcyclopropanecarboxamide,
46) (1R,2S)-2-(3,4-difluorophenyl)-2-{[(2,4-dimethylpyrimidin-5-yl)oxy]methyl}-N-(5-fluoro-4-methylpyridin-2-yl)cyclopropanecarboxamide,
47) (1R,2S)-2-(3,4-difluorophenyl)-2-{[(2,4-dimethylpyrimidin-5-yl)oxy]methyl}-N-(4-fluorophenyl)cyclopropanecarboxamide,
48) (1R,2S)-2-(3,4-difluorophenyl)-2-{[(2,4-dimethylpyrimidin-5-yl)oxy]methyl}-N-(pyridin-2-yl)cyclopropanecarboxamide,
49) (1R,2S)-N-(5-cyanopyridin-2-yl)-2-(3,4-difluorophenyl)-2-{[(2,4-dimethylpyrimidin-5-yl)oxy]methyl}cyclopropanecarboxamide,
50) (1R,2S)-N-(5-chloropyridin-2-yl)-2-(3,4-difluorophenyl)-2-{[(2,4-dimethylpyrimidin-5-yl)oxy]methyl}cyclopropanecarboxamide,
51) (1R,2S)-2-(3,4-difluorophenyl)-2-{[(2,4-dimethylpyrimidin-5-yl)oxy]methyl}-N-(5-fluoropyridin-2-yl)cyclopropanecarboxamide,
52) (1R,2S)-N,2-bis(3,4-difluorophenyl)-2-{[(2,4-dimethylpyrimidin-5-yl)oxy]methyl}cyclopropanecarboxamide, 53) (1R,2S)-2-(3,4-difluorophenyl)-2-{[(2,4-dimethylpyrimidin-5-yl)oxy]methyl}-N-(5-fluoro-4-methoxypyridin-2-yl)cyclopropanecarboxamide, 54) (1R,2S)-2-{[(2,4-dimethylpyrimidin-5-yl)oxy]methyl}-N-(5-fluoropyridin-2-yl)-2-(3-methoxyphenyl)cyclopropanecarboxamide, 55) (1R,2S)-2-{[(2,4-dimethylpyrimidin-5-yl)oxy]methyl}-N-(5-fluoro-4-methylpyridin-2-yl)-2-(3-methoxyphenyl)cyclopropanecarboxamide, 56) (1R,2S)-N-(3,4-difluorophenyl)-2-{[(2,4-dimethylpyrimidin-5-yl)oxy]methyl}-2-(3-methoxyphenyl)cyclopropanecarboxamide, 57) (1R,2S)-2-(3-fluorophenyl)-N-(5-fluoropyridin-2-yl)-2-[(4-methoxymethyl-2-methylpyrimidin-5-yl)oxymethyl]cyclopropanecarboxamide, 58) (1R,2S)-2-(3-fluorophenyl)-N-(4-fluorophenyl)-2-{[(4-methoxymethyl-2-methylpyrimidin-5-yl)oxy]methyl}cyclopropanecarboxamide, 59) (1R,2S)-2-(3-fluorophenyl)-2-{[(4-methoxymethyl-2-methylpyrimidin-5-yl)oxy]methyl}-N-(pyridin-2-yl)cyclopropanecarboxamide, 60) (1R,2S)-N-(3,4-difluorophenyl)-2-(3-fluorophenyl)-2-{[(4-methoxymethyl-2-methylpyrimidin-5-yl)oxy]methyl}cyclopropanecarboxamide, 61) (1R,2S)-N,2-bis(3-fluorophenyl)-2-{[(4-methoxymethyl-2-methylpyrimidin-5-yl)oxy]methyl}cyclopropanecarboxamide, 62) (1R,2S)-N-(2,4-difluorophenyl)-2-(3-fluorophenyl)-2-{[(4-methoxymethyl-2-methylpyrimidin-5-yl)oxy]methyl}cyclopropanecarboxamide, 63) (1R,2S)-N-(2,5-difluorophenyl)-2-(3-fluorophenyl)-2-{[(4-methoxymethyl-2-methylpyrimidin-5-yl)oxy]methyl}cyclopropanecarboxamide, 64) (1R,2S)-N-(5-chloropyridin-2-yl)-2-(3-fluorophenyl)-2-{[(4-methoxymethyl-2-methylpyrimidin-5-yl)oxy]methyl}cyclopropanecarboxamide, 65) (1R,2S)-N-(5-fluoro-4-methylpyridin-2-yl)-2-(3-fluorophenyl)-2-{[(4-methoxymethyl-2-methylpyrimidin-5-yl)oxy]methyl}cyclopropanecarboxamide, 66) (1R,2S)-2-(3-fluorophenyl)-2-{[(4-methoxymethyl-2-methylpyrimidin-5-yl)oxy]methyl}-N-[5-(trifluoromethyl)pyridin-2-yl]cyclopropanecarboxamide, 67) (1R,2S)-2-(4-fluorophenyl)-N-(5-fluoropyridin-2-yl)-2-{[(4-methoxymethyl-2-methylpyrimidin-5-yl)oxy]methyl}cyclopropanecarboxamide, 68) (1R,2S)-N,2-bis(4-fluorophenyl)-2-{[(4-methoxymethyl-2-methylpyrimidin-5-yl)oxy]methyl}cyclopropanecarboxamide, 69) (1R,2S)-N-(5-chloropyridin-2-yl)-2-(4-fluorophenyl)-2-{[(4-methoxymethyl-2-methylpyrimidin-5-yl)oxy]methyl}cyclopropanecarboxamide, 70) (1R,2S)-N-(5-fluoro-4-methylpyridin-2-yl)-2-(4-fluorophenyl)-2-{[(4-methoxymethyl-2-methylpyrimidin-5-yl)oxy]methyl}cyclopropanecarboxamide, 71) (1R,2S)-N-(3,4-difluorophenyl)-2-(4-fluorophenyl)-2-{[(4-methoxymethyl-2-methylpyrimidin-5-yl)oxy]methyl}cyclopropanecarboxamide, 72) (1R,2S)-2-(3,4-difluorophenyl)-2-{[(4-methoxymethyl-2-methylpyrimidin-5-yl)oxy]methyl}-N-(pyridin-2-yl)cyclopropanecarboxamide, 73) (1R,2S)-2-(3,4-difluorophenyl)-N-(5-fluoro-4-methylpyridin-2-yl)-2-{[(4-methoxymethyl-2-methylpyrimidin-5-yl)oxy]methyl}cyclopropanecarboxamide, 74) (1R,2S)-N,2-bis(3,4-difluorophenyl)-2-{[(4-methoxymethyl-2-methylpyrimidin-5-yl)oxy]methyl}cyclopropanecarboxamide, 75) (1R,2S)-N-(2,4-difluorophenyl)-2-(3,4-difluorophenyl)-2-{[(4-methoxymethyl-2-methylpyrimidin-5-yl)oxy]methyl}cyclopropanecarboxamide, 76) (1R,2S)-2-(3,5-difluorophenyl)-2-{[(4-methoxymethyl-2-methylpyrimidin-5-yl)oxy]methyl}-N-(pyridin-2-yl)cyclopropanecarboxamide, 77) (1R,2S)-2-(3,5-difluorophenyl)-N-(4-fluorophenyl)-2-{[(4-methoxymethyl-2-methylpyrimidin-5-yl)oxy]methyl}cyclopropanecarboxamide, 78) (1R,2S)-N-(3,4-difluorophenyl)-2-(3,5-difluorophenyl)-2-{[(4-methoxymethyl-2-methylpyrimidin-5-yl)oxy]methyl}cyclopropanecarboxamide, 79) (1R,2S)-2-(3-chlorophenyl)-2-{[(4-methoxymethyl-2-methylpyrimidin-5-yl)oxy]methyl}-N-(pyridin-2-yl)cyclopropanecarboxamide, 80) (1R,2S)-2-(3-chlorophenyl)-N-(5-fluoro-4-methylpyridin-2-yl)-2-{[(4-methoxymethyl-2-methylpyrimidin-5-yl)oxy]methyl}cyclopropanecarboxamide, 81) (1R,2S)-N-(5-fluoro-4-methylpyridin-2-yl)-2-(3-fluorophenyl)-2-{[(4-methoxyethyl-2-methylpyrimidin-5-yl)oxy]methyl}cyclopropanecarboxamide, 82) (1R,2S)-2-(3-fluoro-5-methoxyphenyl)-N-(4-fluorophenyl)-2-{[(4-methoxymethyl-2-methylpyrimidin-5-yl)oxy]methyl}cyclopropanecarboxamide, 83) (1R,2S)-N-(3,4-difluorophenyl)-2-(3-fluoro-5-methoxyphenyl)-2-{[(4-methoxymethyl-2-methylpyrimidin-5-yl)oxy]methyl}cyclopropanecarboxamide, 84) (1R,2S)-2-(3-fluoro-5-methoxyphenyl)-N-(5-fluoropyridin-2-yl)-2-[(4-methoxymethyl-2-methylpyrimidin-5-yl)oxymethyl]cyclopropanecarboxamide, 85) (1R,2S)-2-(3-fluoro-5-methoxyphenyl)-N-(5-fluoro-4-methylpyridin-2-yl)-2-{[(4-methoxymethyl-2-methylpyrimidin-5-yl)oxy]methyl}cyclopropanecarboxamide, 86) (1R,2S)-2-(3-fluoro-5-methoxyphenyl)-2-[(4-methoxymethyl-2-methylpyrimidin-5-yl)oxymethyl]-N-(pyridin-2-yl)cyclopropanecarboxamide, 87) (1R,2S)-2-(3-fluoro-5-methoxyphenyl)-N-(3-fluorophenyl)-2-{[(4-methoxymethyl-2-methylpyrimidin-5-yl)oxy]methyl}cyclopropanecarboxamide, 88) (1R,2S)-2-(4-fluoro-3-methoxyphenyl)-N-(5-fluoro-4-methylpyridin-2-yl)-2-{[(4-methoxymethyl-2-methylpyrimidin-5-yl)oxy]methyl}cyclopropanecarboxamide, 89) (1R,2S)-2-{[(4-ethyl-2-methylpyrimidin-5-yl)oxy]methyl}-2-(3-fluorophenyl)-N-(pyridin-2-yl)cyclopropanecarboxamide, 90) (1R,2S)-2-{[(4-ethyl-2-methylpyrimidin-5-yl)oxy]methyl}-2-(3-fluorophenyl)-N-(5-fluoropyridin-2-yl)cyclopropanecarboxamide, 91) (1R,2S)-N-(5-cyanopyridin-2-yl)-2-{[(4-ethyl-2-methylpyrimidin-5-yl)oxy]methyl}-2-(3-fluorophenyl)cyclopropanecarboxamide, 92) (1R,2S)-N-(5-chloropyridin-2-yl)-2-{[(4-ethyl-2-methylpyrimidin-5-yl)oxy]methyl}-2-(3-fluorophenyl)cyclopropanecarboxamide, 93) (1R,2S)-2-{[(4-ethyl-2-methylpyrimidin-5-yl)oxy]methyl}-N-(5-fluoro-4-methylpyridin-2-yl)-2-(3-fluorophenyl)cyclopropanecarboxamide, 94) (1R,2S)-2-{[(4-ethyl-2-methylpyrimidin-5-yl)oxy]methyl}-2-(4-fluorophenyl)-N-(pyridin-2-yl)cyclopropanecarboxamide, 95) (1R,2S)-2-{[(4-ethyl-2-methylpyrimidin-5-yl)oxy]methyl}-2-(4-fluorophenyl)-N-(5-fluoropyridin-2-yl)cyclopropanecarboxamide, 96) (1R,2S)-N-(4-chloropyridin-2-yl)-2-{[(4-ethyl-2-methylpyrimidin-5-yl)oxy]methyl}-2-(4-fluorophenyl)cyclopropanecarboxamide,
97) (1R,2S)-2-{[(4-ethyl-2-methylpyrimidin-5-yl)oxy]methyl}-N-(5-fluoro-4-methylpyridin-2-yl)-2-(4-fluorophenyl)cyclopropanecarboxamide,
98) (1R,2S)-2-{[(2,4-dimethylpyrimidin-5-yl)oxy]methyl}-2-(3-fluoro-5-methoxyphenyl)-N-(5-fluoro-4-methylpyrimidin-2-yl)cyclopropanecarboxamide,
99) (1R,2S)-2-{[(2,4-dimethylpyrimidin-5-yl)oxy]methyl}-N-(5-fluoropyridin-2-yl)-2-(3-trifluoromethylphenyl)cyclopropanecarboxamide,
100) (1R,2S)-2-(4-bromophenyl)-N-(5-chloropyridin-2-yl)-2-{[(2,4-dimethylpyrimidin-5-yl)oxy]methyl}cyclopropanecarboxamide,
101) (1R,2S)-2-{[(2,4-dimethylpyrimidin-5-yl)oxy]methyl}-N-(5-fluoromethylpyridin-2-yl)-2-(3-fluorophenyl)cyclopropanecarboxamide,
102) (1R,2S)-2-{[(2,4-dimethylpyrimidin-5-yl)oxy]methyl}-N-(5-fluoropyridin-2-yl)-2-(3-iodophenyl)cyclopropanecarboxamide,
103) (1R,2S)-N-(5-fluoropyridin-2-yl)-2-{[(4-hydroxymethyl-2-methylpyrimidin-5-yl)oxy]methyl}-2-(3-fluorophenyl)cyclopropanecarboxamide,
104) (1R,2S)-2-{[(4-ethyl-2-methylpyrimidin-5-yl)oxy]methyl}-2-(3-fluorophenyl)-N-(4-fluorophenyl)cyclopropanecarboxamide,
105) (1R,2S)-2-{[(4-fluoromethyl-2-methylpyrimidin-5-yl)oxy]methyl}-2-(3-fluorophenyl)-N-(5-fluoropyridin-2-yl)cyclopropanecarboxamide,
106) (1R,2S)-2-{[(2,4-dimethylpyrimidin-5-yl)oxy]methyl}-2-(3-fluoro-4-hydroxyphenyl)-N-(5-fluoropyridin-2-yl)cyclopropanecarboxamide,
107) (1R,2S)-2-{[(2,4-dimethylpyrimidin-5-yl)oxy]methyl}-2-(3-fluoro-4-methoxyphenyl)-N-(5-fluoropyridin-2-yl)cyclopropanecarboxamide,
108) (1R,2S)-2-(3-fluorophenyl)-N-(5-fluoropyridin-2-yl)-2-{[(2-hydroxymethyl-4-methylpyrimidin-5-yl)oxy]methyl}cyclopropanecarboxamide,
109) (1R,2S)-2-{[(2,4-dimethylpyrimidin-5-yl)oxy]methyl}-2[5-fluoro-2-hydroxyphenyll-N-(5-fluoropyridin-2-yl)cyclopropanecarboxamide,
110) (1R,2S)-2-{[(2,4-dimethyl-6-oxo-1,6-dihydropyrimidin-5-yl)oxy]methyl}-2-(3-fluorophenyl)-N-(5-fluoropyridin-2-yl)cyclopropanecarboxamide,
111) (1R,2S)-N-(2-cyanopyridin-4-yl)-2-{[(2,4-dimethylpyrimidin-5-yl)oxy]methyl}-2-phenylcyclopropanecarboxamide,
112) (1R,2S)-2-[N-(2,4-dimethylpyrimidin-5-yl)methylaminomethyl]-N-(5-fluoropyridin-2-yl)-2-(3-fluorophenyl) cyclopropanecarboxamide,
113) (1R,2S)-N-(5-chloro-4-methylpyridin-2-yl)-2[N-(2,4-dimethylpyrimidin-5-yl)methylaminomethyl]-2-(3-fluorophenyl) cyclopropanecarboxamide,
114) (1R,2S)-N-(3,4-fluoropyridin-2-yl)-2-[N-(2,4-dimethylpyrimidin-5-yl)methylaminomethyl]-2-(3-fluorophenyl) cyclopropanecarboxamide,
115) (1R,2S)-2-(3-fluorophenyl)-N-(5-fluoropyridin-2-yl)-2-[N-(2-methyl-4-trifluoromethylpyrimidin-5-yl)methylaminomethyl] cyclopropanecarboxamide, and
116) (1R,2S)-2-{[(2,4-dimethylpyrimidin-5-yl)oxy]methyl}-N-(6-fluoro-5-methoxypyridin-3-yl)-2-phenylcyclopropanecarboxamide.

6. A compound, which is selected from the following compounds, or a pharmaceutically acceptable salt thereof:

1) (1R,2S)-2-{[(2,4-dimethylpyrimidin-5-yl)oxy]methyl}-N-(5-fluoropyridin-2-yl)-2-phenylcyclopropanecarboxamide,
11) (1R,2S)-2-{[(2,4-dimethylpyrimidin-5-yl)oxy]methyl}-N-(5-fluoro-4-methylpyridin-2-yl)-2-phenylcyclopropanecarboxamide,
14) (1R,2S)-2-{[(2,4-dimethylpyrimidin-5-yl)oxy]methyl}-N-(5-fluoro-4-methylpyridin-2-yl)-2-(3-fluorophenyl)cyclopropanecarboxamide,
21) (1R,2S)-2-{[(2,4-dimethylpyrimidin-5-yl)oxy]methyl}-2-(3-fluorophenyl)-N-(5-fluoropyridin-2-yl)cyclopropanecarboxamide,
31) (1R,2S)-2-(3,5-difluorophenyl)-2-{[(2,4-dimethylpyrimidin-5-yl)oxy]methyl}-N-(5-fluoro-4-methylpyridin-2-yl)cyclopropanecarboxamide, and
89) (1R,2S)-2-{[(4-ethyl-2-methylpyrimidin-5-yl)oxy]methyl}-2-(3-fluorophenyl)-N-(pyridin-2-yl)cyclopropanecarboxamide.

7. (1R,2S)-2-{[(2,4-Dimethylpyrimidin-5-yl)oxy]methyl}-N-(5-fluoro-4-methylpyridin-2-yl)-2-(3-fluorophenyl)cyclopropanecarboxamide represented by the following formula or a pharmaceutically acceptable salt thereof:

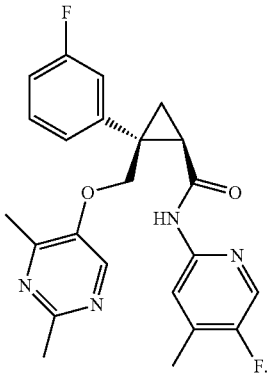

8. (1R,2S)-2-{[(2,4-Dimethylpyrimidin-5-yl)oxy]methyl}-2-(3-fluorophenyl)-N-(5-fluoropyridin-2-yl)cyclopropanecarboxamide represented by the following formula or a pharmaceutically acceptable salt thereof:

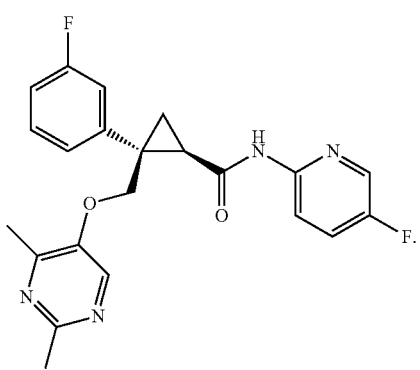

9. (1R,2S)-2-(3,5-Difluorophenyl)-2-{[(2,4-dimethylpyrimidin-5-yl)oxy]methyl}-N-(5-fluoro-4-methylpyridin-2-yl)cyclopropanecarboxamide represented by the following formula or a pharmaceutically acceptable salt thereof:

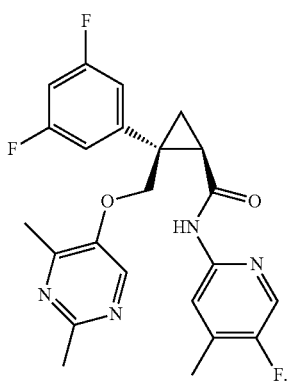

10. A pharmaceutical composition comprising, as an active ingredient, the compound according to claim 2 or a pharmaceutically acceptable salt thereof.

11. A method for treating sleep disorder for which orexin receptor antagonism is effective, which comprises administering the compound according to claim 2 or a pharmaceutically acceptable salt thereof into a subject in need thereof.

12. The method according to claim 11, wherein said sleep disorder is insomnia.

13. A pharmaceutical composition comprising, as an active ingredient, the compound according to claim 3 or a pharmaceutically acceptable salt thereof.

14. A method for treating sleep disorder for which orexin receptor antagonism is effective, which comprises administering the compound according to claim 3 or a pharmaceutically acceptable salt thereof into a subject in need thereof.

15. The method according to claim 14, wherein said sleep disorder is insomnia.

16. A pharmaceutical composition comprising, as an active ingredient, the compound according to claim 5 or a pharmaceutically acceptable salt thereof.

17. A method for treating sleep disorder for which orexin receptor antagonism is effective, which comprises administering the compound according to claim 5 or a pharmaceutically acceptable salt thereof into a subject in need thereof.

18. The method according to claim 17, wherein said sleep disorder is insomnia.

19. A pharmaceutical composition comprising, as an active ingredient, the compound according to claim 7 or a pharmaceutically acceptable salt thereof.

20. A method for treating sleep disorder for which orexin receptor antagonism is effective, which comprises administering the compound according to claim 7 or a pharmaceutically acceptable salt thereof into a subject in need thereof.

21. The method according to claim 20, wherein said sleep disorder is insomnia.

22. A pharmaceutical composition comprising, as an active ingredient, the compound according to claim 8 or a pharmaceutically acceptable salt thereof.

23. A method for treating sleep disorder for which orexin receptor antagonism is effective, which comprises administering the compound according to claim 8 or a pharmaceutically acceptable salt thereof into a subject in need thereof.

24. The method according to claim 23, wherein said sleep disorder is insomnia.

25. A pharmaceutical composition comprising, as an active ingredient, the compound according to claim 9 or a pharmaceutically acceptable salt thereof.

26. A method for treating sleep disorder for which orexin receptor antagonism is effective, which comprises administering the compound according to claim 9 or a pharmaceutically acceptable salt thereof into a subject in need thereof.

27. The method according to claim 26, wherein said sleep disorder is insomnia.

\* \* \* \* \*

UNITED STATES PATENT AND TRADEMARK OFFICE
CERTIFICATE OF CORRECTION

| | | |
|---|---|---|
| PATENT NO. | : 8,268,848 B2 | Page 1 of 3 |
| APPLICATION NO. | : 13/237205 | |
| DATED | : September 18, 2012 | |
| INVENTOR(S) | : Terauchi et al. | |

It is certified that error appears in the above-identified patent and that said Letters Patent is hereby corrected as shown below:

On the Title Page, Item [57] ABSTRACT
Lines 3-4, replace "a potencial of usefulness for" with --a potential use for--.

In the Specification

Column 1
Line 8, replace "Applicaton" with --Application--.

Column 1
Line 29, replace "Patent Documents 14" with --Patent Documents 1-4--.

Column 1
Line 50, replace "whichinvolved" with --which involved--.

Column 4
Line 45, replace "fluoropyridyl" with --furopyridyl--.

Column 6
Line 67, replace "groupor" with --group or--.

Column 18
Line 32, replace "fluoropyridyl" with --furopyridyl--.

Column 19
Line 63, replace "$R_{3a}, R_{3b}, R_{3c}$ and $R_{3b}$" with --$R_{3a}, R_{3b}, R_{3c}$ and $R_{3d}$--.

Signed and Sealed this
Twenty-fifth Day of February, 2014

Michelle K. Lee
*Deputy Director of the United States Patent and Trademark Office*

Column 20
Lines 19-20, replace "$R_{1a}$, $R_{1b}$, $R_{1c}$, $R_{2a}$, $R_{2b}$, $R_{2c}$, $R_{2d}$, $R_{3a}$, $R_{3b}$, $R_{3c}$ and $R_{3b}$" with
--$R_{1a}$, $R_{1b}$, $R_{1c}$, $R_{2a}$, $R_{2b}$, $R_{2c}$, $R_{2d}$, $R_{3a}$, $R_{3b}$, $R_{3c}$ and $R_{3d}$--.

Column 20
Lines 42-43, replace "$R_{1a}$, $R_{1b}$, $R_{1c}$, $R_{2a}$, $R_{2b}$, $R_{2c}$, $R_{2d}$, $R_{3a}$, $R_{3b}$, $R_{3o}$ and $R_{3b}$" with
--$R_{1a}$, $R_{1b}$, $R_{1c}$, $R_{2a}$, $R_{2b}$, $R_{2c}$, $R_{2d}$, $R_{3a}$, $R_{3b}$, $R_{3c}$ and $R_{3d}$--.

Column 49
Lines 2-3, delete "in the sleep experiment by oral administration using mice, which is shown in Test Examples".

Column 49
Line 9, replace "has applicability as a therapeutic agent for" with --has potential use as a therapeutic agent for--.

Column 57
Line 3, replace "range was filtered" with --range by adding ammonia/methanol was filtered--.

Column 73
Line 8, replace "690-696" with --6.90-6.96--.

Column 73
Line 60, replace "10: Ito 0:1" with --10:1 to 0:1--.

Column 122
Line 36, replace "the obtained product of interest" with --the obtained target compound--.

Column 142
Line 2, replace "The obtained product of interest" with --The obtained target compound--.

Column 166
Lines 52-53, replace "the obtained product of interest" with --the obtained target compound--.

Column 169
Line 58, replace "the obtained product of interest" with --the obtained target compound--.

Column 304
Line 17, replace "1050" with --$IC_{50}$--.

Column 308
Line 64, replace "1 nM" with --1nM/L--.

Column 309, Table 74
Example 100, line 15, replace "147" with --146.7--.

CERTIFICATE OF CORRECTION (continued)

U.S. Pat. No. 8,268,848 B2

Column 309, Table 74
Example 119, line 16, replace "21" with --21.3--.

Column 309, Table 74
Example 120, line 17, replace "273" with --273.3--.

Column 309, Table 74
Example 121, line 18, replace "26" with --26.7--.

Column 309
Line 29, replace "6NCrlCrLj" with --6NCrlCrlj--.

Column 310
Line 20, replace "was measured (refer to the following graph)" with --was measured. The results obtained were shown in Figure 1--.

Column 310
Lines 30-31, replace "to be useful for" with --use for--.

In the Claims

Column 312
Lines 53-55, Claim 5, replace "4) (1R,2S)-N-(3-chlorophenyl)-2-{[(2,4-dimethylpyrimidin-5-yl)oxy]methyl}-2phenylcyclopropanecarboxamide" with --4) (1R,2S)-N-(3-chlorophenyl)-2-{[(2,4-dimethylpyrimidin-5-yl)oxy]methyl}-2-phenylcyclopropanecarboxamide--.

Column 317
Lines 42-44, Claim 5, replace "109) (1R,2S)-2-{[(2,4-dimethylpyrimidin-5-yl)oxy]methyl}-2[5-fluoro-2-hydroxyphenyll-N-(5-fluoropyridin-2-yl)cyclopropanecarboxamide" with --109) (1R,2S)-2-{[(2,4-dimethylpyrimidin-5-yl)oxy]methyl}-2-[5-fluoro-2-hydroxyphenyl]-N-(5-fluoropyridin-2-yl)cyclopropanecarboxamide--.

Column 317
Lines 54-56, Claim 5, replace "113) (1R,2S) -N-(5-chloro-4-methylpyridin-2-yl)-2[N-(2,4-dimethylpyrimidin-5-yl)methylaminomethyl] -2-(3-fluorophenyl) cyclopropanecarboxamide" with --113) (1R,2S) -N-(5-chloro-4-methylpyridin-2-yl)-2-[N-(2,4-dimethylpyrimidin-5-yl)methylaminomethyl] -2-(3-fluorophenyl) cyclopropanecarboxamide--.